(12) United States Patent
Collins et al.

(10) Patent No.: US 8,324,226 B2
(45) Date of Patent: Dec. 4, 2012

(54) THERAPEUTIC OXY-PHENYL-ARYL COMPOUNDS AND THEIR USE

(75) Inventors: Ian Collins, Sutton (GB); John Jamieson Caldwell, Sutton (GB); Antony William Oliver, Sutton (GB); Tony Michael Raynham, London (GB); Emma Jane Welsh, Sutton (GB); Cornelius Albertus Johannes Matijssen, Sutton (GB)

(73) Assignee: Cancer Research Technology Limited, London (GB)

( * ) Notice: Subject to any disclaimer, the term of this patent is extended or adjusted under 35 U.S.C. 154(b) by 97 days.

(21) Appl. No.: 12/738,808

(22) PCT Filed: Oct. 23, 2008

(86) PCT No.: PCT/GB2008/003586
§ 371 (c)(1),
(2), (4) Date: Feb. 17, 2011

(87) PCT Pub. No.: WO2009/053694
PCT Pub. Date: Apr. 30, 2009

(65) Prior Publication Data
US 2011/0201592 A1    Aug. 18, 2011

Related U.S. Application Data

(60) Provisional application No. 60/982,203, filed on Oct. 24, 2007.

(51) Int. Cl.
*A01N 43/54* (2006.01)
*A61K 31/517* (2006.01)

(52) U.S. Cl. .............. 514/266.2; 514/256; 514/340; 544/328; 546/268.1

(58) Field of Classification Search ............ 514/266.2, 514/256, 340; 544/328; 546/268.1
See application file for complete search history.

(56) References Cited

U.S. PATENT DOCUMENTS
7,713,983 B2 *   5/2010   Gonzalez et al. .......... 514/266.1

FOREIGN PATENT DOCUMENTS
WO      WO 0224679 A1 *   3/2002
WO      WO 2004078733 A1 *   9/2004

* cited by examiner

*Primary Examiner* — James O Wilson
*Assistant Examiner* — Alexander R Pagano
(74) *Attorney, Agent, or Firm* — Swanson & Bratschun, L.L.C.

(57) ABSTRACT

The present invention pertains generally to the field of therapeutic compounds, and more specifically to certain oxy phenyl aryl compounds (referred to herein as OPA compounds), as described herein, which, inter alia, inhibit Checkpoint Kinase 2 (CHK2) kinase function. The present invention also pertains to pharmaceutical compositions comprising such compounds, and the use of such compounds and compositions, both in vitro and in vivo, to inhibit CHK2 kinase function, and in the treatment of diseases and conditions that are mediated by CHK2, that are ameliorated by the inhibition of CHK2 kinase function, etc., including proliferative conditions such as cancer, etc., optionally in combination with another agent, for example, (a) a DNA topoisomerase I or II inhibitor; (b) a DNA damaging agent; (c) an antimetabolite or TS inhibitor; (d) a microtubule targeted agent; and (e) ionising radiation.

17 Claims, 1 Drawing Sheet

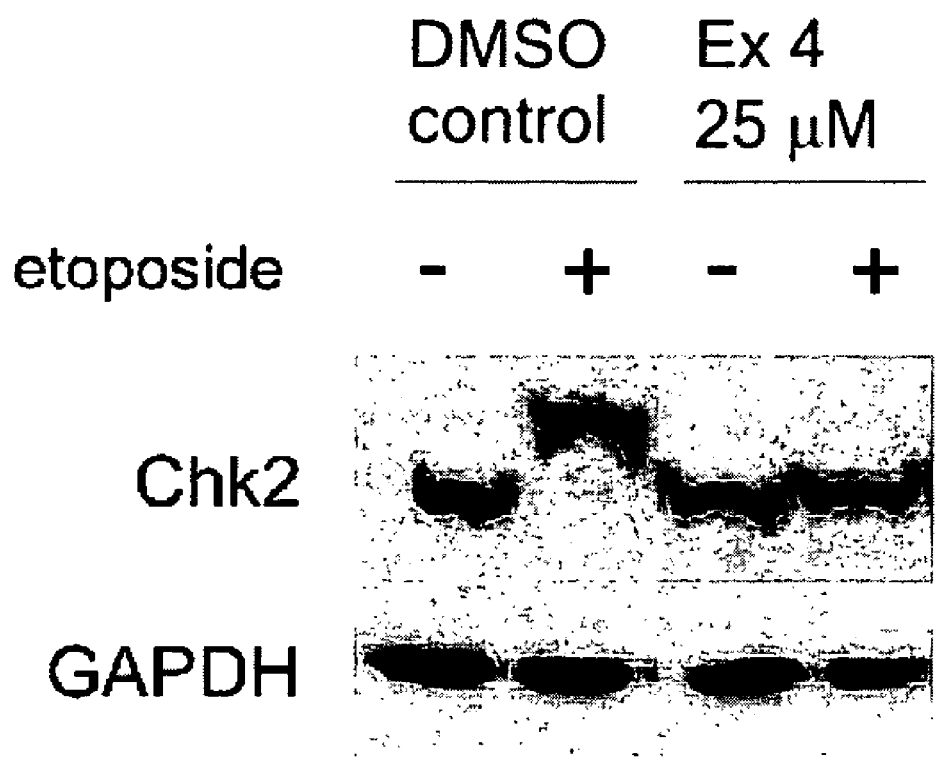

THERAPEUTIC OXY-PHENYL-ARYL COMPOUNDS AND THEIR USE

RELATED APPLICATION

This application is a 35 U.S.C. §371 national phase application of PCT/GB2008/003586 (WO 2009/053694) filed Oct. 23, 2008, entitled "Therapeutic Oxy-Phenyl-Aryl Compounds and Their Use". PCT/GB2008/003586 is a non-provisional application of U.S. provisional patent application No. 60/982,203 filed Oct. 24, 2007, the contents of which are incorporated herein by reference in their entirety.

TECHNICAL FIELD

The present invention pertains generally to the field of therapeutic compounds, and more specifically to certain oxy-phenyl-aryl compounds (referred to herein as OPA compounds), as described herein, which, inter alia, inhibit Checkpoint Kinase 2 (CHK2) kinase function. The present invention also pertains to pharmaceutical compositions comprising such compounds, and the use of such compounds and compositions, both in vitro and in vivo, to inhibit CHK2 kinase function, and in the treatment of diseases and conditions that are mediated by CHK2, that are ameliorated by the inhibition of CHK2 kinase function, etc., including proliferative conditions such as cancer, etc., optionally in combination with another agent, for example, (a) a DNA topoisomerase I or II inhibitor; (b) a DNA damaging agent; (c) an antimetabolite or TS inhibitor; (d) a microtubule targeted agent; and (e) ionising radiation.

Incorporated by reference herein in its entirety is the Sequence Listing entitled "sequence Listing.txt", created Feb. 17, 2011, size of 1 kilobyte.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Checkpoint Kinase 2 (CHK2)

The human genome is subject to continuos attack on its integrity, and as a consequence eukaryotic cells possess distinct strategies with which to respond to DNA damage. In this situation, cells respond by activation of cell cycle checkpoints, which either lead to the repair of the damaged DNA or, if the damage is too severe, to activation of cellular processes leading to cell death. A key component of this response is the cell cycle checkpoint kinase Cds1, which was first identified in the fission yeast *schizosaccharomyces pombe* (see, e.g., Murakami et al., 1995). The human homologue of Cds1 is known as CHK2 and is activated in response to DNA damage by phosphorylation at threonine 68, which requires the PI3-Kinase family member, ATM (see, e.g., Matsuoka et al., 1998; Melchionna et al., 2000). This promotes dimerisation of the protein allowing trans-activation through T-loop exchange (see, e.g., Oliver et al., 2006). Once activated, CHK2 can phosphorylate a number of substrates that regulate cell cycle arrest, DNA repair and cell death. Key substrates include the cell cycle phosphatases, Cdc25A and Cdc25C, which are inactivated through degradation and relocalisation respectively (see, e.g., Pommier et al., 2005). Another important substrate is the p53 protein that is phosphorylated at serine 20, which promotes activation of this important tumour suppressor (see, e.g., Hirao et al., 2000; Chehab et al., 2000). Others include BRCA1, E2F, Plk1 and PML (see, e.g., Pommier et al., 2005).

Inhibition of CHK2 has the potential to offer a number of therapeutic strategies for the treatment of cancer.

All cancers, by definition, have some form of aberrant cell division cycle and frequently the cancer cells possess one or more defective cell cycle checkpoints or harbour defects in a particular DNA repair pathway. These cells are more dependent on the remaining cell cycle checkpoints and repair pathways, compared to normal, non-cancerous cells (where all checkpoints and DNA repair pathways are intact) and their response to DNA damage is frequently a critical determinant of whether they continue to proliferate or activate cell death processes and die. For example, tumour cells that contain a mutant form(s) of the tumour suppressor p53 are defective in the G1 DNA damage checkpoint. Thus CHK2 inhibitors that can abrogate the G2 or S-phase checkpoints (induced by such cancer treatments as ionising radiation or chemotherapeutic anticancer agents) are expected to further cripple the ability of the tumour cell to repair damaged DNA.

Many of the known cancer treatments cause DNA damage by either physically modifying DNA or disrupting vital cellular processes that can affect the fidelity of DNA replication and cell division, such as DNA metabolism, DNA synthesis, DNA transcription and microtubule spindle formation. Such treatments include for example, ionising radiation, which causes DNA strand breaks and a variety of chemotherapeutic agents. A significant limitation to these treatments is drug resistance and one of the most important mechanisms of this resistance is attributed to activation of cell cycle checkpoints, giving the tumour cell time to repair damaged DNA. By abrogating a particular cell cycle checkpoint or inhibiting a particular form of DNA repair by inhibition of CHK2, it may be possible to circumvent tumour cell resistance to these agents and augment tumour cell death induced by DNA damage, thus increasing the therapeutic index of these cancer treatments.

Many tumours already possess activated checkpoint pathway(s), due to intrinsic damaged DNA (see, e.g., Gorgoulis et al., 2005; Bartkova et al., 2005). It may therefore also be possible to administer a CHK2 inhibitor as a single agent and obtain therapeutic activity through inhibition of remaining checkpoint pathway(s) that are in operation.

A major effect of cytotoxic cancer treatments, such as ionising radiation or chemotherapeutic agents, is the death of proliferating cancer cells. However, these agents often have side effects, due to toxicity to normal proliferating tissues. One explanation for this is that cancer cells are often resistant to apoptosis due to defective cell cycle checkpoints. Consequently the doses of a particular cancer treatment that are effective against the tumour may also kill the proliferating normal cells that have intact cell cycle checkpoints and undergo apoptosis. One of the most important signalling pathways involved in activation of cell cycle checkpoints is the p53 pathway. The TP53 gene itself is mutated in 50% of human tumours, whilst other components of this pathway are also found altered in cancer (see, e.g., Gorgoulis et al., 2005; Bartkova et al., 2005). Thus, if p53-dependent apoptosis is temporarily inhibited in normal cells the toxicity/side effects of cancer treatments may be reduced. For example, pifithrin-α a pharmacological inhibitor of p53 function, protects mice from lethal and sub-lethal doses of radiation without causing tumour formation (see, e.g., Komarov et al., 1999). In addition, targeted disruption of CHK2 allows the increased survival of mice exposed to radiation (through resistance to apoptosis) and these animals do not show an increase in spontaneous tumour development compared to the wild-type controls (see, e.g., Takai et al., 2002). Pharmacological inhibition of CHK2 has been shown to have a radioprotective effect on normal human cells (see, e.g., Arienti et al., 2005).

In addition, inhibition of CHK2 alone or in combination with other agents may provide new strategies for treatment or prevention of other diseases, disorders or symptoms thereof in addition to cancer where cell death is associated, such as hypoxia, diabetes, stroke and autoimmune disease.

CHK2 is activated in response to the physiological stress of hypoxia/reoxygenation (see, e.g., Gibson et al., 2005). Loss or inhibition of CHK2 sensitises cells to hypoxia/reoxygenation. Therefore inhibition of CHK2 in this context may have particular therapeutic value in the treatment of solid tumours, which are often hypoxic.

SUMMARY OF THE INVENTION

One aspect of the invention pertains to certain oxy-phenyl-aryl compounds (referred to herein as OPA compounds), as described herein.

Another aspect of the invention pertains to a composition (e.g., a pharmaceutical composition) comprising an OPA compound, as described herein, and a pharmaceutically acceptable carrier or diluent.

Another aspect of the invention pertains to method of preparing a composition (e.g., a pharmaceutical composition) comprising the step of admixing an OPA compound, as described herein, and a pharmaceutically acceptable carrier or diluent.

Another aspect of the present invention pertains to a method of inhibiting CHK2 kinase function in a cell, for example, in vitro or in vivo, comprising contacting the cell with an effective amount of an OPA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a method of regulating (e.g., inhibiting) cell proliferation (e.g., proliferation of a cell), inhibiting cell cycle progression, promoting apoptosis, or a combination of one or more these, for example, in vitro or in vivo, comprising contacting a cell with an effective amount of an OPA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a method of treatment comprising administering to a subject in need of treatment a therapeutically-effective amount of an OPA compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to an OPA compound as described herein for use in a method of treatment of the human or animal body by therapy.

In one embodiment, the method of treatment comprises treatment with both (i) an OPA compound and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to use of an OPA compound, as described herein, in the manufacture of a medicament for use in treatment.

In one embodiment, the treatment comprises treatment with both (i) a medicament comprising an OPA compound and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

In one embodiment, the treatment is treatment of a disease or condition that is mediated by CHK2.

In one embodiment, the treatment is treatment of a disease or condition that is ameliorated by the inhibition of CHK2 kinase function.

In one embodiment, the treatment is treatment of a proliferative condition.

In one embodiment, the treatment is treatment of cancer.

In one embodiment, the treatment is treatment of p53 negative cancer.

In one embodiment, the treatment is treatment of lung cancer, breast cancer, ovarian cancer, colorectal cancer, melanoma, or glioma.

Another aspect of the present invention pertains to a method of radio-protecting a cell (e.g., a non-cancerous cell) comprising contacting the cell with an effective amount of an OPA compound, as described herein.

Another aspect of the present invention pertains to a method of reducing or eliminating damaging effects of ionising radiation on a cell (e.g., a non-cancerous cell) that has been exposed to ionising radiation, or will be exposed to ionising radiation, comprising contacting the cell with an effective amount of an OPA compound, as described herein.

Another aspect of the present invention pertains to a method of radio-protecting cells (e.g., non-cancerous cells) (e.g., protecting cells, e.g., non-cancerous cells, from damaging effects of ionising radiation) in a patient undergoing treatment with ionizing radiation (e.g., radiotherapy) (e.g., in a patient that has had, is having, or will have treatment with ionizing radiation, e.g., radiotherapy), comprising administering to the patient a therapeutically-effective amount of an OPA compound, as described herein, preferably in the form of a pharmaceutical composition.

Another aspect of the present invention pertains to an OPA compound, as described herein, for use in a method of radio-protecting cells (e.g., non-cancerous cells) (e.g., protecting cells, e.g., non-cancerous cells, from damaging effects of ionising radiation) in a patient undergoing treatment with ionizing radiation (e.g., radiotherapy) (e.g., in a patient that has had, is having, or will have treatment with ionizing radiation, e.g., radiotherapy).

Another aspect of the present invention pertains to use of an OPA compound, as described herein, in the manufacture of a medicament for use in a method of radio-protecting cells (e.g., non-cancerous cells) (e.g., protecting cells, e.g., non-cancerous cells, from damaging effects of ionising radiation) in a patient undergoing treatment with ionizing radiation (e.g., radiotherapy) (e.g., in a patient that has had, is having, or will have treatment with ionizing radiation, e.g., radiotherapy).

Another aspect of the present invention pertains to a kit comprising (a) an OPA compound, as described herein, preferably provided as a pharmaceutical composition and in a suitable container and/or with suitable packaging; and (b) instructions for use, for example, written instructions on how to administer the compound.

In one embodiment, the kit further comprises one or more other agents selected from: (a) a DNA topoisomerase I or II inhibitor; (b) a DNA damaging agent; (c) an antimetabolite or TS inhibitor; and (d) a microtubule targeted agent.

Another aspect of the present invention pertains to an OPA compound obtainable by a method of synthesis as described herein, or a method comprising a method of synthesis as described herein.

Another aspect of the present invention pertains to an OPA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

BRIEF DESCRIPTION OF THE DRAWINGS

FIG. 1 is a photograph of a gel obtained using the CHK2 band shift assay described herein and showing bands for Chk2 and GAPDH, with lanes for a DMSO control (without and with etoposide) and for 25 µM compound A-004 (denoted "Ex 4") (again, without and with etoposide). Compound A-004 prevented the etoposide-induced CHK2 band shift on the gel when the cells were exposed to a concentration of 25 µM of the compound.

DETAILED DESCRIPTION OF THE INVENTION

Compounds

One aspect of the present invention pertains to compounds selected from compounds of the following formula and phar-maceutically acceptable salts, hydrates, and solvates thereof (collectively referred to herein as "oxy-phenyl-aryl compounds" or "OPA compounds"):

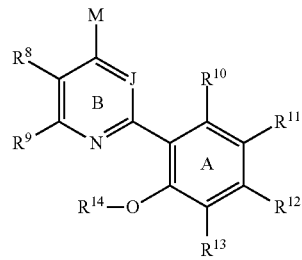

wherein
=J- is independently =N— or =CH—;
—$R^{10}$ is independently —H or -$G^1$;
—$R^{11}$ is independently —H or -$G^1$;
—$R^{12}$ is independently —H or -$G^1$;
—$R^{13}$ is independently —H or -$G^1$; and
—$R^{14}$ is independently —H or -$G^2$;
and wherein
either (i):
—$R^8$ is independently —$R^{19}$; and
—$R^9$ is independently —$R^{20}$;
wherein
—$R^{19}$ is independently —H or -$G^3$; and
—$R^{20}$ is independently —H or -$G^4$;
or (ii):
the group:

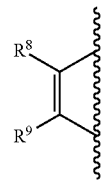

is independently a group:

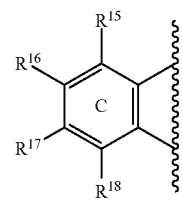

wherein
—$R^{15}$ is independently —H or -$G^5$;
—$R^{16}$ is independently —H or -$G^5$;
—$R^{17}$ is independently —H or -$G^5$; and
—$R^{18}$ is independently —H or -$G^5$;

and wherein

-M is independently selected from:

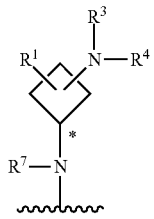
(MX-4)

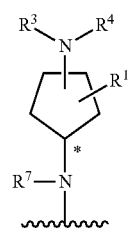
(MX-5)

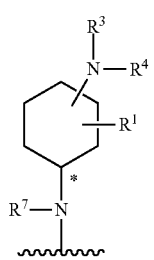
(MX-6)

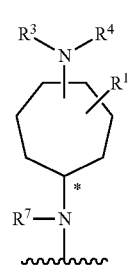
(MX-7)

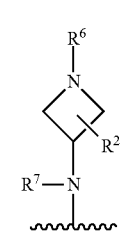
(MN-4)

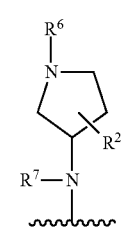
(MN-5)

-continued

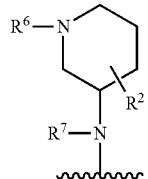
(MN-6-m)

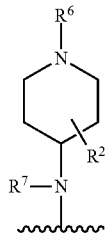
(MN-6-p)

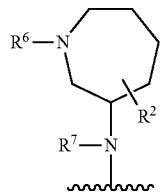
(MN-7-m)

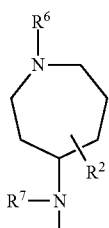
(MN-7-p)

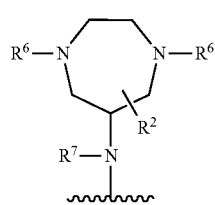
(MNN-7)

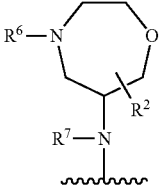
(MNO-7)

wherein
- $-R^1$, if present, is independently —H or a group $-D^1$;
- $-R^2$, if present, is independently —H or a group $-D^1$;
- the group —$NR^3R^4$, if present, is attached to a ring carbon atom other than the ring carbon atom to which is attached the group —$NR^7$—;
- if —$R^3$ and —$R^4$ are present, then:
- either: each of —$R^3$ and —$R^4$ is independently —H or -$D^2$;
- or: —$R^3$ and —$R^4$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
—$R^5$, if present, is independently —H or -$D^2$;
—$R^6$, if present, is independently —H or -$D^2$; and
—$R^7$ is independently —H or -$D^2$;
wherein -$G^1$, -$G^2$, -$G^3$, -$G^4$, -$G^5$, -$D^1$, and -$D^2$ are as defined herein;
and optionally with one or more provisos, for example, one or more provisos as discussed below under the heading "Optional Provisos".

For the avoidance of doubt, it is intended that Ring A and Ring B are only linked as shown in the formula above. For example, it is not intended that -M and —$R^{10}$ together form one group.

Similarly, it is intended that Ring C, if present, is linked to Ring A only as shown, specifically, through Ring B. For example, it is not intended that —$R^{18}$ and —$R^{14}$ together form one group.

Optional Provisos

In one or more aspects of the present invention (e.g., compounds, compositions, methods of treatment, compounds for use in therapy, use of compounds in the manufacture of a medicament, etc.), the compounds are optionally as defined herein, but with one or more optional provisios, as defined in this section.

In one embodiment, the proviso is that the compound is not a compound selected from compounds (PR-A) through (PR-L).

In one embodiment, the proviso is that the compound is not a compound selected from compounds (PR-A) through (PR-L), or a salt, solvate, or hydrate thereof.

In one embodiment, if: —$R^{16}$ is —F, then: —$R^{17}$ is not —H.

In one embodiment, if: —$R^{16}$ is —H, then: —$R^{17}$ is not —Cl.

In one embodiment, if: —$R^{16}$ is —H, then: —$R^{17}$ is not -Me.

In one embodiment, if: —$R^{16}$ is —F, —Cl, —Br, or —I, then: —$R^{17}$ is not —H.

In one embodiment, if: —$R^{16}$ is —H, then: —$R^{17}$ is not —F, —Cl, —Br, or —I.

In one embodiment, if: —$R^{16}$ is —H, then: —$R^{17}$ is not saturated aliphatic $C_{1-4}$alkyl.

In one embodiment, if —$R^{19}$ is —CN, then —$R^{20}$ is not a group that is attached via a nitrogen atom. Examples of groups that are attached via a nitrogen atom include —$NH_2$, —NHMe, —$NMe_2$, —NHC(=O)Me, and morpholino.

| Code No. | Name | Structure | Citation |
|---|---|---|---|
| (PR-A) | 2-{4-[(1-Benzyl-pyrrolidin-3-yl)-methyl-amino]-6-fluoro-quinazolin-2-yl}-phenol | 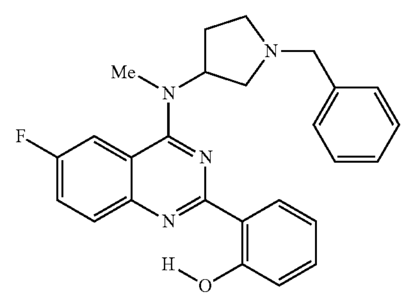 | WO 2004/078733 |
| (PR-B) | 2-{4-[((S)-1-Benzyl-pyrrolidin-3-yl)-methyl-amino]-7-chloro-quinazolin-2-yl}-phenol | 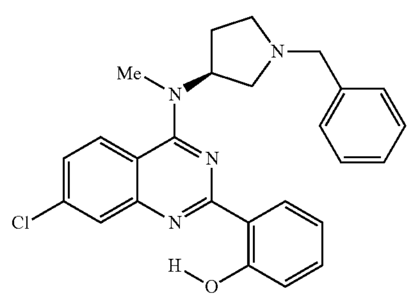 | WO 2004/078733 |
| (PR-C) | 2-{4-[((S)-1-Benzyl-pyrrolidin-3-yl)-methyl-amino]-7-methyl-quinazolin-2-yl}-phenol | 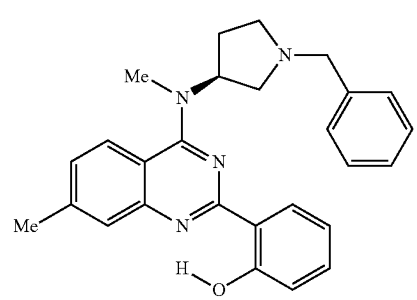 | WO 2004/078733 |

-continued

| Code No. | Name | Structure | Citation |
|---|---|---|---|
| (PR-D) | 2-{4-[((S)-1 Benzyl-pyrrolidin-3-yl)-methyl-amino]-6-fluoro-quinazolin-2-yl}-phenol | 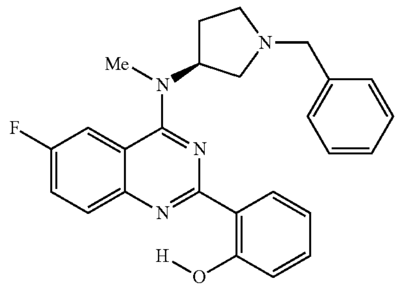 | WO 2004/078733 |
| (PR-E) | 2-{7-Chloro-4-[methyl-(1-methyl-pyrrolidin-3-yl)-amino]-quinazolin-2-yl}-phenol | 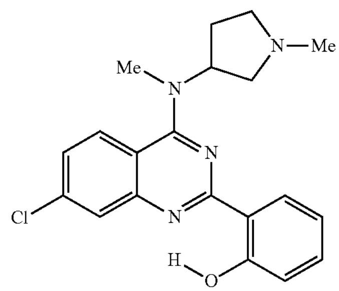 | WO 2004/078733 |
| (PR-F) | 2-{7-Methyl-4-[methyl-(1-methyl-pyrrolidin-3-yl)-amino]-quinazolin-2-yl}-phenol | 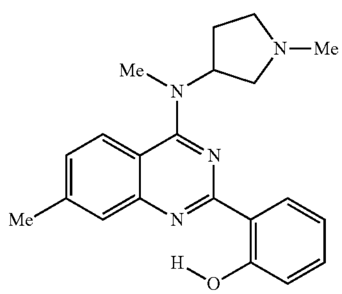 | WO 2004/078733 |
| (PR-G) | 2-{6-Fluoro-4-[methyl-(1-methyl-pyrrolidin-3-yl)-amino]-quinazolin-2-yl}-phenol | 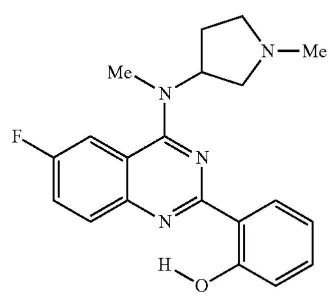 | WO 2004/078733 |
| (PR-H) | 2-{7-Chloro-4-[methyl-(1-methyl-piperidin-4-yl)-amino]-quinazolin-2-yl}-phenol | 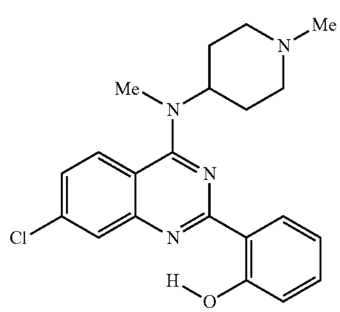 | WO 2004/078733 |

-continued

| Code No. | Name | Structure | Citation |
|---|---|---|---|
| (PR-I) | 2-{7-Methyl-4-[methyl-(1-methyl-piperidin-4-yl)-amino]-quinazolin-2-yl}-phenol | 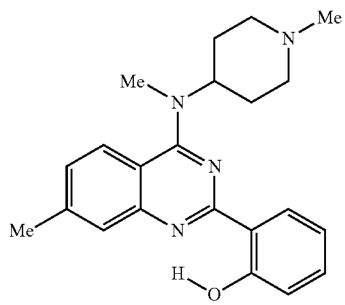 | WO 2004/078733 |
| (PR-J) | 2-{6-Fluoro-4-[methyl-(1-methyl-piperidin-4-yl)-amino]-quinazolin-2-yl}-phenol | 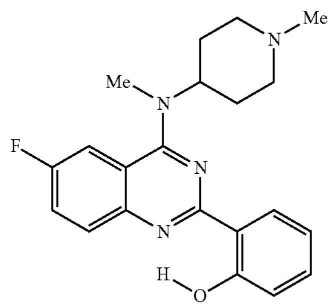 | WO 2004/078733 |
| (PR-K) | 2-Amino-6-(2-hydroxy-phenyl)-4-(piperidin-3-ylamino)-nicotinonitrile | 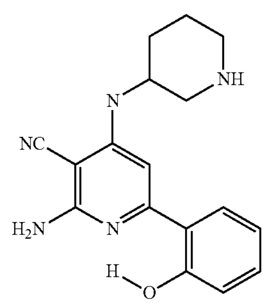 | WO 2002/024679 |
| (PR-L) | 2-Amino-6-(2-hydroxy-phenyl)-4-(piperidin-4-ylamino)-nicotinonitrile | 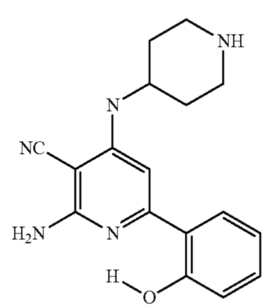 | WO 2002/024679 |

Stereoisomerism

Many of the chemical structures shown herein indicate one or more specific stereoisomeric configurations. Similarly, many of the chemical structures shown herein are silent in this respect, and do not indicate any stereoisomeric configuration. Similarly, many of the chemical structures shown herein indicate the specific stereoisomeric configurations at one or more positions, but are silent with respect to one or more other positions. Where a chemical structure herein is silent with respect to the stereoisomeric configuration at a position, that structure is intended to depict all possible stereoisomeric configuration at that position, both individually, as if each possible stereoisomeric configuration was individually recited, and also as a mixture (e.g., a racemic mixture) of stereoisomers. For example, S1 denotes each of S2 and S3. Similarly, S2 denotes both S4 and S5; and S3 denotes both S6 and S7.

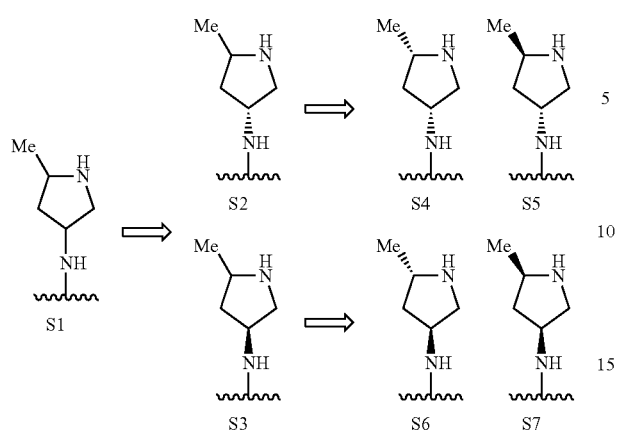

The Group =J-

In one embodiment, =J- is independently =N— or =CH—.

In one embodiment, =J- is independently =N—.

In one embodiment, =J- is independently =CH—.

The Groups —R⁸ and —R⁹: Ring C is Absent

In one embodiment, —R⁸ is independently —R¹⁹ and —R⁹ is independently —R²⁰, for example, as in the following groups:

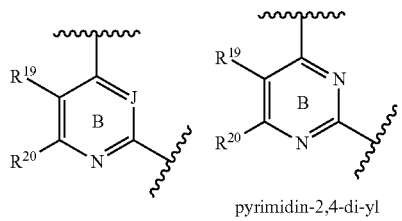

pyrimidin-2,4-di-yl

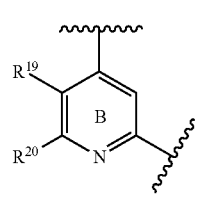

pyridin-2,4-di-yl

In one embodiment, additionally, —R²⁰ is independently —H, as in, for example, the following groups:

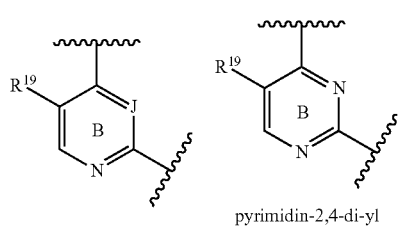

pyrimidin-2,4-di-yl

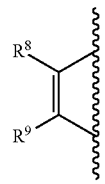

pyridin-2,4-di-yl

For the avoidance of doubt, it is not intended that —R¹⁹ and —R²⁰, if present, form a fused ring with Ring B.

The Groups —R⁸ and —R⁹: Ring C is Present

In one embodiment, the group:

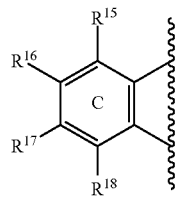

is independently a group:

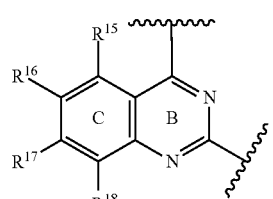

as in, for example, the following groups:

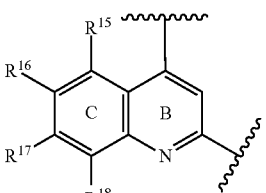

quinazolin-2,4-di-yl quinolin-2,4-di-yl

In one embodiment, each of —R¹⁵, —R¹⁶, —R¹⁷, and —R¹⁸ is independently —H, as in, for example, the following groups:

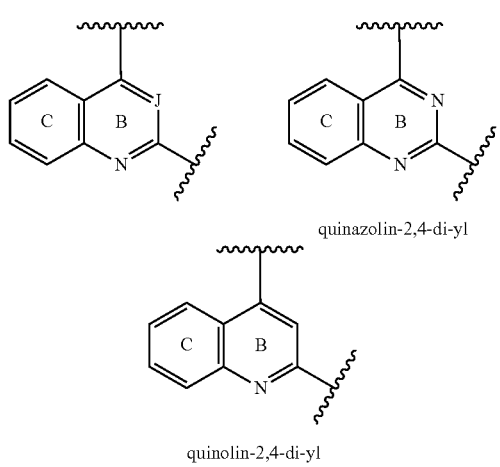

quinazolin-2,4-di-yl

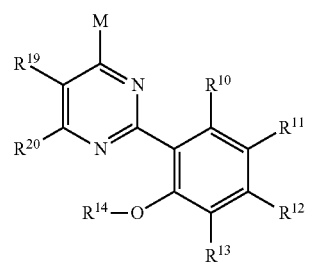

quinolin-2,4-di-yl

For the avoidance of doubt, it is not intended that two or more of —$R^{15}$, —$R^{16}$, —$R^{17}$, and —$R^{18}$, if present, form a fused ring with Ring C.

The Heteroaromatic Core

In one embodiment, the compounds are selected from:
compounds of Formula (I),
compounds of Formula (II),
compounds of Formula (III), and
compounds of Formula (IV);
and pharmaceutically acceptable salts, hydrates, and solvates thereof:

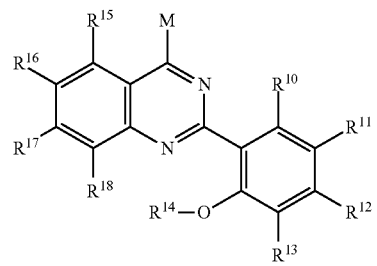
(I)

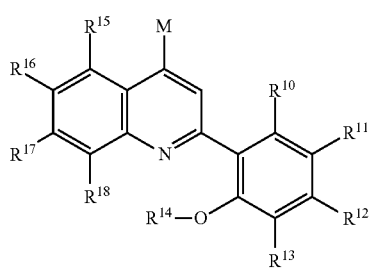
(II)

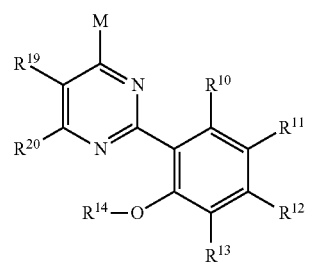
(III)

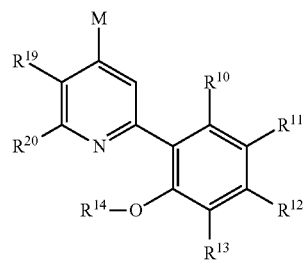
(IV)

In one embodiment, the compounds are selected from: compounds of Formula (I) and pharmaceutically acceptable salts, hydrates, and solvates thereof.

In one embodiment, the compounds are selected from: compounds of Formula (II) and pharmaceutically acceptable salts, hydrates, and solvates thereof.

In one embodiment, the compounds are selected from: compounds of Formula (III) and pharmaceutically acceptable salts, hydrates, and solvates thereof.

In one embodiment, the compounds are selected from: compounds of Formula (IV) and pharmaceutically acceptable salts, hydrates, and solvates thereof.

The Amino Group -M

In one embodiment, -M is independently selected from:

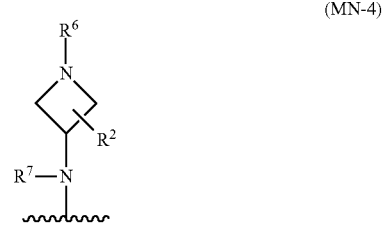
(MN-4)

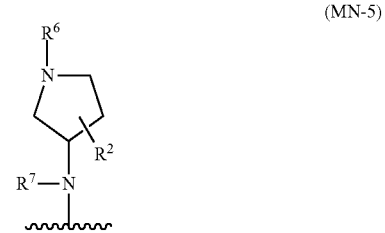
(MN-5)

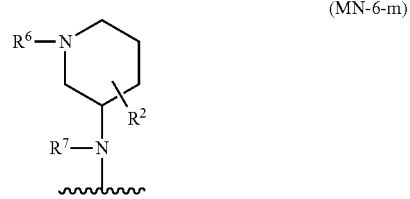
(MN-6-m)

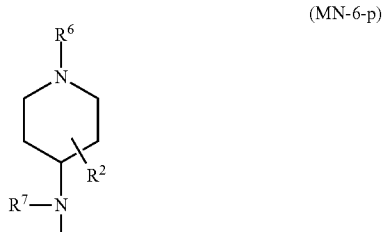
(MN-6-p)

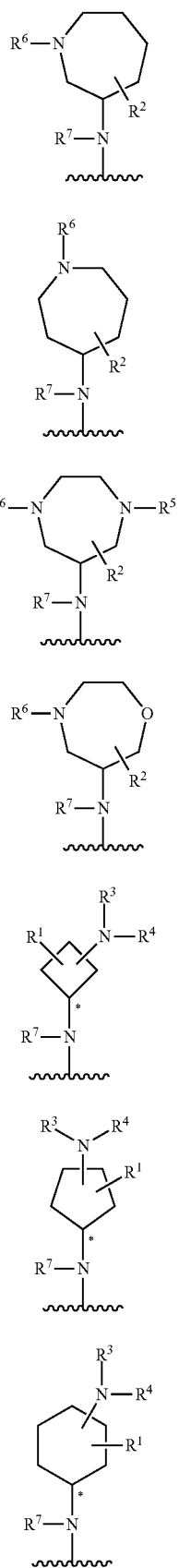

(MN-7-m)

(MN-7-p)

(MNN-7)

(MNO-7)

(MX-4)

(MX-5)

(MX-6)

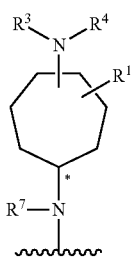

(MX-7)

wherein
- —R¹, if present, is independently —H or a group -D¹;
- —R², if present, is independently —H or a group -D¹;
- the group —NR³R⁴, if present, is attached to a ring carbon atom other than the ring carbon atom to which is attached the group —NR⁷—;
- if —R³ and —R⁴ are present, then:
  either: each of —R³ and —R⁴ is independently —H or -D²;
  or: —R³ and —R⁴, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
- —R⁵, if present, is independently —H or -D²;
- —R⁶, if present, is independently —H or -D²; and
- —R⁷ is independently —H or -D².

Note that the group —NR³R⁴, if present, is attached to a ring carbon atom other than the ring carbon atom to which is attached the group —NR⁷—. The ring carbon atom to which is attached the group —NR⁷— may conveniently be referred to as the "apex" carbon atom. This apex carbon atom is shown by an asterisk in Formulae (MX-4), (MX-5), (MX-6), and (MX-7).

The Amino Group: "Exo-Endo"

In one embodiment, -M is independently selected from:
groups of Formula (MN-4),
groups of Formula (MN-5),
groups of Formula (MN-6-m),
groups of Formula (MN-6-p),
groups of Formula (MN-7-m),
groups of Formula (MN-7-p),
groups of Formula (MNN-7), and
groups of Formula (MNO-7).

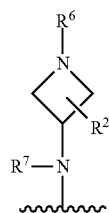

(MN-4)

(MN-5)
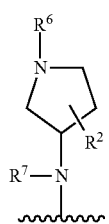

(MN-6-m)
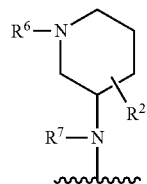

(MN-6-p)
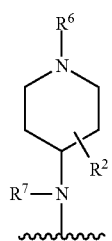

(MN-7-m)
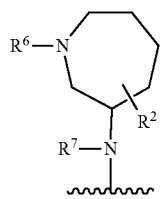

(MN-7-p)
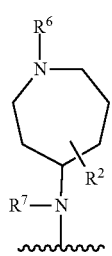

(MNN-7)
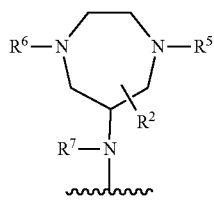

(MNO-7)
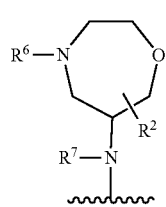

In one embodiment, -M is independently selected from:
groups of Formula (MN-5),
groups of Formula (MN-6-m), and
groups of Formula (MN-6-p).

In one embodiment, -M is independently selected from: groups of Formula (MN-5).

In one embodiment, -M is independently selected from: groups of Formula (MN-6-m).

In one embodiment, -M is independently selected from: groups of Formula (MN-6-p).

In one embodiment, -M is independently selected from: groups of Formula (MN-5u).

In one embodiment, -M is independently selected from: groups of Formula (MN-5d).

(MN-5u)
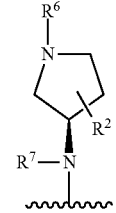

(MN-5d)
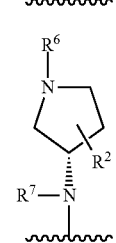

In one embodiment, -M is independently selected from: groups of Formula (MN-6u-m).

In one embodiment, -M is independently selected from: groups of Formula (MN-6d-m).

(MN-6u-m)
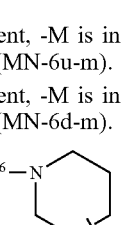

(MN-6d-m)
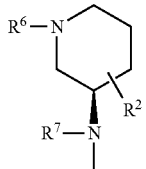

In one embodiment, -M is independently selected from: groups of Formula (MN-6u-p).

In one embodiment, -M is independently selected from: groups of Formula (MN-6d-p).

(MN-6u-p)
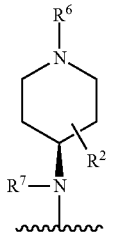

-continued

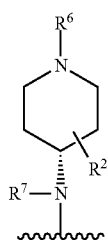
(MN-d-p)

In one embodiment, -M is independently selected from: groups of Formula (MN-6-m-a).

In one embodiment, -M is independently selected from: groups of Formula (MN-6-m-b).

In one embodiment, -M is independently selected from: groups of Formula (MN-6-m-c).

In one embodiment, -M is independently selected from: groups of Formula (MN-6-m-e).

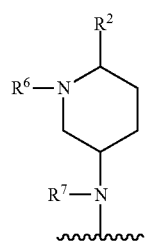
(MN-6-m-a)

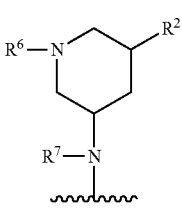
(MN-6-m-b)

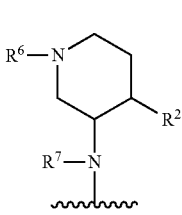
(MN-6-m-c)

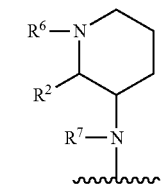
(MN-6-m-e)

In one embodiment, -M is independently selected from: groups of Formula (MN-6-p-a).

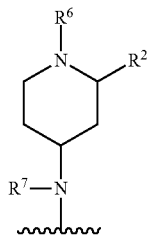
(MN-6-p-a)

In one embodiment, -M is independently selected from: groups of Formula (MN-5-a).

In one embodiment, -M is independently selected from: groups of Formula (MN-5-b).

In one embodiment, -M is independently selected from: groups of Formula (MN-5-c).

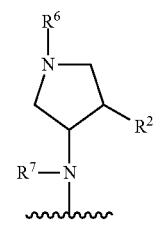
(MN-5-a)

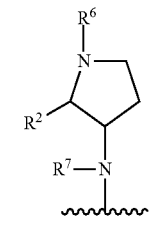
(MN-5-b)

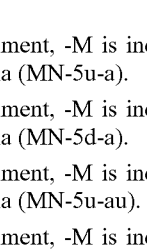
(MN-5-c)

In one embodiment, -M is independently selected from: groups of Formula (MN-5u-a).

In one embodiment, -M is independently selected from: groups of Formula (MN-5d-a).

In one embodiment, -M is independently selected from: groups of Formula (MN-5u-au).

In one embodiment, -M is independently selected from: groups of Formula (MN-5u-ad).

In one embodiment, -M is independently selected from: groups of Formula (MN-5d-au).

In one embodiment, -M is independently selected from: groups of Formula (MN-5d-ad).

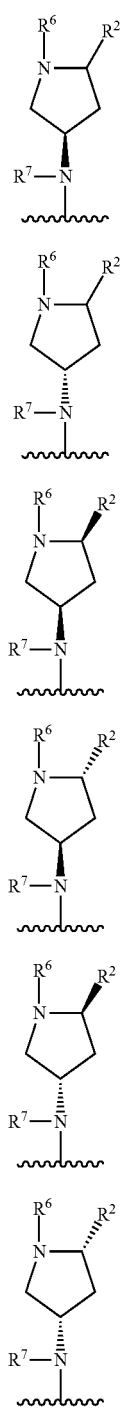
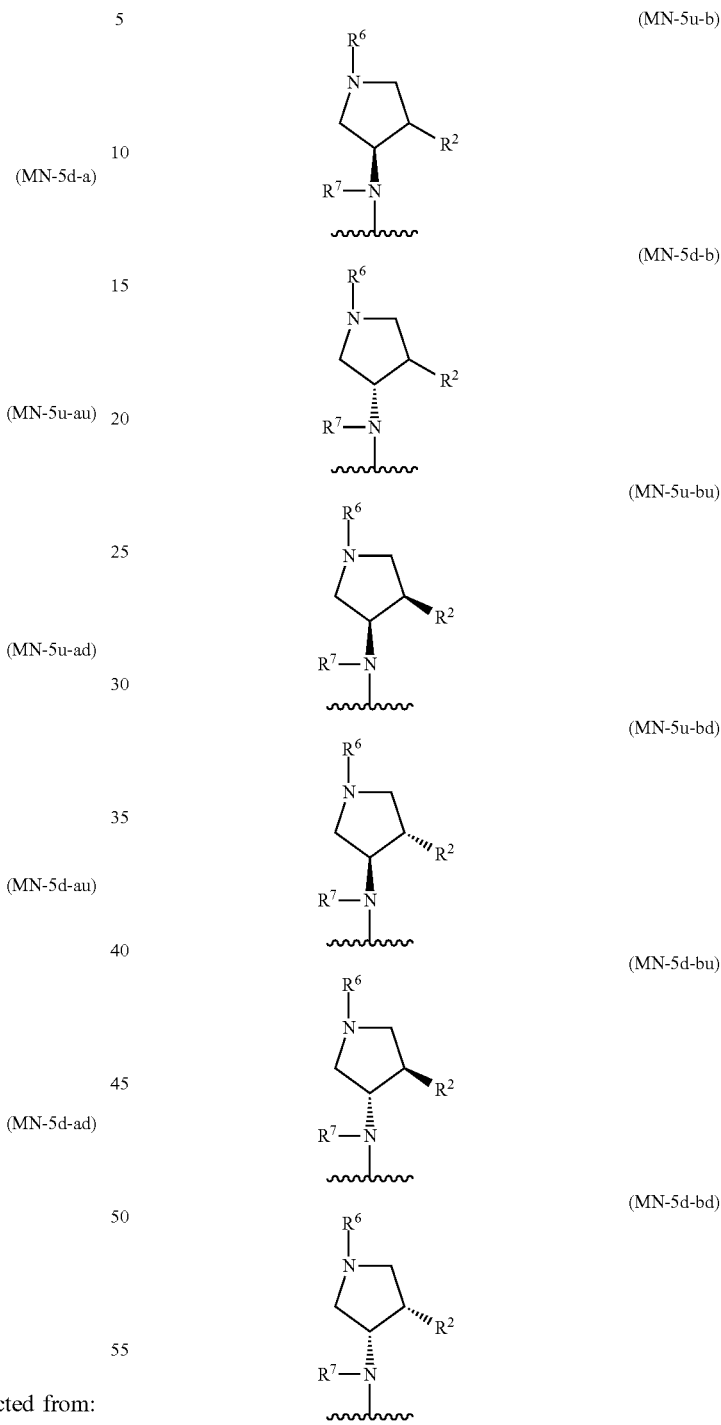

In one embodiment, -M is independently selected from: groups of Formula (MN-5u-b).

In one embodiment, -M is independently selected from: groups of Formula (MN-5d-b).

In one embodiment, -M is independently selected from: groups of Formula (MN-5u-bu).

In one embodiment, -M is independently selected from: groups of Formula (MN-5u-bd).

In one embodiment, -M is independently selected from: groups of Formula (MN-5d-bu).

In one embodiment, -M is independently selected from: groups of Formula (MN-5d-bd).

In one embodiment, -M is independently selected from: groups of formula (MN-5u-c).

In one embodiment, -M is independently selected from: groups of Formula (MN-5d-c).

In one embodiment, -M is independently selected from: groups of Formula (MN-5u-cu).

In one embodiment, -M is independently selected from: groups of Formula (MN-5u-cd).

In one embodiment, -M is independently selected from: groups of Formula (MN-5d-cu).

In one embodiment, -M is independently selected from: groups of Formula (MN-5d-cd).

(MN-5u-c)
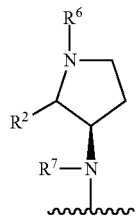

(MN-5d-c)
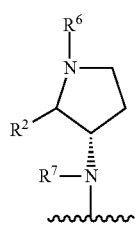

(MN-5u-cu)
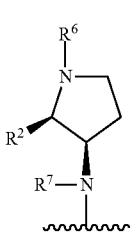

(MN-5u-cd)
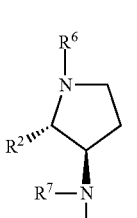

(MN-5d-cu)
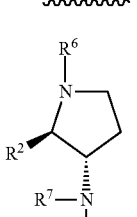

(MN-5d-cd)
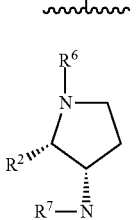

In one embodiment, -M is independently selected from: groups of Formula (MN-6u-m-a).

In one embodiment, -M is independently selected from: groups of Formula (MN-6d-m-a).

(MN-6u-m-a)
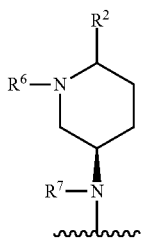

(MN-6ud-m-a)
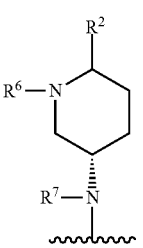

In one embodiment, -M is independently selected from: groups of Formula (MN-6u-m-b).

In one embodiment, -M is independently selected from: groups of Formula (MN-6d-m-b).

(MN-6u-m-b)
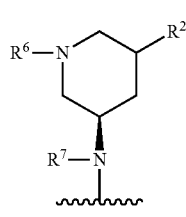

(MN-6d-m-b)
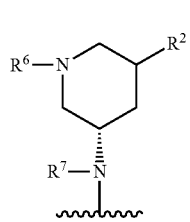

In one embodiment, -M is independently selected from: groups of Formula (MN-6u-m-c).

In one embodiment, -M is independently selected from: groups of Formula (MN-6d-m-c).

(MN-6u-m-c)
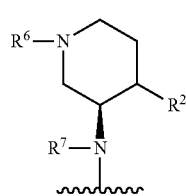

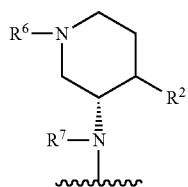 (MN-6d-m-c)

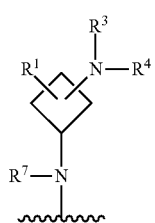 (MX-4)

In one embodiment, -M is independently selected from: groups of Formula (MN-6u-m-e).
In one embodiment, -M is independently selected from: groups of Formula (MN-6d-m-e).

(MX-5)

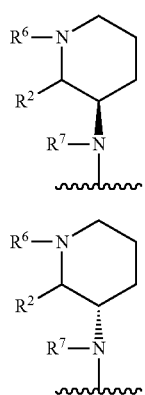 (MN-6u-m-e)

(MX-6)

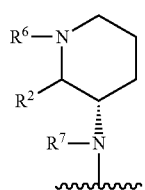 (MN-6d-m-e)

In one embodiment, -M is independently selected from: groups of Formula (MN-6u-p-a).
In one embodiment, -M is independently selected from: groups of Formula (MN-6d-p-a).

(MX-7)

 (MN-6u-p-a)

In one embodiment, -M is independently selected from:
groups of Formula (MX-5), and
groups of Formula (MX-6).

In one embodiment, -M is independently selected from: groups of Formula (MX-5).

In one embodiment, -M is independently selected from: groups of Formula (MX-6).

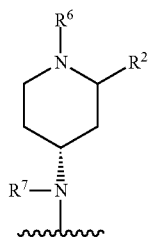 (MN-6d-p-a)

In one embodiment, -M is independently selected from: groups of Formula (MX-5-a).

In one embodiment, -M is independently selected from: groups of Formula (MX-6-a).

The Amino Group: "Exo-Exo"
In one embodiment, -M is independently selected from:
groups of Formula (MX-4),
groups of Formula (MX-5),
groups of Formula (MX-6), and
groups of Formula (MX-7).

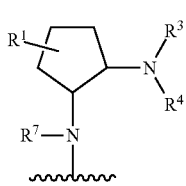 (MX-5-a)

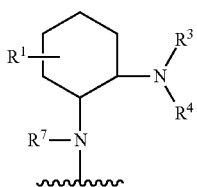
(MX-6-a)

In one embodiment, -M is independently selected from: groups of Formula (MX-5u).

In one embodiment, -M is independently selected from: groups of Formula (MX-5d).

In one embodiment, -M is independently selected from: groups of Formula (MX-6u).

In one embodiment, -M is independently selected from: groups of Formula (MX-6d).

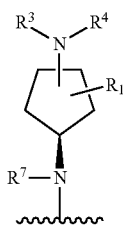
(MX-5u)

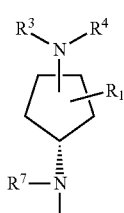
(MX-5d)

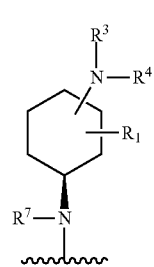
(MX-6u)

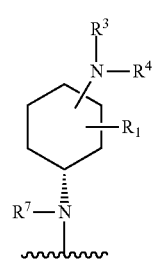
(MX-6d)

In one embodiment, -M is independently selected from: groups of Formula (MX-5u-a).

In one embodiment, -M is independently selected from: groups of Formula (MX-5d-a).

In one embodiment, -M is independently selected from: groups of Formula (MX-6u-a).

In one embodiment, -M is independently selected from: groups of Formula (MX-6d-a).

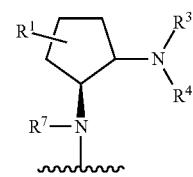
(MX-5u-a)

(MX-5d-a)

(MX-6u-a)

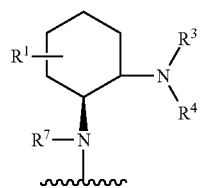
(MX-6d-a)

The Group —$R^1$

In one embodiment, —$R^1$, if present, is independently —H or -$D^1$.

In one embodiment, —$R^1$, if present, is independently —H.

In one embodiment, —$R^1$, if present, is independently -$D^1$.

The Group —$R^2$

In one embodiment, —$R^2$, if present, is independently —H or -$D^1$.

In one embodiment, —$R^2$, if present, is independently —H.

In one embodiment, —$R^2$, if present, is independently -$D^1$.

The Groups —$R^3$ and —$R^4$

In one embodiment, if —$R^3$ and —$R^4$ are present, then: either: each of —$R^3$ and —$R^4$ is independently —H or -$D^2$; or: —$R^3$ and —$R^4$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, if —$R^3$ and —$R^4$ are present, then: either: each of —$R^3$ and —$R^4$ is independently —H or -$D^2$; or: —$R^3$ and —$R^4$, taken together with the nitrogen atom to which they are attached, form azetidino, pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.

In one embodiment, if —$R^3$ and —$R^4$ are present, then: either: each of —$R^3$ and —$R^4$ is independently —H or -$D^2$;

or: —$R^3$ and —$R^4$, taken together with the nitrogen atom to which they are attached, form pyrrolidino, piperidino, piperizino, or morpholino, and is optionally substituted, for example, with one or more groups selected from $C_{1-3}$alkyl and —$CF_3$.

In one embodiment, if —$R^3$ and —$R^4$ are present, then: each of —$R^3$ and —$R^4$ is independently —H or -$D^2$.

In one embodiment, if —$R^3$ and —$R^4$ are present, then: each of —$R^3$ and —$R^4$ is independently —H.

The Group —$R^5$

In one embodiment, —$R^5$, if present, is independently —H or -$D^2$.

In one embodiment, —$R^5$, if present, is independently —H.

In one embodiment, —$R^5$, if present, is independently -$D^2$.

The Group —$R^6$

In one embodiment, —$R^6$, if present, is independently —H or -$D^2$.

In one embodiment, —$R^6$, if present, is independently —H.

In one embodiment, —$R^6$, if present, is independently -$D^2$.

The Group —$R^7$

In one embodiment, —$R^7$, if present, is independently —H or -$D^2$.

In one embodiment, —$R^7$, if present, is independently —H.

In one embodiment, —$R^7$, if present, is independently -$D^2$.

The Group -$D^1$

In one embodiment, each -$D^1$, if present, is independently
—$R^{5A1}$,
—OH, -$L^{5A}$-OH,
—$OR^{5A1}$, -$L^{5A}$-$OR^{5A1}$,
—$NH_2$, —$NHR^{5A1}$, —$NR^{5A1}{}_2$, —$NR^{5A2}R^{5A3}$,
-$L^{5A}$-$NH_2$, -$L^{5A}$-$NHR^{5A1}$, -$L^{5A1}$-$NR^{5A1}{}_2$, -$L^{5A}$-$NR^{5A2}R^{5A3}$,
—C(=O)OH, —C(=O)$OR^{5A1}$,
—C(=O)$NH_2$, —C(=O)$NHR^{5A1}$, —C(=O)$NR^{5A1}{}_2$, —C(=O)$NR^{5A2}R^{5A3}$, or
—C(=O)$R^{5A1}$;
with the limitation that if a -$D^1$ is —OH, —$OR^{5A1}$, —$NH_2$, —$NHR^{5A1}$, —$NR^{5A1}{}_2$, or —$NR^{5A2}R^{5A3}$, then that -$D^1$ is not attached to a carbon atom that is attached to a nitrogen atom; wherein
each -$L^{5A}$- is independently saturated aliphatic $C_{1-5}$alkylene;
in each group —$NR^{5A2}R^{5A3}$, —$R^{5A2}$ and —$R^{5A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{5A1}$ is independently
—$R^{5B1}$, —$R^{5B2}$, —$R^{5B3}$, —$R^{5B4}$, —$R^{5B5}$, —$R^{5B6}$, —$R^{5B7}$, —$R^{5B8}$,
-$L^{5B}$-$R^{5B4}$, -$L^{5B}$-$R^{5B5}$, -$L^{5B}$-$R^{5B6}$, -$L^{5B}$-$R^{5B7}$, or -$L^{5B}$-$R^{5B8}$;
wherein
each —$R^{5B1}$ is independently saturated aliphatic $C_{1-6}$alkyl;
each —$R^{5B2}$ is independently aliphatic $C_{2-6}$alkenyl;
each —$R^{5B3}$ is independently aliphatic $C_{2-6}$alkynyl;
each —$R^{5B4}$ is independently saturated $C_{3-6}$cycloalkyl;
each —$R^{5B5}$ is independently $C_{3-6}$cycloalkenyl;
each —$R^{5B6}$ is independently non-aromatic $C_{3-7}$heterocyclyl;
each —$R^{5B7}$ is independently $C_{6-10}$-carboaryl;

each —$R^{5B5}$ is independently $C_{6-10}$heteroaryl;
each -$L^{5B}$- is independently saturated aliphatic $C_{1-3}$alkylene;
and wherein
each —$R^{5B4}$, —$R^{5B5}$, —$R^{5B6}$, $R^{5B7}$, and —$R^{5B5}$ is optionally substituted, for example, with one or more substituents —$R^{5C1}$ and/or one or more substituents —$R^{1C2}$, and
each —$R^{5B1}$, —$R^{5B2}$, —$R^{5B3}$, and -$L^{5B}$- is optionally substituted, for example, with one or more substituents —$R^{5C2}$,
wherein
each —$R^{5C1}$ is independently saturated aliphatic $C_{1-4}$alkyl, phenyl, or benzyl;
each —$R^{5C2}$ is independently
—F, —Cl, —Br, —I,
—$CF_3$, —$OCF_3$,
—OH, -$L^{5D}$-OH, —O-$L^{5D}$-OH,
—$OR^{5D1}$, -$L^{5D}$-$OR^{5D1}$, —O-$L^{5D}$-$OR^{5D1}$,
—SH, —$SR^{5D1}$,
—CN,
—$NO_2$,
—$NH_2$, —$NHR^{5D1}$, —$NR^{5D1}{}_2$, —$NR^{5D2}R^{5D3}$,
-$L^{5D}$-$NH_2$, -$L^{5D}$-$NHR^{5D1}$, -$L^{5D}$-$NR^{5D1}{}_2$, -$L^{5D}$-$NR^{5D2}R^{5D3}$,
—O-$L^{5D}$-$NH_2$, —O-$L^{5D}$-$NHR^{5D1}$, —O-$L^{5D}$-$NR^{5D1}{}_2$, —O-$L^{5D}$-$NR^{5D2}R^{5D3}$,
—C(=O)OH, —C(=O)$OR^{5D1}$,
—C(=O)$NH_2$, —C(=O)$NHR^{5D1}$, —C(=O)$NR^{5D1}{}_2$, or —C(=O)$NR^{5D2}R^{5D3}$;
wherein
each —$R^{5D1}$ is independently saturated aliphatic $C_{1-4}$alkyl, phenyl, or benzyl;
each -$L^{5D}$- is independently saturated aliphatic $C_{1-5}$alkylene; and
in each group —$NR^{5D2}R^{5D3}$, —$R^{5D2}$ and —$R^{5D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

The above limitation (that if a -$D^1$ is —OH, —$OR^{5A1}$, —$NH_2$, —$NHR^{5A1}$, —$NR^{5A1}{}_2$, or —$NR^{5A2}R^{5A3}$, then that -$D^1$ is not attached to a carbon atom that is attached to a nitrogen atom) is illustrated by the following examples, where the candidate -$D^1$ group is —$NH_2$:

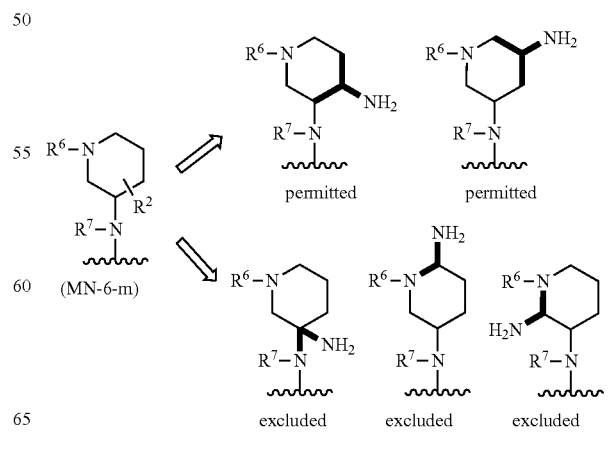

(MN-6-m)

In one embodiment, each -D$^1$, if present, is independently
—R$^{5A1}$,
—OR$^{5A1}$, -L$^{5A}$-OR$^{5A1}$,
-L$^{5A}$-NH$_2$, -L$^{5A}$-NHR$^{5A1}$-L$^{5A1}$NR$^{5A1}$$_2$, -L$^{5A}$-NR$^{5A2}$R$^{5A3}$,
—C(=O)OH, —C(=O)OR$^{5A1}$,
—C(=O)NH$_2$, —C(=O)NHR$^{5A1}$, —C(=O)NR$^{5A1}$$_2$, or
—C(=O)NR$^{5A2}$R$^{5A3}$.

In one embodiment, each -D$^1$, if present, is independently
—C(=O)OH,
—C(=O)OR$^{5A1}$,
—C(=O)NH$_2$, —C(=O)NHR$^{5A1}$, —C(=O)NR$^{5A1}$$_2$, or
—C(=O)NR$^{5A2}$R$^{5A3}$.

In one embodiment, each -D$^1$, if present, is independently
—R$^{5A1}$.

In one embodiment, each -L$^{5A}$-, if present, is independently saturated aliphatic C$_{1-3}$alkylene.

In one embodiment, each —NR$^{5A2}$R$^{5A3}$, if present, is independently azetidino, pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{5A2}$R$^{5A3}$, if present, is independently pyrrolidino, piperidino, piperizino, or morpholino, and is optionally substituted, for example, with one or more groups selected from C$_{1-3}$alkyl and —CF$_3$.

In one embodiment, each —R$^{5A1}$, if present, is independently
—R$^{5B1}$, —R$^{5B4}$, —R$^{5B6}$, —R$^{5B7}$, —R$^{5B8}$,
-L$^{5B}$-R$^{5B4}$, -L$^{5B}$-R$^{5B6}$, -L$^{5B}$-R$^{5B7}$, or -L$^{5B}$-R$^{5B8}$.

In one embodiment, each —R$^{5A1}$, if present, is independently —R$^{5B1}$.

In one embodiment, each —R$^{5A1}$, if present, is independently —R$^{5B8}$ or -L$^{5B}$-R$^{5B8}$.

In one embodiment, each -L$^{5B}$-, if present, is independently —CH$_2$—.

In one embodiment, each —R$^{5B6}$, if present, is independently azetidino, pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.

In one embodiment, each —R$^{5B7}$, if present, is independently phenyl, and is optionally substituted.

In one embodiment, each —R$^{5B8}$, if present, is independently C$_{5-6}$heteroaryl, and is optionally substituted.

In one embodiment, each —R$^{5B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, pyrazinyl, or pyridazinyl, and is optionally substituted.

In one embodiment, each —R$^{5C1}$, if present, is independently -Me, -Et, -Ph, or —CH$_2$Ph.

In one embodiment, each —R$^{5C2}$, if present, is independently
—F, —Cl, —Br, —I,
—CF$_3$, —OCF$_3$,
—OH, -L$^{5D}$-OH,
—OR$^{5D1}$, -L$^{5D}$-OR$^{5D1}$,
—NH$_2$, —NHR$^{5D1}$, —NR$^{5D1}$$_2$, —NR$^{4D2}$R$^{5D3}$,
-L$^{5D}$-NH$_2$, -L$^{5D}$-NHR$^{5D1}$, -L$^{5D}$-NR$^{5D1}$$_2$, -L$^{5D}$-NR$^{5D2}$R$^{5D3}$,
—C(=O)OH, —C(=O)OR$^{5D1}$,
—C(=O)NH$_2$, —C(=O)NHR$^{5D1}$, —C(=O)NR$^{5D1}$$_2$, or
—C(=O)NR$^{5D2}$R$^{5D3}$.

In one embodiment, each -L$^{5D}$-, if present, is independently saturated aliphatic C$_{1-3}$alkylene.

In one embodiment, each —R$^{5D1}$, if present, is independently C$_{1-4}$alkyl.

In one embodiment, each —NR$^{5D2}$R$^{5D3}$, if present, is independently azetidino, pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{5D2}$R$^{5D3}$, if present, is independently pyrrolidino, piperidino, piperizino, or morpholino, and is optionally substituted, for example, with one or more groups selected from C$_{1-3}$alkyl and —CF$_3$.

In one embodiment, each —R$^{5D2}$, if present, is independently —F, —Cl, —Br, —I, —CF$_3$, —OCF$_3$, —OH, —CH$_2$CH$_2$OH, —O—CH$_2$CH$_2$OH, —OMe, —OEt, —CH$_2$CH$_2$OMe, —O—CH$_2$CH$_2$OMe, —SMe, —CN, —NO$_2$, —NH$_2$, —NHMe, —NMe$_2$, —CH$_2$CH$_2$NH$_2$, —CH$_2$— (morpholino), —O—CH$_2$CH$_2$NH$_2$, —O—CH$_2$CH$_2$— (morpholino), —C(=O)OH, —C(=O)OMe, —C(=O)NH$_2$, —C(=O)NHMe, —C(=O)NMe$_2$, —S(=O)$_2$NH$_2$, —S(=O)$_2$NHMe, —S(=O)$_2$NMe$_2$, or —S(=O)$_2$Me.

In one embodiment, each -D$^1$, if present, is independently —C(=O)OH, —C(=O)OMe, —C(=O)OEt, —C(=O)NHMe, or —C(=O)NMe$_2$.

In one embodiment, each -D$^1$, if present, is independently —C(=O)OH or —C(=O)OMe.

In one embodiment, each -D$^1$, if present, is independently —C(=O)OMe.

In one embodiment, each -D$^1$, if present, is independently —C(=O)NHMe or —C(=O)NMe$_2$.

In one embodiment, each -D$^1$, if present, is independently selected from those substituents exemplified under the heading "Some Preferred Embodiments."

The Group -D$^2$

In one embodiment, each -D$^2$, if present, is independently saturated aliphatic C$_{1-4}$alkyl.

In one embodiment, each -D$^2$, if present, is independently -Me, -Et, -nPr, -iPr, or -tBu.

The Groups —R$^{10}$, —R$^{11}$, —R$^{12}$, and —R$^{13}$

In one embodiment, —R$^{10}$ is independently —H or -G$^1$.
In one embodiment, —R$^{10}$ is independently —H.
In one embodiment, —R$^{10}$ is independently -G$^1$.
In one embodiment, —R$^{11}$ is independently —H or -G$^1$.
In one embodiment, —R$^{11}$ is independently —H.
In one embodiment, —R$^{11}$ is independently -G$^1$.
In one embodiment, —R$^{12}$ is independently —H or -G$^1$.
In one embodiment, —R$^{12}$ is independently —H.
In one embodiment, —R$^{12}$ is independently -G$^1$.
In one embodiment, —R$^{13}$ is independently —H or -G$^1$.
In one embodiment, —R$^{13}$ is independently —H.
In one embodiment, —R$^{13}$ is independently -G$^1$.

In one embodiment:
—R$^{10}$ is independently —H; and
—R$^{13}$ is independently —H.

In one embodiment:
—R$^{10}$ is independently —H;
—R$^{11}$ is independently —H; and
—R$^{13}$ is independently —H.

In one embodiment:
—R$^{10}$ is independently —H;
—R$^{12}$ is independently —H; and
—R$^{13}$ is independently —H.

In one embodiment:
—R$^{11}$ is independently —H;
—R$^{12}$ is independently —H; and
—R$^{13}$ is independently —H.

In one embodiment:
—$R^{10}$ is independently —H;
—$R^{11}$ is independently —H;
—$R^{12}$ is independently —H; and
—$R^{13}$ is independently —H.

The Group —$R^{14}$
In one embodiment, —$R^{14}$ is independently —H or -$G^2$.
In one embodiment, —$R^{14}$ is independently —H.
In one embodiment, —$R^{14}$ is independently -$G^2$.

The Groups —$R^{15}$, —$R^{16}$, —$R^{17}$, and —$R^{18}$
In one embodiment, —$R^{15}$, if present, is independently —H or -$G^5$.
In one embodiment, —$R^{15}$, if present, is independently —H.
In one embodiment, —$R^{15}$, if present, is independently -$G^5$.
In one embodiment, —$R^{16}$, if present, is independently —H or -$G^5$.
In one embodiment, —$R^{16}$, if present, is independently —H.
In one embodiment, —$R^{16}$, if present, is independently -$G^5$.
In one embodiment, —$R^{17}$, if present, is independently —H or -$G^5$.
In one embodiment, —$R^{17}$, if present, is independently —H.
In one embodiment, —$R^{17}$, if present, is independently -$G^5$.
In one embodiment, —$R^{18}$, if present, is independently —H or -$G^5$.
In one embodiment, —$R^{18}$, if present, is independently —H.
In one embodiment, —$R^{18}$, if present, is independently -$G^5$.

In one embodiment.
—$R^{15}$, if present, is independently —H; and
—$R^{18}$, if present, is independently —H.

In one embodiment,
—$R^{15}$, if present, is independently —H;
—$R^{17}$, if present, is independently —H; and
—$R^{18}$, if present, is independently —H.

In one embodiment,
—$R^{15}$, if present, is independently —H;
—$R^{16}$, if present, is independently —H; and
—$R^{18}$, if present, is independently —H.

In one embodiment,
—$R^{15}$, if present, is independently —H;
—$R^{16}$, if present, is independently —H;
—$R^{17}$, if present, is independently —H; and
—$R^{18}$, if present, is independently —H.

The Groups —$R^{19}$ and —$R^{20}$
In one embodiment, —$R^{19}$, if present, is independently —H or -$G^3$.
In one embodiment, —$R^{19}$, if present, is independently —H.
In one embodiment, —$R^{19}$, if present, is independently -$G^3$.
In one embodiment, —$R^{20}$, if present, is independently —H or -$G^4$.
In one embodiment, —$R^{20}$, if present, is independently —H.
In one embodiment, —$R^{20}$, if present, is independently -$G^4$.

The Group -$G^1$
In one embodiment, each -$G^1$, if present, is independently
—F, —Cl, —Br, —I,
—$R^{1A1}$,
—$CF_3$, —$OCF_3$,
—OH, -$L^{1A}$-OH, —O-$L^{1A}$-OH,
—$OR^{1A1}$, -$L^{1A}$-$OR^{1A1}$, —O-$L^{1A}$-$OR^{1A1}$,
—SH, —$SR^{1A1}$,
—CN,
—$NO_2$,
—$NH_2$, —$NHR^{1A1}$, —$NR^{1A1}{}_2$, —$NR^{1A2}R^{1A3}$,
-$L^{1A}$-$NH_2$, -$L^{1A}$-$NHR^{1A1}$, -$L^{1A}$-$NR^{1A1}{}_2$, -$L^{1A}$-$NR^{1A2}R^{1A3}$,
—O-$L^{1A}$-$NH_2$, —O-$L^{1A}$-$NHR^{1A1}$, —O-$L^{1A}$-$NR^{1A1}{}_2$, —O-$L^{1A}$-$NR^{1A2}R^{1A3}$,
—C(=O)OH, —C(=O)$OR^{1A1}$,
—C(=O)$NH_2$, —C(=O)$NHR^{1A1}$, —C(=O)$NR^{1A1}{}_2$, —C(=O)$NR^{1A2}R^{1A3}$,
—C(=O)$NHOR^{1A1}$, —C(=O)$NR^{1A1}$C(=O)$R^{1A1}$,
—NHC(=O)$R^{1A1}$, —$NR^{1A1}$C(=O)$R^{1A1}$,
—NHC(=O)$OR^{1A1}$, —$NR^{1A1}$C(=O)$OR^{1A1}$,
—OC(=O)$NH_2$, —OC(=O)$NHR^{1A1}$, —OC(=O)$NR^{1A1}{}_2$, —OC(=O)$NR^{1A2}R^{1A3}$,
—C(=O)$R^{1A1}$,
—NHC(=O)$NH_2$, —NHC(=O)$NHR^{1A1}$, —NHC(=O)$NR^{1A1}{}_2$, —NHC(=O)$NR^{1A2}R^{1A3}$,
—$NR^{1A1}$C(=O)$NH_2$, —$NR^{1A1}$C(=O)$NHR^{1A1}$,
—$NR^{1A1}$C(=O)$NR^{1A1}{}_2$, —$NR^{1A1}$C(=O)$NR^{1A2}R^{1A3}$,
—NHS(=O)$_2R^{1A1}$, —$NR^{1A1}$, —$NR^{1A1}$S(=O)$_2R^{1A1}$,
—S(=O)$_2NH_2$, —S(=O)$_2NHR^{1A1}$, —S(=O)$_2NR^{1A1}{}_2$, —S(=O)$_2NR^{1A2}R^{1A3}$,
—S(=O)$R^{1A1}$, —S(=O)$_2R^{1A1}$, —OS(=O)$_2R^{1A1}$, or —S(=O)$_2OR^{1A1}$;

wherein
each -$L^{1A}$- is independently saturated aliphatic $C_{1-5}$alkylene;
in each group —$NR^{1A2}R^{1A3}$, —$R^{1A2}$ and —$R^{1A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{1A1}$ is independently
—$R^{1B1}$, —$R^{1B2}$, —$R^{1B3}$, —$R^{1B5}$, —$R^{1B6}$, —$R^{1B7}$, —$R^{1B8}$,
-$L^{1B}$-$R^{1B4}$, -$L^{1B}$-$R^{1B5}$, -$L^{1B}$-$R^{1B6}$, -$L^{1B}$-$R^{1B7}$, or -$L^{1B}$-$R^{1B8}$;

wherein
each —$R^{1B1}$ is independently saturated aliphatic $C_{1-6}$alkyl;
each —$R^{1B2}$ is independently aliphatic $C_{2-6}$alkenyl;
each —$R^{1B3}$ is independently aliphatic $C_{2-6}$alkynyl;
each —$R^{1B4}$ is independently saturated $C_{3-6}$cycloalkyl;
each —$R^{1B6}$ is independently $C_{3-6}$cycloalkenyl;
each —$R^{1B6}$ is independently non-aromatic $C_{3-7}$heterocyclyl;
each —$R^{1B7}$ is independently $C_{6-10}$carboaryl;
each —$R^{1B8}$ is independently $C_{5-10}$heteroaryl;
each -$L^{1B}$- is independently saturated aliphatic $C_{1-3}$alkylene;

and wherein
each —$R^{1B4}$, —$R^{1B5}$, —$R^{1B6}$, $R^{1B7}$, and —$R^{1B8}$ is optionally substituted, for example, with one or more substituents —$R^{1C1}$ and/or one or more substituents —$R^{1C2}$, and
each —$R^{1B1}$, —$R^{1B2}$, —$R^{1B3}$, and -$L^{1B}$- is optionally substituted, for example, with one or more substituents —$R^{1C2}$, wherein
each —$R^{1C1}$ is independently saturated aliphatic $C_{1-4}$alkyl, phenyl, or benzyl;
each —$R^{1C2}$ is independently
- —F, —Cl, —Br, —I,
- —$CF_3$, —$OCF_3$,
- —OH, -$L^{1D}$-OH, —O-$L^{1D}$-OH,
- —$OR^{1D1}$, -$L^{1D}$-$OR^{1D1}$, —O-$L^{1D}$-$OR^{1D1}$,
- —SH, —$SR^{1D1}$,
- —CN,
- —$NO_2$,
- —$NH_2$, —$NHR^{1D1}$, —$NR^{1D1}{}_2$, —$NR^{1D2}R^{1D3}$,
- -$L^{1D}$-$NH_2$, -$L^{1D}$-$NHR^{1D1}$, or -$L^{1D}$-$NR^{1D1}{}_2$, or -$L^{1D}$-$NR^{1D2}R^{1D3}$,
- —O-$L^{1D}$-$NH_2$—O-$L^{1D}$-$NHR^{1D1}$, —O-$L^{1D}$-$NR^{1D2}R^{1D3}$,
- —C(=O)OH, —C(=O)$OR^{1D1}$,
- —C(=O)$NH_2$, —C(=O)$NHR^{1D1}$, —C(=O)$NR^{1D1}{}_2$, —C(=O)$NR^{1D2}R^{1D3}$,
- —S(=O)$_2NH_2$, —S(=O)$_2NHR^{1A1}$, —S(=O)$_2NR^{1A1}{}_2$, —S(=O)$_2NR^{1A2}R^{1A3}$, or
- —S(=O)$_2R^{1A1}$;

wherein
each —$R^{1D1}$ is independently saturated aliphatic $C_{1-4}$alkyl, phenyl, or benzyl;
each -$L^{1D}$- is independently saturated aliphatic $C_{1-5}$alkylene; and
in each group —$NR^{1D2}R^{1D3}$, —$R^{1D2}$ and —$R^{1D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each -$G^1$, if present, is independently
- —F, —Cl, —Br, —I,
- —$R^{1A1}$,
- —$CF_3$, —$OCF_3$,
- —OH, -$L^{1A}$-OH, —O-$L^{1A}$-OH,
- —$OR^{1A1}$, -$L^{1A}$-$OR^{1A1}$, —O-$L^{1A}$-$OR^{1A1}$,
- —SH, —$SR^{1A1}$,
- —CN,
- —$NH_2$, —$NHR^{1A1}$, —$NR^{1A1}{}_2$, —$NR^{1A2}R^{1A3}$,
- -$L^{1A}$-$NH_2$, -$L^{1A}$-$NHR^{1A1}$, -$L^{1A}$-$NR^{1A1}{}_2$, -$L^{1A}$-$NR^{1A2}R^{1A3}$,
- —O-$L^{1A}$-$NH_2$, —O-$L^{1A}$-$NHR^{1A1}$, —O-$L^{1A}$-$NR^{1A1}{}_2$,
- —O-$L^{1A}$-$NR^{1A2}R^{1A3}$,
- —C(=O)OH, —C(=O)$OR^{1A1}$,
- —C(=O)$NH_2$, —C(=O)$NHR^{1A1}$, —C(=O)$NR^{1A1}{}_2$,
- —C(=O)$NR^{1A2}R^{1A3}$,
- —C(=O)$NHOR^{1A1}$,
- —NHC(=O)$R^{1A1}$, —$NR^{1A1}$C(=O)$R^{1A1}$, or
- —C(=O)$R^{1A1}$.

In one embodiment, each -$G^1$, if present, is independently
- —F, —Cl, —Br, —I,
- —$R^{1A1}$,
- —$CF_3$, —$OCF_3$,
- —OH, -$L^{1A}$-OH, —O-$L^{1A}$-OH,
- —$OR^{1A1}$, -$L^{1A}$-$OR^{1A1}$, —O-$L^{1A}$-$OR^{1A1}$,
- —SH, —$SR^{1A1}$,
- —CN,
- —$NH_2$, —$NHR^{1A1}$, —$NR^{1A1}{}_2$, —$NR^{1A2}R^{1A3}$,
- -$L^{1A}$-$NH_2$, -$L^{1A}$-$NR^{1A1}$, -$L^{1A}$-$NR^{1A1}{}_2$, -$L^{1A}$-$NR^{1A2}R^{1A3}$,
- —O-$L^{1A}$-$NH_2$, —O-$L^{1A}$-$NHR^{1A1}$, —O-$L^{1A}$-$NR^{1A1}{}_2$,
- —O-$L^{1A}$-$NR^{1A2}R^{1A3}$,
- —C(=O)$OR^{1A1}$,
- —C(=O)$NH_2$, —C(=O)$NHR^{1A1}$, —C(=O)$NR^{1A1}{}_2$,
- —C(=O)$NR^{1A2}R^{1A3}$,
- —C(=O)$NHOR^{1A1}$,
- —NHC(=O)$R^{1A1}$, or —$NR^{1A1}$C(=O)$R^{1A1}$.

In one embodiment, each -$G^1$, if present, is independently
- —F, —Cl, —Br, —I,
- —$R^{1A1}$,
- —$CF_3$, —$OCF_3$,
- —$OR^{1A1}$, -$L^{1A}$-$OR^{1A1}$,
- —CN,
- —$NH_2$, —$NHR^{1A1}$, —$NR^{1A1}{}_2$, —$NR^{1A2}R^{1A3}$,
- -$L^{1A}$-$NH_2$, -$L^{1A}$-$NHR^{1A1}$, -$L^{1A}$-$NR^{1A1}{}_2$, -$L^{1A}$-$NR^{1A2}R^{1A3}$,
- —C(=O)$OR^{1A1}$,
- —C(=O)$NH_2$, —C(=O)$NHR^{1A1}$, —C(=O)$NR^{1A1}{}_2$,
- —C(=O)$NR^{1A2}R^{1A3}$, or
- —C(=O)$NHOR^{1A1}$.

In one embodiment, each -$G^1$, if present, is independently —F, —Cl, —Br, —I, —$R^{1A1}$, —$CF_3$, —C(=O)$OR^{1A1}$, or —C(=O)$NHOR^{1A1}$.

In one embodiment, each -$G^1$, if present, is independently —F, —Cl, —Br, —I, —$R^{1A1}$, or —C(=O)$OR^{1A1}$.

In one embodiment, each -$L^{1A}$-, if present, is independently saturated aliphatic $C_{1-3}$alkylene.

In one embodiment, each —$NR^{1A2}R^{1A3}$, if present, is independently azetidino, pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.

In one embodiment, each —$NR^{1A2}R^{1A3}$, if present, is independently pyrrolidino, piperidino, piperizino, or morpholino, and is optionally substituted, for example, with one or more groups selected from $C_{1-3}$alkyl and —$CF_3$.

In one embodiment, each —$R^{1A1}$, if present, is independently
- —$R^{1B1}$, —$R^{1B4}$, —$R^{1B6}$, —$R^{1B7}$, —$R^{1B8}$,
- -$L^{1B}$-$R^{1B4}$, -$L^{1B}$-$R^{1B6}$, -$L^{1B}$-$R^{1B7}$, or -$L^{1B}$-$R^{1B8}$.

In one embodiment, each —$R^{1A1}$, if present, is independently
- —$R^{1B1}$, $R^{1B4}$, —$R^{1B6}$, —$R^{1B7}$,
- -$L^{1B}$-$R^{1B4}$, -$L^{1B}$-$R^{1B6}$, or -$L^{1B}$-$R^{1B7}$.

In one embodiment, each —$R^{1A1}$, if present, is independently —$R^{1B1}$, —$R^{1B6}$, or —$R^{1B7}$.

In one embodiment, each —$R^{1A1}$, if present, is independently —$R^{1B8}$.

In one embodiment, each —$R^{1A1}$, if present, is independently —$R^{1B1}$.

In one embodiment, each -$L^{1B}$-, if present, is independently —$CH_2$—.

In one embodiment, each —$R^{1B8}$, if present, is independently azetidino, pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.

In one embodiment, each —$R^{1B7}$, if present, is independently phenyl, and is optionally substituted.

In one embodiment, each —$R^{1B8}$, if present, is independently $C_{5-6}$heteroaryl, and is optionally substituted.

In one embodiment, each —$R^{1B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, pyrazinyl, or pyridazinyl, and is optionally substituted.

In one embodiment, each —$R^{1C1}$, if present, is independently -Me, -Et, -Ph, or —$CH_2$Ph.

In one embodiment, each —$R^{1C2}$, if present, is independently
- —F, —Cl, —Br, —I,
- —$CF_3$, —$OCF_3$,
- —OH, -$L^{1D}$-OH, —O-$L^{1D}$-OH,
- —$OR^{1D1}$, -$L^{1D}$-$OR^{1D1}$, —O-$L^{1D}$-$OR^{1D1}$, —$NH_2$, —$NHR^{1D1}$, —$NR^{1D1}{}_2$, —$NR^{1D2}R^{1D3}$,
-$L^{1D}$-$NH_2$, -$L^{1D}$-$NHR^{1D1}$, -$L^{1D}$-$NR^{1D2}R^{1D3}$,
—C(=O)OH, —C(=O)$OR^{1D1}$,
—C(=O)$NH_2$, —C(=O)$NHR^{1D1}$, —C(=O)$NR^{1D1}{}_2$, or
—C(=O)$NR^{1D2}R^{1D3}$.

In one embodiment, each -$L^{1D}$-, if present, is independently saturated aliphatic $C_{1-3}$alkylene.

In one embodiment, each —$R^{1D1}$, if present, is independently $C_{1-4}$alkyl.

In one embodiment, each —$NR^{1D2}R^{1D3}$, if present, is independently azetidino, pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.

In one embodiment, each —$NR^{1D2}R^{1D3}$, if present, is independently pyrrolidino, piperidino, piperizino, or morpholino, and is optionally substituted, for example, with one or more groups selected from $C_{1-3}$alkyl and —$CF_3$.

In one embodiment, each —$R^{1C2}$, if present, is independently —F, —Cl, —Br, —I, —$CF_3$, —$OCF_3$, —OH, —$CH_2CH_2OH$, —O—$CH_2CH_2OH$, —OMe, —OEt, —$CH_2CH_2OMe$, —O—$CH_2CH_2OMe$, —SMe, —CN, —$NO_2$, —$NH_2$, —NHMe, —$NMe_2$, —$CH_2CH_2NH_2$, —$CH_2$— (morpholino), —O—$CH_2CH_2NH_2$, —O—$CH_2CH_2$— (morpholino), —C(=O)OH, —C(=O)OMe, —C(=O)$NH_2$, —C(=O)NHMe, —C(=O)$NMe_2$, —S(=O)$_2NH_2$, —S(=O)$_2$NHMe, —S(=O)$_2NMe_2$, or —S(=O)$_2$Me.

In one embodiment, each -$G^1$, if present, is independently —F, —Cl, —Br, -Me, -Et, -nPr, -iPr, -nBu, -iBu, -sBu, -tBu, —$CF_3$, —C(=O)OMe, or —C(=O)OEt.

In one embodiment, each -$G^1$, if present, is independently selected from those substituents exemplified under the heading "Some Preferred Embodiments."

The Group -$G^2$

In one embodiment, -$G^2$, if present, is independently saturated aliphatic $C_{1-4}$alkyl.

In one embodiment, -$G^2$, if present, is independently -Me, -Et, -nPr, -iPr, or -tBu.

The Group -$G^3$

In one embodiment, -$G^3$, if present, is independently -$G^{3A}$, -$G^{3B}$, or -$G^{3C}$, wherein
-$G^{3A}$ is independently -$G^A$;
-$G^{3B}$ is independently -$G^B$; and
-$G^{3C}$ is independently -$G^C$.

In one embodiment, -$G^3$, if present, is independently -$G^{3A}$.
In one embodiment, -$G^3$, if present, is independently -$G^{3B}$ or -$G^{3C}$.
In one embodiment, -$G^3$, if present, is independently -$G^{3B}$.
In one embodiment, -$G^3$, if present, is independently -$G^{3C}$.
In one embodiment, -$G^3$, if present, is independently -$G^{3A}$; and -$G^4$, if present, is independently -$G^{4B}$ or -$G^{4C}$.
In one embodiment, -$G^3$, if present, is independently -$G^{3B}$ or -$G^{3C}$; and -$G^4$, if present, is independently -$G^{4A}$.

The Group -$G^4$

In one embodiment, -$G^4$, if present, is independently -$G^{4A}$, -$G^{4B}$, or -$G^{4C}$, wherein
$G^{4A}$ is independently -$G^A$;
-$G^{4B}$ is independently -$G^B$; and
-$G^{4C}$ is independently -$G^{4C}$.

In one embodiment, -$G^4$, if present, is independently -$G^{4A}$.
In one embodiment, -$G^4$, if present, is independently -$G^{3B}$ or -$G^{3C}$.
In one embodiment, -$G^4$, if present, is independently -$G^{4B}$.
In one embodiment, -$G^4$, if present, is independently -$G^{4C}$.
In one embodiment, -$G^4$, if present, is independently -$G^{4A}$; and -$G^3$, if present, is independently -$G^{3B}$ or -$G^{3C}$.

In one embodiment, -$G^4$, if present, is independently -$G^{4B}$ or -$G^{4C}$; and -$G^3$, if present, is independently -$G^{3A}$.

The Group -$G^A$

In one embodiment, each -$G^A$, if present, is independently —F, —Cl, —Br, —I,
—$R^{2A1}$,
—$CF_3$, —$OCF_3$,
—OH, -$L^{2A}$-OH, —O-$L^{2A}$-OH,
—$OR^{2A1}$, -$L^{2A}$-$OR^{2A1}$, —O-$L^{2A}$-$OR^{2A1}$,
—SH, —$SR^{2A1}$,
—CN,
—$NO_2$,
—$NH_2$, —$NHR^{2A1}$, —$NR^{2A1}{}_2$, —$NR^{2A2}R^{2A3}$,
-$L^{2A}$-$NH_2$, -$L^{2A}$-$NHR^{2A1}$, -$L^{2A}$-$NR^{2A1}{}_2$, -$L^{2A}$-$NR^{2A2}R^{2A3}$,
—O-$L^{2A}$-$NH_2$, —O-$L^{2A}$-$NHR^{2A1}$, —O-$L^{2A}$-$NR^{2A1}{}_2$, —O-$L^{2A}$-$NR^{2A2}R^{2A3}$,
—C(=O)OH, —C(=O)$OR^{2A1}$,
—C(=O)$NH_2$, —C(=O)$NHR^{2A1}$, —C(=O)$NR^{2A1}{}_2$, —C(=O)$NR^{2A2}R^{2A3}$,
—NHC(=O)$R^{2A1}$, —$NR^{2A1}$C(=O)$R^{2A1}$,
—NHC(=O)$OR^{2A1}$, —$NR^{2A1}$C(=O)$OR^{2A1}$,
—OC(=O)$NH_2$, —OC(=O)$NHR^{2A1}$, —OC(=O)$NR^{2A1}{}_2$, —OC(=O)$NR^{2A2}R^{2A3}$,
—C(=O)$R^{21}$,
—NHC(=O)$NH_2$, —NHC(=O)$NHR^{2A1}$,
—NHC(=O)$NR^{2A1}{}_2$, —NHC(=O)$NR^{2A2}R^{2A3}$,
—$NR^{2A1}$C(=O)$NH_2$, —$NR^{2A1}$C(=O)$NHR^{2A1}$,
—$NR^{2A1}$C(=O)$NR^{2A1}{}_2$, —$NR^{2A1}$C(=O)$NR^{2A2}R^{2A3}$,
—NHS(=O)$_2R^{2A1}$, —$NR^{2A1}$S(=O)$_2R^{2A1}$,
—S(=O)$_2NH_2$, —S(=O)$_2NHR^{2A1}$, —S(=O)$_2NR^{2A1}{}_2$,
—S(=O)$_2NR^{2A2}R^{2A3}$,
—S(=O)$R^{2A1}$, —S(=O)$_2R^{2A1}$, —OS(=O)$_2R^{2A1}$, or
—S(=O)$_2OR^{2A1}$;
wherein
each -$L^{2A}$- is independently saturated aliphatic $C_{1-5}$alkylene;
in each group —$NR^{2A2}R^{2A3}$, —$R^{2A2}$ and —$R^{2A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{2A1}$ is independently
—$R^{2B1}$, —$R^{2B2}$, —$R^{2B3}$, —$R^{2B4}$, —$R^{2B5}$, —$R^{2B6}$, —$R^{2B7}$, —$R^{2B8}$,
-$L^{2B}$-$R^{2B4}$, -$L^{2B}$-$R^{2B5}$, -$L^{2B}$-$R^{2B6}$, -$L^{2B}$-$R^{2B8}$;
wherein
each —$R^{2B1}$ is independently saturated aliphatic $C_{1-6}$alkyl;
each —$R^{2B2}$ is independently aliphatic $C_{1-6}$alkenyl;
each —$R^{2B3}$ is independently aliphatic $C_{2-6}$alkynyl;
each —$R^{2B4}$ is independently saturated $C_{3-6}$cycloalkyl;
each —$R^{2B5}$ is independently $C_{3-6}$cycloalkenyl;
each —$R^{2B6}$ is independently non-aromatic $C_{3-7}$heterocyclyl;
each —$R^{2B7}$ is independently $C_{6-10}$carboaryl;
each —$R^{2B8}$ is independently $C_{5-10}$heteroaryl;
each -$L^{2B}$- is independently saturated aliphatic $C_{1-3}$alkylene;
and wherein
each —$R^{2B4}$, —$R^{2B5}$, $R^{2B6}$, $R^{2B7}$, and —$R^{2B8}$ is optionally substituted, for example, with one or more substituents —$R^{2C1}$ and/or one or more substituents —$R^{2C2}$, and
each —$R^{2B1}$, —$R^{2B2}$, $R^{2B3}$, and -$L^{2B}$- is optionally substituted, for example, with one or more substituents —$R^{2C2}$, wherein each —$R^{2C1}$ is independently saturated aliphatic $C_{1-4}$alkyl, phenyl, or benzyl;

each —$R^{2C2}$ is independently
- —F, —Cl, —Br, —I,
- —$CF_3$, —$OCF_3$,
- —OH, -$L^{2D}$-OH,
- —$OR^{2D}$, -$L^{2D}$-$OR^{2D1}$,
- —SH, —$SR^{2D1}$,
- —CN,
- —$NO_2$,
- —$NH_2$, —$NHR^{2D1}$, —$NR^{2D1}{}_2$, —$NR^{2D2}R^{2D3}$,
- -$L^{2D}$-$NH_2$, -$L^{2D}$-$NHR^{2D1}$, -$L^{2D}$-$NR^{2D1}{}_2$, -$L^{2D}$-$NR^{2D2}R^{2D3}$,
- —C(=O)OH, —C(=O)$OR^{2D1}$,
- —C(=O)$NH_2$, —C(=O)$NHR^{2D1}$, —C(=O)$NR^{2D1}{}_2$, or —C(=O)$NR^{2D2}R^{2D3}$;

wherein each —$R^{2D1}$ is independently saturated aliphatic $C_{1-4}$alkyl, phenyl, or benzyl;

each -$L^{2D}$- is independently saturated aliphatic $C_{1-5}$alkylene; and in each group —$NR^{2D2}R^{2D3}$, —$R^{2D2}$ and —$R^{2D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each -$G^A$, if present, is independently
- —F, —Cl, —Br, —I,
- —$R^{2A1}$,
- —$CF_3$, —$OCF_3$,
- —OH, -$L^{2A}$-OH, —O-$L^{2A}$-OH,
- —$OR^{2A1}$, -$L^{2A}$-$OR^{2A1}$, —O-$L^{2A}$-$OR^{2A1}$,
- —SH, —$SR^{2A1}$,
- —CN,
- —$NH_2$, —$NHR^{2A1}$, —$NR^{2A1}{}_2$, —$NR^{2A2}R^{2A3}$,
- -$L^{2A}$-$NH_2$, -$L^{2A}$-$NHR^{2A1}$, -$L^{2A}$-$NR^{2A1}{}_2$, -$L^{2A}$-$NR^{2A2}R^{2A3}$,
- —O-$L^{2A}$-$NH_2$, —O-$L^{2A}$-$NHR^{2A1}$, —O-$L^{2A}$-$NR^{2A1}{}_2$,
- —O-$L^{2A}$-$NR^{2A2}R^{2A3}$,
- —C(=O)OH, —C(=O)$OR^{2A1}$,
- —C(=O)$NH_2$, —C(=O)$NHR^{2A1}$, —C(=O)$NR^{2A1}{}_2$,
- —C(=O)$NR^{2A2}R^{2A3}$,
- —NHC(=O)$R^{2A1}$, —$NR^{2A1}$C(=O)$R^{2A1}$, or
- —C(=O)$R^{2A1}$.

In one embodiment, each -$G^A$, if present, is independently
- —F, —Cl, —Br, —I,
- —$R^{2A1}$,
- —$CF_3$, —$OCF_3$,
- —OH, -$L^{2A}$-OH, —O-$L^{2A}$-OH,
- —$OR^{2A1}$, -$L^{2A}$-$OR^{2A1}$, —O-$L^{2A}$-$OR^{2A1}$,
- —CN,
- —$NH_2$, —$NHR^{2A1}$, —$NR^{2A1}{}_2$, —$NR^{2A2}R^{2A3}$,
- -$L^{2A}$-$NH_2$, -$L^{2A}$-$NHR^{2A1}$, -$L^{2A}$-$NR^{2A1}{}_2$, -$L^{2A}$-$NR^{2A2}R^{2A3}$,
- —O-$L^{2A}$-$NH_2$, —O-$L^{2A}$-$NHR^{2A1}$, —O-$L^{2A}$-$NR^{2A1}{}_2$,
- —O-$L^{2A}$-$NR^{2A2}R^{2A3}$,
- —NHC(=O)$R^{2A1}$, or —$NR^{2A1}$C(=O)$R^{2A1}$.

In one embodiment, each -$G^A$, if present, is independently
- —F, —Cl, —Br, —I,
- —$R^{2A1}$,
- —$CF_3$, —$OCF_3$,
- -$L^{2A}$-OH, —O-$L^{2A}$-OH,
- —$OR^{2A1}$, -$L^{2A}$-$OR^{2A1}$, —O-$L^{2A}$-$OR^{2A1}$,
- —CN,
- —$NH_2$, —$NHR^{2A1}$, —$NR^{2A1}{}_2$, —$NR^{2A2}R^{2A3}$,
- -$L^{2A}$-$NH_2$, -$L^{2A}$-$NHR^{2A1}$, -$L^{2A}$-$NR^{2A1}{}_2$, -$L^{2A}$-$NR^{2A2}R^{2A3}$,
- —O-$L^{2A}$-$NH_2$, —O-$L^{2A}$-$NHR^{2A1}$, —O-$L^{2A}$-$NR^{2A1}{}_2$, or
- —O-$L^{2A}$-$NR^{2A2}R^{2A3}$.

In one embodiment, each -$L^{2A}$-, if present, is independently saturated aliphatic $C_{1-3}$alkylene.

In one embodiment, each —$NR^{2A2}R^{2A3}$, if present, is independently azetidino, pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.

In one embodiment, each —$NR^{2A2}R^{2A3}$, if present, is independently pyrrolidino, piperidino, piperizino, or morpholino, and is optionally substituted, for example, with one or more groups selected from $C_{1-3}$alkyl and —$CF_3$.

In one embodiment, each —$R^{2A1}$, if present, is independently
- —$R^{2B1}$, —$R^{2B4}$, —$R^{2B6}$, —$R^{2B7}$, —$R^{2B8}$,
- -$L^{2B}$-$R^{2B4}$, -$L^{2B}$-$R^{2B6}$, -$L^{2B}$-$R^{2B7}$, or -$L^{2B}$-$R^{2B8}$.

In one embodiment, each —$R^{2A1}$, if present, is independently —$R^{2B1}$.

In one embodiment, each -$L^{2B}$-, if present, is independently —$CH_2$—.

In one embodiment, each —$R^{2B6}$, if present, is independently azetidino, pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.

In one embodiment, each —$R^{2B7}$, if present, is independently phenyl, and is optionally substituted.

In one embodiment, each —$R^{2B8}$, if present, is independently $C_{5-6}$heteroaryl, and is optionally substituted.

In one embodiment, each —$R^{2B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, pyrazinyl, or pyridazinyl, and is optionally substituted.

In one embodiment, each —$R^{2C1}$, if present, is independently -Me, -Et, -Ph, or —$CH_2$Ph.

In one embodiment, each —$R^{2C2}$, if present, is independently
- —F, —Cl, —Br, —I,
- —$CF_3$, —$OCF_3$,
- —OH, -$L^{2D}$-OH,
- —$OR^{2D1}$, -$L^{2D}$-$OR^{2D1}$,
- —$NH_2$, —$NHR^{2D1}$, —$NR^{2D1}{}_2$, —$NR^{2D2}R^{2D3}$,
- -$L^{2D}$-$NH_2$, -$L^{2D}$-$NHR^{2D1}$, -$L^{2D}$-$NR^{2D1}{}_2$, -$L^{2D}$-$NR^{2D2}R^{2D3}$.
- —C(=O)OH, —C(=O)$OR^{2D1}$,
- —C(=O)$NH_2$, —C(=O)$NHR^{2D1}$, —C(=O)$NR^{2D1}{}_2$, or —C(=O)$NR^{2D2}R^{2D3}$.

In one embodiment, each -$L^{2D}$-, if present, is independently saturated aliphatic $C_{1-3}$alkylene.

In one embodiment, each —$R^{2D1}$, if present, is independently $C_{1-4}$alkyl.

In one embodiment, each —$NR^{2D2}R^{2D3}$, if present, is independently azetidino, pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.

In one embodiment, each —$NR^{2D2}R^{2D3}$, if present, is independently pyrrolidino, piperidino, piperizino, or morpholino, and is optionally substituted, for example, with one or more groups selected from $C_{1-3}$alkyl and —$CF_3$.

In one embodiment, each —$R^{2C2}$, if present, is independently —F, —Cl, —Br, —I, —$CF_3$, —$OCF_3$, —OH, —$CH_2CH_2OH$, —O—$CH_2CH_2OH$, —OMe, —OEt, —CH$_2$CH$_2$OMe, —O—CH$_2$CH$_2$OMe, —SMe, —CN, —NO$_2$, —NH$_2$, —NHMe, —NMe$_2$, —CH$_2$CH$_2$NH$_2$, —CH$_2$— (morpholino), —O—CH$_2$CH$_2$NH$_2$, —O—CH$_2$CH$_2$— (morpholino), —C(=O)OH, —C(=O)OMe, —C(=O)NH$_2$, —C(=O)NHMe, —C(=O)NMe$_2$, —S(=O)$_2$NH$_2$, —S(=O)$_2$NHMe, —S(=O)$_2$NMe$_2$, or —S(=O)$_2$Me.

In one embodiment, each -G$^A$, if present, is independently selected from those substituents exemplified under the heading "Some Preferred Embodiments."

The Group -G$^B$

In one embodiment, each -G$^B$, if present, is independently phenyl, and is optionally substituted, for example, with one or more substituents, -Q$^1$.

In one embodiment, each -G$^B$, if present, is unsubstituted.

In one embodiment, each -G$^B$, if present, is substituted.

The Group -G$^C$

In one embodiment, each -G$^C$, if present, is independently C$_{5-6}$heteroaryl, and is optionally substituted, for example, with one or more substituents, -Q$^1$.

In one embodiment, each -G$^C$, if present, is independently pyrazolyl, imidazolyl, triazolyl, pyridinyl, pyrimidinyl, pyrazinyl, or pyridazinyl; and is optionally substituted, for example, with one or more substituents, -Q$^1$.

In one embodiment, each -G$^C$, if present, is independently pyrazol-3-yl, pyrazol-4-yl, imidazol-2-yl, imidazol-4-yl, 1,2,3-triazol-4-yl, 1,2,4-triazol-3-yl, pyridin-2-yl, pyridin-3-yl, pyridine-4-yl, pyrimidin-2-yl, pyrimidin-4-yl, pyrimidin-5-yl, pyrazin-2-yl, pyridazin-3-yl, or pyridazin-4-yl; and is optionally substituted, for example, with one or more substituents, -Q$^1$.

In one embodiment, each -G$^C$, if present, is unsubstituted.

In one embodiment, each -G$^C$, if present, is substituted.

The Group -Q$^1$

In one embodiment, each -Q$^1$, if present, is independently
- —F, —Cl, —Br, —I,
- —R$^{3A1}$,
- —CF$_3$, —OCF$_3$,
- —OH, -L$^{3A}$-OH, —O-L$^{3A}$-OH,
- —OR$^{3A1}$, -L$^{3A}$-OR$^{3A1}$, —O-L$^{3A}$-OR$^{3A1}$,
- —SH, —SR$^{3A1}$,
- —CN,
- —NO$_2$,
- —NH$_2$, —NHR$^{3A1}$, —NR$^{3A1}{}_2$, —NR$^{3A2}$R$^{3A3}$,
- -L$^{3A}$-NH$_2$, -L$^{3A}$-NHR$^{3A1}$, -L$^{3A}$-NR$^{3A1}{}_2$, -L$^{3A}$-NR$^{3A2}$R$^{3A3}$,
- —O-L$^{3A}$-NH$_2$, —O-L$^{3A}$-NHR$^{3A1}$, —O-L$^{3A}$-NR$^{3A1}{}_2$, —O-L$^{3A}$-NR$^{3A2}$R$^{3A3}$,
- —C(=O)OH, —C(=O)OR$^{3A1}$,
- —C(=O)NH$_2$, —C(=O)NHR$^{3A1}$, —C(=O)NR$^{3A1}{}_2$, —C(=O)NR$^{3A2}$R$^{3A3}$,
- —C(=O)NHOR$^{3A1}$, —C(=O)NR$^{3A1}$OR$^{3A1}$,
- —NHC(=O)R$^{3A1}$, —NR$^{3A1}$C(=O)R$^{3A1}$,
- —NHC(=O)OR$^{3A1}$, —NR$^{3A1}$C(=O)OR$^{3A1}$,
- —OC(=O)NH$_2$, —OC(=O)NHR$^{3A1}$, —OC(=O)NR$^{3A1}{}_2$, —OC(=O)NR$^{3A2}$R$^{3A3}$,
- —C(=O)R$^{3A1}$,
- —NHC(=O)NH$_2$, —NHC(=O)NHR$^{3A1}$, —NHC(=O)NR$^{3A1}{}_2$, —NHC(=O)NR$^{3A2}$R$^{3A3}$,
- —NR$^{3A1}$C(=O)NH$_2$, —NR$^{3A1}$C(=O)NHR$^{3A1}$, —NR$^{3A1}$C(=O)NR$^{3A1}{}_2$, NR$^{3A1}$C(=O)NR$^{3A2}$R$^{3A3}$,
- —NHS(=O)$_2$R$^{3A1}$, —NR$^{3A1}$S(=O)$_2$R$^{3A1}$,
- —S(=O)$_2$NH$_2$, —S(=O)$_2$NHR$^{3A1}$, —S(=O)$_2$NR$^{3A1}{}_2$, —S(=O)$_2$NR$^{3A2}$R$^{3A3}$,
- —S(=O)R$^{3A1}$, —S(=O)$_2$R$^{3A1}$, —OS(=O)$_2$R$^{3A1}$, or —S(=O)$_2$OR$^{3A1}$;

wherein
each -L$^{3A}$- is independently saturated aliphatic C$_{1-6}$alkylene;

in each group —NR$^{3A2}$R$^{3A3}$, —R$^{3A2}$ and —R$^{3A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —R$^{3A1}$ is independently
—R$^{3B1}$, —R$^{3B2}$, —R$^{3B3}$, —R$^{3B4}$, —R$^{3B5}$, —R$^{3B6}$, —R$^{3B7}$, —R$^{3B8}$,
-L$^{3B}$-R$^{3B4}$, -L$^{3B}$R$^{3B5}$, L$^{3B}$R$^{3B6}$, -L$^{3B}$-R$^{3B7}$, or -L$^{3B}$-R$^{3B8}$;

wherein
each —R$^{3B1}$ is independently saturated aliphatic C$_{1-6}$alkyl;
each —R$^{3B2}$ is independently aliphatic C$_{2-6}$alkenyl;
each —R$^{3B3}$ is independently aliphatic C$_{2-6}$alkynyl;
each —R$^{3B4}$ is independently saturated C$_{3-6}$cycloalkyl;
each —R$^{3B6}$ is independently C$_{3-6}$cycloalkenyl;
each —R$^{3B6}$ is independently non-aromatic C$_{3-4}$heterocyclyl;
each —R$^{3B7}$ is independently C$_{6-10}$carboaryl;
each —R$^{3B6}$ is independently C$_{6-10}$heteroaryl;
each -L$^{3B}$- is independently saturated aliphatic C$_{1-3}$alkylene;

and wherein
each —R$^{3B5}$, —R$^{3B5}$, —R$^{3B6}$, —R$^{3B7}$, and —R$^{3B8}$ is optionally substituted, for example, with one or more substituents —R$^{3C1}$ and/or one or more substituents —R$^{1C2}$, and each —R$^{3B1}$, —R$^{3B2}$, R$^{3B3}$, and -L$^{3B}$- is optionally substituted, for example, with one or more substituents —R$^{3C2}$, wherein
each —R$^{3C1}$ is independently saturated aliphatic C$_{1-4}$alkyl, phenyl, or benzyl;
each —R$^{3C2}$ is independently
- —F, —Cl, —Br, —I,
- —CF$_3$, —OCF$_3$,
- —OH, -L$^{3D}$-OH, —O-L$^{3D}$-OH,
- —OR$^{3D1}$, -L$^{3D}$-OR$^{3D1}$, —O-L$^{3D}$-OR$^{3D1}$,
- —SH, —SR$^{3D1}$,
- —CN,
- —NO$_2$,
- —NH$_2$, —NHR$^{3D1}$, —NR$^{3D1}{}_2$, —NR$^{3D2}$R$^{3D3}$,
- -L$^{3D}$-NH$_2$, -L$^{3D}$-NHR$^{3D1}$, -L$^{3D}$-NR$^{3D1}{}_2$, or -L$^{3D}$-NR$^{3D2}$R$^{3D3}$,
- —O-L$^{3D}$-NHR$^{3D1}$, —O-L$^{3D}$-NR$^{3D1}{}_2$, —O-L$^{3D}$-NR$^{3D2}$R$^{3D3}$,
- —C(=O)OH, —C(=O)OR$^{3D1}$,
- —C(=O)NH$_2$, —C(=O)NHR$^{3D1}$, —C(=O)NR$^{3D1}{}_2$, —C(=O)NR$^{3D2}$R$^{3D3}$,
- —S(=O)$_2$NH$_2$, —S(=O)$_2$NHR$^{3A1}$, —S(=O)$_2$NR$^{3A1}{}_2$, —S(=O)$_2$NR$^{3A2}$R$^{3A3}$, or
- —S(=O)$_2$R$^{3A1}$;

wherein
each —R$^{3D1}$ is independently saturated aliphatic C$_{1-4}$alkyl, phenyl, or benzyl;
each -L$^{3D}$- is independently saturated aliphatic C$_{1-5}$alkylene; and
in each group —NR$^{3D2}$R$^{3D3}$, —R$^{3D2}$ and —R$^{3D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroa- In one embodiment, each -Q$^1$, if present, is independently
—F, —Cl, —Br, —I,
—R$^{3A1}$,
—CF$_3$, —OCF$_3$,
—OH, -L$^{3A}$-OH, —O-L$^{3A}$-OH,
—OR$^{3A1}$, -L$^{3A}$-OR$^{3A1}$, —O-L$^{3A}$-OR$^{3A1}$,
—SH, —SR$^{3A1}$,
—CN,
—NH$_2$, —NHR$^{3A1}$, —NR$^{3A1}{}_2$, —NR$^{3A2}$R$^{3A3}$,
-L$^{3A}$-NH$_2$, -L$^{3A}$-NHR$^{3A1}$, -L$^{3A}$-NR$^{3A1}{}_2$, -L$^{3A}$-NR$^{3A2}$R$^{3A3}$,
—O-L$^{3A}$-NH$_2$, —O-L$^{3A}$-NHR$^{3A1}$, —O-L$^{3A}$-NR$^{3A1}{}_2$,
—O-L$^{3A}$-NR$^{3A2}$R$^{3A3}$,
—C(=O)OH, —C(=O)OR$^{3A1}$,
—C(=O)NH$_2$, —C(=O)NHR$^{3A1}$, —C(=O)NR$^{3A1}{}_2$,
—C(=O)NR$^{3A2}$R$^{3A3}$,
—NHC(=O)R$^{3A1}$, —NR$^{3A1}$C(=O)R$^{3A1}$, or
—C(=O)R$^{3A1}$.

In one embodiment, each -Q$^1$, if present, is independently
—F, —Cl, —Br, —I,
—R$^{3A1}$,
—CF$_3$, —OCF$_3$,
—OH, -L$^{3A}$-OH, —O-L$^{3A}$-OH,
—OR$^{3A1}$, -L$^{3A}$-OR$^{3A1}$, —O-L$^{3A}$-OR$^{3A1}$,
—CN,
—NH$_2$, —NHR$^{3A1}$, —NR$^{3A1}{}_2$, —NR$^{3A2}$R$^{3A3}$,
-L$^{3A}$-NH$_2$, -L$^{3A}$-NHR$^{3A1}$, -L$^{3A}$-NR$^{3A1}{}_2$, -L$^{3A}$-NR$^{3A2}$R$^{3A3}$,
—O-L$^{3A}$-NH$_2$, —O-L$^{3A}$-NHR$^{3A1}$, —O-L$^{3A}$-NR$^{3A1}{}_2$,
—O-L$^{3A}$-NR$^{3A2}$R$^{3A3}$,
—NHC(=O)R$^{3A1}$, or —NR$^{3A1}$C(=O)R$^{3A1}$.

In one embodiment, each -Q$^1$, if present, is independently
—F, —Cl, —Br, —I,
—R$^{3A1}$,
—CF$_3$, —OCF$_3$,
—O-L$^{3A}$-OH,
—OR$^{3A1}$, —O-L$^{3A}$-OR$^{3A1}$,
—CN,
—O-L$^{3A}$-NH$_2$, —O-L$^{3A}$-NHR$^{3A1}$, —O-L$^{3A}$-NR$^{3A1}{}_2$, or
—O-L$^{3A}$-NR$^{3A2}$R$^{3A3}$.

In one embodiment, each -L$^{3A}$-, if present, is independently saturated aliphatic C$_{1-3}$alkylene.

In one embodiment, each —NR$^{3A2}$R$^{3A3}$, if present, is independently azetidino, pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{3A2}$R$^{3A3}$, if present, is independently pyrrolidino, piperidino, piperizino, or morpholino, and is optionally substituted, for example, with one or more groups selected from C$_{1-3}$alkyl and —CF$_3$.

In one embodiment, each —R$^{3A1}$, if present, is independently
—R$^{3B1}$, —R$^{3B4}$, —R$^{3B6}$, —R$^{3B7}$, R$^{3B8}$,
-L$^{3B}$-R$^{3B4}$, -L$^{3B}$-R$^{3B6}$, -L$^{3B}$-R$^{3B7}$, or -L$^{3B}$-R$^{3B8}$.

In one embodiment, each —R$^{3A1}$, if present, is independently —R$^{3B1}$.

In one embodiment, each -L$^{3B}$-, if present, is independently —CH$_2$—.

In one embodiment, each —R$^{3B8}$, if present, is independently azetidino, pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.

In one embodiment, each —R$^{3B7}$, if present, is independently phenyl, and is optionally substituted.

In one embodiment, each —R$^{3B8}$, if present, is independently C$_{5-6}$heteroaryl, and is optionally substituted.

In one embodiment, each —R$^{3B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, pyrazinyl, or pyridazinyl, and is optionally substituted.

In one embodiment, each —R$^{3C1}$, if present, is independently -Me, -Et, -Ph, or —CH$_2$Ph.

In one embodiment, each —R$^{3C2}$, if present, is independently
—F, —Cl, —Br, —I,
—CF$_3$, —OCF$_3$,
—OH, -L$^{3D}$-OH,
—OR$^{3D1}$, -L$^{3D}$-OR$^{3D1}$,
—NH$_2$, —NHR$^{3D1}$, —NR$^{3D1}{}_2$, —NR$^{3D2}$R$^{3D3}$,
-L$^{3D}$-NH$_2$, -L$^{3D}$-NHR$^{3D1}$, -L$^{3D}$-NR$^{3D1}{}_2$, -L$^{3D}$-NR$^{3D2}$R$^{3D3}$,
—C(=O)OH, —C(=O)OR$^{3D1}$,
—C(=O)NH$_2$, —C(=O)NHR$^{3D1}$, —C(=O)NR$^{3D1}{}_2$, or
—C(=O)NR$^{3D2}$R$^{3D3}$.

In one embodiment, each -L$^{3D}$-, if present, is independently saturated aliphatic C$_{1-3}$alkylene.

In one embodiment, each —R$^{3D1}$, if present, is independently C$_{1-4}$alkyl.

In one embodiment, each —NR$^{3D2}$R$^{3D3}$, if present, is independently azetidino, pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{3D2}$R$^{3D3}$, if present, is independently pyrrolidino, piperidino, piperizino, or morpholino, and is optionally substituted, for example, with one or more groups selected from C$_{1-3}$alkyl and —CF$_3$.

In one embodiment, each —R$^{3C2}$, if present, is independently —F, —Cl, —Br, —I, —CF$_3$, —OCF$_3$, —OH, —CH$_2$CH$_2$OH, —O—CH$_2$CH$_2$OH, —OMe, —OEt, —CH$_2$CH$_2$OMe, —O—CH$_2$CH$_2$OMe, —SMe, —CN, —NO$_2$, —NH$_2$, —NHMe, —NMe$_2$, —CH$_2$CH$_2$NH$_2$, —CH$_2$— (morpholino), —O—CH$_2$CH$_2$NH$_2$, —O—CH$_2$CH$_2$— (morpholino), —C(=O)OH, —C(=O)OMe, —C(=O)NH$_2$, —C(=O)NHMe, —C(=O)NMe$_2$, —S(=O)$_2$NH$_2$, —S(=O)$_2$NHMe, —S(=O)$_2$NMe$_2$, or —S(=O)$_2$Me.

In one embodiment, each -Q$^1$, if present, is independently
—F, —Cl, —Br, —I,
-Me, -Et, -nPr, -iPr, -nBu, -sBu, -tBu,
—OMe, —OEt
—SMe,
—CN,
—NO$_2$,
—NH$_2$, —NHMe, —NMe$_2$
—C(=O)OH,
—C(=O)OMe,
—C(=O)NH$_2$, —C(=O)NHMe, —C(=O)NMe$_2$,
—S(=O)$_2$NH$_2$, —S(=O)$_2$NHMe, —S(=O)$_2$NMe$_2$, or
—S(=O)$_2$Me.

In one embodiment, each -Q$^1$, if present, is independently selected from those substituents exemplified under the heading "Some Preferred Embodiments."

The Group -G$^5$

In one embodiment, each -G$^5$, if present, is independently
—F, —Cl, —Br, —I,
—R$^{4A1}$,
—CF$_3$, —OCF$_3$,
—OH, -L$^{4A}$-OH, —O-L$^{4A}$-OH,
—OR$^{4A1}$, -L$^{4A}$-OR$^{4A1}$, —O-L$^{4A}$OR$^{4A1}$, —SH, —SR$^{4A1}$,
—CN,
—NO$_2$,
—NH$_2$, —NHR$^{4A1}$, —NR$^{4A1}_2$, —NR$^{4A2}$R$^{4A3}$,
-L$^{4A}$-NH$_2$, -L$^{4A}$-NHR$^{4A1}$, -L$^{4A}$-NR$^{4A1}_2$, R$^{4A2}$R$^{4A3}$,
—O-L$^{4A}$-NH$_2$, —O-L$^{4A}$-NHR$^{4A1}$, —O-L$^{4A}$-NR$^{4A1}_2$,
—O-L$^{4A}$-NR$^{4A2}$R$^{4A3}$,
—C(=O)OH, —C(=O)OR$^{4A1}$,
—C(=O)NH$_2$, —C(=O)NHR$^{4A1}$, —C(=O)NR$^{4A1}_2$,
—C(=O)NR$^{4A2}$R$^{4A3}$,
—NHC(=O)Ram, —NR$^{4A1}$C(=O)R$^{4A1}$,
—OC(=O)NH$_2$, —OC(=O)NHR$^{4A1}$, —OC(=O)NR$^{4A1}_2$, —OC(=O)NR$^{4A2}$R$^{4A3}$,
—C(=O)R$^{4A1}$,
—NHC(=O)NH$_2$, —NHC(=O)NHR$^{4A1}$,
—NHC(=O)NR$^{4A1}_2$, —NHC(=O)NR$^{4A2}$R$^{4A3}$,
—NR$^{4A1}$C(=O)NH$_2$, —NR$^{4A1}$C(=O)NHR$^{4A1}$,
—NR$^{4A1}$C(=O)NR$^{4A1}_2$, —NR$^{4A1}$C(=O)NR$^{4A2}$R$^{4A3}$,
—NHS(=O)$_2$R$^{4A1}$, —NR$^{4A1}$S(=O)$_2$R$^{4A1}$,
—S(=O)$_2$NH$_2$, —S(=O)$_2$NHR$^{4A1}$, —S(=O)$_2$NR$^{4A1}_2$,
—S(=O)$_2$NR$^{4A2}$R$^{4A3}$,
—S(=O)R$^{4A1}$, —S(=O)$_2$R$^{4A1}$, —S(=O)$_2$R$^{4A1}$, or
—S(=O)$_2$OR$^{4A1}$;

wherein
  each -L$^{4A}$- is independently saturated aliphatic C$_{1-6}$alkylene;
  in each group —NR$^{4A2}$R$^{4A3}$, —R$^{4A2}$ and —R$^{4A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
  each —R$^{4A1}$ is independently
    —R$^{4B1}$, —R$^{4B2}$, —R$^{4B3}$, —R$^{4B4}$, —R$^{4B5}$, —R$^{4B6}$, —R$^{4B7}$, —R$^{4B8}$,
    -L$^{4B}$-R$^{4B4}$, -L$^{4B}$-R$^{4B5}$, -L$^{4B}$-R$^{4B6}$, -L$^{4B}$-R$^{4B7}$, or -L$^{4B}$-R$^{4B8}$;
  wherein
    each —R$^{4B1}$ is independently saturated aliphatic C$_{1-6}$alkyl;
    each —R$^{4B2}$ is independently aliphatic C$_{2-6}$alkenyl;
    each —R$^{4B3}$ is independently aliphatic C$_{2-6}$alkynyl;
    each —R$^{4B4}$ is independently saturated C$_{3-6}$cycloalkyl;
    each —R$^{4B5}$ is independently C$_{3-6}$cycloalkenyl;
    each —R$^{4B6}$ is independently non-aromatic C$_{3-7}$heterocyclyl;
    each —R$^{4B7}$ is independently C$_{6-10}$carboaryl;
    each —R$^{4B8}$ is independently C$_{6-10}$heteroaryl;
    each -L$^{4B}$- is independently saturated aliphatic C$_{1-3}$alkylene;
  and wherein
    —R$^{4B4}$, R$^{4B5}$, —R$^{4B6}$, R$^{4B7}$, R$^{4B8}$ is optionally substituted, for example, with one or more substituents —R$^{4C1}$ and/or one or more substituents —R$^{4C2}$, and
    each —R$^{4B1}$, —R$^{4B2}$, R$^{4B3}$, and -L$^{4B}$- is optionally substituted, for example, with one or more substituents —R$^{4C2}$,
  wherein
    each —R$^{4C1}$ is independently saturated aliphatic C$_{1-4}$alkyl, phenyl, or benzyl;
    each —R$^{4C2}$ is independently
      —F, —Cl, —Br, —I,
      —CF$_3$, —OCF$_3$,
      —OH, -L$^{4D}$-OH,
      —OR$^{4D1}$, -L$^{4D}$-OR$^{4D1}$,
      —SH, —SR$^{4D1}$,
      —CN,
      —NO$_2$,
      —NH$_2$, —NHR$^{4D1}$, —NR$^{4D1}_2$, —NR$^{4D2}$R$^{4D3}$,
      -L$^{4D}$-NH$_2$, -L$^{4D}$-NHR$^{4D1}$, -L$^{4D}$-NR$^{4D1}_2$, -L$^{4D}$-NR$^{4D2}$R$^{4D3}$,
      —C(=O)OH, —C(=O)OR$^{4D1}$,
      —C(=O)NH$_2$, —C(=O)NHR$^{4D1}$, —C(=O)NR$^{4D1}_2$,
      or —C(=O)NR$^{4D2}$R$^{4D3}$;
    wherein
      each —R$^{4D1}$ is independently saturated aliphatic C$_{1-4}$alkyl, phenyl, or benzyl;
      each -L$^{4D}$- is independently saturated aliphatic C$_{1-5}$alkylene; and
      in each group —NR$^{4D2}$R$^{4D3}$, —R$^{4D2}$ and —R$^{4D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each -G$^5$, if present, is independently
—F, —Cl, —Br, —I,
—R$^{4A1}$,
—CF$_3$, —OCF$_3$,
—OH, -L$^{4A}$-OH, —O-L$^{4A}$-OH,
—OR$^{4A1}$, -L$^{4A}$-OR$^{4A1}$, —O-L$^{4A}$-OR$^{4A1}$,
—CN,
—NH$_2$, —NHR$^{4A1}$, —NR$^{4A1}_2$, —NR$^{4A2}$R$^{4A3}$,
-L$^{4A}$-NH$_2$, -L$^{4A}$-NHR$^{4A1}$, -L$^{4A}$-NR$^{4A2}$R$^{4A3}$,
—O-L$^{4A}$-NH$_2$, —O-L$^{4A}$-NHR$^{4A1}$, —O-L$^{4A}$-NR$^{4A1}_2$,
—O-L-NR$^{4A2}$R$^{4A3}$,
—C(=O)OH, —C(=O)OR$^{4A1}$,
—C(=O)NH$_2$, —C(=O)NHR$^{4A1}$, —C(=O)NR$^{4A1}_2$,
—C(=O)NR$^{4A2}$R$^{4A3}$,
—NHC(=O)R$^{4A1}$, —NR$^{4A1}$C(=O)R$^{4A1}$, or
—C(=O)R$^{4A1}$.

In one embodiment, each -G$^5$, if present, is independently
—F, —Cl, —Br, —I,
—R$^{4A1}$,
—CF$_3$, —OCF$_3$,
—OH, -L$^{4A}$-OH, —O-L$^{4A}$-OH,
—OR$^{4A1}$, -L$^{4A}$-OR$^{4A1}$, —O-L$^{4A}$OR$^{4A1}$,
—CN,
—NH$_2$, —NHR$^{4A1}$, —NR$^{4A1}_2$, —NR$^{4A2}$R$^{4A3}$,
-L$^{4A}$-NH$_2$, -L$^{4A}$-NHR$^{4A1}$, -L$^{4A}$-NR$^{4A1}_2$, -L$^{4A}$-NR$^{4A2}$R$^{4A3}$,
—O— L$^{4A}$-NH$_2$, —O-L$^{4A}$-NHR$^{4A1}$, —O-L$^{4A}$-NR$^{4A1}_2$,
—O-L$^{4A}$-NR$^{4A2}$R$^{4A3}$,
—C(=O)OH, —C(=O)OR$^{4A1}$,
—NHC(=O)R$^{4A1}$, or —NR$^{4A1}$C(=O)R$^{4A1}$.

In one embodiment, each -G$^5$, if present, is independently
—F, —Cl, —Br, —I,
—R$^{4A1}$,
—CF$_3$,
-L$^{4A}$-OH, —O-L$^{4A}$-OH,
—OR$^{4A1}$, -L$^{4A}$-OR$^{4A1}$, —O-L$^{4A}$-OR$^{4A1}$,
—CN,
—NH$_2$, —NHR$^{4A1}$, —NR$^{4A1}_2$, —NR$^{4A2}$R$^{4A3}$,
-L$^{4A}$-N$_{H2}$, -L$^{4A}$-NHR$^{4A1}$, -L$^{4A}$-NR$^{4A1}_2$, -L$^{4A}$-NR$^{4A2}$R$^{4A3}$,
—O-L$^{4A}$-NH$_2$, —O-L$^{4A}$-NHR$^{4A1}$, —O-L$^{4A}$-NR$^{4A1}_2$, or
—O-L$^{4A}$-NR$^{4A2}$R$^{4A3}$.

In one embodiment, each -L$^{4A}$-, if present, is independently saturated aliphatic C$_{1-3}$alkylene.

In one embodiment, each —NR$^{4A2}$R$^{4A3}$, if present, is independently azetidino, pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{4A2}$R$^{4A3}$, if present, is independently pyrrolidino, piperidino, piperizino, or morpholino, and is optionally substituted, for example, with one or more groups selected from $C_{1-3}$alkyl and —CF$_3$.

In one embodiment, each —R$^{4A1}$, if present, is independently
—R$^{4B1}$, —R$^{4B3}$, —R$^{4B4}$, —R$^{4B6}$, —R$^{4B7}$, —R$^{4B8}$, -L$^{4B}$-R$^{4B4}$, -L$^{4B}$-R$^{4B6}$, -L$^{4B}$-R$^{4B7}$, or -L$^{4B}$-R$^{4B8}$.

In one embodiment, each —R$^{4A1}$, if present, is independently —R$^{AB1}$.

In one embodiment, each —R$^{4A1}$, if present, is independently —R$^{4B2}$.

In one embodiment, each —R$^{4A1}$, if present, is independently —R$^{4B3}$.

In one embodiment, each —R$^{4A1}$, if present, is independently —R$^{4B8}$.

In one embodiment, each -L$^{4B}$-, if present, is independently —CH$_2$—.

In one embodiment, each —R$^{4B6}$, if present, is independently azetidino, pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.

In one embodiment, each —R$^{4B7}$, if present, is independently phenyl, and is optionally substituted.

In one embodiment, each —R$^{4B8}$, if present, is independently $C_{5-6}$heteroaryl, and is optionally substituted.

In one embodiment, each —R$^{4B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, pyrazinyl, or pyridazinyl, and is optionally substituted.

In one embodiment, each —R$^{4C1}$, if present, is independently -Me, -Et, -Ph, or —CH$_2$Ph.

In one embodiment, each —R$^{4C2}$, if present, is independently
—F, —Cl, —Br, —I,
—CF$_3$, —OCF$_3$,
—OH, -L$^{4D}$-OH,
—OR$^{4D1}$, -L$^{4D}$-OR$^{4D1}$,
—NH$_2$, NHR$^{4D1}$, —NR$^{4D1}{}_2$, —NR$^{4D2}$R$^{4D3}$,
-L$^{4D}$-NH$_2$, -L$^{4D}$-NHR$^{4D1}$, -L$^{4D}$-NR$^{4D1}{}_2$, -L$^{4D}$-NR$^{4D2}$R$^{4D3}$,
—C(=O)OH, —C(=O)OR$^{4D1}$,
—C(=O)NH$_2$, —C(=O)NHR$^{4D1}$, —C(=O)NR$^{4D1}{}_2$, or —C(=O)NR$^{4D2}$R$^{4D3}$.

In one embodiment, each -L$^{4D}$-, if present, is independently saturated aliphatic $C_{1-3}$alkylene.

In one embodiment, each —R$^{4D1}$, if present, is independently $C_{1-4}$alkyl.

In one embodiment, each —NR$^{4D2}$R$^{4D3}$, if present, is independently azetidino, pyrrolidino, imidazolidino, pyrazolidino, piperidino, piperizino, morpholino, azepino, or diazepino, and is optionally substituted, for example, with one or more groups selected from $C_{1-3}$alkyl and —CF$_3$.

In one embodiment, each —NR$^{4D2}$R$^{4D3}$, if present, is independently pyrrolidino, piperidino, piperizino, or morpholino, and is optionally substituted, for example, with one or more groups selected from $C_{1-3}$alkyl and —CF$_3$.

In one embodiment, each —R$^{4C2}$, if present, is independently —F, —Cl, —Br, —I, —CF$_3$, —OCF$_3$, —OH, —CH$_2$CH$_2$OH, —O—CH$_2$CH$_2$OH, —OMe, —OEt, —CH$_2$CH$_2$OMe, —O—CH$_2$CH$_2$OMe, —SMe, —CN, —NO$_2$, —NH$_2$, —NHMe, —NMe$_2$, —CH$_2$CH$_2$NH$_2$, —CH$_2$— (morpholino), —O—CH$_2$CH$_2$NH$_2$, —O—CH$_2$CH$_2$— (morpholino), —C(=O)OH, —C(=O)OMe, —C(=O)NH$_2$, —C(=O)NHMe, —C(=O)NMe$_2$, —S(=O)$_2$NH$_2$, —S(=O)$_2$NHMe, —S(=O)$_2$NMe$_2$, or —S(=O)$_2$Me.

In one embodiment, each -G$^5$, if present, is independently selected from those substituents exemplified under the heading "Some Preferred Embodiments."

Molecular Weight

In one embodiment, the compound has a molecular weight of 229 to 800.

In one embodiment, the bottom of range is 230; 250; 275; 325; 350; 375; 400; 425; 450.

In one embodiment, the top of range is 700; 600; 500.

In one embodiment, the range is 250 to 800.

In one embodiment, the range is 250 to 700.

In one embodiment, the range is 250 to 600.

In one embodiment, the range is 250 to 500.

Combinations

All compatible combinations of the embodiments described herein are explicitly disclosed herein, as if each and every compatible combination was individually and explicitly recited.

Some Preferred Embodiments

In one embodiment, the compound is selected from the following compounds, and pharmaceutically acceptable salts, hydrates, and solvates thereof:

| Synthesis | ID No. | Structure |
|---|---|---|
| 1-D | A-001 | 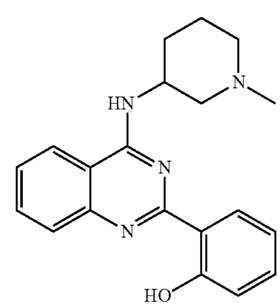 |
| 2-B | A-002 | 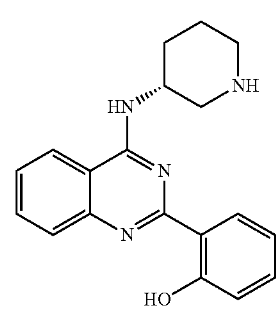 |

| Synthesis | ID No. | Structure |
|---|---|---|
| 3 | A-003 | 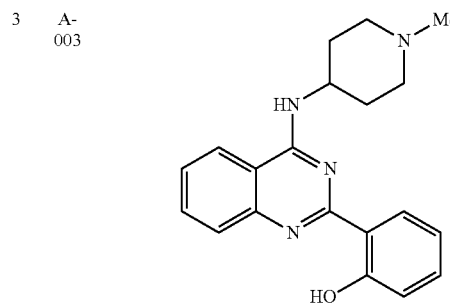 |
| 4 | A-004 | 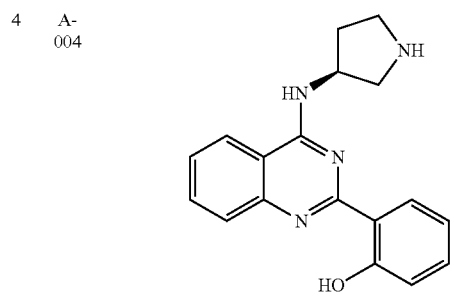 |
| 5 | A-005 | 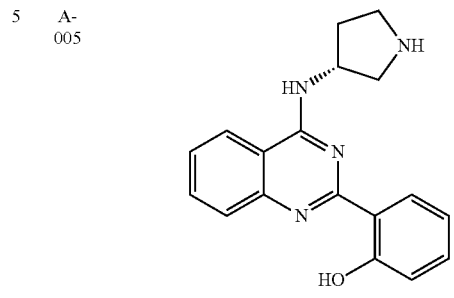 |
| 6 | A-006 | 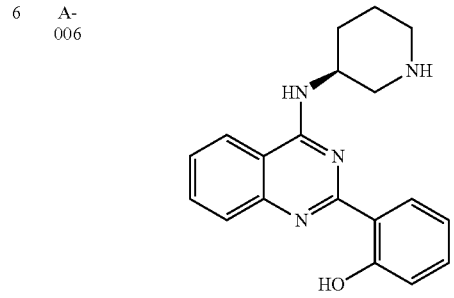 |
| 7 | A-007 | 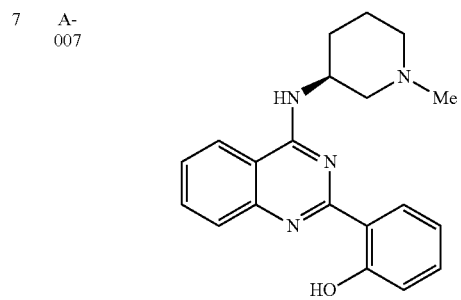 |
| 8 | A-008 | 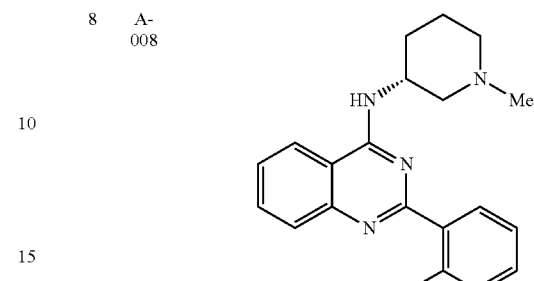 |
| 9 | A-009 | 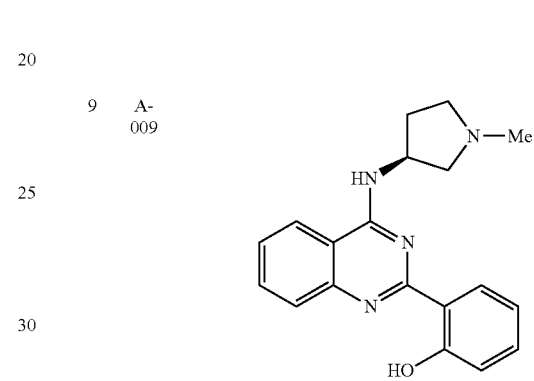 |
| 10 | A-010 | 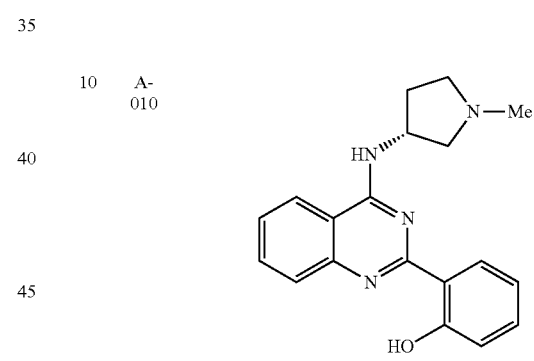 |
| 11 | A-011 | 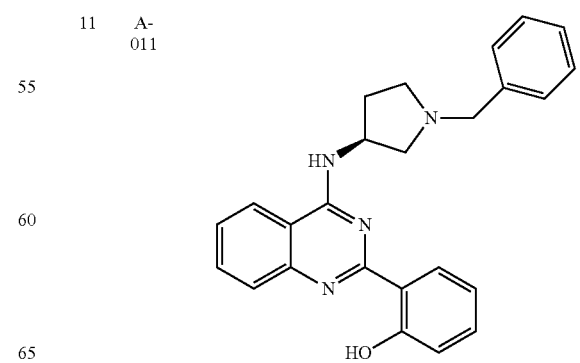 |

-continued

| Synthesis | ID No. | Structure |
|---|---|---|
| 12 | A-012 | (methyl pyrrolidine-2-carboxylate with NH linked to 2-(2-hydroxyphenyl)quinazolin-4-yl) |
| 18 | A-013 | ((R)-piperidin-3-ylamino linked to 2-(5-chloro-2-hydroxyphenyl)quinazolin-4-yl) |
| 19 | A-014 | ((R)-piperidin-3-ylamino linked to 2-(5-fluoro-2-hydroxyphenyl)quinazolin-4-yl) |
| 20 | A-015 | ((R)-pyrrolidin-3-ylamino linked to 2-(5-fluoro-2-hydroxyphenyl)quinazolin-4-yl) |
| 22 | A-016 | ((R)-pyrrolidin-3-ylamino linked to 6-bromo-2-(2-hydroxyphenyl)quinazolin-4-yl) |

-continued

| Synthesis | ID No. | Structure |
|---|---|---|
| 23 | A-017 | (methyl pyrrolidine-2-carboxylate with NH linked to 2-(2-hydroxyphenyl)quinazolin-4-yl) |
| 24 | A-018 | (methyl pyrrolidine-2-carboxylate with NH linked to 2-(2-hydroxyphenyl)quinazolin-4-yl) |
| 25 | A-019 | ((S)-pyrrolidin-3-ylamino linked to 2-(5-chloro-2-hydroxyphenyl)quinazolin-4-yl) |
| 27 | A-020 | ((S)-pyrrolidin-3-ylamino linked to 7-phenyl-2-(2-hydroxyphenyl)quinazolin-4-yl) |

| Synthesis | ID No. | Structure |
|---|---|---|
| 28 | A-021 | 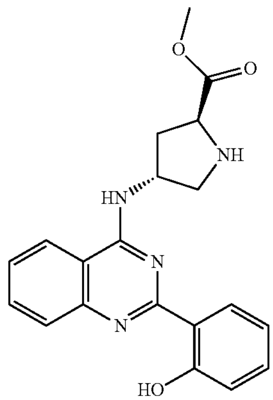 |
| 29 | A-022 | 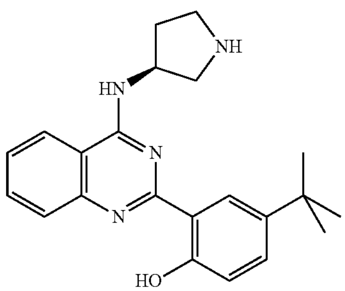 |
| 30-C | A-023 | 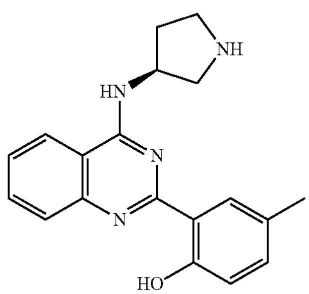 |
| 31 | A-024 | 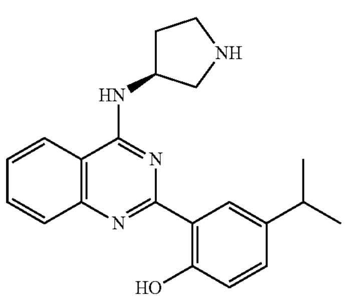 |
| 32-B | A-025 | 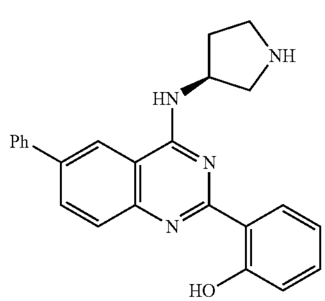 |
| 33 | A-026 | |
| 34 | A-027 | |
| 35 | A-028 | |
| 36 | A-029 | |
| 37-D | A-030 | |

-continued
| Synthesis | ID No. | Structure |
|---|---|---|
| 38 | A-031 | 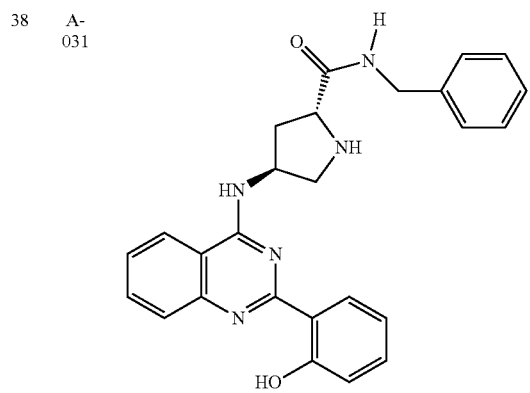 |
| 39 | A-032 | 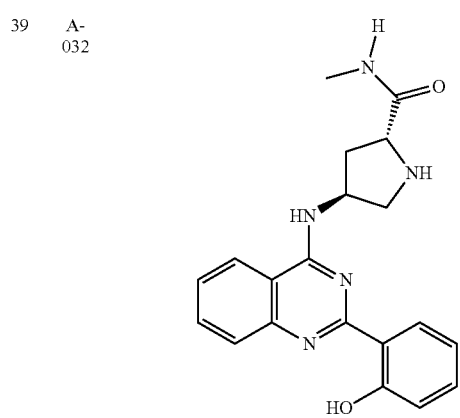 |
| 40-B | A-033 | 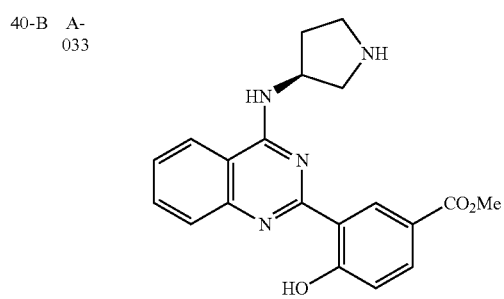 |
| 41 | A-034 | 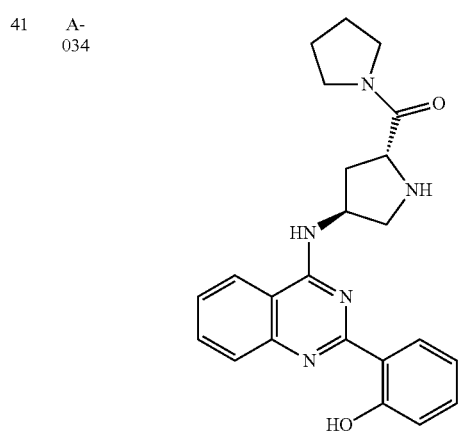 |
-continued
| Synthesis | ID No. | Structure |
|---|---|---|
| 42 | A-035 | 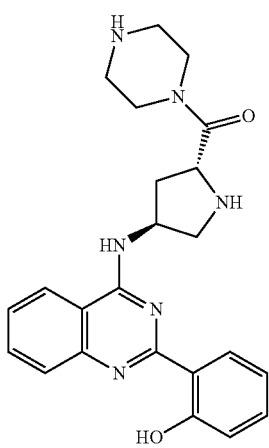 |
| 43 | A-036 | 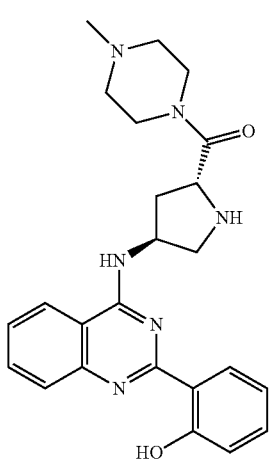 |
| 44 | A-037 | 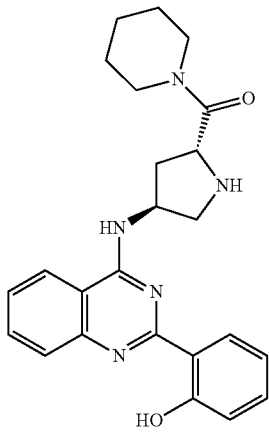 |

| Synthesis | ID No. | Structure |
|---|---|---|
| 45 | A-038 | 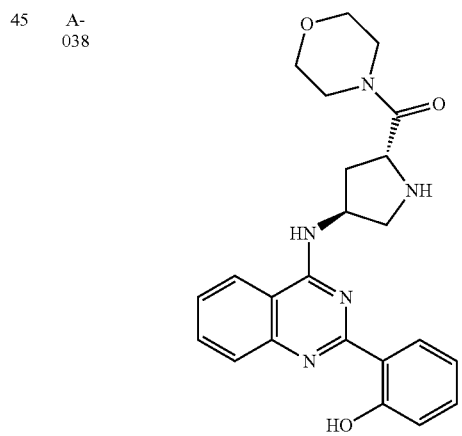 |
| 46 | A-039 | 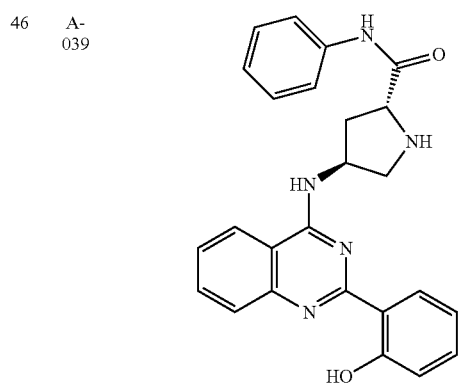 |
| 47 | A-040 | 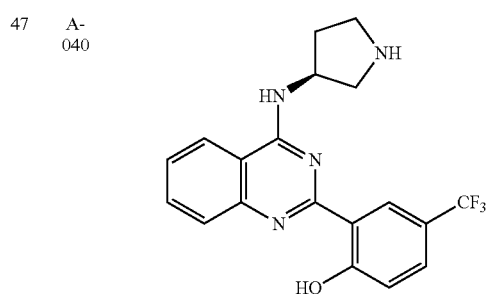 |
| 48 | A-041 | 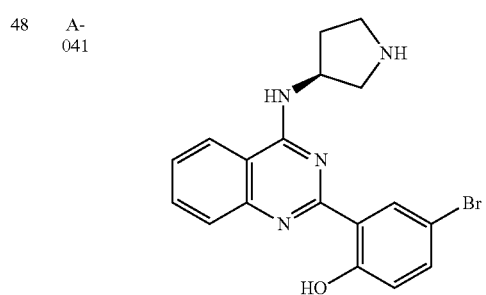 |
| Synthesis | ID No. | Structure |
|---|---|---|
| 49 | A-042 | 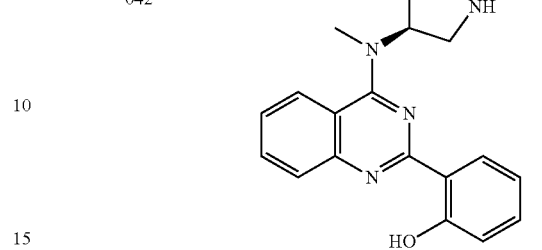 |
| 50 | A-043 | 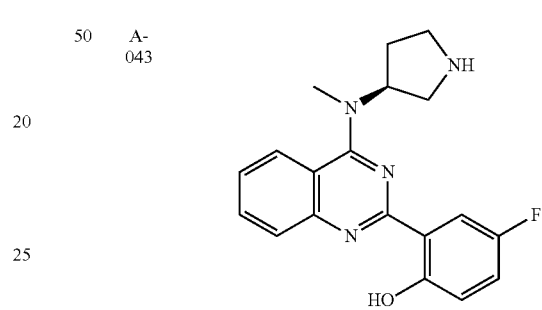 |
| 51 | A-044 | 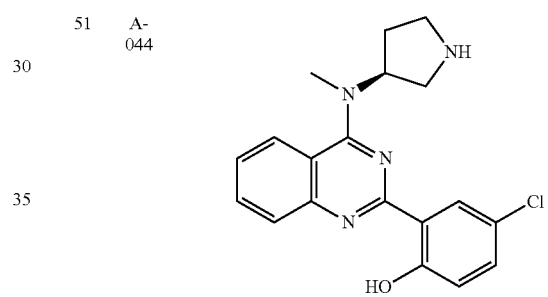 |
| 52-B | A-045 | 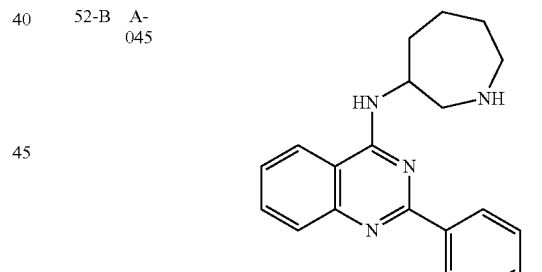 |
| 53 | A-046 | 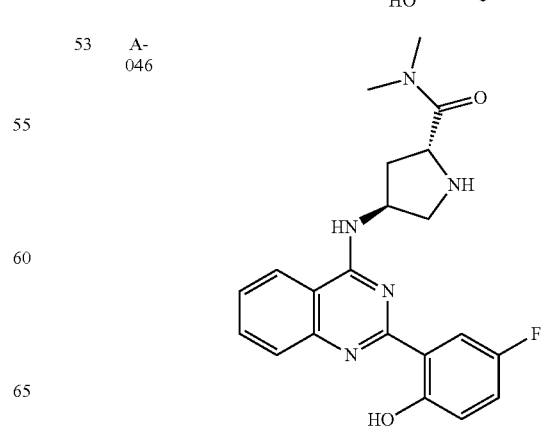 |

| Synthesis | ID No. | Structure |
|---|---|---|
| 54 | A-047 | 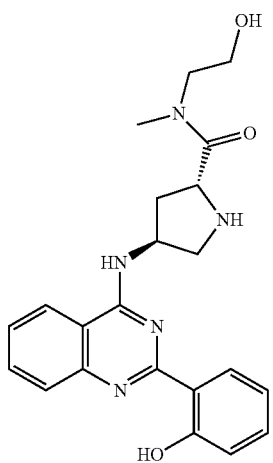 |
| 55 | A-048 | 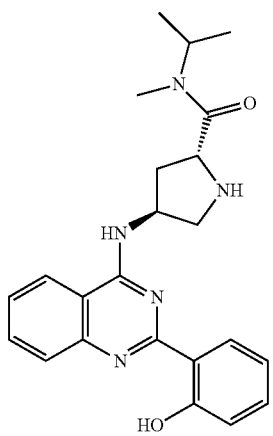 |
| 56 | A-049 | 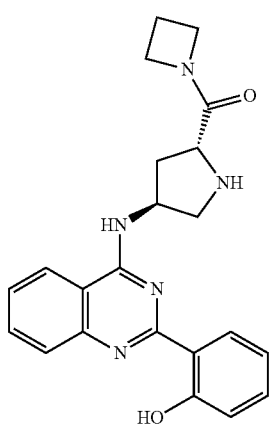 |
| Synthesis | ID No. | Structure |
|---|---|---|
| 57 | A-050 | 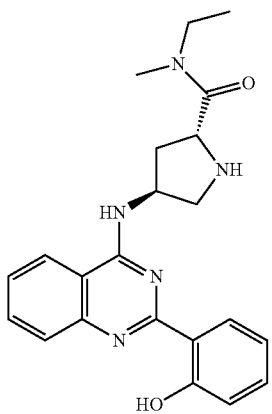 |
| 58 | A-051 | 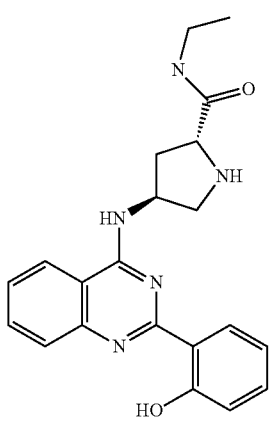 |
| 59-B | A-052 | 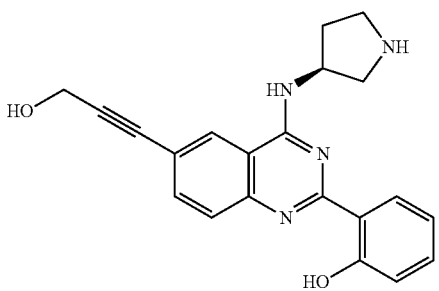 |
| 60 | A-053 | 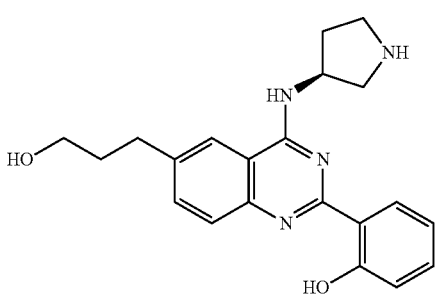 |

-continued
| Synthesis | ID No. | Structure |
|---|---|---|
| 61 | A-054 | 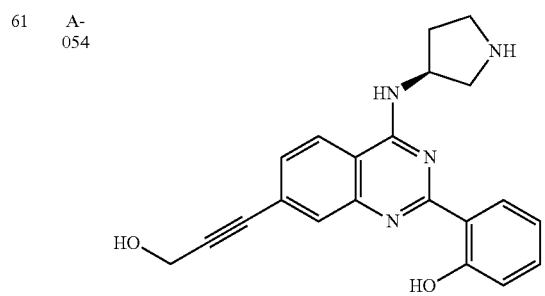 |
| 62 | A-055 | 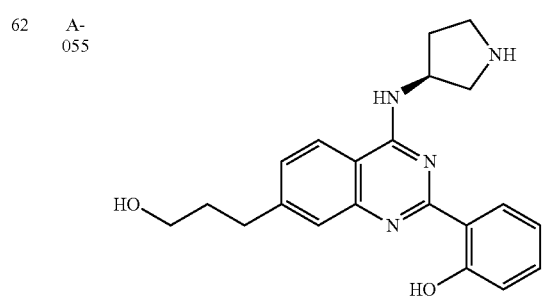 |
| 63 | A-056 | 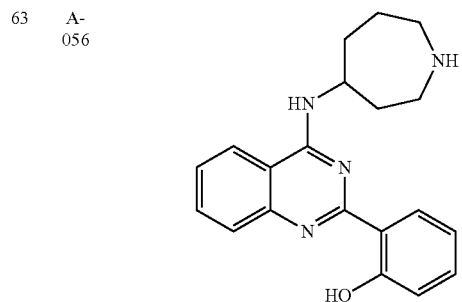 |
| 64 | A-057 | 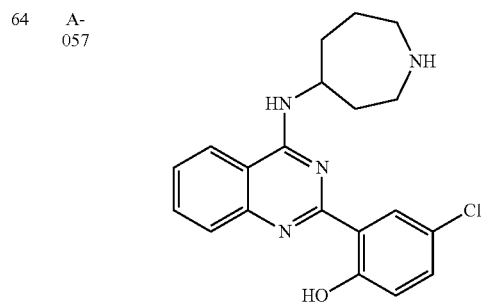 |
| 65 | A-058 | 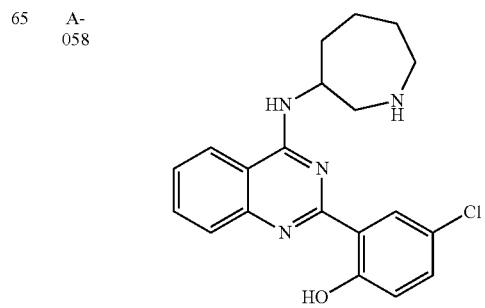 |
-continued
| Synthesis | ID No. | Structure |
|---|---|---|
| 66 | A-059 | 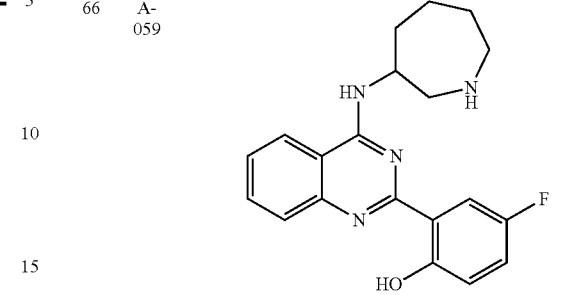 |
| 67 | A-060 | 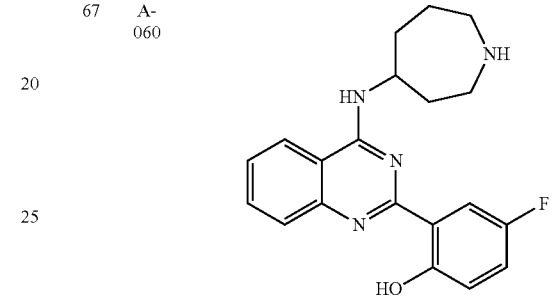 |
| 68 | A-061 | 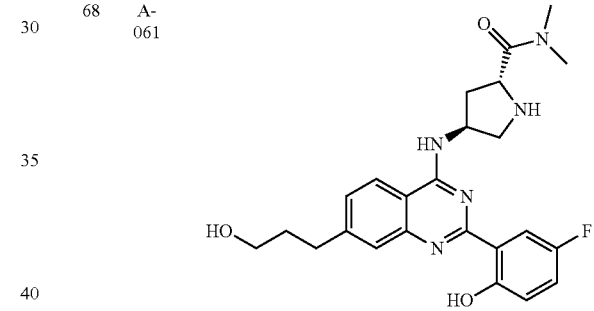 |
| 69 | A-062 | 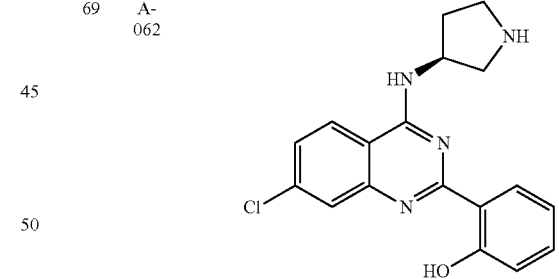 |
| 70 | A-063 | 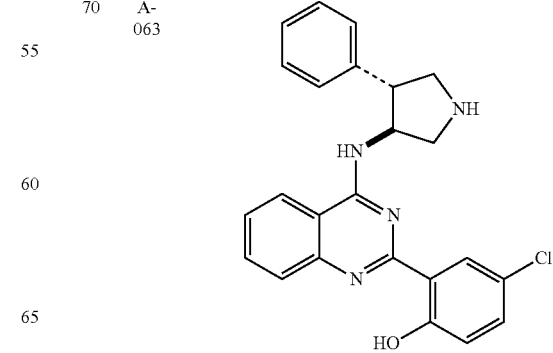 |

| Syn-thesis | ID No. | Structure |
|---|---|---|
| 71 | A-064 | 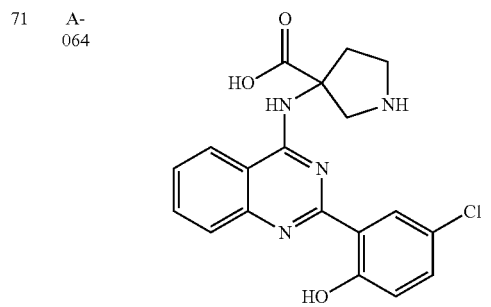 |
| 72-B | A-065 | 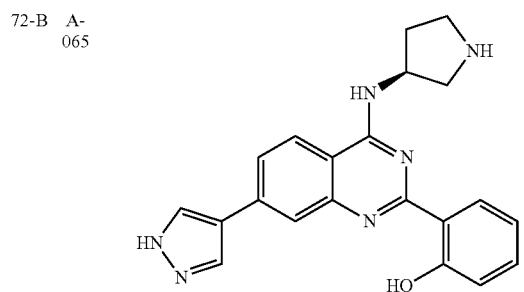 |
| 73 | A-066 | 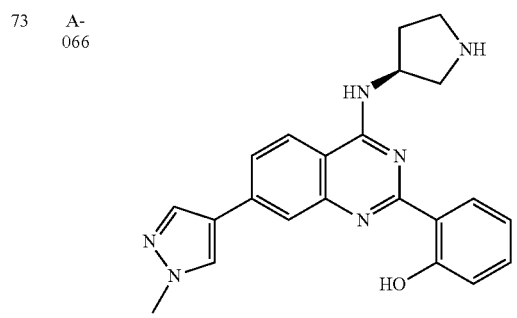 |
| 74-B | A-067 | 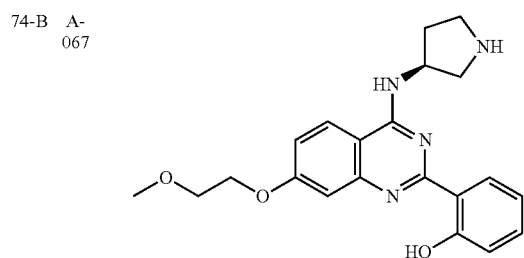 |
| 75 | A-068 | 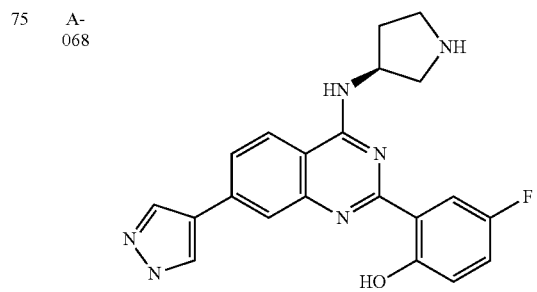 |
| Syn-thesis | ID No. | Structure |
|---|---|---|
| 76-B | A-069 | 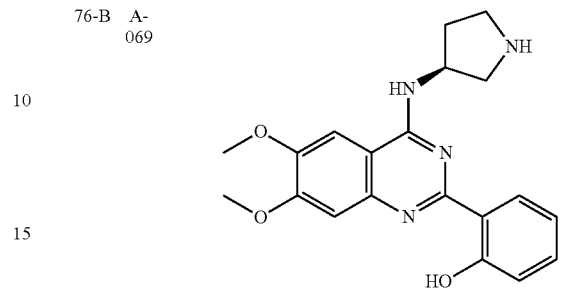 |
| 77 | A-070 | 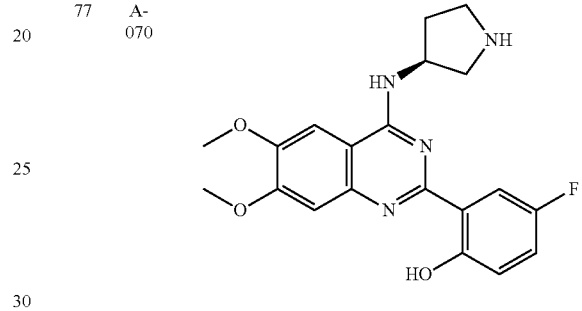 |
| 78 | A-071 | 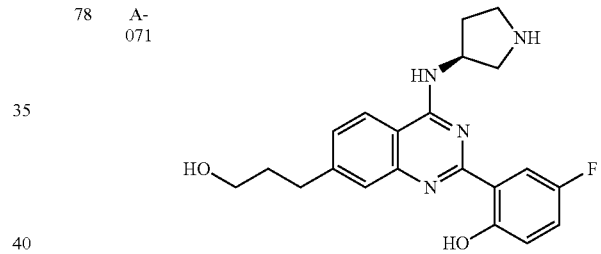 |
| 79 | A-072 | 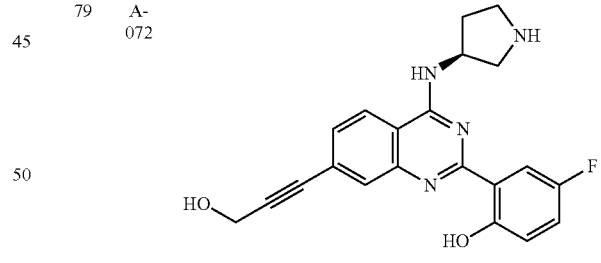 |
| 80-B | A-073 | 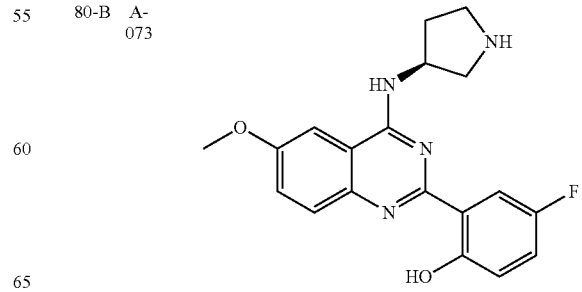 |

| Synthesis | ID No. | Structure |
|---|---|---|
| 81 | A-074 | 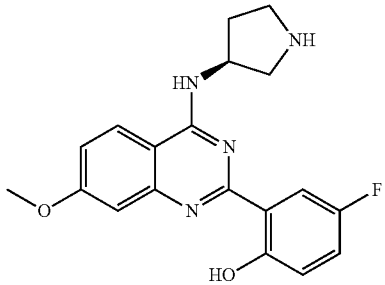 |
| 82 | A-075 | 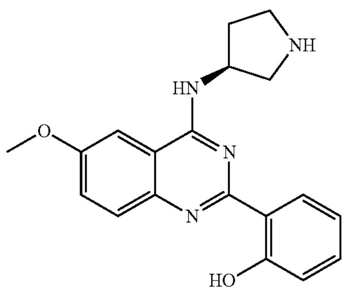 |
| 83 | A-076 | 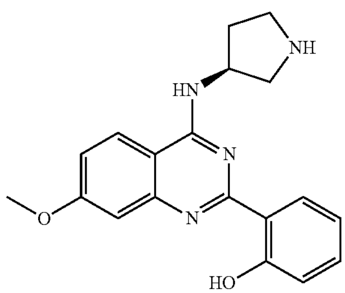 |
| 84 | A-077 | 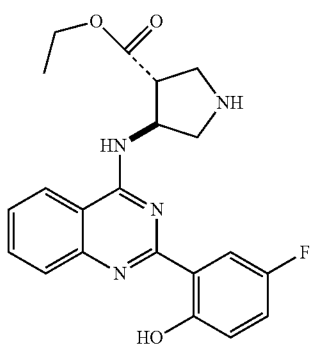 |
| 85-B | A-078 | 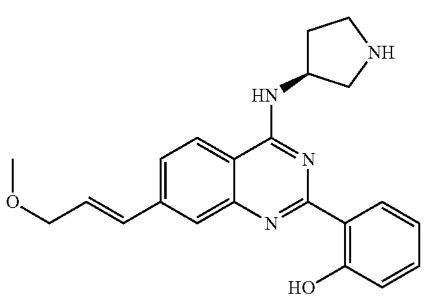 |
| 86 | A-079 | |
| 87 | A-080 | |
| 88 | A-081 | |
| 89-B | A-082 | |

-continued

| Synthesis | ID No. | Structure |
|---|---|---|
| 90 | A-083 | 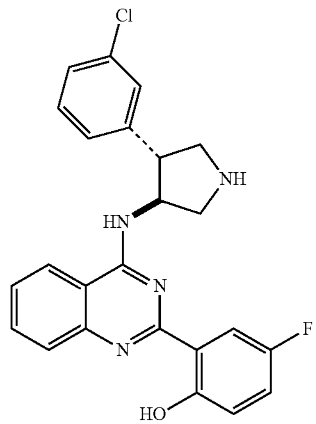 |
| 91 | A-084 | 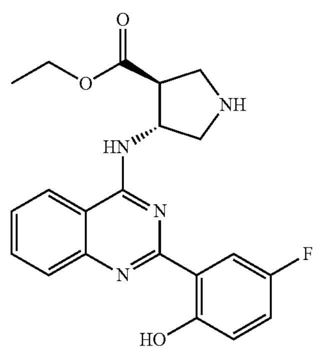 |
| 92 | A-085 | 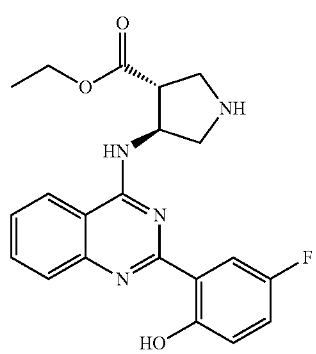 |
| 93 | A-086 | 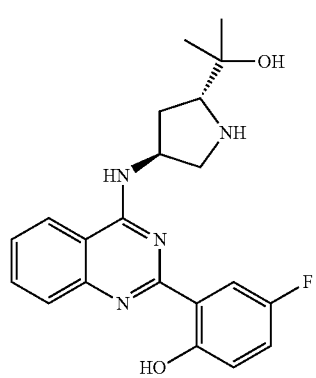 |
| 94 | A-087 | |
| 95-B | A-088 | |
| 96 | A-089 | |
| 97-D | A-090 | |

| Synthesis | ID No. | Structure |
|---|---|---|
| 98 | A-091 | 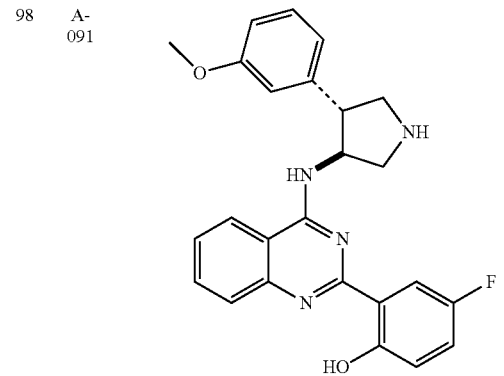 |
| 99 | A-092 | 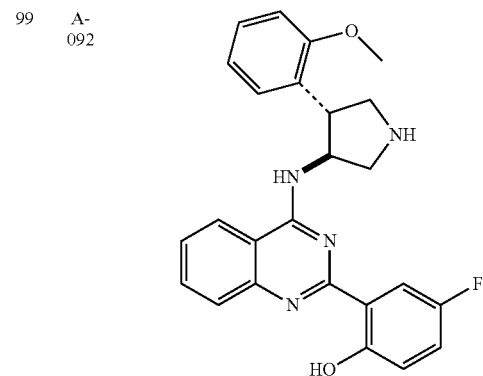 |
| 100 | A-093 | 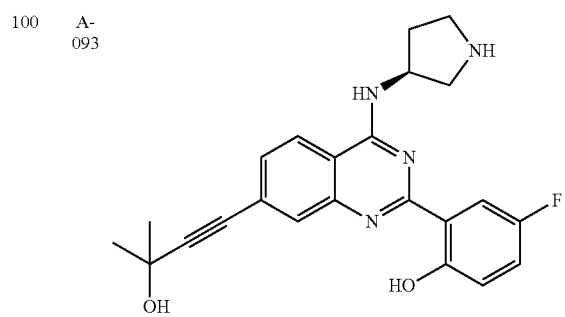 |
| 101 | A-094 | 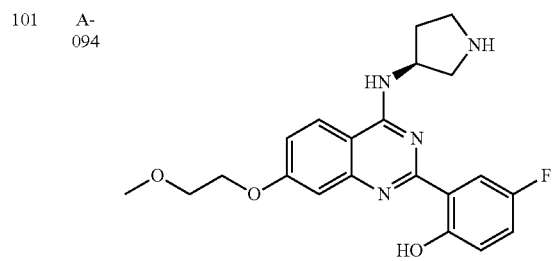 |
| 102 | A-095 | 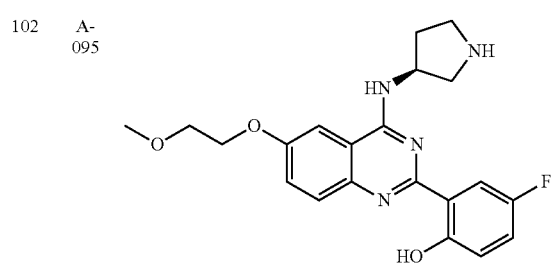 |
| 103 | A-096 | 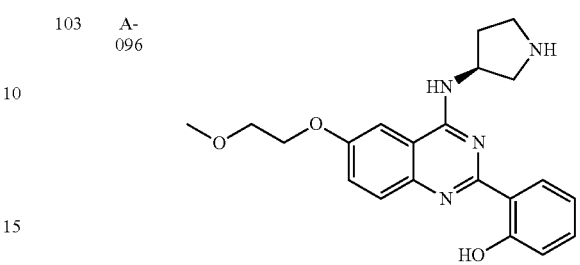 |
| 104 | A-097 | 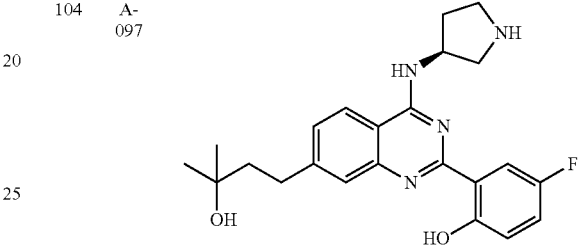 |
| 105 | A-098 | 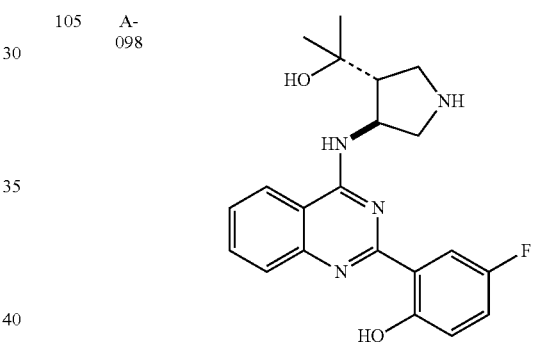 |
| 106 | A-099 | 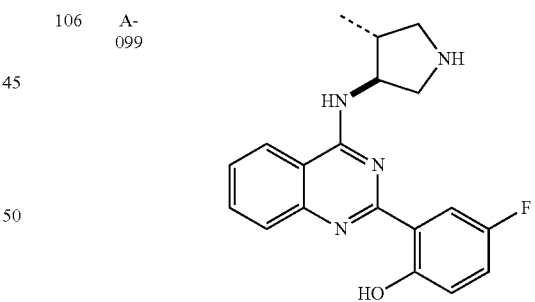 |
| 107 | A-100 | 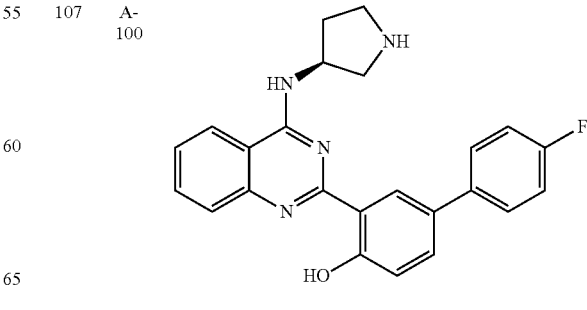 |

| Synthesis | ID No. | Structure |
|---|---|---|
| 108 | A-101 | 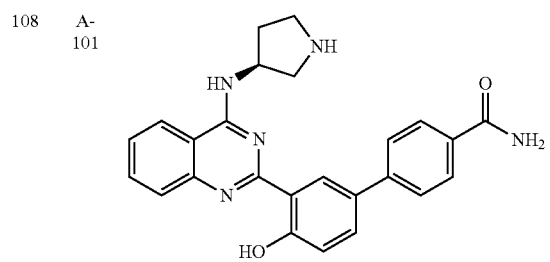 |
| 109 | A-102 | 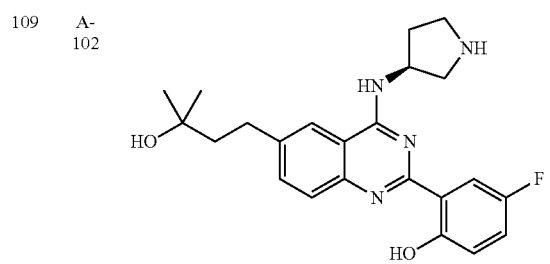 |
| 110-D | A-103 | 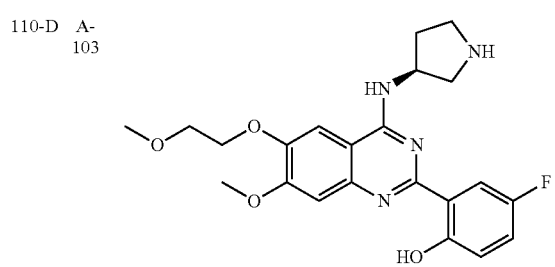 |
| 111-C | A-104 | 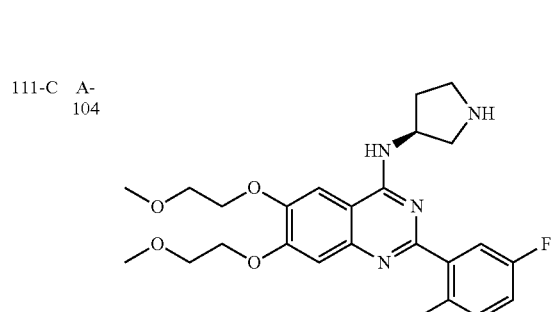 |
| 112 | A-105 | 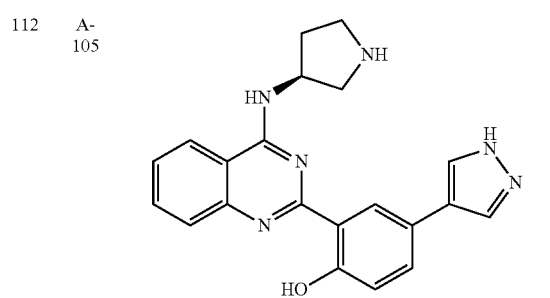 |
| 113 | A-106 | 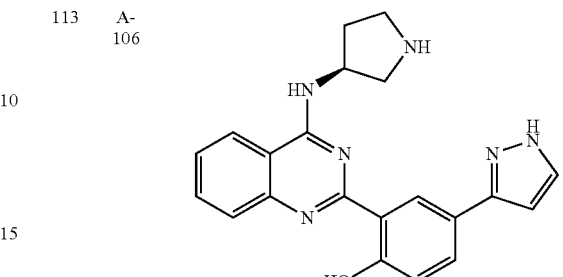 |
| 114 | A-107 | 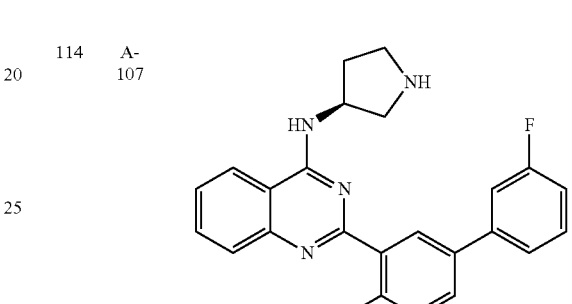 |
| 115 | A-108 | 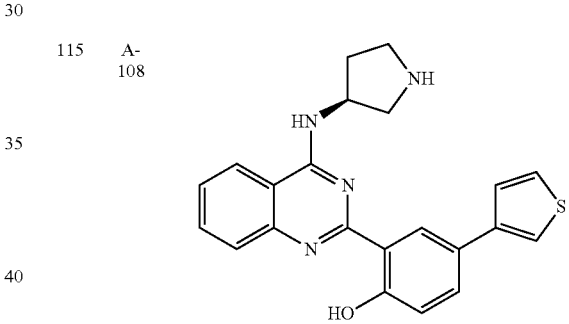 |
| 116 | A-109 | 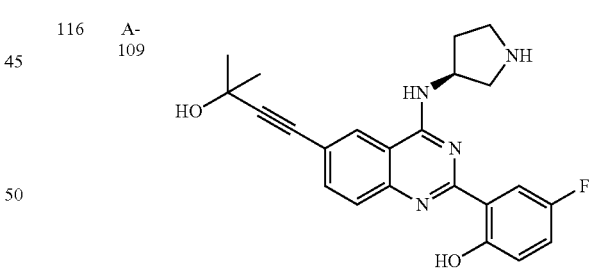 |
| 117-B | A-110 | 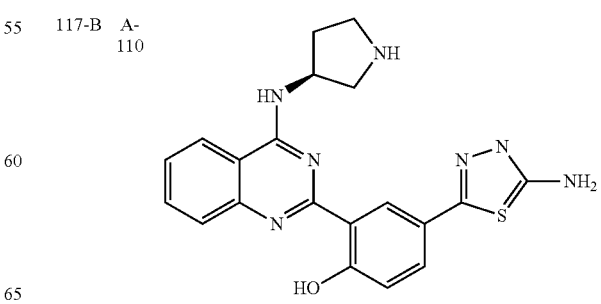 |

| Synthesis | ID No. | Structure |
|---|---|---|
| 118-B | A-111 | (structure) |
| 119 | A-112 | (structure) |
| 120 | A-113 | (structure) |
| 121 | A-114 | (structure) |

| Synthesis | ID No. | Structure |
|---|---|---|
| 122 | A-115 | (structure) |
| 123 | A-116 | (structure) |
| 124 | A-117 | (structure) |
| 125 | A-118 | (structure) |

In one embodiment, the compound is selected from the following compounds, and pharmaceutically acceptable salts, hydrates, and solvates thereof:

| Synthesis | ID No. | Structure |
|---|---|---|
| 13 | B-001 | *(4-aminocyclohexyl)amino-2-(2-hydroxyphenyl)quinazoline)* |
| 14 | B-002 | *((1S,2S)-2-aminocyclohexyl)amino-2-(2-hydroxyphenyl)quinazoline* |
| 15 | B-003 | *((1R,2S)-2-aminocyclohexyl)amino-2-(2-hydroxyphenyl)quinazoline* |
| 16 | B-004 | *(3-aminocyclohexyl)amino-2-(2-hydroxyphenyl)quinazoline* |

In one embodiment, the compound is selected from the following compounds, and pharmaceutically acceptable salts, hydrates, and solvates thereof:

| Synthesis | ID No. | Structure |
|---|---|---|
| 26-C | C-001 | *(S)-pyrrolidin-3-ylamino-2-(2-hydroxyphenyl)quinoline* |

In one embodiment, the compound is selected from the following compounds, and pharmaceutically acceptable salts, hydrates, and solvates thereof:

| Synthesis | ID No. | Structure |
|---|---|---|
| 17-D | D-001 | *(S)-pyrrolidin-3-ylamino-5-phenyl-2-(2-hydroxyphenyl)pyrimidine* |
| 21-C | D-002 | *(S)-pyrrolidin-3-ylamino-2-(2-hydroxyphenyl)pyrimidine* |

Substantially Purified Forms

One aspect of the present invention pertains to OPA compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

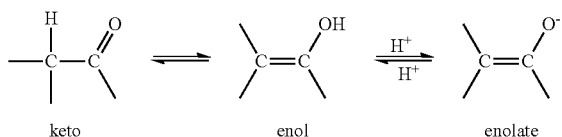

keto enol enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COON may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CF_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O●).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Methods for the chemical synthesis of OPA compounds of the present invention are described herein. These and/or other well-known methods may be modified and/or adapted in known ways in order to facilitate the synthesis of additional OPA compounds of the present invention.

In one approach, appropriate anthranilo-nitriles are first reacted with appropriate 2-methoxybenzoyl chlorides to give the corresponding intermediate amides, which are subsequently cyclised to provide the corresponding 4-hydroxyquinazolines. The 4-hydroxyl group is activated by conversion to the chloride, for example, by using phosphorus oxychloride. This is followed by deprotection of the anisole functionality to provide the corresponding phenols. Final displacement of the 4-chloro group by appropriate amines provides the corresponding quinazolines. An example of such a method is shown in the following scheme.

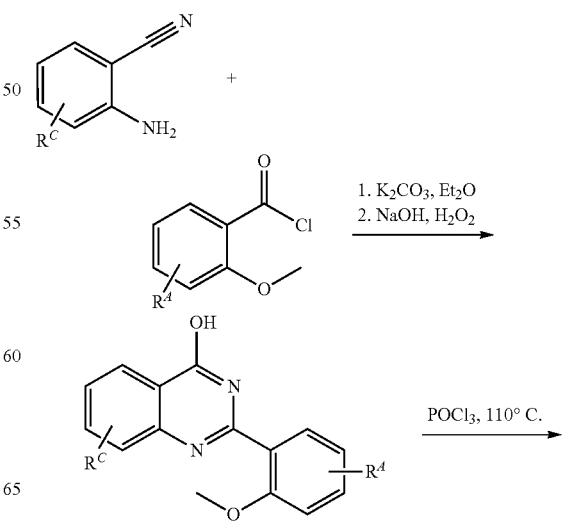

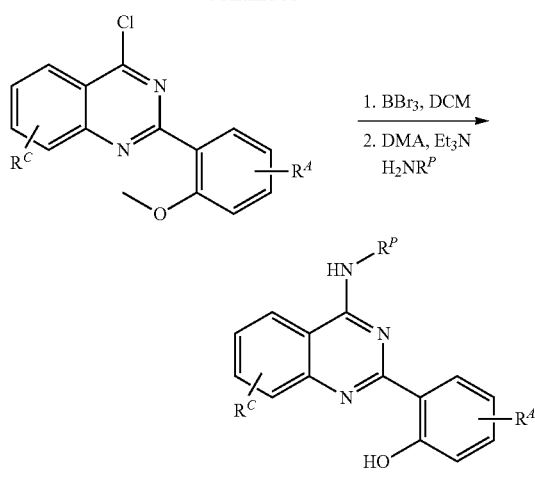

In another approach, appropriate 2,4-quinolinediols are reacted, for example, with phosphorus oxychloride, to give the corresponding 2-4-dichloroquinolines, which undergo selective palladium-catalysed coupling with appropriate 2-hydroxyphenylboronic acids at the 2-chloro substitutent. Subsequent amine displacement of the 4-chloro substituent, for example, under microwave heating with appropriate amines, provides the corresponding quinolines. An example of such a method is shown in the following scheme.

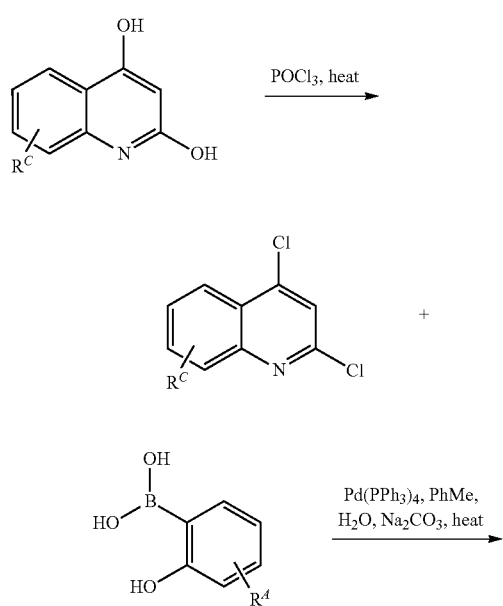

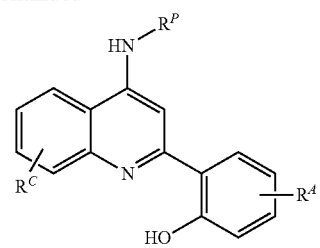

In another approach, appropriate 2,4-dichloropyrimidines are reacted with appropriate amines to selectively displace the 4-chloro substituent. The resulting 2-chloro-pyrimidines undergo palladium-catalysed coupling with appropriate 2-hydroxyphenylboronic acids to give the corresponding pyrimidines. An example of such a method is shown in the following scheme.

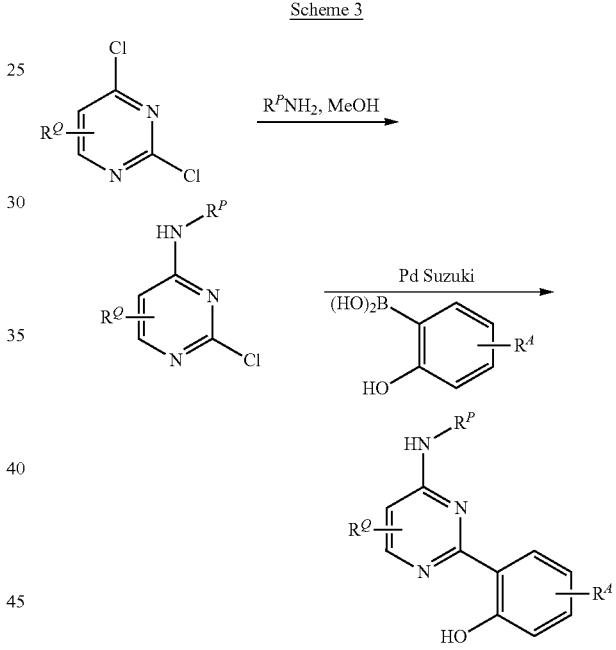

In another approach, appropriate 2,4-dichloropyridines are reacted with appropriate 2-hydroxyphenylboronic acids under palladium-catalysis to give selectively reaction at the 2-chloro substituent. The corresponding 4-chloro-pyridines are displaced with appropriate amines to give the corresponding pyridines. An example of such a method is shown in the following scheme.

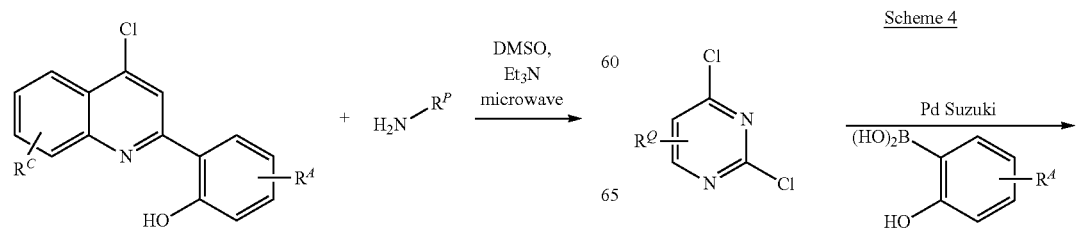

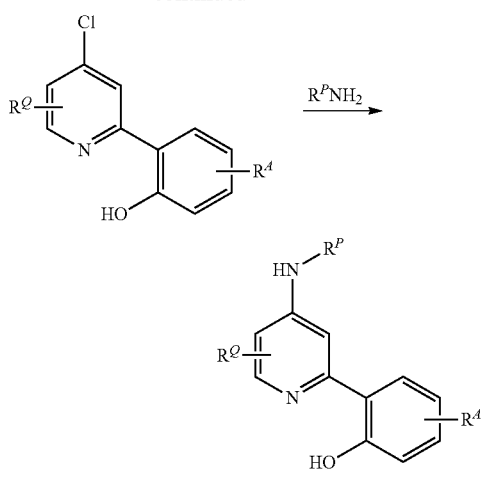

In another approach, appropriate 2,4-quinazolinediols are reacted, for example, with phosphorus oxychloride, to give the corresponding 2,4-dichloroquinazolines, which are reacted with appropriate amines to selectively displace the 4-chloro substituent. The resulting 2-chloro-quinazolines undergo palladium-catalysed coupling with appropriate 2-hydroxyphenylboronic acids to give the corresponding quinazolines. An example of such a method is shown in the following scheme.

Scheme 5

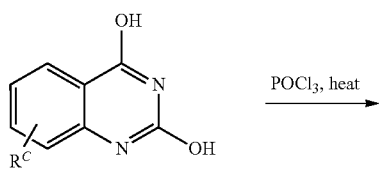

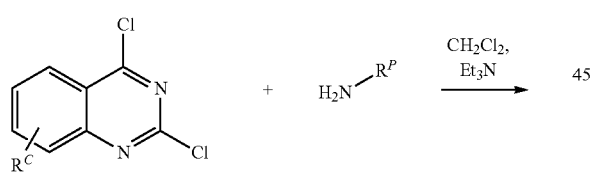

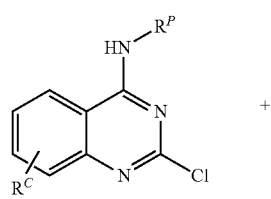

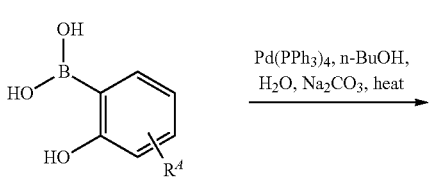

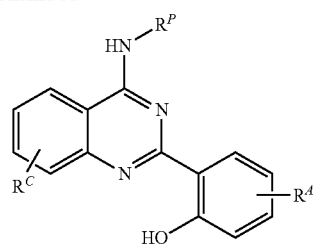

In another approach, appropriate halo-substituted 2-(4-amino)quinazolin-2-yl)phenols are reacted, for example, with alkynes in the presence of a palladium catalyst. An example of such a method is shown in the following scheme.

Scheme 6

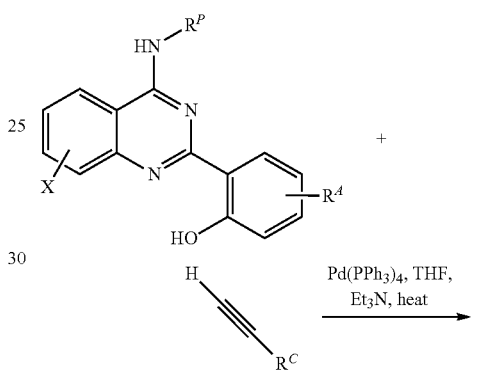

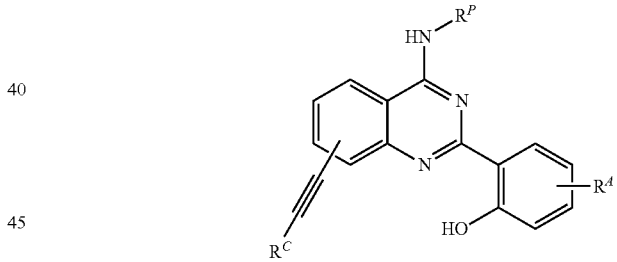

In another approach, appropriate alkynyl-substituted 2-(2-hydroxyphenyl)-quinazolines are reduced with, for example, hydrogen in the presence of a palladium catalyst. An example of such a method is shown in the following scheme.

Scheme 7

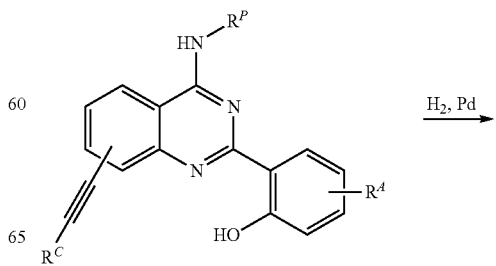

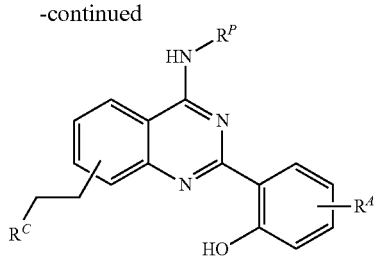

In another approach, appropriate 4-amino-2-(2-methoxyphenyl)-quinazolines are alkylated with, for example, an alkyl or benzyl halide in the presence of sodium hydride. The resulting 4-(dialkylamino)-2-(2-methoxyphenyl)-quinazolines undergo O-demethylation with, for example, boron tribromide to give the corresponding quinazolines. An example of such a method is shown in the following scheme.

Scheme 8

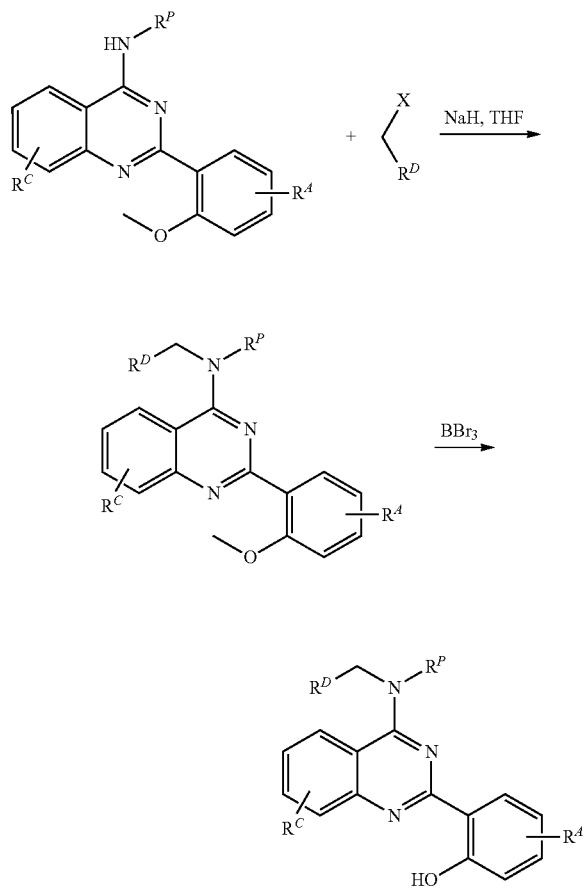

In another approach, appropriate halo-substituted 2-(4-amino)quinazolin-2-yl)phenols are reacted, for example, with boronic acids in the presence of a palladium catalyst. An example of such a method is shown in the following scheme.

Scheme 9

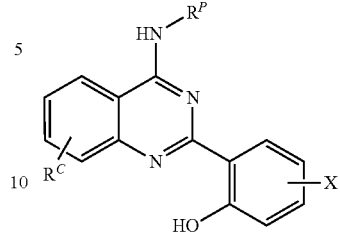

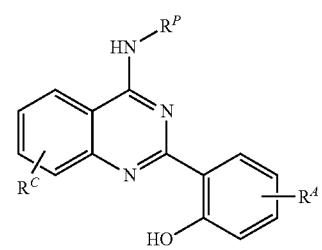

Compositions

One aspect of the present invention pertains to a composition (e.g., a pharmaceutical composition) comprising an OPA compound, as described herein, and a pharmaceutically acceptable carrier, diluent, or excipient.

Another aspect of the present invention pertains to a method of preparing a composition (e.g., a pharmaceutical composition) comprising admixing an OPA compound, as described herein, and a pharmaceutically acceptable carrier, diluent, or excipient.

Uses

The compounds described herein are useful, for example, in the treatment of diseases and conditions that are ameliorated by the inhibition of CHK2 kinase function, such as, for example, proliferative conditions, cancer, etc.

Use in Methods of Inhibiting CHK2

One aspect of the present invention pertains to a method of inhibiting CHK2 kinase function, for example, in vitro or in vivo, comprising contacting a CHK2 kinase with an effective amount of an OPA compound, as described herein.

One aspect of the present invention pertains to a method of inhibiting CHK2 kinase function in a cell, for example, in vitro or in vivo, comprising contacting the cell with an effective amount of an OPA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Suitable assays for determining CHK2 kinase function inhibition are described herein and/or are known in the art.

Use in Methods of Inhibiting Cell Proliferation, Etc.

The OPA compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, for example, in vitro or in vivo, comprising contacting a cell with an effective amount of an OPA compound, as described herein.

In one embodiment, the method is a method of regulating (e.g., inhibiting) cell proliferation (e.g., proliferation of a cell), for example, in vitro or in vivo, comprising contacting a cell with an effective amount of an OPA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

In one embodiment, the method is performed in vitro.

In one embodiment, the method is performed in vivo.

In one embodiment, the OPA compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Radio-Protection Etc.

Another aspect of the present invention pertains to a method of radio-protecting a cell (e.g., a non-cancerous cell) comprising contacting the cell with an effective amount of an OPA compound, as described herein.

Another aspect of the present invention pertains to a method of reducing or eliminating damaging effects of ionising radiation on a cell (e.g., a non-cancerous cell) that has been exposed to ionising radiation, or will be exposed to ionising radiation, comprising contacting the cell with an effective amount of an OPA compound, as described herein.

In one embodiment, the cell is exposed to ionising radiation before being contacted with the OPA compound. In one embodiment, the cell is exposed to ionising radiation after being contacted with the OPA compound.

In embodiment, the method if performed in vivo.

In embodiment, the method if performed in vitro.

Use in Methods of Therapy

Another aspect of the present invention pertains to an OPA compound, as described herein, for use in a method of treatment of the human or animal body by therapy.

In one embodiment, the method of treatment comprises treatment with both (i) an OPA compound, as described herein, and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to (a) a DNA topoisomerase I or II inhibitor, (b) a DNA damaging agent, (c) an antimetabolite or TS inhibitor, or (d) a microtubule targeted agent, as described herein, for use in a method of treatment of the human or animal body by therapy, wherein the method of treatment comprises treatment with both (i) an OPA compound, as described herein, and (a) the DNA topoisomerase I or II inhibitor, (b) the DNA damaging agent, (c) the antimetabolite or TS inhibitor, or (d) the microtubule targeted agent.

Use in the Manufacture of Medicaments

Another aspect of the present invention pertains to use of an OPA compound, as described herein, in the manufacture of a medicament for use in treatment.

In one embodiment, the medicament comprises the OPA compound.

In one embodiment, the treatment comprises treatment with both (i) a medicament comprising an OPA compound, as described herein, and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to use of (a) a DNA topoisomerase I or II inhibitor, (b) a DNA damaging agent, (c) an antimetabolite or TS inhibitor, or (d) a microtubule targeted agent, as described herein, in the manufacture of a medicament for use in a treatment, wherein the treatment comprises treatment with both (i) an OPA compound, as described herein, and (a) the DNA topoisomerase I or II inhibitor, (b) the DNA damaging agent, (c) the antimetabolite or TS inhibitor, or (d) the microtubule targeted agent.

Methods of Treatment

Another aspect of the present invention pertains to a method of treatment comprising administering to a patient in need of treatment a therapeutically effective amount of an OPA compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Conditions Treated—Conditions Mediated by CHK2

In one embodiment (e.g., of use in methods of therapy, of use in the manufacture of medicaments, of methods of treatment), the treatment is treatment of a disease or condition that is mediated by CHK2.

Conditions Treated—Conditions Ameliorated by the Inhibition of CHK2 Kinase Function In one embodiment (e.g., of use in methods of therapy, of use in the manufacture of medicaments, of methods of treatment), the treatment is treatment of: a disease or condition that is ameliorated by the inhibition of CHK2 kinase function.

Conditions Treated—Proliferative Conditions and Cancer

In one embodiment (e.g., of use in methods of therapy, of use in the manufacture of medicaments, of methods of treatment), the treatment is treatment of: a proliferative condition.

The term "proliferative condition," as used herein, pertains to an unwanted or uncontrolled cellular proliferation of excessive or abnormal cells which is undesired, such as, neoplastic or hyperplastic growth.

In one embodiment, the treatment is treatment of: a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of: cancer.

In one embodiment, the treatment is treatment of: p53 negative cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the treatment is treatment of:
a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
a hematopoietic tumor of myeloid lineage, for example acute and chronic myelogenous leukemias, myelodysplastic syndrome, or promyelocytic leukemia;
a tumour of mesenchymal origin, for example fibrosarcoma or habdomyosarcoma;
a tumor of the central or peripheral nervous system, for example astrocytoma, neuroblastoma, glioma or schwannoma;
melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of: lung cancer, breast cancer, ovarian cancer, colorectal cancer, melanoma, or glioma.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Conditions Treated—Radio-Protection and the Damaging Effects of Ionising Radiation The OPA compounds, as described herein, may also be used as a preventive (e.g., in preventive treatment) to provide a protective effect for normal, undiseased (e.g., non-cancerous) tissue in combination with treatment with ionising radiation (e.g., radiotherapy).

In one embodiment, the treatment is treatment to radio-protect cells (e.g., non-cancerous cells) (e.g., to protect cells, e.g., non-cancerous cells, from damaging effects of ionising radiation) (e.g., in a patient undergoing treatment with ionizing radiation, e.g., radiotherapy) (e.g., in a patient that has had, is having, or will have treatment with ionizing radiation, radiotherapy).

In one embodiment, the treatment is treatment to reduce or eliminate damaging effects of ionising radiation on cells (e.g., non-cancerous cells) that have been, are being, or will be exposed to ionising radiation in a patient undergoing treatment with ionizing radiation, e.g., radiotherapy (e.g., in a patient that has had, is having, or will have treatment with ionizing radiation, e.g., radiotherapy).

Thus, one aspect of the present invention pertains to a method of radio-protecting cells (e.g., non-cancerous cells) (e.g., protecting cells, e.g., non-cancerous cells, from damaging effects of ionising radiation) in a patient undergoing treatment with ionizing radiation (e.g., radiotherapy) (e.g., in a patient that has had, is having, or will have treatment with ionizing radiation, e.g., radiotherapy), comprising administering to the patient a therapeutically-effective amount of an OPA compound, as described herein, preferably in the form of a pharmaceutical composition.

Another aspect of the present invention pertains to a method of reducing or eliminating damaging effects of ionising radiation on cells (e.g., non-cancerous cells) in a patient undergoing treatment with ionizing radiation (e.g., radiotherapy) (e.g., in a patient that has had, is having, or will have treatment with ionizing radiation, e.g., radiotherapy), comprising administering to the patient a therapeutically-effective amount of an OPA compound, as described herein, preferably in the form of a pharmaceutical composition.

Another aspect of the present invention pertains to an OPA compound, as described herein, for use in a method of radio-protecting cells (e.g., non-cancerous cells) (e.g., protecting cells, e.g., non-cancerous cells, from damaging effects of ionising radiation) in a patient undergoing treatment with ionizing radiation (e.g., radiotherapy) (e.g., in a patient that has had, is having, or will have treatment with ionizing radiation, e.g., radiotherapy).

Another aspect of the present invention pertains to an OPA compound, as described herein, for use in a method of reducing or eliminating damaging effects of ionising radiation on cells (e.g., non-cancerous cells) in a patient undergoing treatment with ionizing radiation (e.g., radiotherapy) (e.g., in a patient that has had, is having, or will have treatment with ionizing radiation, e.g., radiotherapy).

Another aspect of the present invention pertains to use of an OPA compound, as described herein, in the manufacture of a medicament for use in a method of radio-protecting cells (e.g., non-cancerous cells) (e.g., protecting cells, e.g., non-cancerous cells, from damaging effects of ionising radiation) in a patient undergoing treatment with ionizing radiation (e.g., radiotherapy) (e.g., in a patient that has had, is having, or will have treatment with ionizing radiation, e.g., radiotherapy).

Another aspect of the present invention pertains to use of an OPA compound, as described herein, in the manufacture of a medicament for use in a method of reducing or eliminating damaging effects of ionising radiation on cells (e.g., non-cancerous cells) in a patient undergoing treatment with ionizing radiation (e.g., radiotherapy) (e.g., in a patient that has had, is having, or will have treatment with ionizing radiation, e.g., radiotherapy).

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development.

One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Combination Therapies Employing DNA Damaging Agents

As discussed herein, in some embodiments, the OPA compound is employed in combination with (e.g., in conjunction with) with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

When both an OPA compound and one or more other agents are employed, they may be used (e.g., contacted, administered, etc.) in any order. Furthermore, they may be used (e.g., contacted, administered, etc.) together, as part of a single formulation, or separately, as separate formulations.

For example, in regard to methods of treatment employing both an OPA compound and one or more other agents, treatment with (e.g., administration of) the OPA compound may be prior to, concurrent with, or may follow, treatment with (e.g., administration of) the one or more other agents, or a combination thereof.

In one embodiment, treatment with (e.g., administration of) an OPA compound is concurrent with, or follows, treatment with (e.g., administration of) the one or more other agents.

In one embodiment, the one or more other agents is a DNA topoisomerase I or II inhibitor; for example, Etoposide, Toptecan, Camptothecin, Irinotecan, SN-38, Doxorubicin, Daunorubicin.

In one embodiment, the one or more other agents is a DNA damaging agent; for example, alkylating agents, platinating agents, or compounds that generate free radicals; for example, Temozolomide, Cisplatin, Carboplatin, Mitomycin C, Cyclophosphamide, BCNU, CCNU, Bleomycin.

In one embodiment, the one or more other agents is an antimetabolite or TS inhibitor; for example, 5-fluorouracil, hydroxyurea, Gemcitabine, Arabinosylcytosine, Fludarabine, Tomudex, ZD9331.

In one embodiment, the one or more other agents is a microtubule targeted agent; for example, Paclitaxel, Docetaxel, Vincristine, Vinblastine.

In one embodiment, the one or more other agents is ionising radiation (e.g., as part of radiotherapy).

Other Uses

The OPA compounds described herein may also be used as cell culture additives to inhibit CHK2 kinase function, e.g., to inhibit cell proliferation, etc.

The OPA compounds described herein may also be used as part of an in vitro assay, for example, in order to determine whether a candidate host is likely to benefit from treatment with the compound in question.

The OPA compounds described herein may also be used as a standard, for example, in an assay, in order to identify other compounds, other CHK2 kinase function inhibitors, other anti-proliferative agents, other anti-cancer agents, etc.

Kits

One aspect of the invention pertains to a kit comprising (a) an OPA compound as described herein, or a composition comprising an OPA compound as described herein, e.g., preferably provided in a suitable container and/or with suitable packaging; and (b) instructions for use, e.g., written instructions on how to administer the compound or composition.

In one embodiment, the kit further comprises one or more other agents selected from: (a) a DNA topoisomerase I or II inhibitor; (b) a DNA damaging agent; (c) an antimetabolite or TS inhibitor; and (d) a microtubule targeted agent.

The written instructions may also include a list of indications for which the active ingredient is a suitable treatment.

Routes of Administration

The OPA compound or pharmaceutical composition comprising the OPA compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the OPA compound to be administered alone, it is preferable to present it as a pharmaceutical formulation (e.g., composition, preparation, medicament) comprising at least one OPA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one OPA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Reminaton's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the OPA compounds, and compositions comprising the OPA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular OPA compound, the route of administration, the time of administration, the rate of excretion of the OPA compound, the duration of the treatment, other drugs, compounds, and/or materials used in combination, the severity of the condition, and the species, sex, age, weight, condition, general health, and prior medical history of the patient. The amount of OPA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the OPA compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Liquid Chromatography-Mass Spectrometry (LC-MS) Methods

LC-MS (LCT1) analyses were performed on a Micromass LCT/Water's Alliance 2795 HPLC system with a Discovery 5 μm, C18, 50 mm×4.6 mm or 30 mm×4.6 mm i.d. column from Supelco at a temperature of 22° C. and a flow rate of 1 mL/minute using the following solvent gradient:
  Solvent A: Methanol.
  Solvent B: 0.1% Formic acid in water.
  0.0-0.5 minutes 10% A/90% B.
  0.5-1.0 minutes 10% A/90% B to 20% A/80% B.
  1.0-7.5 minutes 20% A/80% B to 90% A/10% B.
  7.5-9.0 minutes 90% A/10% B.
  9.0-9.5 minutes 90% A/10% B to 10% A/90% B.
  9.5-10 minutes 10% A/90% B.

LC-MS (LCT2) analyses were performed on a Micromass LCT/Water's Alliance 2795 HPLC system with a Discovery 5 μm, C18, 50 mm×4.6 mm or 30 mm×4.6 mm i.d. column from Supelco at a temperature of 22° C. and a flow rate of 1 mL/minute using the following solvent gradient:
  Solvent A: Methanol.
  Solvent B: 0.1% Formic acid in water.
  0.0-0.3 minutes 10% A/90% B.
  0.3-0.6 minutes 10% A/90% B to 20% A/80% B.
  0.6-4.5 minutes 20% A/80% B to 90% A/10% B.
  4.5-5.4 minutes 90% A/10% B.
  5.4-5.7 minutes 90% A/10% B to 10% A/90% B.
  5.7-6.0 minutes 10% A/90% B.

LC-MS (LCT2B) analyses were performed on a Micromass LCT/Water's Alliance 2795 HPLC system with a Discovery 5 μm, C18, 50 mm×4.6 mm or 30 mm×4.6 mm i.d. column from Supelco at a temperature of 22° C. and a flow rate of 1 mL/minute using the following solvent gradient:
  Solvent A: Methanol.
  Solvent B: 0.1% Formic acid in water.
  0.0-0.3 minutes 10% A/90% B.
  0.3-0.6 minutes 10% A/90% B to 20% A/80% B.
  0.6-3.0 minutes 20% A/80% B to 90% A/10% B.
  3.0-5.4 minutes 90% A/10% B.
  5.4-5.7 minutes 90% A/10% B to 10% A/90% B.
  5.7-6.0 minutes 10% A/90% B.

LC-MS (LCT3) analyses were performed on a Micromass LCT/Water's Alliance 2795 HPLC system with a Discovery 5 μm, C18, 50 mm×4.6 mm or 30 mm×4.6 mm i.d. column from Supelco at a temperature of 22° C. and a flow rate of 1 mL/minute using the following solvent gradient:
  Solvent A: Methanol.
  Solvent B: 0.1% Formic acid in water.
  0.0-0.3 minutes 10% A/90% B.
  0.3-0.6 minutes 10% A/90% B to 20% A/80% B.
  0.6-3.0 minutes 20% A/80% B to 90% A/10% B.
  3.0-5.4 minutes 90% A/10% B.
  5.4-5.7 minutes 90% A/10% B to 10% A/90% B.
  5.7-6.0 minutes 10% A/90% B.

LC-MS (LCT3B) analyses were performed on a Micromass LCT/Water's Alliance 2795 HPLC system with a Chromolith SpeedROD RP-18e 50×4.6 mm i.d. column from Merck at a temperature of 30° C. and a flow rate of 2 mL/minute using the following solvent gradient:
  Solvent A: Methanol.
  Solvent B: 0.1% Formic acid in water.
  0.0-2.3 minutes 10% A/90% B.
  2.3-3.0 minutes 90% A/10% B.
  3.0-3.3 minutes 90% A/10% B.
  3.3-3.5 minutes 10% A/90% B.

LC-MS (LCT4) analyses were performed on a Micromass LCT/Water's Alliance 2795 HPLC system with a Chromolith SpeedROD RP-18e 50×4.6 mm i.d. column from Merck at a temperature of 30° C. and a flow rate of 2 mL/minute using the following solvent gradient:
  Solvent A: Methanol.
  Solvent B: 0.1% Formic acid in water.
  0.0-1.8 minutes 10% A/90% B.
  1.8-3.0 minutes 90% A/10% B.
  3.0-3.3 minutes 90% A/10% B.
  3.3-3.5 minutes 10% A/90% B.

LC-MS (LCT5) analyse were performed on an Aglient 1200 series HPLC system with a CHIRALCEL OD-H 250× 4.6 mm i.d. column at a temperature of 20° C. and a flow rate of 0.5 mL/minute using 20% iso-propanol in hexane.

Gas Chromatography-Mass Spectrometry (GC-MS) Methods

GC-MS (GCMS1) analyses were performed on a Thermo Trace/Finnigan Polaris Q system with a Zebron 15 m×0.25 mm i.d. column with 2.5 μm film thickness using helium as the carrier gas at a flow rate of 1.8 mL/minute and measuring the sample mass following ionisation by EI or CI. A 2 μL sample was injected and the following temperature gradient was applied to the column:
  0.0-1 minutes 80° C.
  1.0-6.0 minutes 80° C. to 300° C.
  6.0-8.0 minutes 300° C.

Synthesis 1-A 2-(2-Methoxy-phenyl)-quinazolin-4-ol

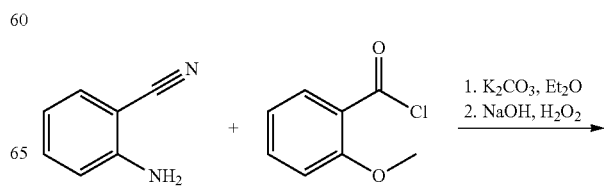

-continued

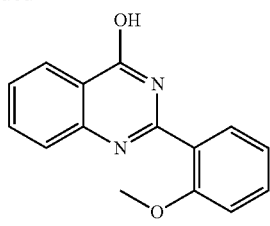

2-Methoxybenzoyl chloride (10.2 mL, 75.81 mmol) was added to a mixture of anthranilonitrile (7.46 g, 63.18 mmol) and potassium carbonate (43.76 g, 315.90 mmol) in diethyl ether (400 mL) at reflux. After 24 hours the solution was cooled and water (60 mL) was added. The resulting white solid was collected and washed with water (20 mL) and diethyl ether (50 mL). The solid was suspended in a mixture of 16% w/v aqueous sodium hydroxide (200 mL) and hydrogen peroxide (50 mL of a 30% v/v aqueous solution) and refluxed for 20 hours. The resulting pale yellow solution was cooled and acidified with acetic acid. The resulting precipitate was collected and washed with water to give the title compound as a white solid (4.94 g, 33%).

LC-MS (LCT1) m/z 253 [M+H$^+$], R$_t$ 4.81 minutes. $^1$H NMR (d$^6$-DMSO) δ 12.06 (s, 1H), 8.15 (dd, J 8.0, 1.0 Hz, 1H), 7.83 (ddd, J 8.5, 7.0, 1.5 Hz, 1H), 7.73-7.69 (m, 2H), 7.55-7.50 (m, 2H), 7.20 (d, J 8.5 Hz, 1H), 7.10 (dt, J 7.5, 1.0 Hz, 1H), 3.29 (s, 3H).

Synthesis 1-B

4-Chloro-2-(2-methoxy-phenyl)-quinazoline

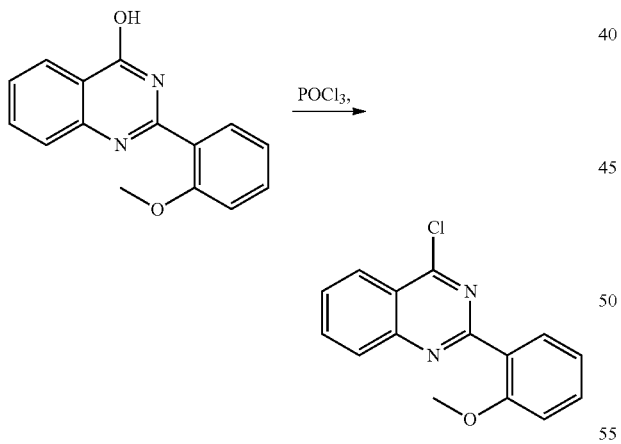

A solution of 2-(2-methoxy-phenyl)-quinazolin-4-ol (2.94 g, 11.65 mmol) in phosphorus oxychloride (60 mL) was heated to reflux for 4.5 hours. The orange reaction mixture was concentrated and the resulting gum was treated with ice-cold saturated sodium bicarbonate (200 mL) and extracted with ethyl acetate (2×200 mL). The organic layers were combined, dried (MgSO$_4$) and concentrated to give the title compound as a yellow solid (2.92 g, 93%).

GC-MS (GCMS1) m/z 270 [M$^+$], R$_t$ 5.02 minutes. $^1$H NMR (d$^6$-DMSO) δ 8.19 (dd, J 8.0, 1.0 Hz, 1H), 7.90-7.88 (m, 1H), 7.82 (d, J 8.5 Hz, 1H), 7.74 (dd, J 7.5, 1.5 Hz, 1H), 7.61 (t, J 8.0 Hz, 1H), 7.25 (d, J 8.5 Hz, 1H), 7.14 (dt, J 7.5, 1.0 Hz, 1H). 3.88 (s, 3H).

Synthesis 1-C

1-Methyl-piperidin-3-yl-amine dihydrochloride

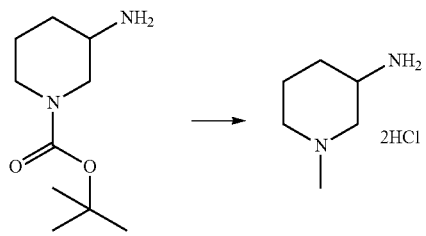

Lithium aluminium hydride (4.99 mL, 1 M solution in THF, 4.993 mmol) was added to a solution of 3-amino-1-Boc-piperidine (0.200 g, 0.999 mmol) in THF at 0° C. under nitrogen. After 15 minutes the solution was heated at reflux for 14 hours. The mixture was cooled, quenched by the sequential addition of water (0.2 mL), 15% aqueous sodium hydroxide (0.2 mL) and water (0.6 mL). The resulting white precipitate was filtered and 4M HCl in dioxane (0.5 mL) was added to the filtrate. Concentration of the filtrate provided the crude title compound that was used without further purification.

Synthesis 1-D

2-[4-(1-Methyl-piperidin-3-yl-amino)-quinazolin-2-yl]-phenol (A-001)

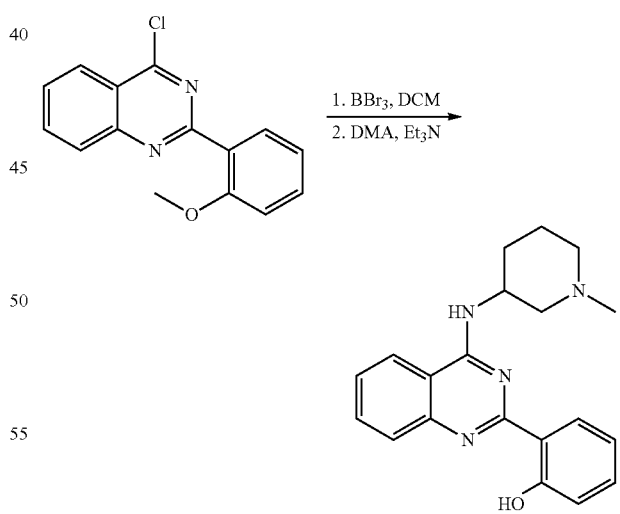

Boron tribromide (7.4 mL, 1 M solution in dichloromethane, 7.4 mmol) was added to a solution of 4-chloro-2-(2-methoxy-phenyl)-quinazoline (0.200 g, 0.739 mmol) in dichloromethane (5 mL) at 0° C. After 24 hours the solution was poured into ice-water (200 mL) and extracted with dichloromethane (2×100 mL). The organic layers were combined, washed with brine (100 mL), dried (MgSO$_4$) and concentrated to give a yellow solid that was used immediately without further purification. Half of the material (0.370 mmol) was dissolved in N,N-dimethylacetamide and 1-methylpiperidine-3-amine dihydrochloride (0.083 g, 0.444 mmol) was added. Triethylamine (258 µL, 1.850 mmol) was added and the reaction was stirred for 1 hour. The mixture was concentrated and purified by ion exchange chromatography on SCX-2 Isolute acidic resin (2 g), eluting with methanol and then 1 M ammonia in methanol. The basic fractions were combined and purified by silica column chromatography, eluting with 10% methanol in dichloromethane, to give the title compound as a yellow solid (0.103 g, 83%).

LC-MS (LCT2) m/z 335 [M+H$^+$], R$_t$ 3.59 minutes. $^1$H NMR (CDCl$_3$) δ 8.53 (d, J 8.0, 2.0 Hz, 1H), 7.83-7.80 (m, 2H), 7.74 (ddd, J 8.0, 7.0, 1.5 Hz, 1H), 7.46 (ddd, J 8.5, 7.0, 1.5 Hz, 1H), 7.37 (ddd, J 8.5, 7.5, 2.0 Hz, 1H), 7.03 (dd, J 8.0, 1.0 Hz, 1H), 6.94 (ddd, J 8.0, 7.0, 1.0 Hz, 1H), 6.66 (br s, 1H), 4.75-4.70 (m, 1H), 2.74-2.55 (m, 3H), 2.24 (br s, 1H), 2.03 (br s, 1H), 1.81-1.64 (4H, m).

Synthesis 2-A (R)-3-[2-(2-Hydroxy-phenyl)-quinazolin-4-yl-amino]-piperidine-1-carboxylic acid tert-butyl ester

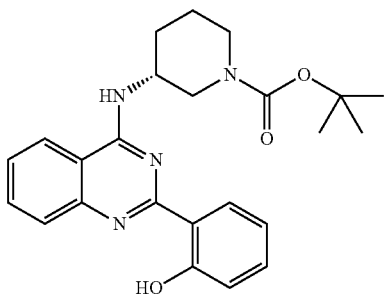

The title compound was prepared from 2-methoxybenzoyl chloride, anthranilonitrile, and (R)-3-amino-piperidine-1-carboxylic acid tert-butyl ester using methods analogous to those described in Synthesis 1, steps 1A, 1B, and 1D.

Synthesis 2-B

2-[4-((R)-Piperidin-3-ylamino)-quinazolin-2-yl]-phenol (A-002)

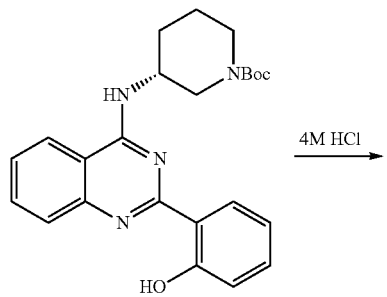

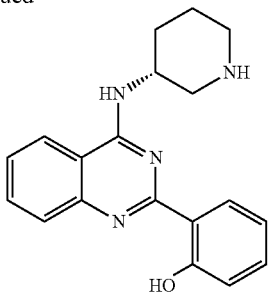

Crude (R)-3-[2-(2-hydroxy-phenyl)-quinazolin-4-yl-amino]-piperidine-1-carboxylic acid tert-butyl ester (~1.0 mmol) was dissolved in methanol (4 mL) and 4M HCl in dioxane (10 mL) was added. After stirring for 24 hours the solution was concentrated and purified by ion exchange chromatography on SCX-2 Isolute acidic resin (5 g), eluting with methanol and then 1 M ammonia in methanol. Further purification by silica column chromatography, eluting with 20% methanol in dichloromethane, gave the title compound as a yellow solid (0.127 g, 40%).

LC-MS (LCT2) m/z 321 [M+H$^+$], R$_t$ 2.58 minutes. $^1$H NMR (CDCl$_3$) δ 8.51 (d, J 8.0 Hz, 1H), 7.89 (d, J 8.0 Hz, 1H), 7.78 (d, J 8.0 Hz, 1H), 7.73-7.70 (m, 1H), 7.43 (dt, J 7.0, 1.0 Hz, 1H), 7.36 (t, J 8.0 Hz, 1H), 7.03 (d, J 8.0 Hz, 1H), 6.93 (t, J 7.5 Hz, 1H), 6.78 (br s, 1H), 4.66 (br s, 1H), 3.26-3.24 (m, 1H), 3.03-2.98 (m, 2H), 2.90-2.86 (m, 1H), 2.07-2.02 (m, 1H), 1.93-1.81 (m, 2H), 1.68-1.62 (m, 1H).

Synthesis 3

2-[4-(1-Methylpiperidin-4-ylamino)-quinazolin-2-yl]-phenol (A-003)

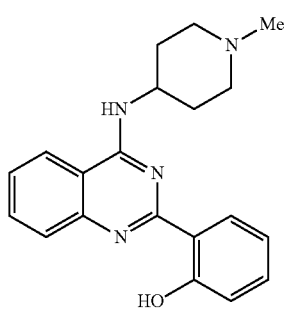

The title compound was prepared using a method analogous to that described in Synthesis 1, replacing 1-methylpiperidine-3-amine dihydrochloride with 1-methylpiperidine-4-amine dihydrochloride in Synthesis 1D.

LC-MS (LCT1) m/z 334 [M+H$^+$], R$_t$ 3.18 minutes. $^1$H NMR (CDCl$_3$) δ 8.49 (dd, J 8.0, 2.0 Hz, 1H), 7.78 (d, J 8.0 Hz, 1H), 7.73-7.69 (m, 2H), 7.43 (ddd, J 8.0, 7.0, 1.0 Hz, 1H), 7.37 (ddd, J 8.0, 7.0, 2.0 Hz, 1H), 7.04 (dd, J 8.5, 1.0 Hz, 1H), 6.95 (ddd, J 8.0, 7.5, 1.0 Hz, 1H), 5.76 (d, J 7.0 Hz, 1H), 4.42-4.34 (m, 1H), 2.94-2.90 (m, 2H), 2.38 (s, 3H), 2.34-2.23 (m, 4H), 1.78-1.70 (m, 2H).

Synthesis 4

2-[4-((S)-Pyrrolidin-3-ylamino)-quinazolin-2-yl]-phenol (A-004)

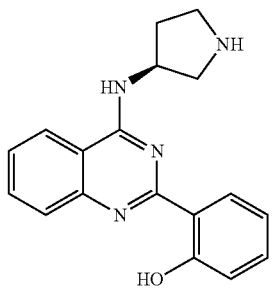

The title compound was prepared using a method analogous to that described in Synthesis 2, replacing (R)-3-aminopiperidine-1-carboxylic acid tert-butyl ester with (S)-3-aminopyrrolidine-1-carboxylic acid tert-butyl ester in Synthesis 2A.

LC-MS (LCT2) m/z 307 [M+H$^+$], R$_t$ 2.49 minutes. $^1$H NMR (CDCl$_3$) δ 8.51 (dd, J 8.0, 2.0 Hz, 1H), 7.94 (d, J 8.0 Hz, 1H), 7.76 (br d, J 8.0 Hz, 1H), 7.69 (ddd, J 8.0, 7.0, 1.0 Hz, 1H), 7.39 (ddd, J 8.0, 7.0, 1.0 Hz, 1H), 7.36 (ddd, J 8.5, 7.0, 2.0 Hz, 1H), 7.03 (dd, J 8.0, 1.0 Hz, 1H), 6.93 (ddd, J 8.0, 7.0, 1.0, 1 H), 6.82 (br d, J 6.0 Hz, 1H), 5.07-5.01 (m, 1H), 3.41-3.10 (m, 4H), 2.47-2.40 (m, 1H), 2.09-2.03 (m, 1H).

Synthesis 5

2-[4-((R)-Pyrrolidin-3-ylamino)-quinazolin-2-yl]-phenol (A-005)

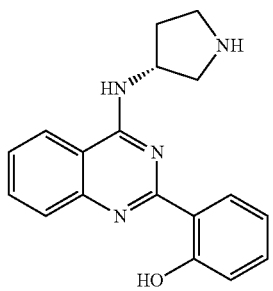

The title compound was prepared using a method analogous to that described in Synthesis 2, replacing (R)-3-aminopiperidine-1-carboxylic acid tert-butyl ester with (S)-3-aminopyrrolidine-1-carboxylic acid tert-butyl ester in Synthesis 2A.

LC-MS (LCT2) m/z 307 [M+H$^+$], R$_t$ 2.49 minutes. $^1$H NMR (CDCl$_3$) δ 8.51 (dd, J 8.0, 2.0 Hz, 1H), 7.94 (d, J 8.0 Hz, 1H), 7.76 (br d, J 8.0 Hz, 1H), 7.69 (ddd, J 8.0, 7.0, 1.0 Hz, 1H), 7.39 (ddd, J 8.0, 7.0, 1.0 Hz, 1H), 7.36 (ddd, J 8.5, 7.0, 2.0 Hz, 1H), 7.03 (dd, J 8.0, 1.0 Hz, 1H), 6.93 (ddd, J 8.0, 7.0, 1.0 Hz, 1H), 6.82 (br d, J 6.0 Hz, 1H), 5.07-5.01 (m, 1H), 3.41-3.10 (m, 4H), 2.47-2.40 (m, 1H), 2.09-2.03 (m, 1H).

Synthesis 6

2-[4-((S)-Piperidin-3-ylamino)-quinazolin-2-yl]-phenol (A-006)

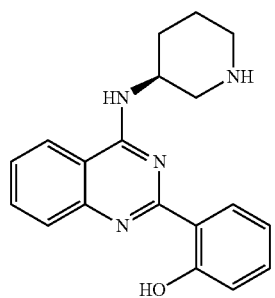

The title compound was prepared using a method analogous to that described in Synthesis 2, replacing (R)-3-aminopiperidine-1-carboxylic acid tert-butyl ester with (S)-3-amino-piperidine-1-carboxylic acid tert-butyl ester in Synthesis 2A.

LC-MS (LCT2) m/z 321 [M+H$^+$], R$_t$ 2.58 minutes. $^1$H NMR (CDCl$_3$) δ 8.51 (d, J 8.0 Hz, 1H), 7.89 (d, J 8.0 Hz, 1H), 7.78 (d, J 8.0 Hz, 1H), 7.73-7.70 (m, 1H), 7.43 (dt, J 7.0, 1.0 Hz, 1H), 7.36 (t, J 8.0 Hz, 1H), 7.03 (d, J 8.0 Hz, 1H), 6.93 (t, J 7.5 Hz, 1H), 6.78 (br s, 1H), 4.66 (br s, 1H), 3.26-3.24 (m, 1H), 3.03-2.98 (m, 2H), 2.90-2.86 (m, 1H), 2.07-2.02 (m, 1H), 1.93-1.81 (m, 2H), 1.68-1.62 (m, 1H).

Synthesis 7

2-[4-((S)-1-Methylpiperidin-3-ylamino)-quinazolin-2-yl]-phenol (A-007)

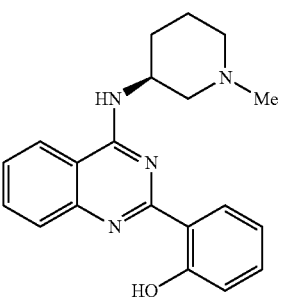

The title compound was prepared using a method analogous to that described in Synthesis 1, replacing 1-methylpiperidine-3-amine dihydrochloride with (S)-1-methylpiperidin-3-ylamine in Synthesis 1D.

LC-MS (LCT2) m/z 335 [M+H$^+$], R$_t$ 2.50 minutes. $^1$H NMR (CDCl$_3$) δ 8.53 (dd, J 8.0, 1.5 Hz, 1H), 7.83 (d, J 8.0 Hz, 1H), 7.80 (d, J 8.5 Hz, 1H), 7.73 (ddd, J 8.0, 7.0, 1.5 Hz, 1H), 7.45 (ddd, J 8.0, 7.0, 1.5 Hz, 1H), 7.37 (ddd, J 8.5, 7.5, 2.0 Hz, 1H), 7.03 (dd, J 8.0, 1.0 Hz, 1H), 6.94 (ddd, J 8.5, 7.5, 1.5 Hz, 1H), 6.68 (br s, 1H), 4.75-4.70 (m, 1H), 2.78-2.55 (m, 3H), 2.35 (s, 3H), 2.28-2.19 (m, 1H), 2.07-1.63 (m, 4H).

Synthesis 8

2-[4-((R)-1-Methylpiperidin-3-ylamino)-quinazolin-2-yl]-phenol (A-008)

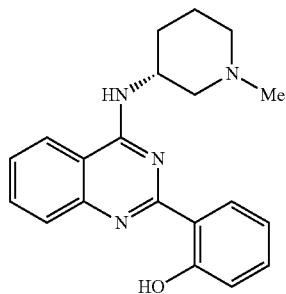

The title compound was prepared using a method analogous to that described in Synthesis 1, replacing 1-methylpiperidine-3-amine dihydrochloride with (R)-1-methylpiperidin-3-ylamine in Synthesis 1D.

LC-MS (LCT2) m/z 335 [M+H$^+$], R$_t$ 2.50 minutes. $^1$H NMR (CDCl$_3$) δ 8.53 (dd, J 8.0, 1.5 Hz, 1H), 7.83 (d, J 8.0 Hz, 1H), 7.80 (d, J 8.5 Hz, 1H), 7.73 (ddd, J 8.0, 7.0, 1.5 Hz, 1H), 7.45 (ddd, J 8.0, 7.0, 1.5 Hz, 1H), 7.37 (ddd, J 8.5, 7.5, 2.0 Hz, 1H), 7.03 (dd, J 8.0, 1.0 Hz, 1H), 6.94 (ddd, J 8.5, 7.5, 1.5 Hz, 1H), 6.68 (br s, 1H), 4.75-4.70 (m, 1H), 2.78-2.55 (m, 3H), 2.35 (s, 3H), 2.28-2.19 (m, 1H), 2.07-1.63 (m, 4H).

Synthesis 9

2-[4-((S)-1-Methylpyrrolidin-3-ylamino)-quinazolin-2-yl]-phenol (A-009)

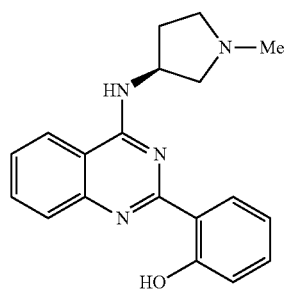

The title compound was prepared using a method analogous to that described in Synthesis 1, replacing 1-methylpiperidine-3-amine dihydrochloride with (S)-1-methylpyrrolidin-3-ylamine in Synthesis 1D.

LC-MS (LCT2) m/z 321 [M+H$^+$], R$_t$ 2.38 minutes. $^1$H NMR (CDCl$_3$) δ 8.54 (dd, J 8.0, 1.5 Hz, 1H), 7.78 (d, J 8.5 Hz, 1H), 7.71 (ddd, J 8.5, 7.0, 1.5 Hz, 1H), 7.42 (ddd, J 8.0, 7.0, 1.0 Hz, 1H), 7.37 (ddd, J 8.0, 7.0, 1.5 Hz, 1H), 7.03 (dd, J 8.0, 1.0 Hz, 1H), 6.94 (ddd, J 8.0, 7.0, 1.0 Hz, 1H), 6.50 (d, J 7.5 Hz, 1H), 5.08-5.02 (m, 1H), 3.05 (dt, J 9.0, 3.5 Hz, 1H), 2.93 (dd, J 10.5, 2.0 Hz, 1H), 2.70 (dd J 10.5, 6.5 Hz, 1H), 2.58 (ddt, J 13.5, 8.5, 3.5 Hz, 1H), 2.44 (s, 3H), 2.33 (q, J 8.5 Hz, 1H), 1.90 (ddt, J 13.5, 8.5, 3.5 Hz, 1H).

Synthesis 10

2-[4-((R)-1-Methylpyrrolidin-3-ylamino)-quinazolin-2-yl]-phenol (A-010)

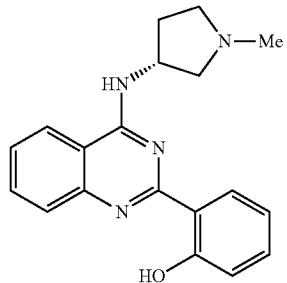

The title compound was prepared using a method analogous to that described in Synthesis 1, replacing 1-methylpiperidine-3-amine dihydrochloride with (R)-1-methylpyrrolidin-3-ylamine in Synthesis 1D.

LC-MS (LCT2) m/z 321 [M+H$^+$], R$_t$ 2.38 minutes. $^1$H NMR (CDCl$_3$) δ 8.54 (dd, J 8.0, 1.5 Hz, 1H), 7.78 (d, J 8.5 Hz, 1H), 7.71 (ddd, J 8.5, 7.0, 1.5 Hz, 1H), 7.42 (ddd, J 8.0, 7.0, 1.0 Hz, 1H), 7.37 (ddd, J 8.0, 7.0, 1.5 Hz, 1H), 7.03 (dd, J 8.0, 1.0 Hz, 1H), 6.94 (ddd, J 8.0, 7.0, 1.0 Hz, 1H), 6.50 (d, J 7.5 Hz, 1H), 5.08-5.02 (m, 1H), 3.05 (dt, J 9.0, 3.5 Hz, 1H), 2.93 (dd, J 10.5, 2.0 Hz, 1H), 2.70 (dd J 10.5, 6.5 Hz, 1H), 2.58 (ddt, J 13.5, 8.5, 3.5 Hz, 1H), 2.44 (s, 3H), 2.33 (q, J 8.5 Hz, 1H), 1.90 (ddt, J 13.5, 8.5, 3.5 Hz, 1H).

Synthesis 11

2-[4-((S)-1-Benzylpyrrolidin-3-ylamino)-quinazolin-2-yl]-phenol (A-011)

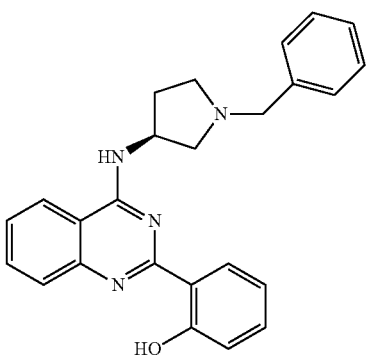

The title compound was prepared using a method analogous to that described in Synthesis 1, using (S)-1-benzylpyrrolidin-3-ylamine in place of 1-methylpiperidin-3-ylamine dihydrochloride in Synthesis 10.

LC-MS (LCT2) m/z 397 [M+H$^+$], R$_t$ 3.20 minutes. $^1$H NMR (CDCl$_3$) δ 8.54 (dd, J 8.0, 1.5 Hz, 1H), 7.79 (dd, J 8.5, 1.0 Hz, 1H), 7.74-7.71 (m, 2H), 7.44 (ddd, J 8.0, 7.0, 1.0 Hz, 1H), 7.38-7.34 (m, 5H), 7.30-7.28 (m, 1H), 7.03 (dd, J 8.0, 1.0 Hz, 1H), 6.94 (ddd, J 8.0, 7.0, 1.0 Hz, 1H), 6.33 (br d, J 7.5 Hz, 1H), 5.09-5.04 (m, 1H), 3.72 (s, 3H), 3.02 (dt, J 8.5, 3.5 Hz, 1H), 2.90 (dd, J 10.0, 3.0 Hz, 1H), 2.85 (dd, J 10.0, 6.5 Hz, 1H), 2.57 (ddt, J 12.5, 8.5, 3.5 Hz, 1H), 2.44 (q, J 8.5 Hz, 1H), 1.90 (ddt, J 13.0, 8.0, 3.5 Hz, 1H).

Synthesis 12

(2S,4S)-4-[2-(2-Hydroxyphenyl)-quinazolin-4-ylamino]-pyrrolidine-2-carboxylic acid methyl ester (A-012)

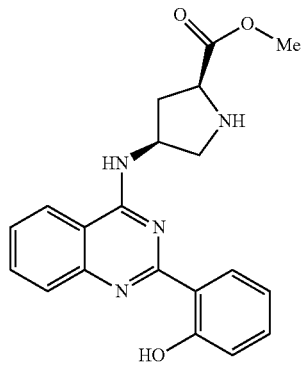

The title compound was prepared using a method analogous to that described in Synthesis 2, replacing (R)-3-aminopiperidine-1-carboxylic acid tert-butyl ester with (2S,4S)-4-aminopyrrolidine-1,2-dicarboxylic acid 1-tert-butyl ester 2-methyl ester in Synthesis 2A.

LC-MS (LCT2) m/z 365 [M+H$^+$], R$_t$ 2.71 minutes. $^1$H NMR (CDCl$_3$) δ 8.54 (dd, J 8.0, 1.5 Hz, 1H), 7.82-7.73 (m, 2H), 7.48 (ddd, J 8.0, 7.0, 1.0 Hz, 1H), 7.37 (ddd, J 8.5, 7.0, 1.5 Hz, 1H), 7.04 (dd, J 8.0, 1.0 Hz, 1H), 6.96-6.91 (m, 2H), 5.19-5.14 (m, 1H), 4.07 (dd, J 9.5, 3.0 Hz, 1H), 3.78 (s, 3H), 3.42 (dd, J, 11.0, 5.0 Hz, 1H), 3.33 (br d, J 11.0 Hz, 1H), 2.59 (ddd, J 14.0, 9.5, 6.5 Hz, 1H), 2.22 (br d, J 14.0 Hz, 1H).

Synthesis 13

2-[4-(4-Aminocyclohexylamino)-quinazolin-2-yl]-phenol (B-001)

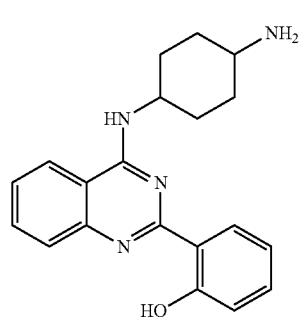

The title compound was prepared using a method analogous to that described in Synthesis 2, replacing (R)-3-aminopiperidine-1-carboxylic acid tert-butyl ester with (4-aminocyclohexyl)-carbamic acid tert-butyl ester in Synthesis 2A.

LC-MS (LCT2) m/z 335 [M+H$^+$], R$_t$ 2.33 minutes. $^1$H NMR (MeOD) δ 8.44 (dd, J 8.0, 1.5 Hz, 1H), 8.12-8.10 (m, 1H), 7.73 (ddd, J 8.0, 6.5, 1.0 Hz, 1H), 7.68-7.66 (m, 1H), 7.43 (ddd, J 8.0, 7.0, 1.0 Hz, 1H), 7.32 (ddd, J 8.0, 7.0, 1.5 Hz, 1H), 6.92-6.88 (m, 2H), 4.29 (tt, J 11.5, 4.0 Hz, 1H), 2.79 (tt, J 11.5, 4.0 Hz, 1H), 2.25-2.21 (m, 2H), 2.06-2.02 (m, 2H), 1.61-1.53 (m, 2H), 1.49-1.41 (m, 2H).

Synthesis 14

2-[4-cis-2-Amino-cyclohexylamino)-quinazolin-2-yl]-phenol (B-002)

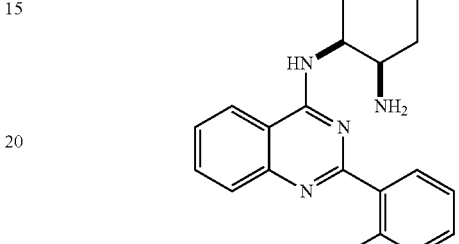

The title compound was prepared using a method analogous to that described in Synthesis 2, replacing (R)-3-aminopiperidine-1-carboxylic acid tert-butyl ester with cis-(2-aminocyclohexyl)-carbamic acid tert-butyl ester in Synthesis 2A.

LC-MS (LCT2) m/z 335 [M+H$^+$], R$_t$ 3.15 minutes. $^1$H NMR (MeOD) δ 8.40 (dd, J 8.0, 1.5 Hz, 1H), 8.17 (br d, J 8.0 Hz, 1H), 7.72 (ddd, J 8.0, 7.0, 1.5 Hz, 1H), 7.66 (br d, J 8.5 Hz, 1H), 7.44 (ddd, J 8.0, 7.0, 1.0 Hz, 1H), 7.31 (ddd, J 8.5, 7.0, 2.0 Hz, 1H), 6.91-6.87 (m, 2H), 4.55 (dt, J 10.0, 4.0 Hz, 1H), 3.58-3.55 (m, 1H), 1.96-1.80 (m, 5H), 1.72-1.63 (m, 1H), 1.60-1.51 (m, 1H).

Synthesis 15

2-[4-(trans-2-Aminocyclohexylamino)-quinazolin-2-yl]-phenol (B-003)

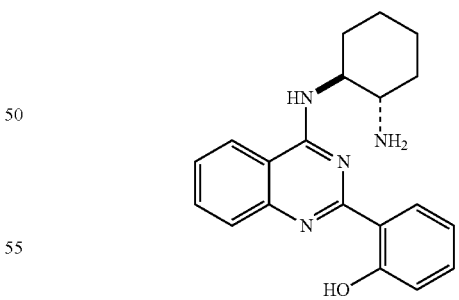

The title compound was prepared using a method analogous to that described in Synthesis 2, replacing (R)-3-aminopiperidine-1-carboxylic acid tert-butyl ester with trans-(2-aminocyclohexyl)-carbamic acid tert-butyl ester in Synthesis 2A.

LC-MS (LCT2) m/z 335 [M+H$^+$], R$_t$ 2.96 minutes. $^1$H NMR (MeOD) δ 8.50 (dd, J 8.0, 2.0 Hz, 1H), 8.22 (br d, J 8.0 Hz, 1H), 7.78 (ddd, J 8.0, 7.0, 1.5 Hz, 1H), 7.73 (br d, J 8.0 Hz, 1H), 7.50 (ddd, J 8.0, 7.0, 1.5 Hz, 1H), 7.34 (ddd, J 8.0, 7.0, 2.0 Hz, 1H), 6.94-6.91 (m, 2H), 4.45 (dt, J 10.5, 4.5 Hz, 1H), 3.14-3.09 (m, 1H), 2.25-2.13 (m, 2H), 1.91-1.87 (m, 2H), 1.57-1.44 (m, 4H).

Synthesis 16

2-[4-(3-Aminocyclohexylamino)-quinazolin-2-yl]-phenol (B-004)

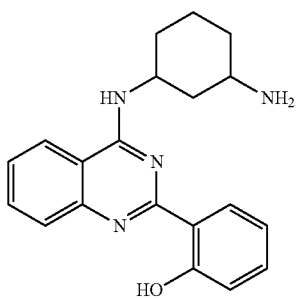

The title compound was prepared using a method analogous to that described in Synthesis 2, replacing (R)-3-aminopiperidine-1-carboxylic acid tert-butyl ester with (3-aminocyclohexyl)-carbamic acid tert-butyl ester in Synthesis 2A.

LC-MS (LCT2) m/z 335 [M+H$^+$], R$_t$ 2.52, 2.63 minutes. $^1$H NMR (MeOD) δ 8.51-8.43 (m, 1H), 8.15-8.10 (m, 1H), 7.73-7.66 (m, 2H), 7.45-7.30 (m, 2H), 6.92-6.88 (m. 2H), 4.73-4.68 & 4.40-4.33 (m, 1H), 3.28-3.24 & 2.96-2.90 (m, 1H), 2.38-2.14 (m, 8H).

Synthesis 17-A

(S)-tert-Butyl 3-(5-bromo-2-chloropyrimidin-4-ylamino)pyrrolidine-1-carboxylate

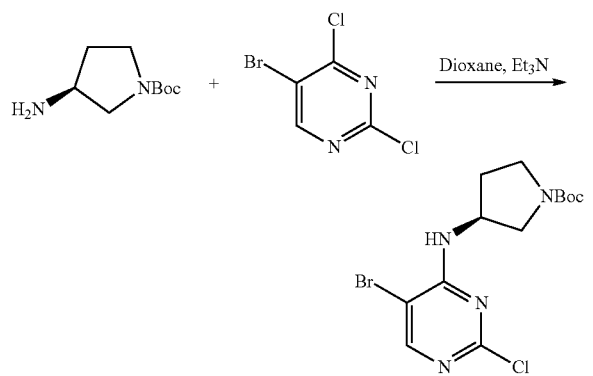

(S)-(−)-1-Boc-3-aminopyrrolidine (0.817 g, 4.39 mmol) and triethylamine (1.22 mL, 8.78 mmol) were added to a solution of 5-bromo-2,4-dichloropyrimidine (1.00 g, 4.39 mmol) in dioxane (22 mL) at 10° C. After 20 hours at room temperature, the solution was concentrated, dissolved in CH$_2$Cl$_2$ (50 mL) and washed with 2 M aqueous K$_2$CO$_3$ (50 mL). The aqueous layer was further extracted with CH$_2$Cl$_2$ (50 mL). The combined organic layers were dried (Na$_2$SO$_4$) and concentrated. The crude product was purified by silica gel chromatography (50% ethyl acetate/hexanes) to give the title compound as an oil (1.106 g, 67%).

LC-MS (LCT2) m/z 321 [M+H-$^t$Bu$^+$], R$_t$ 5.03 minutes. $^1$H NMR (CDCl$_3$) δ 8.17 (s, 1H), 5.45-5.55 (m, 1H), 4.70 (br s, 1H), 3.80-3.76 (m, 1H), 3.58-3.19 (m, 3H), 2.34-2.27 (m, 1H), 1.95 (br s, 1H), 1.49 (s, 9H).

Synthesis 17-B

(S)-tert-Butyl 3-(2-chloro-5-phenylpyrimidin-4-ylamino)pyrrolidine-1-carboxylate

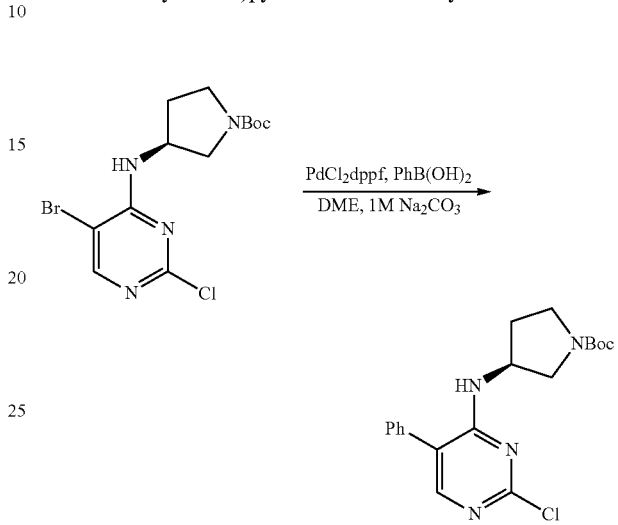

A mixture of (S)-tert-butyl 3-(5-bromo-2-chloropyrimidin-4-ylamino)pyrrolidine-1-carboxylate (0.200 g, 0.539 mmol), phenylboronic acid (0.077 g, 0.636 mmol), PdCl$_2$.dPPf (0.019 g, 0.026 mmol) and 1 M aqueous Na$_2$CO$_3$ (1.06 mL, 1.06 mmol) in DME (5.3 mL) was refluxed for 16 hours. After cooling, water (50 mL) was added and the aqueous phase was extracted with diethyl ether (3×50 mL). The combined organic extracts were dried (MgSO$_4$) and concentrated. The crude product was purified by silica gel chromatography (40% ethyl acetate/hexanes) to give the title compound as an oil (0.163 g, 82%).

LC-MS (LCT2) m/z 375 [M+H$^+$], R$_t$ 5.24 minutes. $^1$H NMR (CDCl$_3$) δ 7.92 (s, 1H), 7.53-7.44 (m, 3H), 7.34-7.32 (m, 2H), 5.15 (d, J 7.0 Hz, 1H), 4.75-4.60 (m, 1H), 3.75 (dd, J 11.5, 6.5 Hz, 1H), 3.48-3.34 (m, 2H), 3.21-3.09 (m, 1H), 2.30-2.21 (m, 1H), 1.87-1.76 (1H, m), 1.46 (s, 9H).

Synthesis 17-C

(S)-tert-butyl 3-(2-(2-hydroxyphenyl)-5-phenylpyrimidin-4-ylamino)pyrrolidine-1-carboxylate

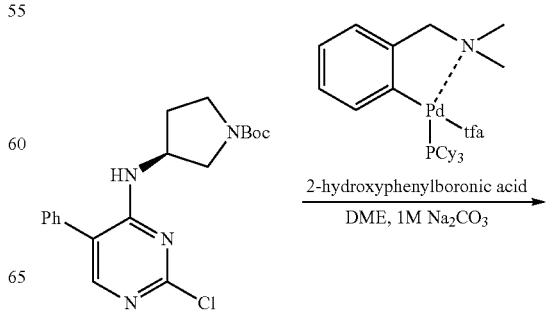

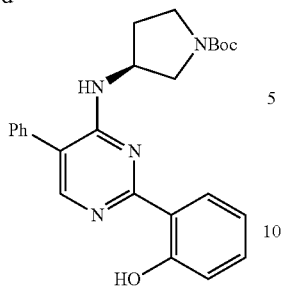

A mixture of (S)-tert-butyl 3-(2-chloro-5-phenylpyrimidin-4-ylamino)pyrrolidine-1-carboxylate (0.153 g, 0.408 mmol), 2-hydroxyphenylboronic acid (0.169 g, 1.24 mmol), palladium catalyst (0.013 g, 0.020 mmol) and 1 M aqueous $Na_2CO_3$ (0.82 mL, 0.82 mmol) in DME (4 mL) was refluxed for 24 hours. After cooling, water (50 mL) was added and the aqueous phase was extracted with diethyl ether (3×50 mL). The combined organic extracts were dried ($MgSO_4$) and concentrated. The crude product was purified by silica gel chromatography (40% ethyl acetate/hexanes) to give the title compound as an oil (0.156 g, 89%).

LC-MS (LCT2) m/z 433 [M+H$^+$], $R_t$ 5.76 minutes. $^1$H NMR (CDCl$_3$) δ 8.43 (dd, J 8.0, 1.5 Hz, 1H), 8.08 (s, 1H), 7.55-7.29 (m, 6H), 7.07-6.93 (m, 3H), 5.20 (d, J 6.0 Hz, 1H), 4.85-4.79 (m, 1H), 3.88-3.81 (m, 1H), 3.54-3.18 (m, 3H), 2.38-2.28 (m, 1H), 1.99-1.87 (m, 1H), 1.47 (s, 9H).

Synthesis 17-D (S)-2-(5-Phenyl-4-pyrrolidin-3-ylamino)pyrimidin-2-yl)phenol (D-001)

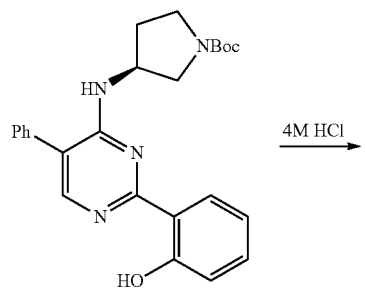

(S)-tert-Butyl 3-(2-(2-hydroxyphenyl)-5-phenylpyrimidin-4-ylamino)pyrrolidine-1-carboxylate (0.147 g, 0.341 mmol) was dissolved in methanol (4 mL) and 4 M HCl in dioxane (10 mL). After stirring for 4 hours, the solution was concentrated and purified by ion exchange chromatography on SCX-2 (solute acidic resin (2 g), eluting with methanol and then 1 M ammonia in methanol. Further purification by preparative thin layer chromatography, eluting with 20% methanol in dichloromethane, gave the title compound as a solid (0.043 g, 38%).

LC-MS (LCT2) m/z 333 [M+H$^+$], $R_t$ 2.88 minutes. $^1$H NMR (CDCl$_3$) δ 8.45 (dd, J 8.0, 2.0 Hz, 1H), 8.06 (s, 1H), 7.55-7.36 (m, 6H), 7.02-7.00 (m, 1H), 6.96-6.93 (m, 1H), 5.36 (d, J 6.5 Hz, 1H), 4.73-4.67 (m, 1H), 3.38 (dd, J 11.5, 6.5 Hz, 1H), 3.10-2.98 (m, 2H), 2.87 (dd, J 11.5, 4.0 Hz, 1H), 2.36-2.29 (m, 1H), 1.70-1.64 (m, 1H).

Synthesis 18

(R)-4-Chloro-2-(4-(piperidin-3-ylamino)quinazolin-2-yl)phenol (A-013)

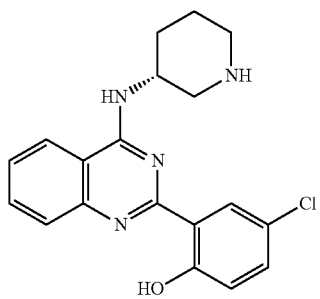

The title compound was prepared using a method analogous to that described in Synthesis 1, replacing 2-methoxybenzoyl chloride with 2-methoxy-4-chlorobenzoyl chloride in Synthesis 1A.

LC-MS-(LCT2) m/z 355 [M+H$^+$], $R_t$ 3.51 minutes. $^1$H NMR (CDCl$_3$) δ 8.44 (d, J 3.0 Hz, 1H), 7.86-7.73 (m, 3H), 7.49-7.46 (m, 1H), 7.29 (d, J 9.0, 3.0 Hz, 1H), 6.96 (d, J 9.0 Hz, 1H), 6.87 (br s, 1H), 4.63 (br s), 3.20-3.17 (m, 1H), 3.04-2.98 (m, 2H), 2.88-2.83 (m, 1H), 2.07-2.02 (m, 1H), 1.92-1.76 (m, 2H), 1.66-1.60 (m, 1H).

Synthesis 19

(R)-4-Fluoro-2-(4-(piperidin-3-ylamino)quinazolin-2-yl)phenol (A-014)

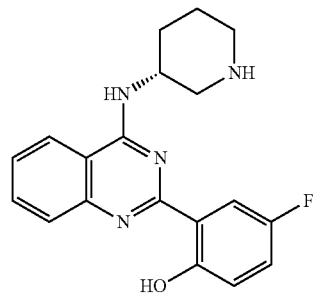

The title compound was prepared using a method analogous to that described in Synthesis 1, replacing 2-methoxybenzoyl chloride with 2-methoxy-4-fluorobenzoyl chloride in Synthesis 1A.

LC-MS (LCT2) m/z 339 [M+H$^+$], $R_t$ 3.05 minutes. $^1$H NMR (CDCl$_3$) δ 8.13 (dd, J 10.0, 3.0 Hz, 1H), 8.02 (d, J 8.0 Hz, 1H), 7.78-7.71 (m, 2H), 7.47-7.43 (m, 1H), 7.06-7.01 (m,

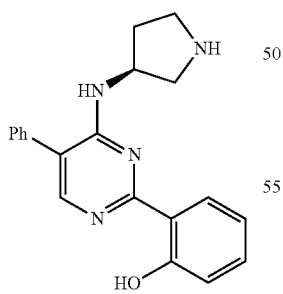

2H), 6.94 (dd, J 9.0, 4.5 Hz, 1H), 4.72 (br s, 1H), 3.26 (dd, J 12.0, 3.0 Hz, 1H), 3.19-3.11 (m, 2H), 2.95-2.89 (m, 1H), 2.13-2.08 (m, 1H), 1.95-1.87 (m, 2H), 1.73-1.69 (m, 1H).

Synthesis 20

(S)-4-Fluoro-2-(4-(pyrrolidin-3-ylamino)quinazolin-2-yl)phenol (A-015)

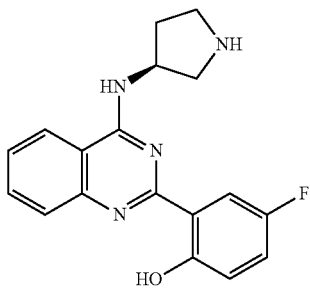

The title compound was prepared using a method analogous to that described in Synthesis 1, replacing 2-methoxybenzoyl chloride with 2-methoxy-4-fluorobenzoyl chloride in Synthesis 1A.

LC-MS (LCT2) m/z 325 [M+H$^+$], R$_t$ 2.98 minutes. $^1$H NMR (CDCl$_3$) δ 8.21 (dd, J 10.0, 3.0 Hz, 1H), 7.82-7.73 (m, 3H), 7.46 (ddd, J 8.0, 7.0, 1.5 Hz, 1H), 7.09 (ddd, J 9.0, 8.0, 3.5 Hz, 1H), 6.97 (dd, J 9.0, 5.0 Hz, 1H), 6.43 (d, J 6.5 Hz, 1H), 5.02-4.97 (m, 1H), 3.41 (dd, J 11.0, 6.5 Hz, 1H), 3.26-3.21 (m, 1H), 3.14-3.07 (m, 2H), 2.49-2.42 (m, 1H), 1.97-1.91 (m, 1H).

Synthesis 21-A (S)-tert-Butyl 3-(2-chloropyrimidin-4-ylamino)pyrrolidine-1-carboxylate

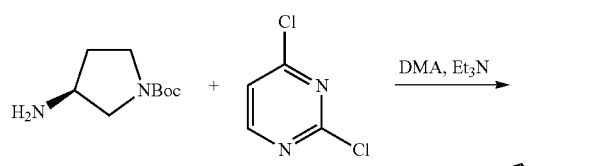

(S)-(−)-1-Boc-3-aminopyrrolidine (0.375 g, 2.014 mmol) and triethylamine (0.561 mL, 4.028 mmol) were added to a solution of 2,4-dichloropyrimidine (0.300 g, 2.014 mmol) in DMA (12 mL) at 0° C. After 24 hours at room temperature, water (150 mL) was added and the aqueous phase was extracted with ethyl acetate (3×40 mL). The combined organic extracts were dried (MgSO$_4$) and concentrated. The crude product was purified by silica gel chromatography (5% methanol in dichloromethane) to give the title compound as an oil (0.540 g, 90%).

LC-MS (LCT2) m/z 243 [M+H-$^t$Bu$^+$], R$_t$ 4.54 minutes. $^1$H NMR (CDCl$_3$) δ 7.99 (br s, 1H), 6.31 (d, J 6.0 Hz, 1H), 5.99 (br s, 1H), 4.55 (br s, 1H), 3.68 (dd, J 11.5, 6.0 Hz, 1H), 3.49-3.42 (m, 2H), 3.33-3.21 (m, 1H), 2.26-2.18 (m, 1H), 1.99-1.88 (m, 1H), 1.45 (s, 9H).

Synthesis 21-B (S)-tert-Butyl 3-(2-(2-hydroxyphenyl)pyrimidin-4-ylamino)pyrrolidine-1-carboxylate

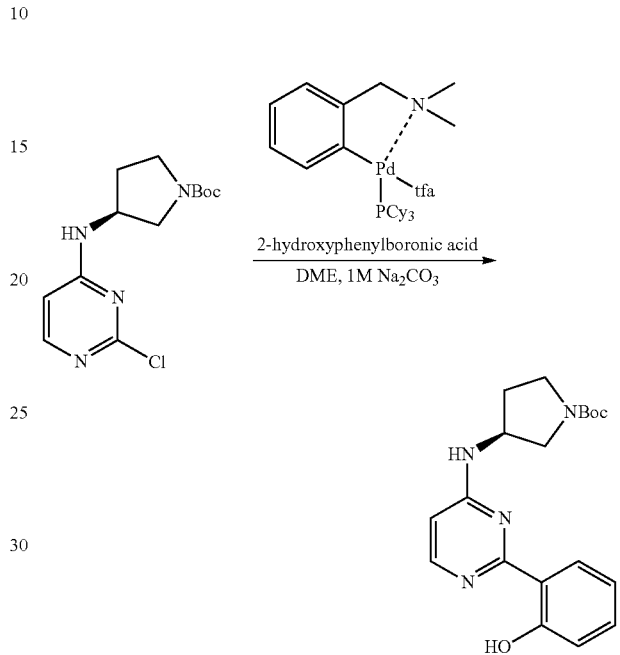

A mixture of (S)-tert-butyl 3-(2-chloropyrimidin-4-ylamino)pyrrolidine-1-carboxylate (0.120 g, 0.400 mmol), 2-hydroxyphenyl boronic acid (0.166 g, 1.20 mmol), palladium catalyst (0.013 g, 0.020 mmol), and 1 M aqueous Na$_2$CO$_3$ (0.80 mL, 0.80 mmol) in DME (4 mL) was refluxed for 24 hours. After cooling, water (50 mL) was added and the aqueous phase was extracted with diethyl ether (3×50 mL). The combined organic extracts were dried (MgSO$_4$) and concentrated. The crude product was purified by silica gel chromatography (66% ethyl acetate/hexanes) to give the title compound as an oil (0.070 g, 49%).

LC-MS (LCT2) m/z 357 [M+H$^+$], R$_t$ 4.51 minutes.

Synthesis 21-C (S)-2-(4-Pyrrolidin-3-ylamino)pyrimidin-2-yl)phenol (D-002)

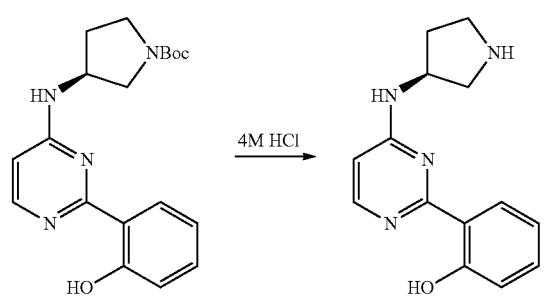

(S)-tert-Butyl 3-(2-(2-hydroxyphenyl)pyrimidin-4-ylamino)pyrrolidine-1-carboxylate (0.070 g, 0.196 mmol) was dissolved in methanol (4 mL) and 4 M HCl in dioxane (10 mL) was added. After stirring for 24 hours, the solution was concentrated and purified by ion exchange chromatography on SCX-2 Isolute acidic resin (2 g), eluting with methanol and then 1 M ammonia in methanol. Further purification by preparative thin layer chromatography, eluting with 20% methanol in dichloromethane, gave the title compound as a solid (0.020 g, 40%).

LC-MS (LCT2) m/z 257 [M+H$^+$], R$_t$ 0.92 minutes. $^1$H NMR (CDCl$_3$) δ 8.38 (d, J 8.0 Hz, 1H), 8.15 (d, J 6.0 Hz, 1H), 7.35 (ddd, J 8.5, 7.0, 2.0 Hz, 1H), 6.99 (dd, J 8.0, 1.0 Hz, 1H), 6.91 (ddd, J 8.0, 7.0, 1.0 Hz, 1H), 6.25 (d, J 6.0 Hz, 1H), 5.50-5.45 (m, 1H), 4.52 (br s, 1H), 3.30 (dd, J 11.0, 6.0 Hz, 1H), 3.19-3.14 (m, 1H), 3.04 (ddd, J 11.0, 8.5, 6.0 Hz, 1H), 2.98 (dd, J 11.0, 3.0 Hz, 1H), 2.34-2.27 (m, 1H), 1.83-1.77 (m, 1H).

Synthesis 22

(S)-2-(6-Bromo-4-(pyrrolidin-3-ylamino)quinazolin-2-yl)phenol (A-016)

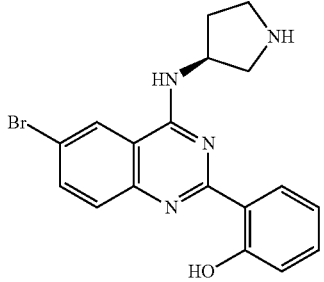

The title compound was prepared using a method analogous to that described in Synthesis 1, replacing anthranilonitrile with 2-amino-5-bromobenzonitrile in Synthesis 1A.

LC-MS (LCT2) m/z 385 [M+H$^+$], R$_t$ 3.40 minutes. $^1$H NMR (MeOD) δ 8.44-8.39 (m, 2H), 7.83 (dd, J 9.0, 2.0 Hz, 1H), 7.60 (d, J 9.0 Hz, 1H), 7.34 (ddd, J 8.5, 7.0, 1.5 Hz, 1H), 6.92-6.86 (m, 2H), 4.89-4.84 (m, 1H), 3.50 (dd, J 12.0, 6.5 Hz, 1H), 3.29-3.25 (m, 1H), 3.19-3.11 (m, 2H), 2.43-2.36 (m, 1H), 2.14-2.07 (m, 1H).

Synthesis 23

(2R,4R)-4-[2-(2-Hydroxyphenyl)-quinazolin-4-ylamino]-pyrrolidine-2-carboxylic acid methyl ester (A-017)

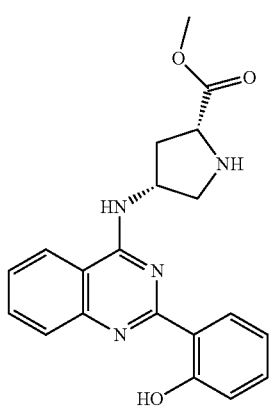

The title compound was prepared using a method analogous to that described in Synthesis 2, replacing (R)-3-aminopiperidine-1-carboxylic acid tert-butyl ester with (2R,4R)-4-aminopyrrolidine-1,2-dicarboxylic acid 1-tert-butyl ester 2-methyl ester in Synthesis 2A.

LC-MS (LCT2) m/z 365 [M+H$^+$], R$_t$ 2.71 minutes. $^1$H NMR (CDCl$_3$) δ 8.54 (dd, J 8.0, 1.5 Hz, 1H), 7.82-7.73 (m, 2H), 7.48 (ddd, J 8.0, 7.0, 1.0 Hz, 1H), 7.37 (ddd, J 8.5, 7.0, 1.5 Hz, 1H), 7.04 (dd, J 8.0, 1.0 Hz, 1H), 6.96-6.91 (m, 2H), 5.19-5.14 (m, 1H), 4.07 (dd, J 9.5, 3.0 Hz, 1H), 3.78 (s, 3H), 3.42 (dd, J 11.0, 5.0 Hz, 1H), 3.33 (br d, J 11.0 Hz, 1H), 2.59 (ddd, J 14.0, 9.5, 6.5 Hz, 1H), 2.22 (br d, J 14.0 Hz, 1H).

Synthesis 24

(2R,4S)-Methyl 4-(2-(2-hydroxyphenyl)quinazolin-4-ylamino)pyrrolidine-2-carboxylate (A-018)

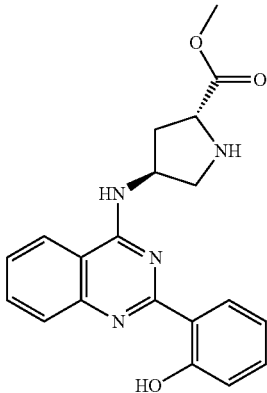

The title compound was prepared using a method analogous to that described in Synthesis 2, replacing (R)-3-aminopiperidine-1-carboxylic acid tert-butyl ester with (2R,4S)-4-aminopyrrolidine-1,2-dicarboxylic acid 1-tert-butyl ester 2-methyl ester in Synthesis 2A.

LC-MS (LCT2) m/z 365 [M+H$^+$], R$_t$ 2.79 minutes. $^1$H NMR (CDCl$_3$) δ 8.52 (dd, J 8.0, 2.0 Hz, 1H), 7.82-7.78 (m, 2H), 7.75 (ddd, J 8.0, 7.0, 1.5 Hz, 1H), 7.45 (ddd, J 8.0, 7.0, 1.5 Hz, 1H), 7.38 (ddd, J 8.5, 7.0, 2.0 Hz, 1H), 7.04 (dd, J 8.0, 1.0 Hz, 1H), 6.94 (ddd, J 8.0, 7.0, 1.0 Hz, 1H), 6.33 (d, J 7.0 Hz, 1H), 5.08-5.02 (m, 1H), 4.04 (dd, J 8.5, 6.5 Hz, 1H), 3.81 (s, 3H), 3.53 (dd, J 11.0, 5.5 Hz, 1H), 3.16 (dd, J 11.0, 2.5 Hz, 1H), 2.54-2.42 (m, 2H).

Synthesis 25

(S)-4-Chloro-2-(4-(pyrrolidin-3-ylamino)quinazolin-2-yl)phenol (A-019)

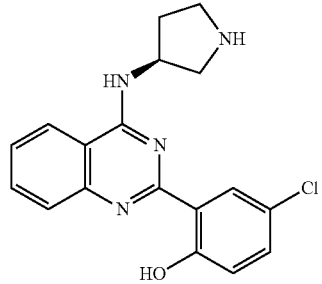

The title compound was prepared using a method analogous to that described in Synthesis 1, replacing 2-methoxybenzoyl chloride with 2-methoxy-4-chlorobenzoyl chloride in Synthesis 1A.

LC-MS (LCT2) m/z 341 [M+H⁺], R$_t$ 3.48 minutes. $^1$H NMR (CDCl$_3$) δ 8.48 (d, J 2.5 Hz, 1H), 7.81-7.74 (m, 3H), 7.47 (ddd, J 8.0, 7.0, 1.5 Hz, 1H), 7.30 (dd, J 9.0, 3.0 Hz, 1H), 6.97 (1H, J 9.0 Hz, 1H), 6.39 (br d, J 6.5 Hz, 1H), 5.04-4.98 (m, 1H), 3.41 (dd, J 11.0, 6.0 Hz, 1H), 3.26-3.21 (m, 1H), 3.13-3.07 (m, 2H), 2.50-2.43 (m, 1H), 1.94-1.90 (m, 1H).

Synthesis 26-A 2-(4-Chloroquinolin-2-yl)phenol

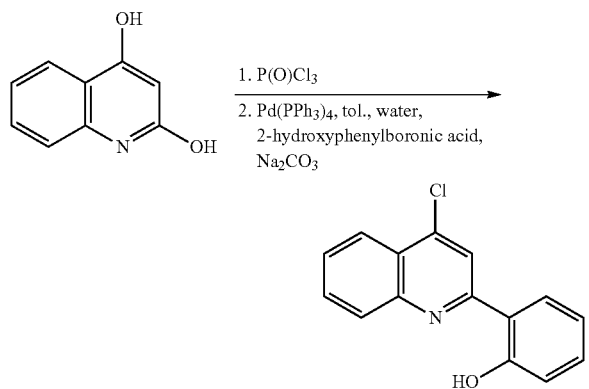

A solution of 2,4-quinolinediol (2.00 g, 12.41 mmol) in phosphorus oxychloride (30 mL) was heated at reflux for 24 hours. The resulting solution was cooled, concentrated, quenched with iced water (100 mL) and extracted with dichloromethane (3×100 mL). The organic layers were combined, washed with brine (100 mL), dried (MgSO$_4$), and concentrated to give 2,4-dichloroquinoline (2.31 g, 94%).

2,4-Dichloroquinoline (0.500 g, 2.525 mmol), 2-hydroxyphenylboronic acid (0.332 g, 2.405 mmol), sodium carbonate (0.510 g, 4.810 mmol) and Pd(PPh$_3$)$_4$ (0.139 g, 120 mmol) were added to a degassed mixture of toluene (5 mL) and water (2 mL), and the mixture was heated for 15 hours. After cooling, water (100 mL) was added and the aqueous layer was extracted with ethyl acetate (2×100 mL). The organic layers were combined, washed with brine (50 mL), dried (MgSO$_4$), and concentrated. The crude product was purified by silica gel chromatography (dichloromethane) to give the title compound (0.322 g, 50%).

LC-MS (LCT2) m/z 256 [M+H⁺], R$_t$ 5.84 minutes.

Synthesis 26-B (S)-tert-Butyl 3-(2-(2-hydroxyphenyl)quinolin-4-ylamino)pyrrolidine-1-carboxylate

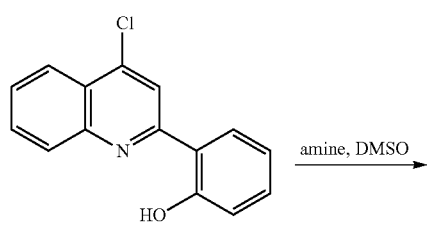

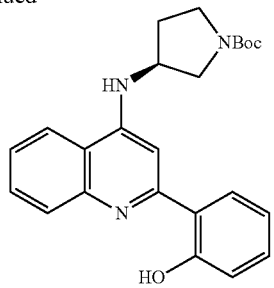

A solution of (S)-3-aminopyrrolidine-1-carboxylic acid tert-butyl ester (0.218 g, 1.173 mmol) and 2-(4-chloroquinolin-2-yl)phenol (0.100 g, 0.391 mmol) in DMSO (2 mL) was heated under microwave conditions at 155° C. for 1.5 hours. The mixture was added to water (50 mL) and extracted with diethyl ether (2×20 mL). The organic layers were combined, dried (MgSO$_4$) and concentrated. The crude product was purified by silica gel chromatography (30-40% ethyl acetate/hexane) to give the title compound (0.067 g, 42%).

LC-MS (LCT2) m/z 406 [M+H⁺], R$_t$ 3.43 minutes.

Synthesis 26-C (S)-2-(4-(Pyrrolidin-3-ylamino)quinolin-2-yl)phenol (C-001)

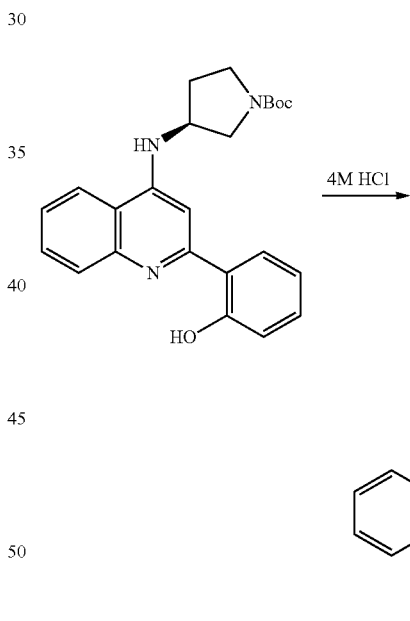

(S)-tert-butyl 3-(2-(2-hydroxyphenyl)quinolin-4-ylamino)pyrrolidine-1-carboxylate (0.050 g, 0.123 mmol) was dissolved in methanol (2 mL) and 4 M HCl in dioxane (5 mL) was added. After stirring for 12 hours, the solution was concentrated and purified by ion exchange chromatography on SCX-2 Isolute acidic resin (2 g), eluting with methanol and then 1 M ammonia in methanol. Further purification by preparative thin layer chromatography, eluting with 20% methanol in dichloromethane, gave the title compound as a solid (0.020 g, 53%).

LC-MS (LCT2) m/z 306 [M+H⁺], R$_t$ 1.04 minutes. $^1$H NMR (MeOD) δ 8.25 (d, J 8.5 Hz, 1H), 7.97 (d, J 8.0 Hz, 1H), 7.84 (d, J 8.5 Hz, 1H), 7.74 (t, J 7.5 Hz, 1H), 7.53 (t, J 8.0 Hz, 1H), 7.35 (t, J 7.5 Hz, 1H), 7.09 (s, 1H), 6.98-6.94 (m, 2H), 4.74-4.70 (m, 1H), 3.76 (dd, J 12.5, 6.5 Hz, 1H), 3.64-3.48 (m, 3H), 2.60-2.53 (m, 1H), 2.38-2.32 (m, 1H).

Synthesis 27

(S)-2-(7-phenyl-4-(pyrrolidinyl-3-yl amino)quinazolin-2-yl)phenol (A-020)

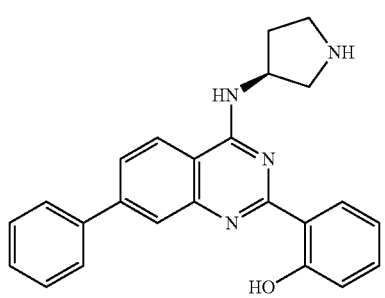

The title compound was prepared from 2-methoxybenzoyl chloride, 2-amino-4-bromobenzonitrile, and (R)-3-amino-piperidine-1-carboxylic acid tert-butyl ester using methods analogous to those described in Synthesis 32.

LC-MS (LCT2) m/z 383 [M+H$^+$], R$_t$ 3.71 minutes. $^1$H NMR (MeOD) δ 8.54 (dd, J 8.0, 1.5 Hz, 1H), 8.27 (d, J 8.5 Hz, 1H), 7.96 (d, J 2.0 Hz, 1H), 7.80-7.78 (m, 3H), 7.55-7.51 (m, 2H), 7.44 (dt, J 7.5, 1.0 Hz, 1H), 7.35 (ddd, J 8.0, 7.0, 1.5 Hz, 1H), 6.95-6.91 (m, 2H), 4.98-4.93 (m, 1H), 3.52 (dd, J 12.0, 7.0 Hz, 1H), 3.28-3.24 (m, 1H), 3.17-3.11 (m, 2H), 2.48-2.40 (m, 1H), 2.15-2.08 (m, 1H).

Synthesis 28

(2S,4R)-Methyl 4-(2-(2-hydroxyphenyl)quinazolin-4-ylamino)pyrrolidine-2-carboxylate (A-021)

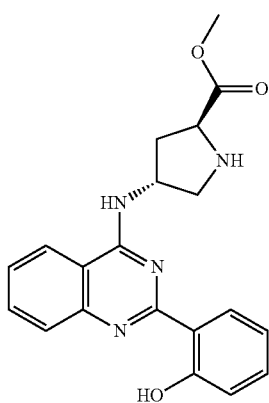

The title compound was prepared using a method analogous to that described in Synthesis 2, replacing (R)-3-aminopiperidine-1-carboxylic acid tert-butyl ester with (2S,4R)-4-aminopyrrolidine-1,2-dicarboxylic acid 1-tert-butyl ester 2-methyl ester in Synthesis 2A.

LC-MS (LCT2) m/z 365 [M+H$^+$], R$_t$ 2.77 minutes. $^1$H NMR (CDCl$_3$) δ 8.52 (dd, J 8.0, 2.0 Hz, 1H), 7.82-7.80 (m, 1H), 7.76 (br s, 1H), 7.74 (ddd, J 8.0, 7.0, 1.5 Hz, 1H), 7.45 (ddd, J 8.0, 7.0, 1.5 Hz, 1H), 7.38 (ddd, J 8.5, 7.0, 2.0 Hz, 1H), 7.04 (dd, J 8.0, 1.0 Hz, 1H), 6.94 (ddd, J 8.0, 7.0, 1.0 Hz, 1H), 6.26 (d, J 7.0 Hz, 1H), 5.08-5.02 (m, 1H), 4.04 (dd, J 8.5, 6.5 Hz, 1H), 3.80 (s, 3H), 3.53 (dd, J 11.0, 5.5 Hz, 1H), 3.13 (dd, J 11.0, 2.5 Hz, 1H), 2.54-2.40 (m, 2H).

Synthesis 29

(S)-4-tert-Butyl-2-(4-(pyrrolidin-3-ylamino)quinazolin-2-yl)phenol (A-022)

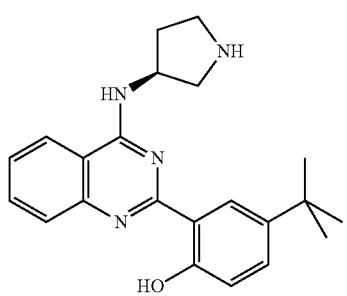

The title compound was prepared using a method analogous to that described in Synthesis 30, replacing 2-methoxy-5-methylphenylboronic acid with 5-tert-butyl-2-methoxyphenylboronic acid.

LC-MS (LCT2) m/z 363 [M+H$^+$], R$_t$ 3.45 minutes. $^1$H NMR (CDCl$_3$) δ 14.40 (br s, 1H), 8.52 (d, J 2.5 Hz, 1H), 8.24 (d, J 8.0 Hz, 1H), 7.77 (d, J 8.0 Hz, 1H), 7.70-7.67 (m, 1H), 7.43 (dd, J 8.5, 2.5 Hz, 1H), 7.40-7.36 (m, 1H), 7.19 (br d, J 6.0 Hz, 1H), 6.97 (d, J 8.5 Hz, 1H), 5.24-5.20 (m, 1H), 3.84 (d, J 12.5 Hz, 1H), 3.68-3.58 (m, 4H), 2.55-2.50 (m, 2H), 1.38 (s, 9H).

Synthesis 30-A (S)-tert-Butyl 3-(2-chloroquinazolin-4-ylamino)pyrrolidine-1-carboxylate

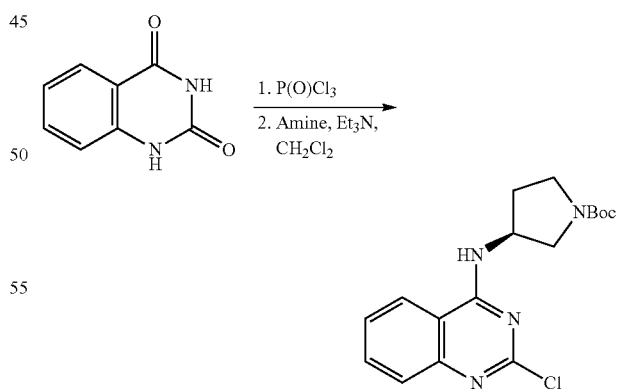

Phosphorous oxychloride (30 mL, 191.00 mmol) was added dropwise over 3 minutes to quinazoline-2,4-dione (2.01 g, 6.17 mmol) at room temperature and the solution was heated at reflux for 48 hours. The reaction mixture was concentrated and the residue was added to iced water (100 mL) and the aqueous phase was extracted with dichloromethane (2×125 mL). The organic layers were combined, dried (MgSO$_4$) and concentrated to give a pale yellow solid (0.944 g, 76%) which was used crude in the next step.

A solution of 2,4-dichloroquinazoline (0.940 g, 4.70 mmol) in dichloromethane (50 mL) was treated with (S)-(−)-1-boc-3-aminopyrrolidine (0.863 mL, 4.70 mmol) followed by triethylamine (2 mL, 14.20 mmol) and the solution was stirred at room temperature for 36 hours. The mixture was diluted with water (20 mL) and extracted with diethyl ether (2×20 mL). The combined organic extracts were dried (MgSO$_4$) and concentrated to give the title compound as a pale brown solid which was used without further purification.

LC-MS (LCT2) m/z 349 [M+H$^+$], R$_t$ 5.07 minutes. $^1$H NMR (CDCl$_3$) δ 7.79 (td, J 8.5, 1.0 Hz, 1H), 7.75 (dd, J 8.5, 1.0 Hz, 1H), 7.70 (d, J 7.5 Hz, 1H), 7.49-7.46 (m, 1H), 5.95-5.85 (m, 1H), 4.95 (br s, 1H), 3.83 (dd, J 11.5, 6.0 Hz, 1H), 3.65-3.33 (m, 1H), 2.40-2.33 (m, 1H), 2.26 (br s, 1H), 1.49 (s, 9H).

Synthesis 30-B (S)-tert-Butyl 3-(2-(2-methoxy-5-methylphenyl)quinazolin-4-ylamino)pyrrolidine-1-carboxylate

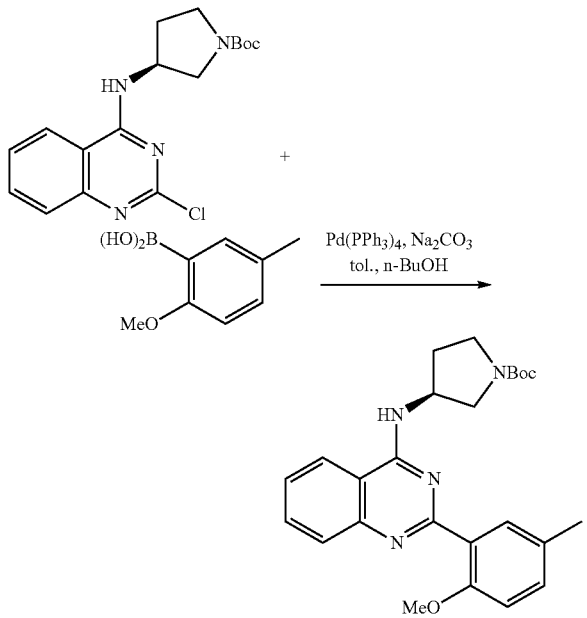

A mixture of toluene (1.8 mL), n-butanol (3 mL) and 2M Na$_2$CO$_3$ (3 mL) was degassed with a stream of nitrogen for 20 minutes. The mixture was transferred onto a degassed mixture of (S)-tert-butyl 3-(2-chloroquinazolin-4-ylamino)pyrrolidine-1-carboxylate (0.300 g, 0.86 mmol), palladium tetrakistriphenyl phosphine (0.0718 g, 0.06 mmol) and 5-methyl-2-methoxyphenylboronic acid (0.143 g, 0.86 mmol) and the solution was heated at reflux. After 17 hours the reaction was cooled, diluted with water (20 mL), and extracted with ethyl acetate (2×20 mL). The combined organic extracts were washed with brine (20 mL), dried (MgSO$_4$), and concentrated. Silica chromatography (6:1-1:1 petroleum ether/ethyl acetate) gave the title compound as a colourless solid (0.329 g, 99%).

LC-MS (LCT2) m/z 435 [M+H$^+$], R$_t$ 3.77 minutes. $^1$H NMR (CDCl$_3$) δ 7.91 (d, J 8.0 Hz, 1H), 7.82 (s, 1H), 7.69 (t, J 8.0 Hz, 1H). 7.54 (s, 1H), 7.39 (t, J 8.0 Hz, 1H), 7.17 (d, J 8.0, 1H), 6.91 (d, J 8.0, 1H), 6.16-6.07 (m, 1H), 4.92 (s, 1H), 3.82 (s, 3H), 3.56 (br s, 1H), 3.48 (br s, 2H), 3.35 (br s, 1H), 2.33 (s, 3H), 2.27 (br s, 1H), 2.08 (br s, 1H), 1.47 (s, 9H).

Synthesis 30-C (S)-4-Methyl-2-(4-(pyrrolidin-3-ylamino)quinazolin-2-yl)phenol (A-023)

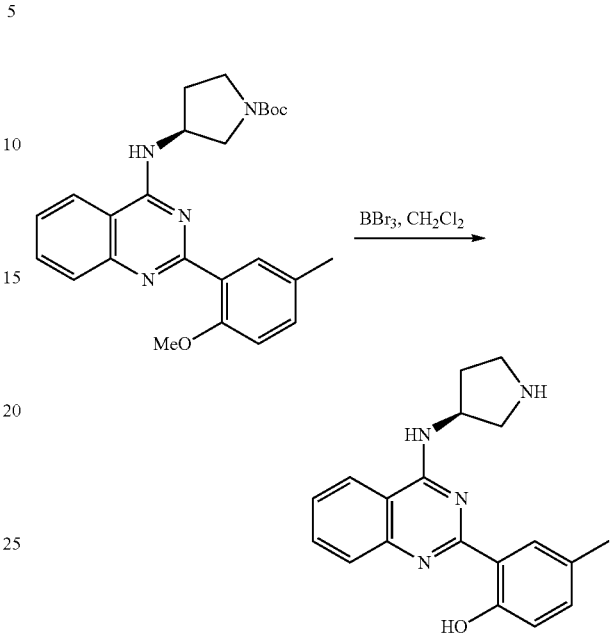

Boron tribromide (0.454 mL of a 1 M solution in dichloromethane, 0.45 mmol) was added to a solution of (S)-tert-butyl 3-(2-(2-methoxy-5-methylphenyl)quinazolin-4-ylamino)pyrrolidine-1-carboxylate (0.079 g, 0.23 mmol) in dichloromethane (2.3 mL). After 16 hours, the reaction was quenched by the addition of methanol (2 mL). Hydrochloric acid (1.5 mL of a 4 M solution in dioxane) was added and the mixture was heated at reflux for 6 hours. The solution was cooled, concentrated, and purified by SCX-2 Isolute column (2 g), eluting first with methanol and finally 1 M ammonia in methanol. Silica column chromatography (5% methanol in DCM) gave the title compound as a yellow solid (0.025 g, 35%).

LC-MS (LCT2) m/z 321 [M+H$^+$], R$_t$ 2.64 minutes. $^1$H NMR (CDCl$_3$) δ 14.52 (br s, 1H), 8.32 (d, J 2.0 Hz, 1H), 7.79 (t, J 9.5, 2H), 7.75-7.72 (m, 1H), 7.47-7.42 (m, 1H), 7.18 (dd, J 8.5, 2.0 Hz, 1H), 6.93 (d, J 8.5 Hz, 1H), 6.26 (br s, 1H), 5.12 (br s, 1H), 3.42 (dd, J 11.0, 6.5 Hz, 1H), 3.27-3.22 (m, 1H), 3.16-3.08 (m, 2H), 2.49-2.42 (m, 1H), 2.37 (s, 3H), 1.98-1.92 (m, 1H).

Synthesis 31

(S)-4-iso-Propyl-2-(4-(pyrrolidin-3-ylamino)quinazolin-2-yl)phenol (A-024)

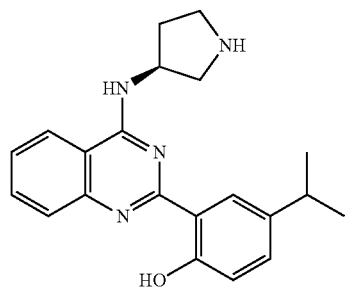

The title compound was prepared using a method analogous to that described in Synthesis 30, replacing 2-methoxy-5-methylphenylboronic acid with 5-iso-propyl-2-methoxyphenylboronic acid.

LC-MS (LCT2) m/z 349 [M+H$^+$], R$_t$ 3.26 minutes. $^1$H NMR (CDCl$_3$) δ 14.45 (br s, 1H), 8.40 (d, J 2.5 Hz, 1H), 7.79 (d, J 4.5 Hz, 1H), 7.78 (d, J 4.5 Hz, 1H), 7.72-7.68 (m, 1H), 7.42-7.38 (m, 1H), 7.23 (dd, J 8.5, 2.5 Hz, 1H), 6.96 (d, J 8.5 Hz, 1H), 6.31 (br d, J 6.0 Hz, 1H), 4.96-4.90 (m, 1H), 3.40 (dd, J 11.0, 6.0 Hz, 1H), 3.24-3.04 (m, 3H), 2.95 (septuplet, J 7.0 Hz, 1H), 2.46-2.39 (m, 1H), 1.98-1.90 (m, 1H), 1.30 (d, J 7.0 Hz, 6H).

Synthesis 32-A (S)-tert-Butyl 3-(6-bromo-2-(2-hydroxyphenyl)quinazolin-4-ylamino)pyrrolidine-1-carboxylate

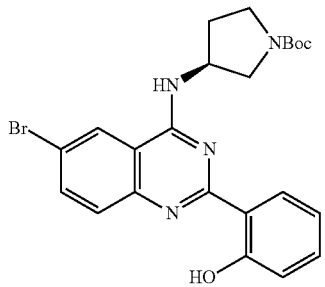

The title compound was prepared from 2-methoxybenzoyl chloride, 2-amino-5-bromobenzonitrile, and (R)-3-amino-piperidine-1-carboxylic acid tert-butyl ester using methods analogous to those described in Synthesis 1, steps 1A, 1B, and 1D.

Synthesis 32-B (S)-2-(6-Phenyl-4-(pyrrolidinyl-3-yl amino)quinazolin-2-yl)phenol (A-025)

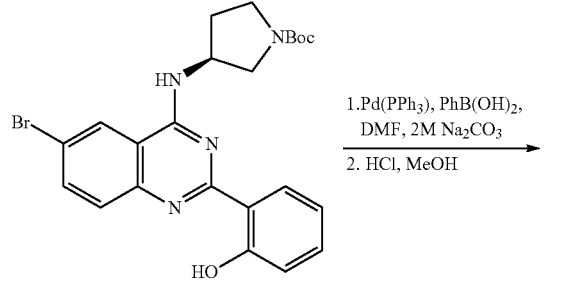

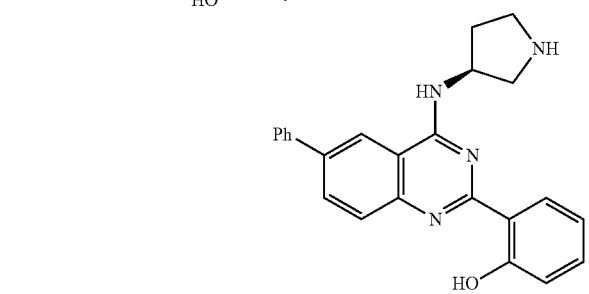

A mixture of (S)-tert-butyl 3-(6-bromo-2-(2-hydroxyphenyl)quinazolin-4-ylamino)pyrrolidine-1-carboxylate (0.097 g, 0.200 mmol), phenylboronic acid (0.073 g, 0.600 mmol), Pd(PPh$_3$)$_4$ (0.014 g, 0.012 mmol) and 2 M aqueous Na$_2$CO$_3$ (1.5 mL, 3.00 mmol) in DMF (2 mL) was heated at 100° C. for 24 hours. After cooling, water (30 mL) was added and the aqueous phase was extracted with ethyl acetate (3×30 mL). The combined organic extracts were dried (MgSO$_4$) and concentrated. The resulting solid was suspended in methanol (3 mL) and 4 M HCl in dioxane (7 mL) was added. After stirring for 24 hours, the solution was concentrated and purified by ion exchange chromatography on SCX-2 Isolute acidic resin (2 g), eluting with methanol and then 1 M ammonia in methanol. Further purification by preparative thin layer chromatography, eluting with 20% methanol in dichloromethane, gave the title compound as a solid (0.028 g, 37%).

LC-MS (LCT2) m/z 383 [M+H$^+$], R$_t$ 3.75 minutes. $^1$H NMR (CDCl$_3$) δ 8.55 (dd, J 8.0, 1.5 Hz, 1H), 7.98-7.95 (m, 2H), 7.85 (d, J 9.0 Hz, 1H), 7.68-7.66 (m, 2H), 7.50-7.46 (m, 2H), 7.41-7.36 (m, 2H), 7.05 (dd, J 8.0, 1.0 Hz, 1H), 6.95 (ddd, J 8.0, 7.0, 1.0 Hz, 1H), 6.55 (br d, J 6.5 Hz, 1H), 5.04-4.99 (m, 1H), 3.44-3.04 (m, 4H), 2.48-2.41 (m, 1H), 2.00-1.94 (m, 1H).

Synthesis 33

(2R,4S)-Methyl 4-(2-(5-chloro-2-hydroxyphenyl)quinazolin-4-ylamino)pyrrolidine-2-carboxylate (A-026)

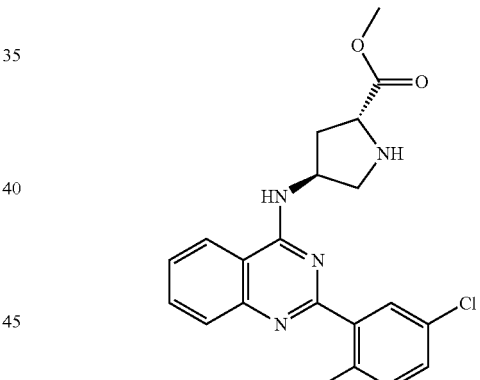

The title compound was prepared using methods analogous to those described in Synthesis 1-A, 1-B and 1-D, replacing 2-methoxybenzoyl chloride with 2-methoxy-4-chlorobenzoyl chloride in Synthesis 1A, and Synthesis 2, replacing (R)-3-aminopiperidine-1-carboxylic acid tert-butyl ester with (2R,4S)-4-aminopyrrolidine-1,2-dicarboxylic acid 1-tert-butyl ester 2-methyl ester in Synthesis 2A.

LC-MS (LCT2) m/z 399 [M+H$^+$], R$_t$ 3.71 minutes. $^1$H NMR (CDCl$_3$) δ 8.43 (d, J 3.0 Hz, 1H), 7.81-7.74 (m, 2H), 7.47 (ddd, J 8.0, 7.0, 1.5 Hz, 1H), 7.30 (dd, J 9.0, 3.0 Hz, 1H), 6.97 (d, J 9.0 Hz, 1H), 6.39 (br d, J 7.0 Hz, 1H), 5.06-5.01 (m, 1H), 4.03 (dd, J 8.5, 6.5 Hz, 1H), 3.82 (s, 3H), 3.52 (dd, J 10.5, 5.5 Hz, 1H), 3.16-3.13 (m, 1H), 2.55-2.50 (m, 1H), 2.44-2.39 (m, 1H).

Synthesis 34

(S)-2-(7-(4-(Morpholinomethyl)phenyl)-4-(pyrrolidin-3-ylamino)quinazolin-2-yl)phenol (A-027)

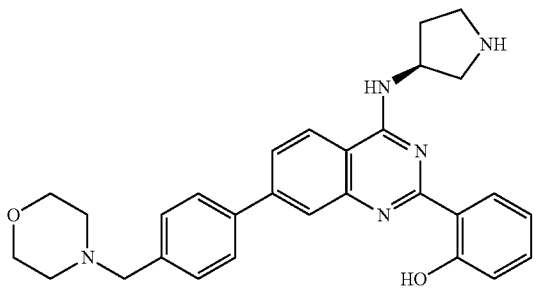

The title compound was prepared using a method analogous to that described in Synthesis 27, replacing phenylboronic acid with 4-(4-morpholinomethyl)phenylboronic acid pinacol ester.

LC-MS (LCT2) m/z 482 [M+H$^+$], R$_t$ 2.22 minutes. $^1$H NMR (CDCl$_3$) δ 8.56 (dd, J 8.0, 2.0 Hz, 1H), 7.98 (d, J 2.0 Hz, 1H), 7.81 (d, J 8.5 Hz, 1H), 7.68-7.65 (m, 3H), 7.47 (d, J 8.5 Hz, 1H), 7.38 (ddd, J 8.5, 7.0, 2.0 Hz, 1H), 7.05 (dd, J 8.0, 1.0 Hz, 1H), 6.95 (ddd, J 8.0, 7.5, 1.0 Hz, 1H), 6.27 (br d, 6.5 Hz, 1H), 5.00-4.95 (m, 1H), 3.76-3.74 (m, 4H), 3.58 (s, 2H), 3.43-3.39 (m, 1H), 3.24-3.19 (m, 1H), 3.11-3.05 (m, 2H), 2.52-2.50 (m, 4H), 2.44 (dddd, J 16.0, 13.5, 8.0, 6.0 Hz, 1H), 1.95-1.89 (m, 1H).

Synthesis 35

(S)-2-(6-(4-(Morpholinomethyl)phenyl)-4-(pyrrolidin-3-ylamino)quinazolin-2-yl)phenol (A-028)

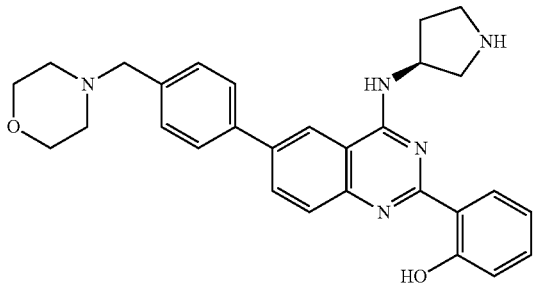

The title compound was prepared using a method analogous to that described in Synthesis 32, replacing phenylboronic acid with 4-(4-morpholinomethyl)phenylboronic acid pinacol ester in Synthesis 32-B.

LC-MS (LCT2) m/z 482 [M+H$^+$], R$_t$ 2.39 minutes. $^1$H NMR (CDCl$_3$) δ 8.54 (dd, J 8.0, 1.5 Hz, 1H), 7.98-7.94 (m, 2H), 7.84 (d, J 8.5 Hz, 1H), 7.61 (d, J 8.0 Hz, 2H), 7.42 (d, J 8.0 Hz, 2H), 7.38 (ddd, J 8.5, 7.0, 2.0 Hz, 1H), 7.04 (dd, J 8.0, 1.0 Hz, 1H), 6.95 (ddd, J 8.0, 7.0, 1.0 Hz, 1H), 6.61 (br d, J 6.0 Hz, 1H), 5.06-5.00 (m, 1H), 3.74-3.72 (m, 4H), 3.53 (s, 2H), 3.41-3.38 (m, 1H), 3.30-3.25 (m, 1H), 3.19-3.17 (m, 1H), 3.13-3.08 (m, 1H), 2.48-2.42 (m, 5H), 2.03-1.98 (m, 1H).

Synthesis 36

(S)-2-(6-(1H-Pyrazol-4-yl)-4-(pyrrolidin-3-ylamino)quinazolin-2-yl)phenol (A-029)

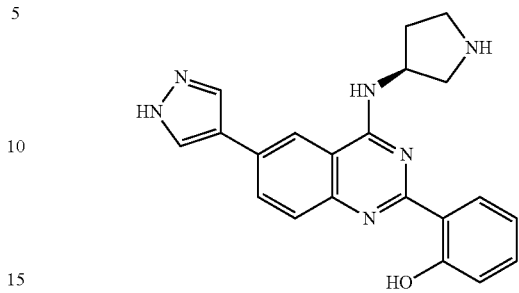

The title compound was prepared using a method analogous to that described in Synthesis 32, replacing phenylboronic acid with 4-(4,4,5,5-tetramethyl-1,3,2-dioxaborolan-2-yl)pyrazole-1-carboxylic acid tert-butyl ester in Synthesis 32-B.

LC-MS (LCT2) m/z 373 [M+H$^+$], R$_t$ 2.95 minutes. $^1$H NMR (CDCl$_3$) δ 8.48 (d, J 8.0 Hz, 1H), 8.40 (s, 1H), 8.11 (s, 2H), 8.00-7.98 (m, 1H), 7.69 (d, J 9.0 Hz, 1H), 7.33 (ddd, J 8.5, 7.0, 1.5 Hz, 1H), 6.93-6.89 (m, 2H), 4.91-4.86 (m, 1H), 3.44 (dd, J 12.0, 7.0 Hz, 1H), 3.23-3.18 (m, 1H), 3.11-3.04 (m, 2H), 2.44-2.37 (m, 1H), 2.10-2.04 (m, 1H).

Synthesis 37-A (2R,4S)-1-tert-butyl 2-methyl 4-(2-(2-methoxyphenyl)quinazolin-4-ylamino)pyrrolidine-1,2-dicarboxylate

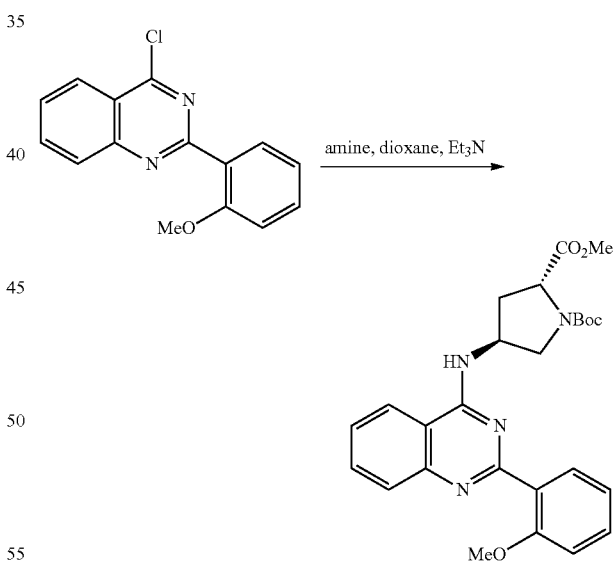

4-Chloro-2-(2-methoxyphenyl)quinazoline (0.463 g, 1.709 mmol), (2R,4S)-4-aminopyrrolidine-1,2-dicarboxylic acid 1-tert-butyl ester 2-methyl ester (0.480 g, 1.709 mmol) and triethylamine (0.715 mL, 5.127 mmol) in dioxane (9 mL) were heated at reflux for 3 days. The mixture was cooled, diluted with dichloromethane (50 mL), and washed with water (50 mL). The organic extracts were dried (MgSO$_4$) and concentrated. Purification by silica gel chromatography (10% methanol in dichloromethane) gave the title compound as a solid (0.423 g, 52%).

LC-MS (LCT2) m/z 479 [M+H$^+$], R$_t$ 3.49 minutes.

Synthesis 37-B

(2R,4S)-1-(tert-Butoxycarbonyl)-4-(2-(2-methoxyphenyl)quinazolin-4-ylamino)pyrrolidine-2-carboxylic acid

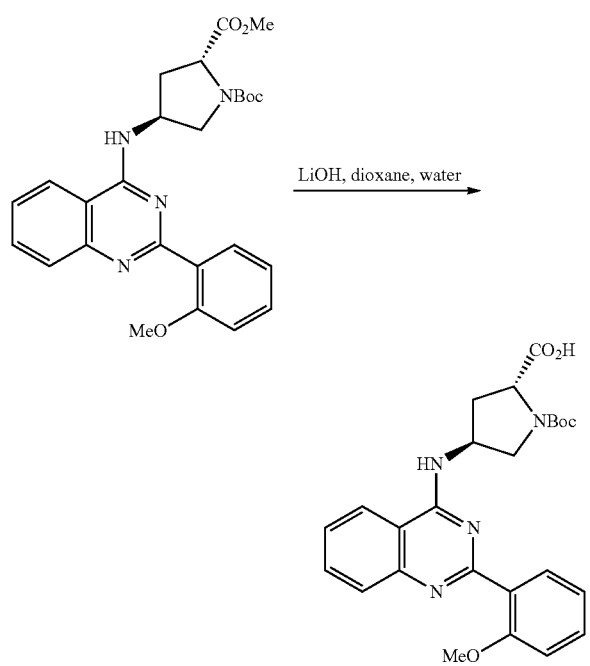

(2R,4S)-1-tert-Butyl 2-methyl 4-(2-(2-methoxyphenyl)quinazolin-4-ylamino)pyrrolidine-1,2-dicarboxylate (0.415 g, 0.851 mmol) and lithium hydroxide monohydrate (0.089 g, 2.128 mmol) were dissolved in water (8 mL) and dioxane (8 mL) and stirred for 1 hour. Water (30 mL) was added and the mixture was acidified to pH 4 with 1M HCl. The aqueous layer was extracted with ethyl acetate (4×30 mL). The combined organic extracts were dried (MgSO$_4$) and concentrated to give the title compound as a solid (0.382 g, 95%).

LC-MS (LCT2) m/z 465 [M+H$^+$], R$_t$ 3.36 minutes.

Synthesis 37-C

(2R,4S)-tert-Butyl 2-(dimethylcarbamoyl)-4-(2-(2-methoxyphenyl)quinazolin-4-ylamino)pyrrolidine-1-carboxylate

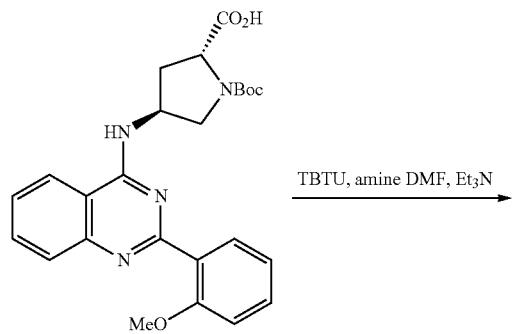

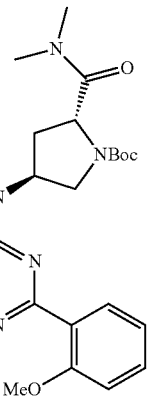

A solution of (2R,4S)-1-(tert-butoxycarbonyl)-4-(2-(2-methoxyphenyl)quinazolin-4-ylamino)pyrrolidine-2-carboxylic acid (0.095 g, 0.204 mmol), dimethylamine hydrochloride (0.017 g, 0.204 mmol), 0-(benzotriazol-1-yl)-N,N,N',N'-tetramethyluronium tetrafluoroborate (0.077 g, 0.204 mmol), and triethylamine (0.037 mL, 0.265 mmol) in DMF (1 mL) was stirred for 24 hours. Water (20 mL) was added and the aqueous layer was extracted with ethyl acetate (3×20 mL). The organic extracts were combined, dried (MgSO$_4$) and concentrated. Purification by silica gel chromatography (10% methanol in dichloromethane) gave the title compound as a solid (0.090 g, 90%).

LC-MS (LCT2) m/z 492 [M+H$^+$], R$_t$ 3.20 minutes.

Synthesis 37-D

(2R,4S)-4-(2-(2-Hydroxyphenyl)quinazolin-4-ylamino)-N,N-dimethylpyrrolidine-2-carboxamide (A-030)

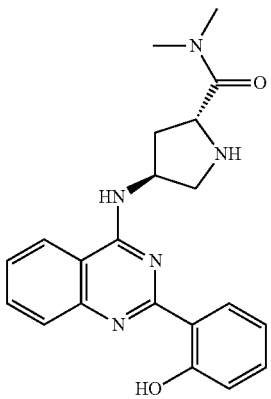

The title compound was prepared using a method analogous to that described in Synthesis 30-C, replacing (S)-tert-butyl 3-(2-(2-methoxy-5-methylphenyl)quinazolin-4-ylamino)pyrrolidine-1-carboxylate with (2R,4S)-tert-butyl 2-(dimethylcarbamoyl)-4-(2-(2-methoxyphenyl)quinazolin-4-ylamino)pyrrolidine-1-carboxylate.

LC-MS (LCT2) m/z 378 [M+H$^+$], R$_t$ 2.68 minutes. $^1$H NMR (CDCl$_3$) δ 8.53 (dd, J 8.0, 2.0 Hz, 1H), 7.85 (br d, J 8.5 Hz, 1H), 7.82 (dd, J 8.5, 1.0 Hz, 1H), 7.76 (ddd, J 8.5, 7.0, 1.0 Hz, 1H), 7.47 (ddd, J 8.0, 7.0, 1.0 Hz, 1H), 7.38 (ddd, J 8.5, 7.0, 2.0 Hz, 1H), 7.04 (dd, J 8.5, 1.0 Hz, 1H), 6.95 (ddd, J 8.0, 7.5, 1.0 Hz, 1H), 6.58 (br d, J 7.0 Hz, 1H), 5.07-5.02 (m, 1H), 4.15 (dt, J 8.0, 1.0 Hz, 1H), 3.60 (dd, J 11.0, 5.0 Hz, 1H), 3.13 (br d, J 11.0 Hz, 1H), 3.02 (s, 3H), 2.99 (s, 3H), 2.52 (dddd, J 13.5, 8.0, 2.5, 1.0 Hz, 1H), 2.25 (ddd, J 14.0, 7.5, 6.5 Hz, 1H).

Synthesis 38

(2R,4S)-N-Benzyl-4-(2-(2-hydroxyphenyl)quinazolin-4-ylamino)pyrrolidine-2-carboxamide (A-031)

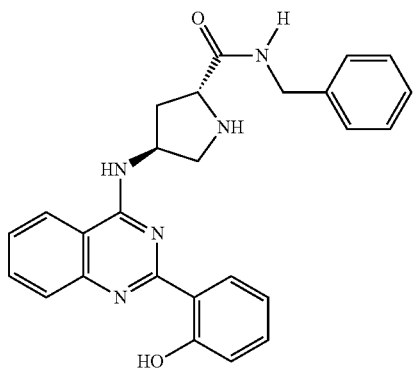

The title compound was prepared using a method analogous to that described in Synthesis 37, replacing dimethylamine hydrochloride with benzylamine in Synthesis 37-C.

LC-MS (LCT2) m/z 440 [M+H$^+$], R$_t$ 3.51 minutes. $^1$H NMR (CDCl$_3$) δ 8.49 (dd, J 8.0, 1.5 Hz, 1H), 7.88-7.74 (m, 4H), 7.44-7.30 (m, 7H), 7.04 (br d, J 8.0 Hz, 1H), 6.93 (dt, J 7.5, 0.5 Hz, 1H), 6.03 (br d, J 5.0 Hz, 1H), 4.90-4.85 (m, 1H), 4.55 (dd, J 15.0, 6.0 Hz, 1H), 4.51 (dd, J 15.0, 6.0 Hz, 1H), 4.18 (t, J 8.0 Hz, 1H), 3.43 (dd, J 12.0, 5.0 Hz, 1H), 3.36 (dd, J 12.0, 3.0 Hz, 1H), 2.53-2.50 (m, 2H).

Synthesis 39

(2R,4S)-4-(2-(2-Hydroxyphenyl)quinazolin-4-ylamino)-N-methylpyrrolidine-2-carboxamide (A-032)

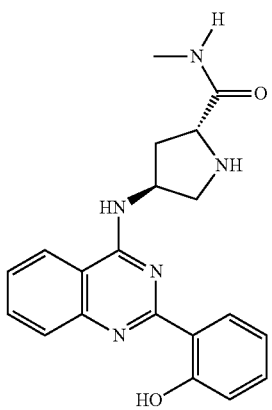

The title compound was prepared using a method analogous to that described in Synthesis 37, replacing dimethylamine hydrochloride with methylamine hydrochloride in Synthesis 37-C.

LC-MS (LCT2) m/z 364 [M+H$^+$], R$_t$ 2.59 minutes. $^1$H NMR (CDCl$_3$) δ 8.50 (dd, J 8.0, 1.5 Hz, 1H), 7.85 (d, J 8.5 Hz, 1H), 7.83 (d, J 9.0 Hz, 1H), 7.78-7.74 (m, 1H), 7.50-7.44 (m, 2H), 7.38 (ddd, J 8.5, 7.0, 1.5 Hz, 1H), 7.04 (d, J 8.0 Hz, 1H), 6.94 (t, J 7.5 Hz, 1H), 6.11 (br d, J 5.0 Hz, 1H), 4.88-4.84 (m, 1H), 4.13 (t, J 8.0 Hz, 1H), 3.43 (dd, J 12.0, 5.0 Hz, 1H), 3.38 (dd, J 12.0, 3.0 Hz, 1H), 2.90 (d, J 5.0 Hz, 3H), 2.54-2.40 (m, 2H).

Synthesis 40-A (S)-tert-Butyl 3-(2-(2-methoxy-5-(trifluoromethyl)phenyl)quinazolin-4-ylamino)pyrrolidine-1-carboxylate

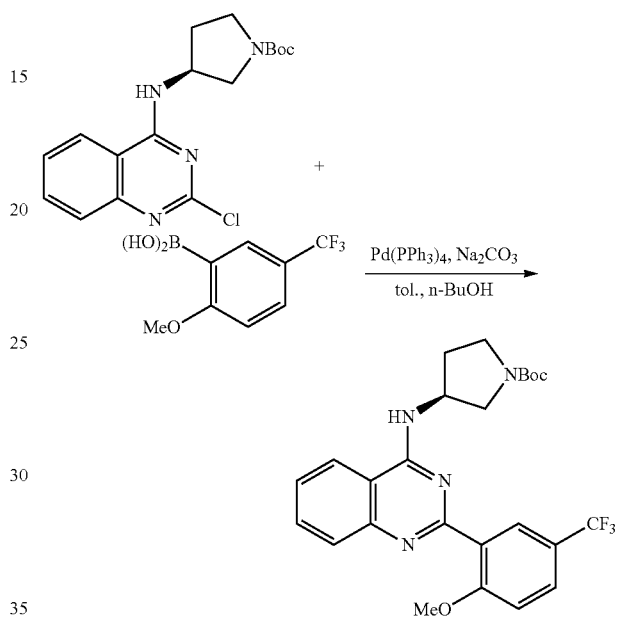

The title compound was prepared using a method analogous to that described in Synthesis 30-B, replacing 2-methoxy-5-methylphenylboronic acid with 2-methoxy-5-(trifluoromethyl)phenylboronic acid.

LC-MS (LCT2) m/z 489 [M+H$^+$], R$_t$ 3.99 minutes. $^1$H NMR (CDCl$_3$) δ 8.04 (d, J 2.0 Hz, 1H), 7.95 (d, J 8.5 Hz, 1H), 7.79-7.75 (m, 1H), 7.72 (d, J 8.5 Hz, 1H), 7.65 (dd, J 8.5, 2.0 Hz, 1H), 7.52-7.47 (m, 1H), 7.09 (d, J 8.0 Hz, 1H), 5.70 (br d, J 5.0 Hz, 1H), 4.90 (br s, 1H), 3.93 (s, 3H), 3.84 (dd, J 11.5, 6.0 Hz, 1H), 3.59-3.37 (br m, 3H), 2.38-2.31 (m, 1H), 2.10 (br s, 1H), 1.47 (s, 9H).

Synthesis 40-B (S)-Methyl 4-hydroxy-3-(4-(pyrrolidin-3-ylamino)quinazolin-2-yl)benzoate (A-033)

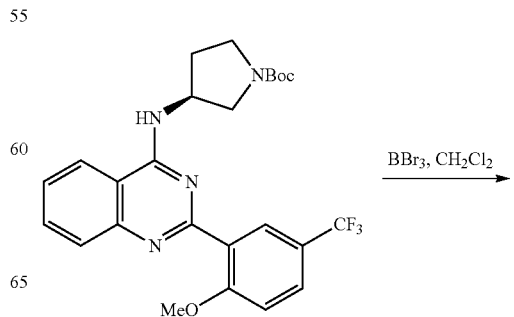

-continued

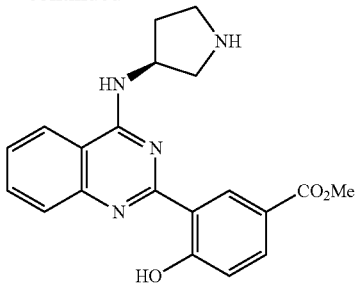

The title compound was prepared using a method analogous to that described in Synthesis 30-C.

LC-MS (LCT2) m/z 365 [M+H$^+$], R$_t$ 3.49 minutes. $^1$H NMR (CDCl$_3$) δ 9.18 (d, J 2.0 Hz, 1H), 8.70 (br s, 1H), 8.33 (br s, 1H), 8.24 (br d, J 7.2 Hz, 1H), 8.01 (dd, J 8.5, 2.0 Hz, 1H), 7.79-7.73 (m, 2H), 7.51-7.47 (m, 1H), 7.02 (d, J 8.5 Hz, 1H), 5.41 (br s, 1H), 3.92 (s, 3H), 3.78-3.39 (m, 4H), 2.56-2.46 (m, 2H).

Synthesis 41

((2R,4S)-4-(2-(2-Hydroxyphenyl)quinazolin-4-ylamino)pyrrolidin-2-yl)(pyrrolidin-1-yl)methanone (A-034)

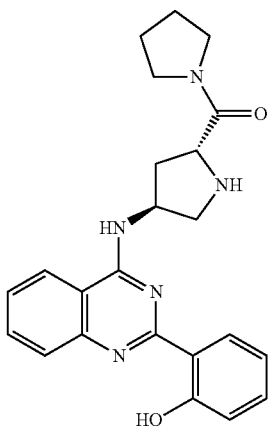

The title compound was prepared using a method analogous to that described in Synthesis 37, replacing dimethylamine hydrochloride with pyrrolidine in Synthesis 37-C.

LC-MS (LCT2) m/z 404 [M+H$^+$], R$_t$ 3.04 minutes. $^1$H NMR (CDCl$_3$) δ 8.53 (dd, J 8.0, 1.5 Hz, 1H), 7.86 (br d, J 8.0 Hz, 1H), 7.81 (dd, J 8.5, 1.0 Hz, 1H), 7.75 (ddd, J 8.0, 7.0, 1.0 Hz, 1H), 7.45 (ddd, J 8.0, 7.0, 1.5 Hz, 1H), 7.38 (ddd, J 8.0, 7.0, 2.0 Hz, 1H), 7.03 (dd, J 8.0, 1.0 Hz, 1H), 6.94 (ddd, J 8.0, 7.0, 1.0 Hz, 1H), 6.66 (br d, J 6.5 Hz, 1H), 5.07-5.03 (m, 1H), 4.01 (t, J 8.0 Hz, 1H), 3.63-3.42 (m, 4H), 3.36-3.30 (m, 1H), 3.13 (dd, J 11.0, 1.0 Hz, 1H), 2.53-2.49 (m, 1H), 2.25 (ddd, J 14.0, 8.0, 6.5 Hz, 1H), 1.97-1.85 (m, 4H).

Synthesis 42

((2R,4S)-4-(2-(2-Hydroxyphenyl)quinazolin-4-ylamino)pyrrolidin-2-yl)(piperazin-1-yl)methanone (A-035)

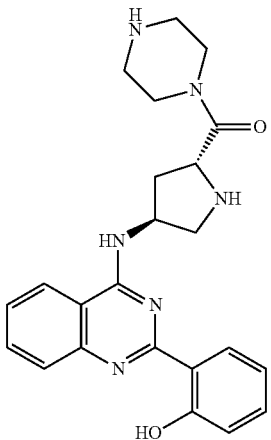

The title compound was prepared using a method analogous to that described in Synthesis 37, replacing dimethylamine hydrochloride with piperazine in Synthesis 37-C.

LC-MS (LCT2) m/z 419 [M+H$^+$], R$_t$ 1.74 minutes. $^1$H NMR (MeOD) δ 8.47 (dd, J 8.0, 1.5 Hz, 1H), 8.16 (br d, J 8.0 Hz, 1H), 7.76 (ddd, J 8.5, 7.0, 1.5 Hz, 1H), 7.72-7.70 (m, 1H), 7.48 (ddd, J 8.0, 7.0, 1.5 Hz, 1H), 7.33 (ddd, J 8.0, 7.0, 2.0 Hz, 1H), 6.93-6.89 (m, 2H), 4.91-4.86 (m, 1H), 4.28 (t, J 8.0 Hz, 1H), 3.71-3.56 (m, 5H), 3.02 (dd, J 11.5, 6.0 Hz, 1H), 2.90-2.80 (m, 4H), 2.41-2.30 (m, 2H).

Synthesis 43

((2R,4S)-4-(2-(2-Hydroxyphenyl)quinazolin-4-ylamino)pyrrolidin-2-yl)(4-methylpiperazin-1-yl)methanone (A-036)

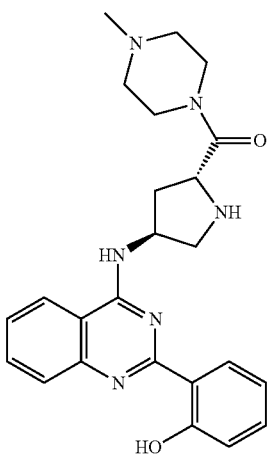

The title compound was prepared using a method analogous to that described in Synthesis 37, replacing dimethylamine hydrochloride with 1-methylpiperazine in Synthesis 37-C.

LC-MS (LCT2) m/z 433 [M+H$^+$], R$_t$ 1.67 minutes. $^1$H NMR (CDCl$_3$) δ 8.52 (dd, J 8.0, 2.0 Hz, 1H), 7.85 (br d, J 8.0 Hz, 1H), 7.79 (dd, J 8.5, 1.0 Hz, 1H), 7.74 (ddd, J 8.0, 7.0, 1.0 Hz, 1H), 7.44, (ddd, J 8.0, 7.0, 1.0 Hz, 1H), 7.38 (ddd, J 8.0, 7.0, 2.0 Hz, 1H), 7.03 (dd, J 8.0, 1.0 Hz, 1H), 6.94 (ddd, J 8.0, 7.0, 1.0 Hz, 1H), 6.69 (br d, J 7.0 Hz, 1H), 5.06-5.01 (m, 1H), 4.11 (t, J 8.0 Hz, 1H), 3.70-3.68 (m, 2H), 3.56 (dd, J 11.0, 5.0 Hz, 1H), 3.43-3.41 (m, 2H), 3.12 (br d, J 11.0, 1H), 2.49-2.23 (m, 6H), 2.30 (s, 3H).

Synthesis 44

((2R,4S)-4-(2-(2-Hydroxyphenyl)quinazolin-4-ylamino)pyrrolidin-2-yl)(piperidin-1-yl)methanone (A-037)

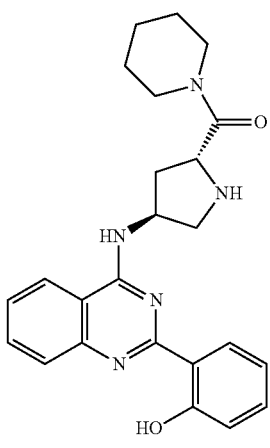

The title compound was prepared using a method analogous to that described in Synthesis 37, replacing dimethylamine hydrochloride with piperidine in Synthesis 37-C.

LC-MS (LCT2) ink 418 [M+H$^+$], R$_t$ 3.37 minutes. $^1$H NMR (CDCl$_3$) δ 8.52 (dd, J 8.0, 2.0 Hz, 1H), 7.90 (br d, J 8.0 Hz, 1H), 7.80 (dd, J 8.5, 1.0 Hz, 1H), 7.75 (ddd, J 8.0, 7.0, 1.0 Hz, 1H), 7.45 (ddd, J 8.5, 7.0, 1.5 Hz, 1H), 7.38 (ddd, J 8.5, 7.5, 2.0 Hz, 1H), 7.04 (dd, J 8.0, 1.0 Hz, 1H), 6.94 (ddd, J 8.0, 7.0, 1.0 Hz, 1H), 6.75 (br d, J 7.0 Hz, 1H), 5.06-5.01 (m, 1H), 4.14 (t, J 8.0 Hz, 1H), 3.64-3.54 (m, 3H), 3.34 (t, J 5.5 Hz, 2H), 3.15 (br d, J 11.0 Hz, 1H), 2.51-2.46 (m, 1H), 2.25 (ddd, J 14.0, 7.5, 6.5 Hz, 1H), 1.68-1.51 (m, 6H).

Synthesis 45

((2R,4S)-4-(2-(2-Hydroxyphenyl)quinazolin-4-ylamino)pyrrolidin-2-yl)(morpholino)methanone (A-038)

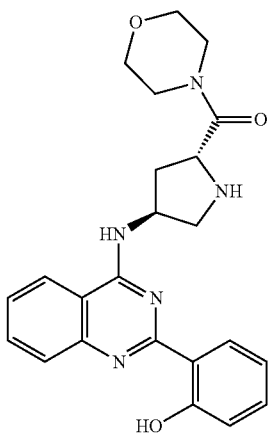

The title compound was prepared using a method analogous to that described in Synthesis 37, replacing dimethylamine hydrochloride with morpholine in Synthesis 37-C.

LC-MS (LCT2) m/z 420 [M+H$^+$], R$_t$ 2.83 minutes. $^1$H NMR (CDCl$_3$) δ 8.52 (dd, J 8.0, 1.5 Hz, 1H), 7.83-7.80 (m, 2H), 7.75 (ddd, J 8.0, 7.0, 1.5 Hz, 1H), 7.46 (ddd, J 8.0, 7.0, 1.5 Hz, 1H), 7.38 (ddd, J 8.5, 7.5, 2.0 Hz, 1H), 7.04 (dd, J 8.0, 1.0 Hz, 1H), 6.95 (ddd, J 8.0, 7.5, 1.0 Hz, 1H), 6.57 (br d, J 6.5 Hz, 1H), 5.06-5.01 (m, 1H), 4.10 (t, J 8.0 Hz, 1H), 3.73-3.64 (m, 6H), 3.58 (dd, J 11.0, 5.5 Hz, 1H), 3.45-3.40 (m, 2H), 3.13 (br d, J 11.0 Hz, 1H), 2.48-2.44 (m, 1H), 2.31-2.26 (m, 1H).

Synthesis 46

(2R,4S)-4-(2-(2-Hydroxyphenyl)quinazolin-4-ylamino)-N-phenylpyrrolidine-2-carboxamide (A-039)

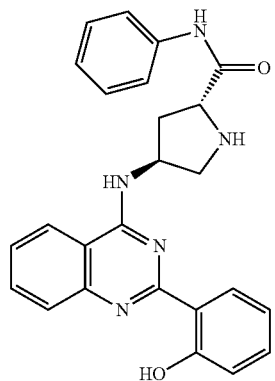

The title compound was prepared using a method analogous to that described in Synthesis 37, replacing dimethylamine hydrochloride with aniline in Synthesis 37-C.

LC-MS (LCT2) m/z 426 [M+H$^+$], R$_t$ 3.70 minutes. $^1$H NMR (MeOD) δ 8.45 (dd, J 8.0, 1.5 Hz, 1H), 8.43 (br s, 1H), 8.22 (d, J 8.0 Hz, 1H), 7.81-7.74 (m, 2H), 7.64 (d, J 8.0 Hz, 2H), 7.52 (t, J 7.5 Hz, 1H), 7.37 (t, J 8.0 Hz, 2H), 7.31 (ddd, J 8.5, 7.5, 1.5 Hz, 1H), 7.16 (t, J 7.5 Hz, 1H), 6.91 (d, J 8.0 Hz, 1H), 6.80 (t, J 7.5 Hz, 1H), 5.09-5.05 (m, 1H), 4.48 (t, J 7.5 Hz, 1H), 3.80 (dd, J 12.0, 6.5 Hz, 1H), 3.50 (dd, J 12.0, 5.0 Hz, 1H), 2.73-2.62 (m, 2H).

Synthesis 47

(S)-2-(4-(Pyrrolidin-3-ylamino)quinazolin-2-yl)-4-(trifluoromethyl)phenol (A-040)

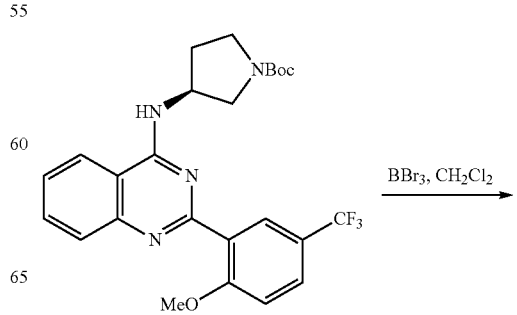

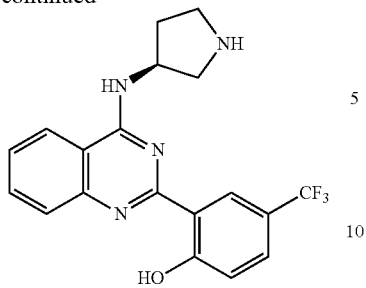

The title compound was prepared using a method analogous to that described in Synthesis 40-B and was isolated from the crude reaction products by preparative HPLC.

LC-MS (LCT2) m/z 375 [M+H$^+$], R$_t$ 3.75 minutes. $^1$H NMR (CDCl$_3$) δ 8.76 (br d, J 2.5 Hz, 1H), 8.56 (br s, 1H), 8.31 (d, J 8.0 Hz, 1H), 7.83-7.76 (m, 2H), 7.60 (dd, J 2.5, 8.5 Hz, 1H), 7.56-7.53 (m, 1H), 7.12-7.10 (d, J 8.5 Hz, 1H), 5.44-5.40 (m, 1H), 3.73 (d, J 11.5 Hz, 1H), 3.63-3.56 (m, 1H), 3.53-3.40 (m, 2H), 2.56-3.40 (m, 2H), 1.80 (br s, 1H).

Synthesis 48

(S)-4-Bromo-2-(4-(pyrrolidin-3-ylamino)quinazolin-2-yl)phenol (A-041)

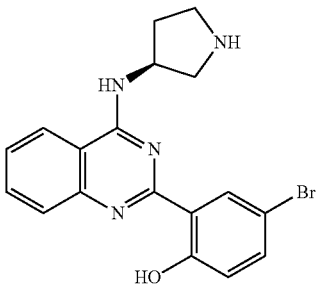

The title compound was prepared using a method analogous to that described in Synthesis 1, replacing 2-methoxybenzoyl chloride with 2-methoxy-4-bromobenzoyl chloride in Synthesis 1A.

LC-MS (LCT1) m/z 385 [M+H$^+$], R$_t$ 5.43 minutes. $^1$H NMR (CDCl$_3$) δ 8.58 (d, J 3.0 Hz, 1H), 8.20 (d, J 8.0 Hz, 1H), 7.81-7.73 (m, 1H), 7.74 (d, J 8.0 Hz, 1H), 7.54-7.50 (m, 1H), 7.41 (dd, J 9.0, 3.0 Hz, 1H), 6.86 (d, J 8.0 Hz, 1H), 4.93-4.88 (m, 1H), 4.86-4.77 (m, 2H), 3.42 (dd, J 12.0, 7.0 Hz, 1H), 3.21-3.15 (m, 1H), 3.10-3.01 (m, 1H), 2.44-2.36 (m, 1H), 2.07-2.00 (m, 1H).

Synthesis 49

(S)-2-(4-(Methyl(pyrrolidin-3-yl)amino)quinazolin-2-yl)phenol (A-042)

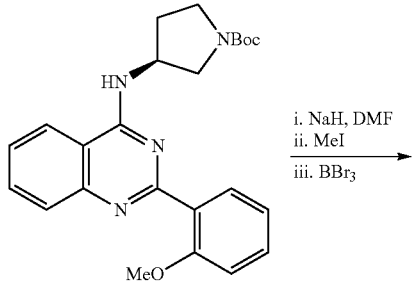

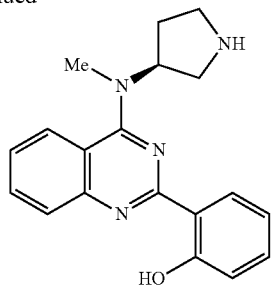

(S)-tert-Butyl 3-(2-(2-methoxyphenyl)quinazolin-4-ylamino)pyrrolidine-1-carboxylate (0.259 g, 0.616 mmol) (prepared by methods analogous to those described in Synthesis 2) was dissolved in DMF (6.16 mL) and cooled to −30° C. NaH (60% dispersion in mineral oil, 0.041 mg, 0.678 mmol) was added and the mixture was stirred at −30° C. for 15 minutes. The mixture was cooled to −78° C. and iodomethane (0.046 mL, 0.727 mmol) was added dropwise. The solution was warmed to room temperature over 2 hours. Water (5 mL) was added and the aqueous phase was extracted with dichloromethane (3×20 mL). The combined organic phases were dried (MgSO$_4$) and concentrated in vacuo. The residue was purified by ion exchange chromatography on SCX-2 Isolute acidic resin (2 g), eluting with methanol and then 1 M ammonia in methanol. The solvents were removed in vacuo and the residue was dissolved in dichloromethane (1.3 mL) and 1 M boron tribromide in dichloromethane (1.3 mL). The solution was stirred at room temperature for 18 hours. Methanol (5 mL) was added and the mixture was purified by ion exchange chromatography on SCX-2 Isolute acidic resin (2 g), eluting with methanol and then 1 M ammonia in methanol. Further purification by silica column chromatography, eluting with a gradient from 3% to 30% methanol in dichloromethane, gave the title compound as a yellow solid (0.028 g, 66%).

LC-MS (LCT3) m/z 321 [M+H$^+$], R$_t$ 2.27 minutes. $^1$H NMR (CDCl$_3$) δ 14.8 (br s, 1H), 8.49 (dd, J 2.0, 8.0 Hz, 1H), 8.00 (d, J 8.5 Hz, 1H), 7.84 (dd, J 8.5, 8.5 Hz, 1H), 7.75-7.70 (m, 1H), 7.43-7.39 (m, 1H), 7.38-7.35 (m, 1H), 7.03 (d, J 8.5 Hz, 1H), 6.94 (t, J 7.5 Hz, 1H), 5.26-5.20 (m, 1H), 3.53-3.48 (m, 1H), 3.39 (s, 3H), 3.26-3.21 (m, 1H), 3.15-3.09 (m, 2H), 2.40-2.34 (m, 1H), 2.10-2.04 (m, 1H), 1.76 (br s, 1H).

Synthesis 50

(S)-4-Fluoro-2-(4-(methyl(pyrrolidin-3-yl)amino)quinazolin-2-yl)phenol (A-043)

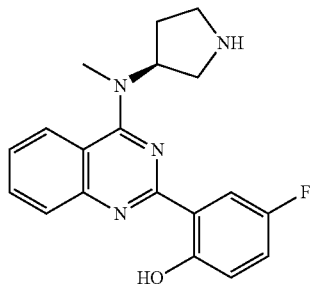

The title compound was prepared using a method analogous to that described in Synthesis 49, starting from (S)-4-fluoro-2-(4-(pyrrolidin-3-ylamino)quinazolin-2-yl)phenol.

LC-MS (LCT3) m/z 339 [M+H$^+$], R$_t$ 2.62 minutes. $^1$H NMR (CDCl$_3$) δ 8.08 (dd, J 3.0, 10.5 Hz, 1H), 8.01 (d, J 8.5 Hz, 1H), 7.87 (d, J 8.5 Hz, 1H), 7.79-7.76 (m, 1H), 7.04-7.00 (m, 1H), 6.92 (dd, J 8.5, 4.0 Hz, 1H), 5.34-5.29 (m, 1H), 3.78-3.73 (m, 1H), 3.53-3.49 (m, 1H), 3.41 (s, 3H), 3.40-3.30 (m, 2H), 2.52-2.46 (m, 1H), 2.32-2.28 (m, 1H), 1.55 (br s, 1H).

Synthesis 51

(S)-4-Chloro-2-(4-(methyl(pyrrolidin-3-yl)amino)quinazolin-2-yl)phenol (A-044)

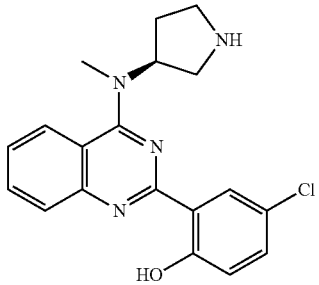

The title compound was prepared using a method analogous to that described in Synthesis 49, starting from (S)-4-chloro-2-(4-(pyrrolidin-3-ylamino)quinazolin-2-yl)phenol.

LC-MS (LCT3) m/z 355 [M+H$^+$], R$_t$ 2.90 minutes. $^1$H NMR (CDCl$_3$) δ 14.8 (br s, 1H), 8.36 (d, J 3.0 Hz, 1H), 8.01 (d, J 8.0 Hz, 1H), 7.85 (d, J 8.5 Hz, 1H), 7.77-7.74 (m, 1H), 7.46-7.44 (m, 1H), 7.29-7.25 (m, 1H), 6.95 (d, J 9.0 Hz, 1H), 5.28-5.24 (m, 1H), 3.63-3.58 (m, 1H), 3.42 (s, 3H), 3.40-3.35 (m, 1H), 3.29-3.18 (m, 2H), 2.45-2.38 (m, 1H), 2.22-2.15 (m, 1H), 1.75 (br s, 1H).

Synthesis 52-A 2-(4-Chloroquinazolin-2-yl)phenol

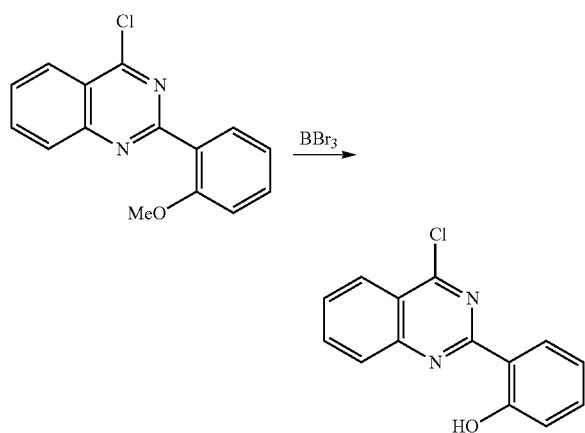

A solution of 4-chloro-2-(2-methoxyphenyl)quinazoline (0.106 g, 0.396 mmol) in dichloromethane (4.0 mL) was treated with 1 M boron tribromide in dichloromethane (4.0 mL, 3.960 mmol) at room temperature. After 18 hours, the reaction was quenched by pouring onto ice/water (100 mL) and the aqueous phase was extracted with ethyl acetate (3×100 mL). The combined organic extracts were dried (MgSO$_4$) and the filtrate was concentrated in vacuo. The residue was used without further purification.

LC-MS (LCT3) m/z 353 [MH+], R$_t$ 4.50 minutes.

Synthesis 52-B 2-(4-(Azepan-3-ylamino)quinazolin-2-yl)phenol (A-045)

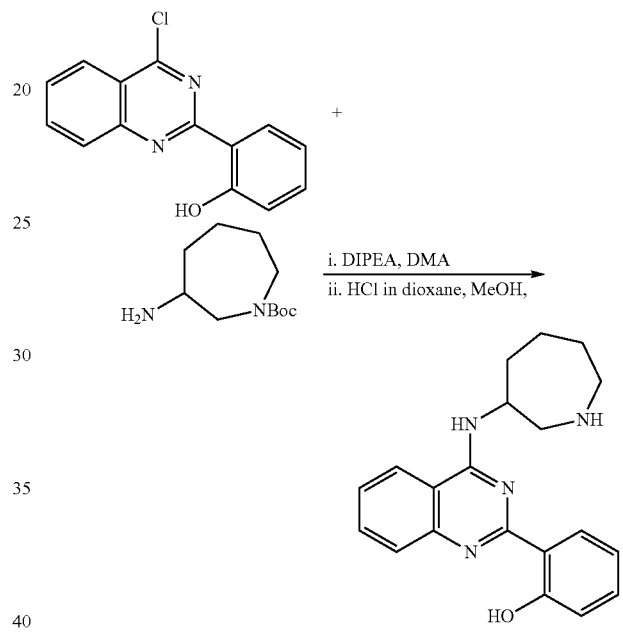

2-(4-Chloroquinazolin-2-yl)phenol (0.093 g, 0.362 mmol) was dissolved in DMA (3.6 mL) and then treated with diisopropylethylamine (0.189 mL, 1.087 mmol) followed by tert-butyl 3-aminoazepane-1-carboxylate (0.078 g, 0.362 mmol) and the solution was heated at 60° C. After 18 hours, the reaction mixture was concentrated in vacuo to remove the excess amine and purified by ion exchange chromatography on SCX-2 Isolute acidic resin (2 g), eluting with methanol and then 1 M ammonia in methanol. The solvent was removed in vacuo and the residue was dissolved in methanol (0.22 mL) and treated with 4 M HCl in dioxane (0.22 mL). After 18 hours, the reaction mixture was concentrated in vacuo and purified by ion exchange chromatography on SCX-2 Isolute acidic resin (2 g), eluting with methanol and then 1 M ammonia in methanol. Further purification by silica column chromatography, eluting with a gradient of 3% to 30% methanol in dichloromethane, gave the title compound as a yellow solid (0.007 g, 6%).

LC-MS (LCT3) m/z 335 [M+H$^+$], R$_t$ 2.47 minutes. $^1$H NMR (CDCl$_3$) δ 8.52 (dd, J 2.0, 8.5 Hz, 1H), 8.17 (d, J 8.0 Hz, 1H), 7.80-7.77 (m, 1H), 7.75-7.72 (m, 1H), 7.52-7.48 (m, 1H), 7.35-7.31 (m, 1H), 6.93-6.89 (m, 2H), 4.76-4.70 (m, 1H), 3.05-2.95 (m, 3H), 2.25-2.20 (m, 1H), 1.95-1.70 (m, 5H).

Synthesis 53

(2R,4S)-4-(2-(5-Fluoro-2-hydroxyphenyl)quinazolin-4-ylamino)-N,N-dimethylpyrrolidine-2-carboxamide (A-046)

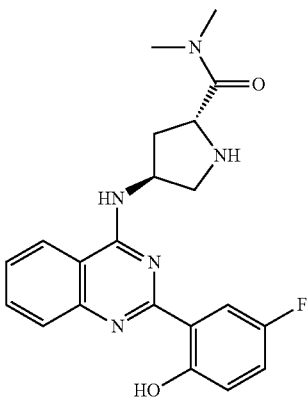

The title compound was prepared using a method analogous to that described in Synthesis 37, replacing 4-chloro-2-(2-methoxyphenyl)quinazoline with 4-chloro-2-(2-methoxy-5-fluorophenyl)quinazoline in Synthesis 37-A.

LC-MS (LCT2) m/z 396 [M+H$^+$], R$_t$ 3.28 minutes. $^1$H NMR (CDCl$_3$) δ 8.15 (dd, J 10.0, 3.5 Hz, 1H), 7.91 (d, J 8.5 Hz, 1H), 7.79-7.72 (m, 2H), 7.45 (ddd, J 8.0, 7.0, 1.5 Hz, 1H), 7.07 (ddd, J 9.0, 8.0, 3.0 Hz, 1H), 6.96 (dd, J 9.0, 4.5 Hz, 1H), 6.84 (br d, J 7.0 Hz, 1H), 5.02-4.97 (m, 1H), 4.16 (t, J 7.5 Hz, 1H), 3.58-3.52 (m, 1H), 3.16 (d, J 10.0 Hz, 1H), 3.01 (s, 3H), 2.97 (s, 3H), 2.54-2.50 (m, 1H), 2.25 (ddd, J 13.5, 7.5, 6.5 Hz, 1H).

Synthesis 54

(2R,4S)-N-(2-Hydroxyethyl)-4-(2-(2-hydroxyphenyl)quinazolin-4-ylamino)-N-methylpyrrolidine-2-carboxamide (A-047)

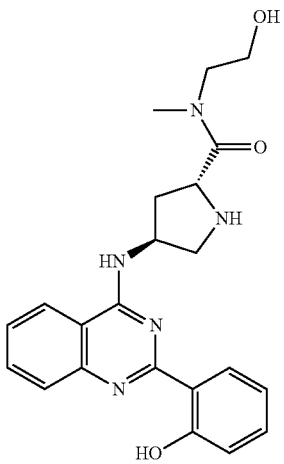

The title compound was prepared using a method analogous to that described in Synthesis 37, replacing dimethylamine hydrochloride with 2-methoxy-N-methylethanamine in Synthesis 37-C.

LC-MS (LCT2) m/z 408 [M+H$^+$], R$_t$ 2.60 minutes. $^1$H NMR (CDCl$_3$) δ 8.50 (ddd, J 8.0, 7.0, 1.5 Hz, 1H), 7.91 (dd, J 12.0, 8.5 Hz, 1H), 7.80-7.67 (m, 2H), 7.44 (ddd, J 8.0, 7.0, 1.0 Hz, 0.5H), 7.39-7.35 (m, 1.5H), 7.25 (d, J 6.5 Hz, 0.5H), 7.03 (d, J 8.0 Hz, 1H), 6.96-6.91 (m, 1H), 6.82 (d, J 6.5 Hz, 0.5H), 5.12-5.08 (m, 0.5H), 5.05-5.00 (m, 0.5H), 4.40-4.37 (m, 0.5H), 4.17-4.14 (m, 0.5H), 3.89-3.49 (m, 5H), 3.19-3.05 (m, 2H), 3.03&3.03 (2×s, 3H), 2.55-2.48 (m, 1H), 2.28-2.22 (m, 1H).

Synthesis 55

(2R,4S)-4-(2-(2-Hydroxyphenyl)quinazolin-4-ylamino)-N-isopropyl-N-methylpyrrolidine-2-carboxamide (A-048)

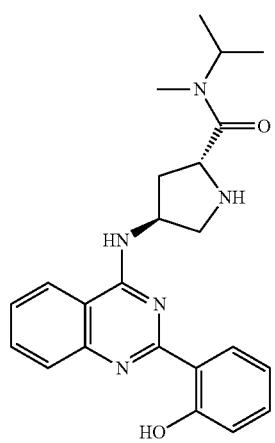

The title compound was prepared using a method analogous to that described in Synthesis 37, replacing dimethylamine hydrochloride with N-methyl-Nisopropylamine in Synthesis 37-C.

LC-MS (LCT2) m/z 406 [M+H$^+$], R$_t$ 3.19 minutes. $^1$H NMR (CDCl$_3$) δ 8.51 (d, J 7.5 Hz, 1H), 7.89 (t, J 8.5 Hz, 1H), 7.77 (d, J 8.5 Hz, 1H), 7.72 (ddd, J 8.0, 7.0. 1.0 Hz, 1H), 7.42 (dd, J 8.0, 7.0 Hz, 1H), 7.37 (ddd, J 8.5, 7.0, 2.0 Hz, 1H), 7.03 (dd, J 8.0, 1.0 Hz, 1H), 6.93 (ddd, J 8.0, 7.0, 1.0 Hz, 1H), 6.71 (d, J 7.0 Hz, 0.5H), 6.69 (d, J 7.0 Hz, 0.5H), 5.05-4.98 (m, 1H), 4.86 (sept, J 7.0 Hz, 0.5H), 4.18 (t, J 8.0 Hz, 0.5H), 4.11 (t, J 8.0 Hz, 0.5H), 4.00 (sept, J 6.5 Hz, 0.5H), 3.61-3.57 (m, 1H), 3.13 (d, J 11.0 Hz, 1H), 2.85&2.76 (2×s, 3H), 2.51-2.44 (m, 1H), 2.28-2.17 (m, 1H), 1.19-1.11 (m, 6H).

Synthesis 56

Azetidin-1-yl((2R,4S)-4-(2-(2-hydroxyphenyl)quinazolin-4-ylamino)pyrrolidin-2-yl)methanone (A-049)

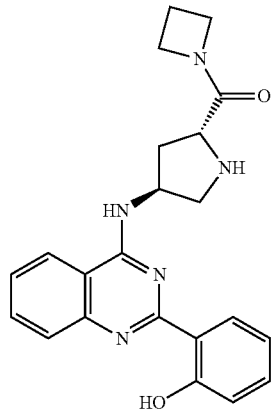

The title compound was prepared using a method analogous to that described in Synthesis 37, replacing dimethylamine hydrochloride with azetidine hydrochloride in Synthesis 37-C.

LC-MS (LCT2) m/z 390 [M+H⁺], R$_t$ 2.80 minutes. ¹H NMR (CDCl$_3$) δ 8.53 (dd, J 8.0, 2.0 Hz, 1H), 7.83 (d, J 8.0 Hz, 1H), 7.79 (d, J 8.5 Hz, 1H), 7.73 (ddd, J 8.5, 7.0, 1.0 Hz, 1H), 7.44 (ddd, J 8.0, 7.0, 1.0 Hz, 1H), 7.38 (ddd, J 8.5, 7.0, 2.0 Hz, 1H), 7.04 (dd, J 8.5, 1.0 Hz, 1H), 6.95 (ddd, J 8.0, 7.0, 1.0 Hz, 1H), 6.50 (d, J 6.5 Hz, 1H), 5.04-5.00 (m, 1H), 4.18-4.04 (m, 4H), 3.85 (t, J 8.0 Hz, 1H), 3.58 (dd, J 10.5, 5.0 Hz, 1H), 3.10 (d, J 10.5 Hz, 1H), 2.42-2.24 (m, 4H).

Synthesis 57

(2R,4S)-N-Ethyl-4-(2-(2-hydroxyphenyl)quinazolin-4-ylamino)-N-methylpyrrolidine-2-carboxamide (A-050)

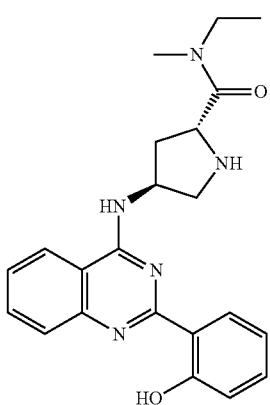

The title compound was prepared using a method analogous to that described in Synthesis 37, replacing dimethylamine hydrochloride with N-methyl-N-ethylamine in Synthesis 37-C.

LC-MS (LCT2) m/z 392 [M+H⁺], R$_t$ 2.97 minutes. ¹H NMR (CDCl$_3$) δ 8.52 (dd, J 8.0, 1.5 Hz, 1H), 7.87 (t, J 8.0 Hz, 1H), 7.80 (dd, J 8.5, 1.0 Hz, 1H), 7.74 (ddd, J 8.0, 7.0. 1.0 Hz, 1H), 7.45 (ddd, J 8.0, 7.0, 1.0 Hz, 1H), 7.38 (ddd, J 8.0, 7.0, 2.0 Hz, 1H), 7.04 (dd, J 8.0, 1.0 Hz, 1H), 6.94 (ddd, 8.0, 7.0, 1.0 Hz, 1H), 6.65 (d, J 6.5 Hz, 0.5H), 6.60 (d, J 6.5 Hz, 0.5H), 5.06-5.00 (m, 1H), 4.15-4.11 (m, 1H), 3.60 (dt, J 12.0, 5.5 Hz, 1H), 3.53-3.22 (m, 2H), 3.13 (br d, J 11.0 Hz, 1H), 2.98&2.93 (2×s, 3H), 2.53-2.46 (m, 1H), 2.30-2.19 (m, 1H), 1.17&1.15 (2×t, J 7.0 Hz, 3H).

Synthesis 58

(2R,4S)-N-Ethyl-4-(2-(2-hydroxyphenyl)quinazolin-4-ylamino)pyrrolidine-2-carboxamide (A-051)

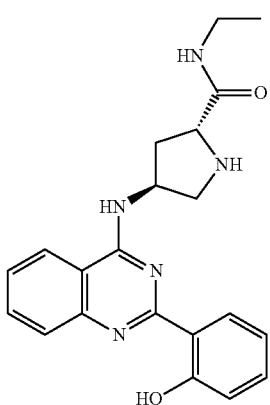

The title compound was prepared using a method analogous to that described in Synthesis 37, replacing dimethylamine hydrochloride with ethylamine in Synthesis 37-C.

LC-MS (LCT2) m/z 378 [M+H⁺], R$_t$ 2.92 minutes. ¹H NMR (d6-DMSO) δ 8.44 (dd, J 8.5, 2.0 Hz, 1H), 8.40 (d, J 8.5 Hz, 1H), 8.35 (d, J 6.0 Hz, 1H), 7.99 (t, J 5.5 Hz, 1H), 7.82 (ddd, J 8.0, 7.0, 1.0 Hz, 1H), 7.76 (dd, J 8.0, 1.0 Hz, 1H), 7.54 (ddd, J 8.0, 7.0, 1.0 Hz, 1H), 7.36 (ddd, J 8.5, 7.0, 2.0 Hz, 1H), 6.93-6.89 (m, 2H), 4.77-4.71 (m, 1H), 3.80 (dd, J 8.5, 6.5 Hz, 1H), 3.23-3.06 (m, 4H), 2.28 (ddd, J 13.0, 8.5, 4.5 Hz, 1H), 2.21-2.16 (m, 1H), 1.06 (t, J 7.0 Hz, 1H).

Synthesis 59-A (S)-tert-butyl 3-(2-(2-hydroxyphenyl)-6-(3-hydroxyprop-1-ynyl)quinazolin-4-ylamino)pyrrolidine-1-carboxylate

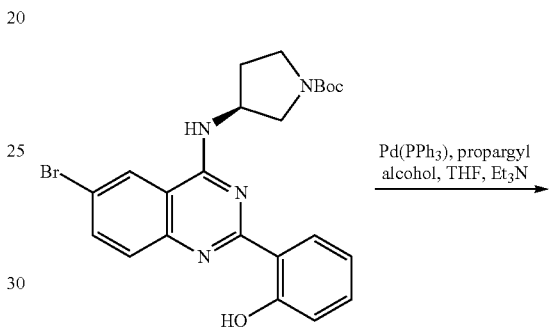

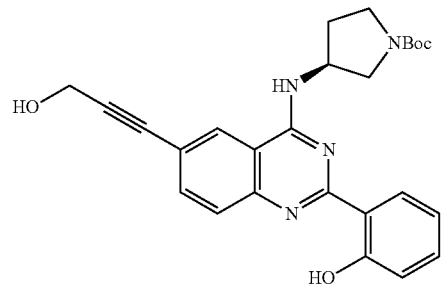

Tetrakis(triphenylphosphine)palladium (0.030 g, 0.026 mmol) was added to a solution of (S)-tert-butyl 3-(6-bromo-2-(2-hydroxyphenyl)quinazolin-4-ylamino)pyrrolidine-1-carboxylate (prepared as described in Synthesis 32-A, 0.250 g, 0.515 mmol), propargyl alcohol (0.043 g, 0.773 mmol) and triethylamine (0.108 mL, 0.773 mmol) in THF (2.5 mL) and the solution heated to reflux for 16 hours. The mixture was cooled then purified by ion exchange chromatography on SCX-2 Isolute acidic resin (5 g), eluting with methanol and then 1 M ammonia in methanol. Further purification by column chromatography, eluting with 5% methanol in dichloromethane, gave the title compound as a solid (0.100 g, 42%).

LC-MS (LCT2) m/z 461 [M+H⁺], R$_t$ 5.69 minutes.

Synthesis 59-B (S)-2-(6-(3-hydroxyprop-1-ynyl)-4-(pyrrolidin-3-ylamino)quinazolin-2-yl)phenol (A-052)

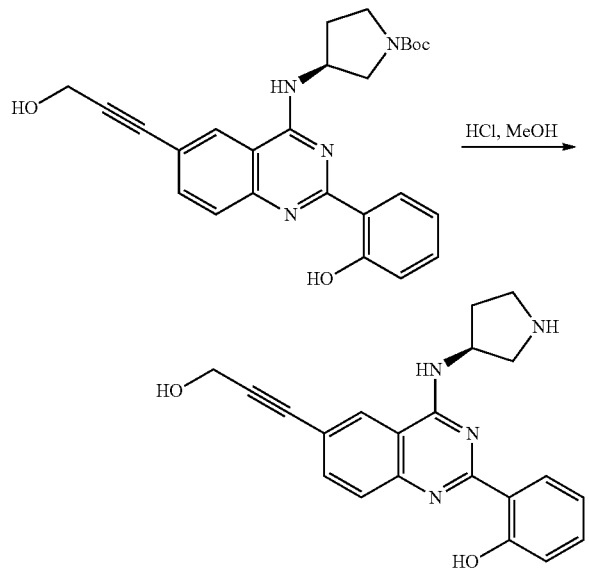

(S)-tert-Butyl 3-(2-(2-hydroxyphenyl)-6-(3-hydroxyprop-1-ynyl)quinazolin-4-ylamino)pyrrolidine-1-carboxylate (0.028 g, 0.061 mmol) was dissolved in methanol (1 mL) and 4 M HCl in dioxane (2 mL) added. After stirring for 12 hours, the solution was concentrated and purified by ion exchange chromatography on SCX-2 (solute acidic resin (2 g), eluting with methanol and then 1 M ammonia in methanol. Further purification by preparative thin layer chromatography, eluting with 20% methanol in dichloromethane, gave the title compound as a yellow solid (0.006 g, 27%).

LC-MS (LCT2) m/z 361 [M+H$^+$], R$_t$ 3.16 minutes. $^1$H NMR (MeOD) δ 8.45 (dd, J 8.0, 2.0 Hz, 1H), 8.27 (d, J 1.5 Hz, 1H), 7.71 (dd, J 8.5, 1.5 Hz, 1H), 7.62 (d, J 8.5 Hz, 1H), 7.33 (ddd, J 8.5, 7.5, 2.0 Hz, 1H), 6.91-6.88 (m, 2H), 4.87-4.83 (m, 1H), 4.45 (s, 2H), 3.42 (dd, J 12.0, 6.5 Hz, 1H), 3.23-3.28 (m, 1H), 3.10-3.03 (m, 2H), 2.41-2.33 (m, 1H), 2.07-2.00 (m, 1H).

Synthesis 60

(S)-2-(6-(3-Hydroxyprop-1-ynyl)-4-(pyrrolidin-3-ylamino)quinazolin-2-yl)phenol (A-053)

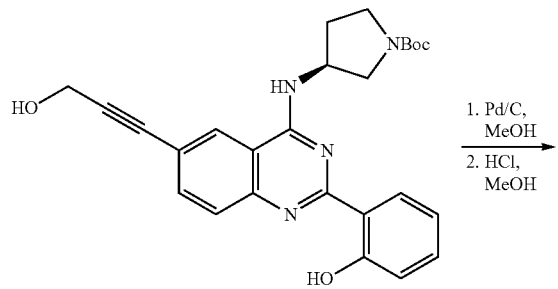

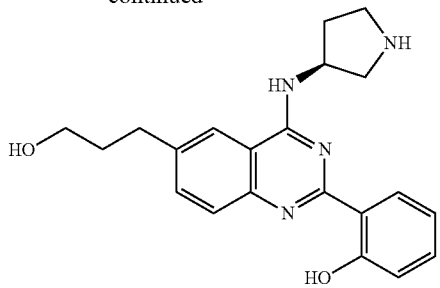

(S)-tert-Butyl 3-(2-(2-hydroxyphenyl)-6-(3-hydroxyprop-1-ynyl)quinazolin-4-ylamino)pyrrolidine-1-carboxylate (prepared as shown in Synthesis 59-A, 0.030 g, 0.065 mmol) in methanol (3 mL) was hydrogenated at atmospheric pressure in the presence of 10% Pd on carbon (0.003 g) for 16 hours. The mixture was filtered through a pad of kieselguhr and concentrated. The crude alcohol was dissolved in methanol (1 mL) and 4 M HCl in dioxane (2 mL) added. After stirring for 12 hours, the solution was concentrated and purified by ion exchange chromatography on SCX-2 (solute acidic resin (2 g), eluting with methanol and then 1 M ammonia in methanol. Further purification by preparative thin layer chromatography, eluting with 20% methanol in dichloromethane, gave the title compound as a yellow solid (0.006 g, 25%).

LC-MS (LCT2) m/z 365 [M+H$^+$], R$_t$ 2.70 minutes. $^1$H NMR (MeOD) δ 8.50 (dd, J 8.0, 1.5 Hz, 1H), 8.04 (s, 1H), 7.69-7.68 (m, 2H), 7.33 (ddd, J 8.0, 7.0, 2.0 Hz, 1H), 6.94-6.90 (m, 2H), 4.97-4.92 (m, 1H), 3.63 (t, J 6.5 Hz, 2H), 3.53 (dd, J 12.0, 6.5 Hz, 1H), 3.30-3.27 (m, 1H), 3.20-2.12 (m, 2H), 2.89 (t, J 7.5 Hz, 2H), 2.47-2.40 (m, 1H), 2.17-2.10 (m, 1H), 1.98-1.92 (m, 2H).

Synthesis 61

(S)-2-(7-(3-Hydroxyprop-1-ynyl)-4-(pyrrolidin-3-ylamino)quinazolin-2-yl)phenol (A-054)

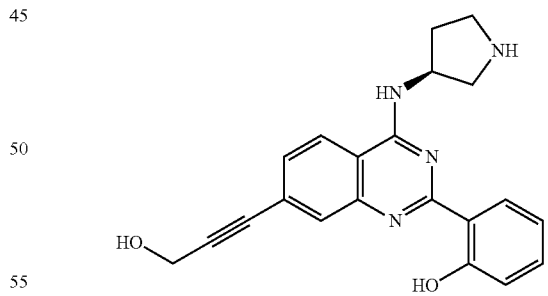

The title compound was prepared using a method analogous to that described in Synthesis 59, replacing (S)-tert-butyl 3-(6-bromo-2-(2-hydroxyphenyl)quinazolin-4-ylamino)pyrrolidine-1-carboxylate with (S)-tert-butyl 3-(7-bromo-2-(2-hydroxyphenyl)quinazolin-4-ylamino)pyrrolidine-1-carboxylate in Synthesis 59-A.

LC-MS (LCT2) m/z 361 [M+H$^+$], R$_t$ 2.95 minutes. $^1$H NMR (MeOD) δ 8.45 (d, J 8.0 Hz, 1H), 8.10 (d, J 8.5 Hz, 1H), 7.72 (s, 1H), 7.44 (d, J 8.5 Hz, 1H), 7.34 (ddd, J 8.5, 7.5, 1.5 Hz, 1H), 6.93-6.89 (m, 2H), 4.91-4.88 (m, 1H), 4.47 (s, 2H), 3.54 (dd, J 12.0, 6.5 Hz, 1H), 3.31-3.28 (m, 2H), 3.21-3.13 (m, 2H), 2.46-2.39 (m, 1H), 2.15-2.09 (m, 1H).

Synthesis 62

(S)-2-(7-(3-Hydroxypropyl)-4-(pyrrolidin-3-ylamino)quinazolin-2-yl)phenol (A-055)

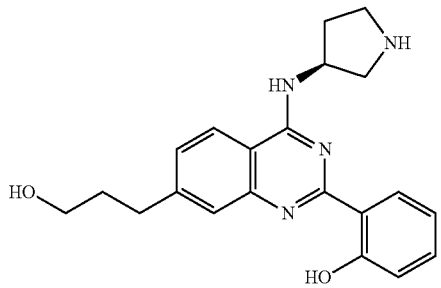

The title compound was prepared using methods analogous to those described in Synthesis 59 and 60, replacing (S)-tert-butyl 3-(6-bromo-2-(2-hydroxyphenyl)quinazolin-4-ylamino)pyrrolidine-1-carboxylate with (S)-tert-butyl 3-(7-bromo-2-(2-hydroxyphenyl)quinazolin-4-ylamino)pyrrolidine-1-carboxylate in Synthesis 59-A.

LC-MS (LCT2) m/z 365 [M+H$^+$], R$_t$ 2.46 minutes. $^1$H NMR (MeOD) δ 8.52 (dd, J 8.0, 1.5 Hz, 1H), 8.16 (d, J 8.5 Hz, 1H), 7.61 (s, 1H), 7.43 (dd, J 8.5, 1.5 Hz, 1H), 7.35 (ddd, J 8.0, 7.5, 1.5 Hz, 1H), 6.95-6.91 (m, 2H), 5.06-5.01 (m, 1H), 3.70 (dd, J 12.0, 6.5 Hz, 1H), 3.65 (t, J 6.5 Hz, 2H), 3.49-3.44 (m, 1H), 3.37-3.31 (m, 2H), 2.90 (t, J 8.0 Hz, 2H), 2.55-2.47 (m, 1H), 2.31-2.24 (m, 1H), 1.99-1.94 (m, 2H).

Synthesis 63

2-(4-(Azepan-4-ylamino)quinazolin-2-yl)phenol (A-056)

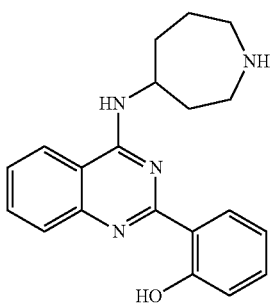

The title compound was prepared using a method analogous to that described in Synthesis 52, replacing tert-butyl-3-aminoazepane-1-carboxylate with tert-butyl 4-aminoazepane-1-carboxylate in Synthesis 52-B.

LC-MS (LCT2B) m/z 335 [M+H$^+$], Rt 2.34 minutes. $^1$H NMR (500 MHz, CDCl$_3$) δ 14.95 (s, 1H), 8.50 (dd, J 8.0, 2.0 Hz, 1H), 7.78-7.65 (m, 3H), 7.42-7.36 (m, 1H), 7.36-7.29 (m, 1H), 7.22 (d, J 8.0 Hz, 1H), 6.99 (dd, J 8.0, 1.0 Hz, 1H), 6.94-6.87 (m, 1H), 4.97 (s, 1H), 3.21-3.05 (m, 2H), 2.98 (dt, J 13.0, 6.5 Hz, 1H), 2.74 (ddd, J 13.0, 9.0, 4.0 Hz, 1H), 2.21-2.11 (m, 1H), 2.11-1.97 (m, 2H), 1.87-1.78 (m, 1H), 1.78-1.68 (m, 2H).

Synthesis 64

2-(4-(Azepan-4-ylamino)quinazolin-2-yl)-4-chlorophenol (A-057)

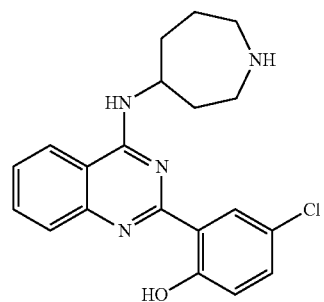

The title compound was prepared using a method analogous to that described in Synthesis 52, replacing 4-chloro-2-(2-methoxyphenyl)quinazoline with 4-chloro-2-(5-chloro-2-methoxyphenyl)quinazoline in Synthesis 52-A and tert-butyl-3-aminoazepane-1-carboxylate with tert-butyl-4-aminoazepane-1-carboxylate in Synthesis 52-B.

LC-MS (LCT2B) m/z 369 [M+H$^+$], Rt 3.05 minutes. $^1$H NMR (500 MHz, MeOD) δ 8.31 (d, J 2.5 Hz, 1H), 8.06 (d, J 8.0 Hz, 1H), 7.72-7.66 (m, 1H), 7.60 (d, J 8.0 Hz, 1H), 7.44-7.37 (m, 1H), 7.22 (dd, J 8.5, 2.5 Hz, 1H), 6.83 (d, J 8.5 Hz, 1H), 4.48 (ddd, J 13.5, 9.5, 4.0 Hz, 1H), 3.10 (tt, J 20.0, 9.0 Hz, 1H), 3.06-2.90 (m, 3H), 2.26 (dd, J 19.0, 12.0 Hz, 1H), 2.19 (dd, J 9.0, 6.0 Hz, 1H), 1.98-1.80 (m, 4H).

Synthesis 65

2-(4-(Azepan-3-ylamino)quinazolin-2-yl)-4-chlorophenol (A-058)

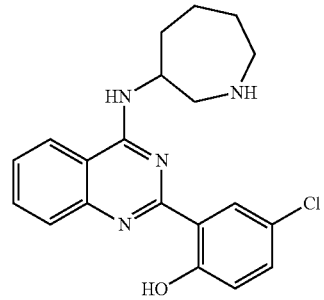

The title compound was prepared using a method analogous to that described in Synthesis 52, replacing 4-chloro-2-(2-methoxyphenyl)quinazoline with 4-chloro-2-(5-chloro-2-methoxyphenyl)quinazoline in Synthesis 52-A.

LC-MS (LCT2B) m/z 369 [M+H$^+$], Rt 3.07 minutes. $^1$H NMR (500 MHz, MeOD) δ 8.45 (d, J 2.0 Hz, 1H), 8.21 (d, J 8.5 Hz, 1H), 7.84-7.77 (m, 1H), 7.75 (d, J 7.5 Hz, 1H), 7.53 (s, 1H), 7.30 (dd, J 8.5, 3.0 Hz, 1H), 6.92 (d, J 8.5 Hz, 1H), 4.83-4.73 (m, 1H) 3.12-2.90 (m, 4H), 2.30-2.20 (m, 1H), 2.01-1.86 (m, 3H), 1.85-1.70 (m, 2H).

Synthesis 66

2-(4-(Azepan-3-ylamino)quinazolin-2-yl)-4-fluorophenol (A-059)

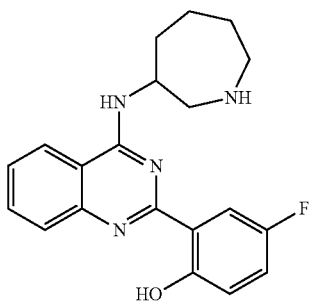

The title compound was prepared using a method analogous to that described in Synthesis 52, replacing 4-chloro-2-(2-methoxyphenyl)quinazoline with 4-chloro-2-(5-fluoro-2-methoxyphenyl)quinazoline in Synthesis 52-A.

LC-MS (LCT2B) m/z 353 [M+H$^+$], Rt 2.85 minutes. $^1$H NMR (500 MHz, MeOD) δ 8.23-8.13 (m, 2H), 7.79 (t, J 7.5 Hz, 1H), 7.74 (d, J 8.5 Hz, 1H), 7.52 (t, J 7.5 Hz, 1H), 7.09 (td, J 3.0, 8.5 Hz, 1H), 6.91 (dd, J 9.0, 4.5 Hz, 1H), 4.78-4.68 (m, 1H), 3.39 (dd, J 13.5, 4.5 Hz, 1H), 3.15-2.97 (m, 3H), 2.32-2.17 (m, 1H), 2.00-1.86 (m, 3H), 1.88-1.68 (m, 2H).

Synthesis 67

2-(4-(Azepan-4-ylamino)quinazolin-2-yl)-4-fluorophenol (A-060)

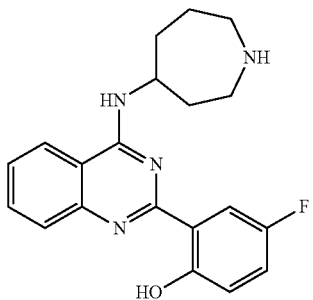

The title compound was prepared using a method analogous to that described in Synthesis 52, replacing 4-chloro-2-(2-methoxyphenyl)quinazoline with 4-chloro-2-(5-fluoro-2-methoxyphenyl)quinazoline in Synthesis 52-A and tert-butyl-3-aminoazepane-1-carboxylate with tert-butyl-4-aminoazepane-1-carboxylate in Synthesis 52-B.

LC-MS (LCT2B) m/z 353 [M+H$^+$], Rt 2.72 minutes. $^1$H NMR (500 MHz, MeOD) δ 8.03 (dd, J 10.0, 3.5 Hz, 2H), 7.70-7.61 (m, 1H), 7.58 (d, J 8.0 Hz, 1H), 7.41-7.33 (m, 1H), 7.06-6.97 (m, 1H), 6.83 (dd, J 9.0, 4.5 Hz, 1H), 4.49 (m, 1H), 3.17-3.05 (m, 1H), 3.05-2.89 (m, 3H), 2.34-2.20 (m, 1H), 2.20-2.11 (m, 1H), 1.97-1.74 (m, 4H).

Synthesis 68

(2R,4S)-4-(2-(5-Fluoro-2-hydroxyphenyl)-7-(3-hydroxypropyl)quinazolin-4-ylamino)-N,N-dimethylpyrrolidine-2-carboxamide (A-061)

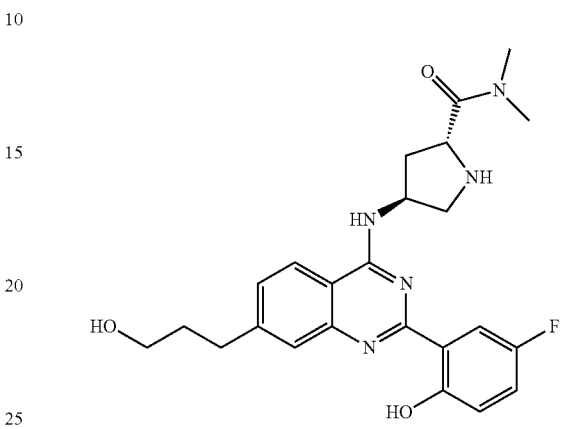

The title compound was prepared using methods analogous to those described in Synthesis 37 and 62, replacing 4-chloro-2-(2-methoxyphenyl)quinazoline with 7-bromo-4-chloro-2-(5-fluoro-2-methoxyphenyl)quinazoline in Synthesis 37-A. 7-Bromo-4-chloro-2-(5-fluoro-2-methoxyphenyl)quinazoline was prepared using methods analogous to those described in Synthesis 1-A, replacing 2-methoxybenzoyl chloride with 5-fluoro-2-methoxybenzoyl chloride and anthranilonitrile with 4-bromo-2-nitrobenzonitrile.

LC-MS (LCT3B) m/z 454 [M+H$^+$], R$_t$ 2.06 minutes. $^1$H NMR (CDCl$_3$) δ 14.61 (br s, 1H), 8.15 (dd, J 10.0, 3.5 Hz, 1H), 7.96 (d, J 8.5 Hz, 1H), 7.60 (s, 1H), 7.32 (dd, J 8.5, 1.5 Hz, 1H), 7.07 (ddd, J 9.0, 8.0, 3.5 Hz, 1H), 6.96 (dd, J 9.0, 4.5 Hz, 1H), 5.06-5.02 (m, 1H), 4.16 (t, J 8.0 Hz, 1H), 3.75 (t, J 6.5 Hz, 2H), 3.52 (dd, J 11.0, 5.0 Hz, 1H), 3.20 (d, J 11.0 Hz, 1H), 3.02 (s, 3H), 2.97 s, 3H), 2.90 (t, J 7.5 Hz, 2H), 2.56 (dd, J 13.5, 8.5 Hz, 1H), 2.22 (ddd, J 13.5, 8.0, 6.0 Hz, 1H), 2.05-1.99 (m, 2H).

Synthesis 69

(S)-2-(7-Chloro-4-(pyrrolidin-3-ylamino)quinazolin-2-yl)phenol (A-062)

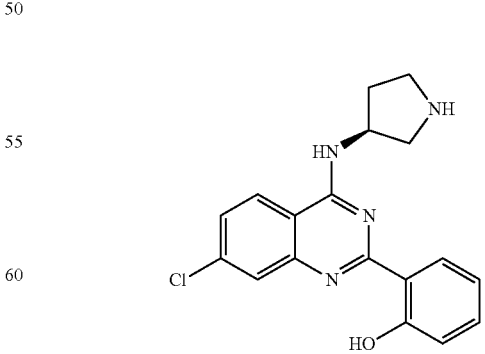

The title compound was prepared using a method analogous to that described in Synthesis 1, replacing anthranilonitrile with 2-amino-4-chlorobenzonitrile in Synthesis 1-A.

LC-MS (LCT2B) m/z 341 [M+H⁺], R$_t$ 3.56 minutes. ¹H NMR (CDCl₃) δ 8.58 (br s, 1H), 8.43-8.40 (m, 2H), 8.16 (d, J 9.0 Hz, 1H), 7.75 (d, J 2.0 Hz, 1H), 7.40 (dd, J 9.0, 2.0 Hz, 1H), 7.36 (ddd, J 8.5, 7.5, 2.0 Hz, 1H), 7.01 (dd, J 8.5, 1.0 Hz, 1H), 6.90 (ddd, J 8.5, 7.5, 1.0 Hz, 1H), 5.35-5.31 (m, 1H), 3.69 (d, J 12.5 Hz, 1H), 3.61-3.55 (m, 1H), 3.47-3.40 (m, 2H), 2.55-2.43 (m, 2H).

Synthesis 70

4-Chloro-2-(4-(trans-4-phenylpyrrolidin-3-ylamino)quinazolin-2-yl)phenol (A-063)

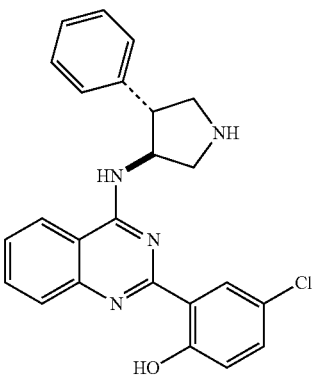

The title compound was prepared using a method analogous to that described in Synthesis 2, replacing (R)-3-amino-piperidine-1-carboxylic acid tert-butyl ester with tert-butyl-trans-3-amino-4-phenylpyrrolidine-1-carboxylate in Synthesis 2-A.

LC-MS (LCT2B) m/z 417 [Cl³⁵M⁺H⁺], Rt 3.35 minutes. ¹H NMR (500 MHz, MeOD) δ 8.20 (d, J 2.5 Hz, 1H), 8.15 (d, J 7.5 Hz, 1H), 7.77-7.70 (m, 1H), 7.64 (d, J 7.5 Hz, 1H), 7.51-7.45 (m, 1H), 7.44 (d, J 7.0 Hz, 2H), 7.32 (t, J 8.0 Hz, 2H), 7.24 (dd, J 8.5, 3.0 Hz, 1H), 7.18 (t, J 7.5 Hz, 1H), 6.86 (d, J 8.5 Hz, 1H), 5.30-5.22 (m, 1H), 3.79-3.58 (m, 2H), 3.58-3.47 (m, 1H), 3.19 (s, 2H).

Synthesis 71

3-(2-(5-Chloro-2-hydroxyphenyl)quinazolin-4-ylamino)pyrrolidine-3-carboxylic acid (A-064)

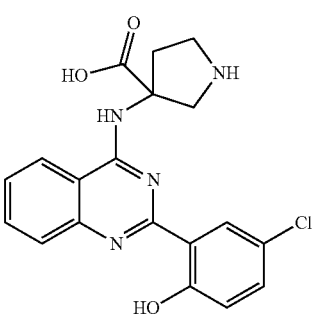

The title compound was prepared in a method analogous to that described in Synthesis 2, replacing 2-methoxybenzoyl chloride and (R)-3-amino-piperidine-1-carboxylic acid tert-butyl ester with 5-chloro-2-methoxybenzoyl chloride and 3-amino-1-(tert-butoxycarbonyl)pyrrolidine-3-carboxylic acid.

LC-MS (LCT2B) m/z 385 [Cl³⁵M⁺H⁺], Rt 2.91 minutes.

Synthesis 72-A (S)-tert-Butyl 3-(7-bromo-2-(2-hydroxyphenyl)quinazolin-4-ylamino)pyrrolidine-1-carboxylate

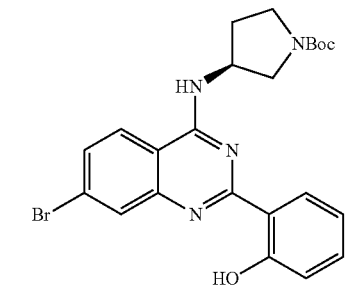

The title compound was prepared from 2-methoxybenzoyl chloride, 2-amino-4-bromobenzonitrile and (S)-3-amino-piperidine-1-carboxylic acid tert-butyl ester using methods analogous to those described in Synthesis 1, steps 1-A, 2-B and 1-D.

Synthesis 72-B (S)-2-(7-(1H-Pyrazol-4-yl)-4-(pyrrolidin-3-ylamino)quinazolin-2-yl)phenol (A-065)

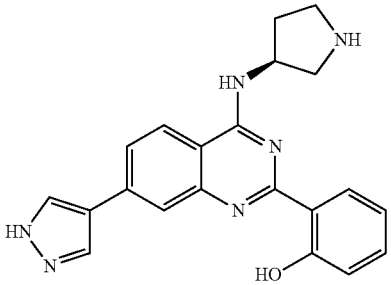

Nitrogen gas was bubbled through a mixture of toluene (1 mL), n-butanol (1.5 mL) and 2M aqueous Na₂CO₃ (1.5 mL) for 30 min. (S)-2-(7-(1H-Pyrazol-4-yl)-4-(pyrrolidin-3-ylamino)quinazolin-2-yl)phenol (0.097 g, 0.200 mmol), Pd(PPh₃)₄ (0.014 g, 0.012 mmol) and tert-butyl 4-(4,4,5,5-tetramethyl-1,3,2-dioxaborolan-2-yl)-1H-pyrazole-1-carboxylate (0.177 g, 0.600 mmol) were added and the resulting mixture heated at 110° C. in a sealed tube. After 6 h, water was added (50 mL) and the mixture extracted with ethyl acetate (2×50 mL). Organic phases were combined, dried (MgSO₄) and concentrated. The crude solid obtained was stirred with methanol (3 mL) and 4M HCl in dioxane (7 mL) for 24 h. The mixture was concentrated and the crude purified by ion exchange chromatography on SCX-2 Isolute acidic resin (2 g), eluting with methanol and then 1 M ammonia in methanol. Further purification by preparative thin layer chromatography, eluting with 20% methanol in dichloromethane, gave the title compound as a solid (0.023 g, 31%).

LC-MS (LCT3B) m/z 373 [M+H⁺], R$_t$ 1.77 minutes. ¹H NMR (MeOD) δ 8.44 (dd, J 8.0, 1.5 Hz, 1H), 8.11 (s, 2H), 8.04 (d, J 8.5 Hz, 1H), 7.78 (d, J 1.5 Hz, 1H), 7.63 (dd, J 8.5, 1.5 Hz, 1H), 7.32 (ddd, J 8.5, 7.0, 1.5 Hz, 1H), 6.92-6.87 (m, 2H), 4.79-4.74 (m, 1H), 3.36 (dd, J 12.0, 6.5 Hz, 1H), 3.17-3.12 (m, 1H), 3.04-2.95 (m, 2H), 2.36-2.29 (m, 1H), 2.01-1.95 (m, 1H).

Synthesis 73

(S)-2-(7-(1-Methyl-1H-pyrazol-4-yl)-4-(pyrrolidin-3-ylamino)quinazolin-2-yl)phenol (A-066)

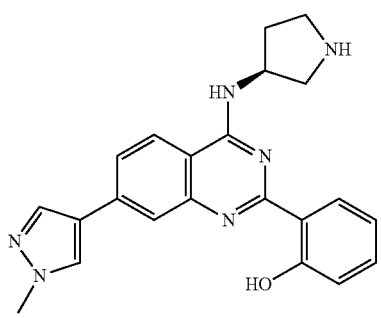

The title compound was prepared from 2-methoxybenzoyl chloride, 2-amino-4-bromobenzonitrile, (S)-3-amino-piperidine-1-carboxylic acid tert-butyl ester and 1-methyl-4-(4,4,5,5-tetramethyl-1,3,2-dioxaborolan-2-yl)-1H-pyrazole using methods analogous to those described in Synthesis 72.

LC-MS (LCT3B) m/z 387 [M+H⁺], R$_t$ 1.88 minutes. ¹H NMR (MeOD) δ 8.42 (dd, J 8.0, 1.5 Hz, 1H), 8.00 (s, 1H), 7.99 (d, J 8.5 Hz), 7.89 (s, 1H), 7.65 (s, 1H), 7.54 (d, J 8.5 Hz, 1H), 7.32 (ddd, J 8.5, 7.5, 1.5 Hz, 1H), 6.91-6.87 (m, 2H), 4.77-4.73 (m, 1H), 3.91 (s, 3H), 3.37-3.33 (m, 1H), 3.17-3.11 (m, 1H), 3.04-2.94 (m, 2H), 2.36-2.28 (m, 1H), 1.99-1.93 (m, 1H).

Synthesis 74-A 7-(2-Methoxyethoxy)quinazoline-2,4-diol

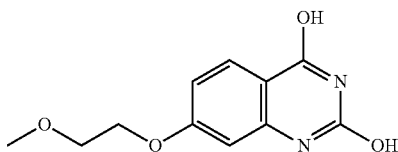

Sodium hydride (0.803 g of a 60% dispersion in mineral oil, 20.084 mmol) was added to a solution of methyl 4-fluoro-2-nitrobenzoate (1.000 g, 5.021 mmol) and 2-methoxyethoxyethanol (1.58 mL, 20.084 mmol) in DMF (25 mL) at 0° C. After heating to 90° C. for 24 h, the reaction mixture was cooled, water (250 mL) added and the aqueous layer washed with ethyl acetate (50 mL). The aqueous phase was acidified to pH 2 using 1M HCl and extracted with ethyl acetate (3×50 mL). The combined organic extracts were dried (MgSO$_4$) and concentrated. The resulting oil was dissolved in ethanol (22 mL), palladium on carbon (0.060 g, 5 wt %) added and the mixture stirred under a hydrogen atmosphere for 2 h. The reaction mixture was filtered through a pad of celite, washing with ethanol, and the filtrate concentrated. The crude aniline obtained was heated with urea (2.91 g, 48.51 mmol) to 150° C. for 14 h. Water (30 mL) was cautiously added to the melt and allowed to cool. Exhaustive extraction with ethyl acetate and concentration of the organic extracts gave the crude title compound (0.710 g, 60% crude yield).

LC-MS (LCT2B) m/z 237 [M+H⁺], R$_t$ 2.96 minutes.

Synthesis 74-B (S)-2-(7-(2-Methoxyethoxy)-4-(pyrrolidin-3-ylamino)quinazolin-2-yl)phenol (A-067)

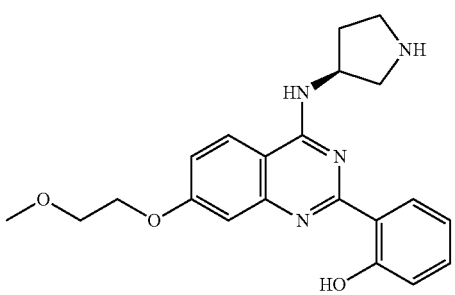

The title compound was prepared using methods analogous to those described in Synthesis 30-A, 30-B and 2-B, replacing 5-methyl-2-methoxyphenylboronic acid with 2-hydroxyphenylboronic acid in Synthesis 30-B.

LC-MS (LCT3B) m/z 381 [M+H⁺], R$_t$ 1.75 minutes. ¹H NMR (MeOD) δ 8.48 (dd, J 8.0, 1.5 Hz, 1H), 8.01 (d, J 9.0 Hz, 1H), 7.32 (ddd, J 8.5, 7.5, 1.5 Hz, 1H), 7.06-7.03 (m, 2H), 6.92-6.86 (m, 2H), 4.81-4.79 (m, 1H), 4.24-4.22 (m, 2H), 3.80-3.78 (m, 2H), 3.45 (s, 3H), 3.44-3.38 (m, 1H), 3.21-3.16 (m, 1H), 3.09-2.99 (m, 2H), 2.39-2.32 (m, 1H), 2.04-1.98 (m, 1H).

Synthesis 75

(S)-2-(7-(1H-Pyrazol-4-yl)-4-(pyrrolidin-3-ylamino)quinazolin-2-yl)-4-fluorophenol (A-068)

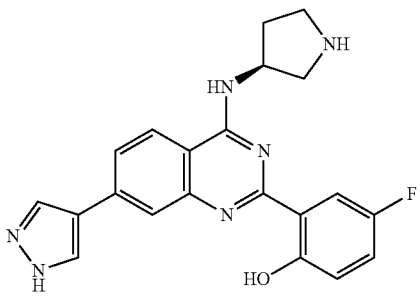

The title compound was prepared from 5-fluoro-2-methoxybenzoyl chloride, 2-amino-4-bromobenzonitrile, (S)-3-amino-piperidine-1-carboxylic acid tert-butyl ester and tert-butyl 4-(4,4,5,5-tetramethyl-1,3,2-dioxaborolan-2-yl)-1H-pyrazole-1-carboxylate using methods analogous to those described in Synthesis 72.

LC-MS (LCT3B) m/z 391 [M+H⁺], R$_t$ 2.01 minutes. ¹H NMR (MeOD) δ 8.13 (s, 2H), 8.12-8.07 (m, 2H), 7.82 (s, 1H), 7.68 (d, J 8.5 Hz, 1H), 7.06 (ddd, J 8.5, 8.0, 3.5 Hz, 1H), 6.88 (dd, J 9.0, 4.5 Hz, 1H), 4.80-4.84 (m, 1H, partially obscured by water peak), 3.40-3.36 (m, 1H), 3.18-3.13 (m, 1H), 3.06-3.01 (m, 1H), 2.98 (dd, J 12.0, 5.0 Hz, 1H), 2.39-2.32 (m, 1H), 2.02-1.96 (m, 1H).

Synthesis 76-A (S)-tert-Butyl 3-(2-chloro-6,7-dimethoxyquinazolin-4-ylamino)pyrrolidine-1-carboxylate

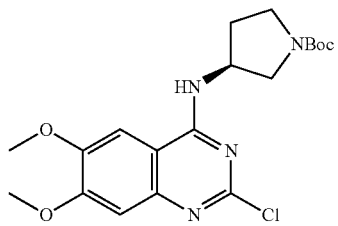

The title compound was prepared using a method analogous to that described in Synthesis 30-A, replacing quinazoline-2,4-dione with 6,7-dimethoxyquinazoline-2,4-diol.
LC-MS (LCT3B) m/z 409 [M+H$^+$], R$_t$ 2.72 minutes.

Synthesis 76-B (S)-2-(6,7-Dimethoxy-4-(pyrrolidin-3-ylamino)quinazolin-2-yl)phenol (A-069)

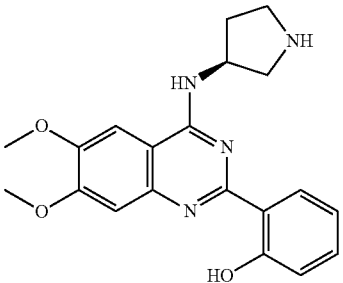

(S)-2-(6,7-Dimethoxy-4-(pyrrolidin-3-ylamino)quinazolin-2-yl)phenol (0.818 g, 2.000 mmol), 2-hydroxyphenylboronic acid (0.276 g, 2.000 mmol), sodium carbonate (0.636 g, 6.000 mmol) and Pd(PPh$_3$)$_4$ (0.116 g, 0.100 mmol) were added to a degassed mixture of toluene (5 mL) and water (2 mL), and the mixture heated for 24 hours. After cooling, water (100 mL) was added and the aqueous layer was extracted with ethyl acetate (2×100 mL). The organic layers were combined, dried (MgSO$_4$), and concentrated. The crude product was purified by silica gel chromatography (5% methanol in dichlormethane) to give the Boc-protected product (0.383 g, 41%). A portion (0.100 g, 0.214 mmol) was stirred with methanol (3 mL) and 4M HCl in dioxane (7 mL) for 20 h. The mixture was concentrated and the crude purified by ion exchange chromatography on SCX-2 Isolute acidic resin (2 g), eluting with methanol and then 1 M ammonia in methanol. Further purification by silica column chromatography (3 cm plug of silica), eluting with 20% methanol in dichloromethane, gave the title compound as a solid (0.058 g, 74%).

LC-MS (LCT3B) m/z 367 [M+H$^+$], R$_t$ 1.69 minutes. $^1$H NMR (CDCl$_3$) δ 8.53 (dd, J 8.0, 1.5 Hz, 1H), 7.35 (ddd, J 8.5, 7.0, 1.5 Hz, 1H), 7.16 (s, 1H), 7.03 (dd, J 8.0, 1.0 Hz, 1H), 7.00 (s, 1H), 6.96-6.92 (m, 1H), 6.00 (d, J 6.5 Hz, 1H), 5.00-4.94 (m, 1H), 4.04 (s, 3H), 4.03 (s, 3H), 3.38 (dd, J 11.0, 6.0 Hz, 1H), 3.24-3.19 (m, 1H), 3.12-3.03 (m, 2H), 2.48-2.40 (m, 1H), 1.96-1.90 (m, 1H, partially obscured by water peak).

Synthesis 77

(S)-2-(6,7-Dimethoxy-4-(pyrrolidin-3-ylamino)quinazolin-2-yl)-4-fluorophenol (A-070)

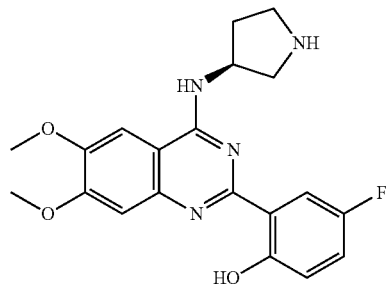

The title compound was prepared using a method analogous to that described in Synthesis 76, replacing 2-hydroxyphenylboronic acid with 5-fluoro-2-hydroxyphenylboronic acid in Synthesis 76-B.
LC-MS (LCT3B) m/z 385 [M+H$^+$], R$_t$ 2.01 minutes. $^1$H NMR (CDCl$_3$) δ 8.18 (dd, J 10.0, 3.5 Hz, 1H), 7.12 (s, 1H), 7.07-7.03 (m, 1H), 7.05 (s, 1H), 6.95 (dd, J 9.0, 5.0 Hz, 1H), 6.26 (d, J 7.0 Hz, 1H), 4.99-4.94 (m, 1H), 4.02 (s, 3H), 4.02 (s, 3H), 3.32 (dd, J 11.0, 6.0 Hz, 1H), 3.22-3.17 (m, 1H), 3.10-3.02 (m, 2H), 2.46-2.39 (m, 1H), 1.95-1.89 (m, 1H).

Synthesis 78

(S)-4-Fluoro-2-(7-(3-hydroxypropyl)-4-(pyrrolidin-3-ylamino)quinazolin-2-yl)phenol (A-071)

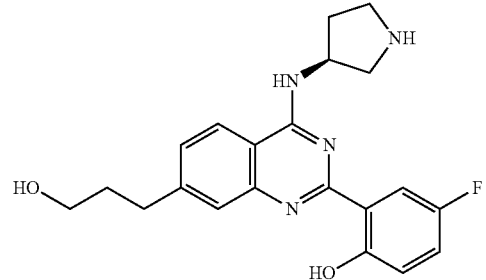

The title compound was prepared using methods analogous to those described in Synthesis 59 and 60, replacing (S)-tert-butyl 3-(6-bromo-2-(2-hydroxyphenyl)quinazolin-4-ylamino)pyrrolidine-1-carboxylate with (S)-tert-butyl 3-(7-bromo-2-(5-fluoro-2-hydroxyphenyl)quinazolin-4-ylamino)pyrrolidine-1-carboxylate in Synthesis 59-A.

LC-MS (LCT3B) m/z 383 [M+H$^+$], R$_t$ 1.96 minutes. $^1$H NMR (DMSO) δ 8.36 (br s, 1H), 8.33 (d, J 8.5 Hz, 1H), 8.14 (dd, J 10.0, 3.5 Hz, 1H), 7.57 (s, 1H), 7.42 (dd, J 8.5, 1.5 Hz, 1H), 7.21 (dt, J 8.5, 1.5 Hz, 1H), 6.93 (dd, J 9.0, 5.0 Hz, 1H), 4.72 (br s, 1H), 4.50 (br s, 1H), 4.06 (br s, 1H), 3.46-3.43 (m, 1H), 3.20-3.15 (m, 1H), 3.00-2.95 (m, 1H), 2.87-2.82 (m, 2H), 2.80 (t, J 8.0 Hz, 2H), 2.21-2.14 (m, 1H), 1.89-1.79 (m, 3H).

Synthesis 79

(S)-4-Fluoro-2-(7-(3-hydroxyprop-1-ynyl)-4-(pyrrolidin-3-ylamino)quinazolin-2-yl)phenol (A-072)

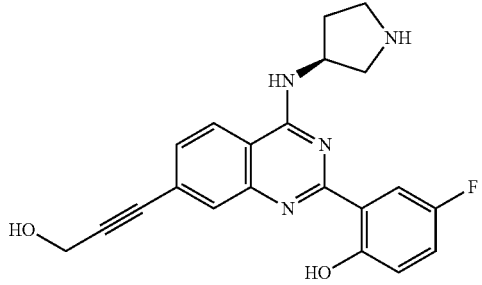

The title compound was prepared using methods analogous to those described in Synthesis 59, replacing (S)-tert-butyl 3-(6-bromo-2-(2-hydroxyphenyl)quinazolin-4-ylamino)pyrrolidine-1-carboxylate with (S)-tert-butyl 3-(7-bromo-2-(5-fluoro-2-hydroxyphenyl)quinazolin-4-ylamino)pyrrolidine-1-carboxylate in Synthesis 59-A.

LC-MS (LCT3B) m/z 379 [M+H$^+$], R$_t$ 2.09 minutes. $^1$H NMR (DMSO) δ 8.52 (br, s, 1H), 8.42 (d, J 9.0 Hz, 1H), 8.13 (dd, J 10.0, 3.5 Hz, 1H), 7.79 (d, J 1.5 Hz, 1H), 7.55 (dd, J 8.5, 1.5 Hz, 1H), 7.23 (dt, J 8.5, 3.5 Hz, 1H), 6.94 (dd, J 9.0, 5.0 Hz, 1H), 5.42 (br s, 1H), 4.71 (br s, 1H), 4.37 (s, 2H), 3.21-3.19 (m, 1H), 3.00-2.94 (m, 1H), 2.88-2.82 (m, 2H), 2.21-2.14 (m, 1H), 1.90-1.83 (m, 1H).

Synthesis 80-A

6-Methoxyquinazoline-2,4-diol

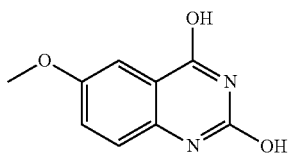

2-Amino-5-methoxybenzoic acid (5.090 g, 30.45 mmol) was heated with urea (18.300 g, 304.50 mmol) to 150° C. for 24 h. Water (150 mL) was cautiously added to the melt and allowed to cool. The resulting precipitate was filtered off and dried to give a solid (4.189 g, 72%).

LC-MS (LCT3B) m/z 193 [M+H$^+$], R$_t$ 1.60 minutes. $^1$H NMR (DMSO) δ 7.33 (d, J 3.0 Hz, 1H), 7.27 (dd, J 9.0, 3.0 Hz, 1H), 7.12 (d, J 9.0 Hz, 1H), 3.78 (s, 3H).

Synthesis 80-B (S)-4-Fluoro-2-(6-methoxy-4-(pyrrolidin-3-ylamino)quinazolin-2-yl)phenol (A-073)

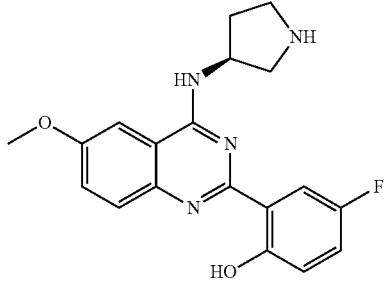

The title compound was prepared using methods analogous to those described in Synthesis 30-A and 76, replacing quinazoline-2,4-dione with 6-methoxyquinazoline-2,4-diol in Synthesis 30-A and replacing 2-hydroxyphenylboronic acid with 5-fluoro-2-hydroxyphenylboronic acid in Synthesis 76-B.

LC-MS (LCT3B) m/z 355 [M+H$^+$], R$_t$ 2.19 minutes. $^1$H NMR (DMSO) δ 8.27 (br s, 1H), 8.12 (dd, J 10.0, 3.5 Hz, 1H), 7.82 (d, J 2.5 Hz, 1H), 7.73 (d, J 9.0 Hz, 1H), 7.46 (dd, J 9.0, 2.5 Hz, 1H), 7.19 (dt, J 9.0, 3.5 Hz, 1H), 6.92 (dd, J 9.0, 5.0 Hz, 1H), 4.75-4.69 (m, 1H), 3.93 (s, 3H), 3.25 (dd, J 11.5, 7.0 Hz, 1H), 3.01-2.96 (m, 1H), 2.91-2.83 (m, 2H), 2.24-2.17 (m, 1H), 1.90-1.84 9m, 1H).

Synthesis 81

(S)-4-Fluoro-2-(7-methoxy-4-(pyrrolidin-3-ylamino)quinazolin-2-yl)phenol (A-074)

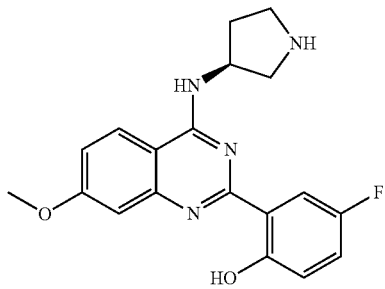

The title compound was prepared using a method analogous to that described in Synthesis 80, replacing 2-amino-5-methoxybenzoic acid with 2-amino-4-methoxybenzoic acid in Synthesis 80-A.

LC-MS (LCT3B) m/z 355 [M+H$^+$], R$_t$ 2.13 minutes. $^1$H NMR (DMSO) δ 8.35-8.30 (m, 2H), 8.13 (dd, J 10.0, 3.0, 1H), 7.23-7.19 (m, 2H), 7.14 (dd, J 9.0, 2.5 Hz, 1H), 6.93 (dd, J 9.0, 5.0 Hz, 1H), 4.70 (br s, 1H), 3.93 (s, 3H), 3.20-3.16 (m, 1H), 3.01-2.96 (m, 1H), 2.89-2.83 (m, 2H), 2.21-2.14 (m, 1H), 1.89-1.82 (m, 1H).

Synthesis 82

(S)-2-(6-Methoxy-4-(pyrrolidin-3-ylamino)quinazolin-2-yl)phenol (A-075)

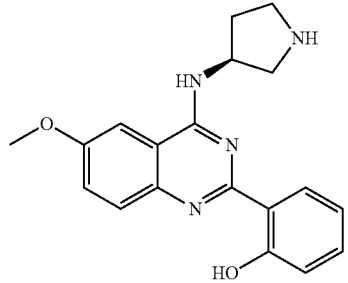

The title compound was prepared using a method analogous to that described in Synthesis 80, replacing 5-fluoro-2-hydroxyphenylboronic acid with 2-hydroxyphenylboronic acid.

LC-MS (LCT3B) m/z 337 [M+H$^+$], R$_t$ 2.06 minutes. $^1$H NMR (MeOD) δ 8.40 (dd, J 8.0, 1.5 Hz, 1H), 7.54 (d, J 9.0 Hz, 1H), 7.47 (d, J 2.5 Hz, 1H), 7.32-7.28 (m, 2H), 6.91-6.86 (m, 2H), 4.82-4.78 (m, 1H), 3.89 (s, 3H), 3.47-3.43 (m, 1H), 3.26-3.20 (m, 1H), 3.13-3.05 (m, 2H), 2.41-2.34 (m, 1H), 2.09-2.03 (m, 1H).

Synthesis 83

(S)-2-(7-Methoxy-4-(pyrrolidin-3-ylamino)quinazolin-2-yl)phenol (A-076)

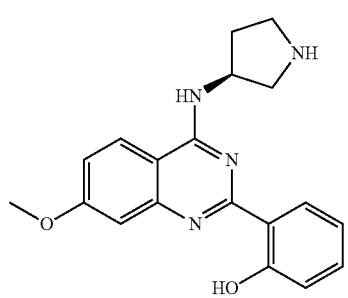

The title compound was prepared using a method analogous to that described in Synthesis 80, replacing 2-amino-5-methoxybenzoic acid and 5-fluoro-2-hydroxyphenylboronic acid with 2-amino-4-methoxybenzoic acid and 2-hydroxyphenylboronic acid.

LC-MS (LCT3B) m/z 337 [M+H$^+$], R$_t$ 1.81 minutes. $^1$H NMR (MeOD) δ 8.44 (dd, J 8.0, 1.5 Hz, 1H), 7.96 (d, J 9.0 Hz, 1H), 7.33-7.30 (m, 1H), 7.00-6.97 (m, 2H), 6.91-6.86 (m, 2H), 4.78-4.73 (m, 1H), 3.89 (s, 3H), 3.37-3.32 (m, 1H), 3.16-3.10 (m, 1H), 3.03-2.94 (m, 2H), 2.35-2.28 (m, 1H), 1.99-1.92 (m, 1H).

Synthesis 84 trans-Ethyl 4-(2-(5-fluoro-2-hydroxyphenyl)quinazolin-4-ylamino)pyrrolidine-3-carboxylate (A-077)

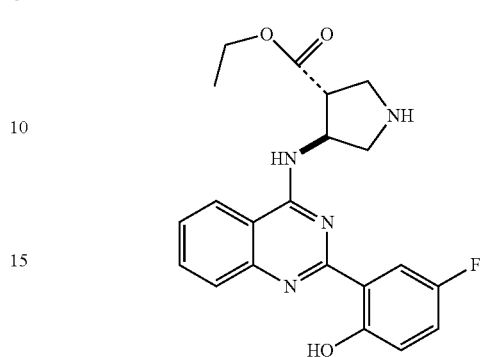

The title compound was prepared using methods analogous to those described in Synthesis 1-A, 1-B, 1-D and 2, replacing 2-methoxybenzoyl chloride with 2-methoxy-4-fluorobenzoyl chloride in Synthesis 1A, and replacing (R)-3-aminopiperidine-1-carboxylic acid tert-butyl ester with trans-1-tert-butyl 3-ethyl 4-(2-(5-fluoro-2-hydroxyphenyl)-3,4-dihydroquinazolin-4-ylamino)pyrrolidine-1,3-dicarboxylate in Synthesis 2-A.

LC-MS (LCT3B) m/z 397 [M+H$^+$], Rt 2.22 minutes. $^1$H NMR (500 MHz, CDCl$_3$) δ 8.22 (dd, J 10.0, 3.0 Hz, 1H), 7.98 (d, J 8.5 Hz, 1H), 7.83 (d, J 7.5 Hz, 1H), 7.78 (t, J 7.0 Hz, 1H), 7.50 (t, J 7.0 Hz, 1H), 7.13-7.07 (m, 1H), 6.98 (dd, J 9.0, 4.5 Hz, 1H), 6.79-6.68 (m, 1H), 5.38-5.20 (m, 1H), 4.45-4.21 (m, 2H), 3.72-3.62 (m, 1H), 3.57-3.42 (m, 2H), 3.32 (d, J 12.0 Hz, 1H), 3.28-3.18 (m, 1H), 1.30 (t, J 7.0 Hz, 3H).

Synthesis 85-A

(S,E)-tert-Butyl 3-(2-(2-hydroxyphenyl)-7-(3-methoxyprop-1-enyl)quinazolin-4-ylamino)pyrrolidine-1-carboxylate

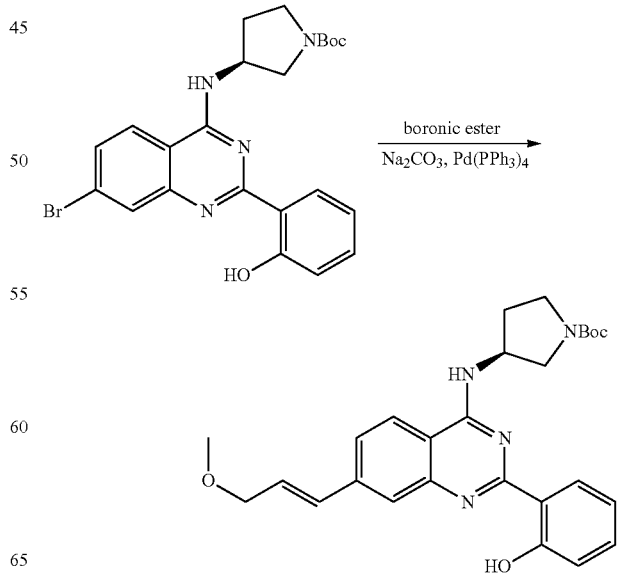

(S)-tert-Butyl 3-(7-bromo-2-(2-hydroxyphenyl)quinazolin-4-ylamino)pyrrolidine-1-carboxylate (0.099 g, 0.20 mmol), trans-3-methoxy-1-propenylboronic acid pinacol ester (0.051 g, 0.23 mmol), Na₂CO₃ (0.066 g, 0.62 mmol), palladium tetrakistriphenyl phosphine (0.012 g, 0.011 mmol) was dissolved in a toluene (1 mL) and water (0.3 mL) and the mixture was degassed in a sealed tube. The reaction mixture was heated at 110° C. for 16 h. The reaction mixture was cooled and diluted with water (50 mL) and extracted with ethyl acetate (3×50 mL). The combined organic extracts were dried (MgSO₄) and concentrated in vacuo. Further purification by silica column chromatography eluting with a gradient from 1% to 10% methanol in dichloromethane, gave the title compound as a yellow solid (0.071 g, 27%).

LC-MS (LCT3B) m/z 477 [M+H⁺], Rt 3.07 minutes.

Synthesis 85-B (S,E)-2-(7-(3-Methoxyprop-1-enyl)-4-(pyrrolidin-3-ylamino)quinazolin-2-yl)phenol (A-078)

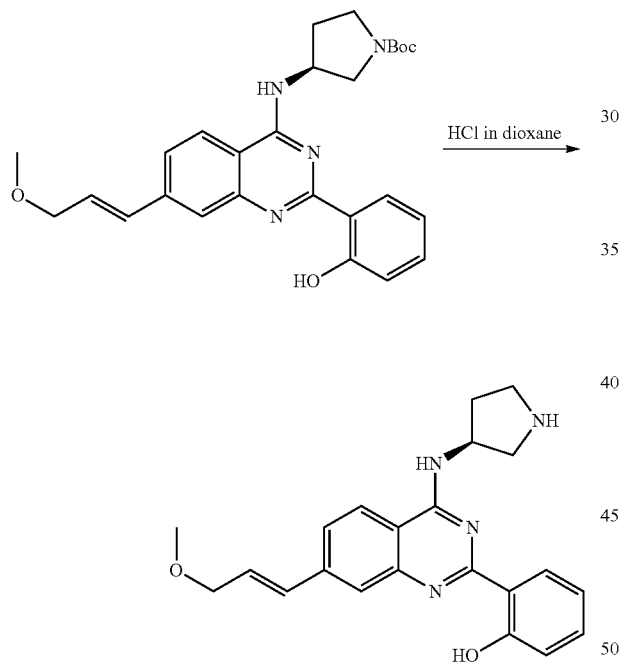

The title compound was prepared using a method analogous to that described in Synthesis 59-B, replacing (S)-tert-butyl 3-(2-(2-hydroxyphenyl)-6-(3-hydroxyprop-1-ynyl)quinazolin-4-ylamino)pyrrolidine-1-carboxylate with (S,E)-tert-butyl 3-(2-(2-hydroxyphenyl)-7-(3-methoxyprop-1-enyl)quinazolin-4-ylamino)pyrrolidine-1-carboxylate.

LC-MS (LCT4) m/z 377 [M+H⁺], Rt 1.75 minutes. ¹H NMR (500 MHz, CDCl₃) δ 14.79 (br. s, 1H), 8.53 (d, J 6.0 Hz, 1H), 7.79-7.67 (m, 2H), 7.49 (d, J 8.5 Hz, 1H), 7.37 (t, J 7.5 Hz, 1H), 7.03 (d, J 8.2 Hz, 1H), 6.94 (t, J 7.5 Hz, 1H), 6.74 (d, J 16.0 Hz, 1H), 6.49 (dt, J 16.0, 5.5 Hz, 1H), 6.36 (m, 1H), 5.04-4.90 (m, 1H), 4.16 (d, J 4.3 Hz, 2H), 3.45 (s, 3H), 3.28-3.15 (m, 1H), 3.17-3.02 (m, 3H), 2.50-2.30 (m, 1H), 2.01-1.85 (m, 1H).

Synthesis 86

(S)-2-(7-(3-Methoxypropyl)-4-(pyrrolidin-3-ylamino)quinazolin-2-yl)phenol (A-079)

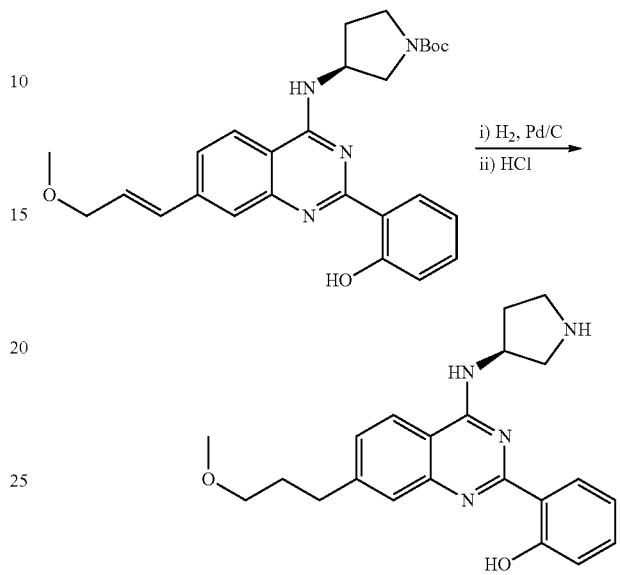

The title compound was synthesised using methods analogous to those described in Synthesis 60 and 85-A, with (S)-tert-butyl 3-(2-(2-hydroxyphenyl)-6-(3-hydroxyprop-1-ynyl)quinazolin-4-ylamino)pyrrolidine-1-carboxylate replaced with (S,E)-2-(7-(3-methoxyprop-1-enyl)-4-(pyrrolidin-3-ylamino)quinazolin-2-yl)phenol in Synthesis 60.

LC-MS (LCT2B) m/z 379 [M+H⁺], Rt 2.10 minutes. ¹H NMR (500 MHz, CDCl₃) δ 14.85 (br. s, 1H), 8.53 (d, J 6.5 Hz, 1H), 7.72 (d, J 8.0 Hz, 1H), 7.59 (s, 1H), 7.36 (t, J 7.0 Hz, 1H), 7.27 (d, J 8.0 Hz, 1H), 7.03 (d, J 8.0 Hz, 1H), 6.93 (t, J 7.5 Hz, 1H), 6.30 (br. s, 1H), 4.97 (br. s, 1H), 3.46-3.37 (m, 3H), 3.36 (s, 3H), 3.27-3.16 (m, 1H), 3.16-3.02 (m, 2H), 2.87-2.81 (m, 2H), 2.49-2.29 (m, 1H), 2.02-1.86 (m, 3H).

Synthesis 87

(S)-4-Fluoro-2-(6-methoxy-7-(2-methoxyethoxy)-4-(pyrrolidin-3-ylamino)quinazolin-2-yl)Phenol (A-080)

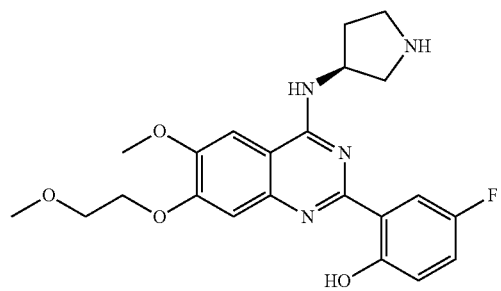

The title compound was prepared using a method analogous to that described in Synthesis 80, replacing 2-amino-5-methoxybenzoic acid with 2-amino-4-(2-methoxyethoxy)-5-methoxybenzoic acid in Synthesis 80-A.

LC-MS (LCT3B) m/z 429 [M+H⁺], R_t 2.08 minutes. ¹H NMR (MeOD) δ 8.02 (dd, J 10.0, 3.0 Hz, 1H), 7.42 (s, 1H), 7.02 (dt, J 8.0, 3.0 Hz, 1H), 6.99 (s, 1H), 6.84 (dt, J 9.0, 4.5 Hz, 1H), 4.77-4.72 (m, 1H), 4.23-4.21 (m, 2H), 3.95 (s, 3H), 3.84-3.82 (m, 2H), 3.47 (s, 3H), 3.40 (dd, J 12.0, 6.5 Hz, 1H), 3.21-3.15 (m, 1H), 3.10-3.04 (m, 1H), 3.00 (dd, J 12.0, 4.5 Hz, 1H), 2.39-2.32 (m, 1H), 2.04-1.97 (m, 1H).

Synthesis 88

(S)-2-(6-Methoxy-7-(2-methoxyethoxy)-4-(pyrrolidin-3-ylamino)quinazolin-2-yl)phenol (A-081)

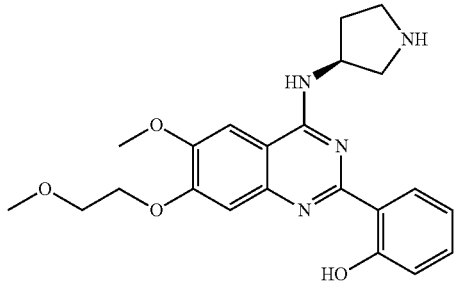

The title compound was prepared using a method analogous to that described in Synthesis 80, replacing 2-amino-5-methoxybenzoic acid with 2-amino-4-(2-methoxyethoxy)-5-methoxybenzoic acid in Synthesis 80-A, and replacing 5-fluoro-2-hydroxyphenylboronic acid with 2-hydroxyphenylboronic acid.

LC-MS (LCT3B) m/z 411 [M+H⁺], R_t 1.92 minutes. ¹H NMR (MeOD) δ 8.42 (dd, J 8.0, 1.5 Hz, 1H), 7.46 (s, 1H), 7.31 (ddd, J 8.5, 7.0, 1.5 Hz, 1H), 7.02 (s, 1H), 6.95-6.87 (m, 2H), 4.81-4.76 (m, 1H), 4.24-4.22 (m, 2H), 3.96 (s, 3H), 3.84-3.82 (m, 2H), 3.47 (s, 3H), 3.25-3.19 (m, 1H), 3.13-3.02 (m, 2H), 2.40-2.33 (m, 1H), 2.08-2.01 (m, 1H).

Synthesis 89-A (2R,4S)-1-tert-butyl 2-methyl 4-(2-(5-fluoro-2-hydroxyphenyl)quinazolin-4-ylamino)pyrrolidine-1,2-dicarboxylate

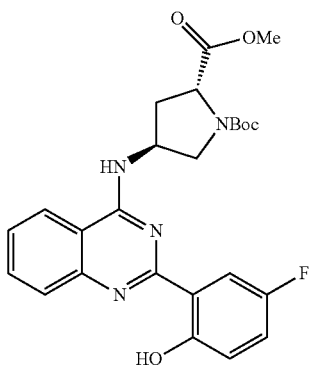

The title compound was prepared using methods analogous to those described in Synthesis 1-A, 1-B, 1-D and 2, replacing 2-methoxybenzoyl chloride with 2-methoxy-4-fluorobenzoyl chloride in Synthesis 1A, and replacing (R)-3-aminopiperidine-1-carboxylic acid tert-butyl ester with (2R,4S)-4-aminopyrrolidine-1,2-dicarboxylic acid 1-tert-butyl ester 2-methyl ester in Synthesis 2-A.

LC-MS (LCT2B) m/z 483 [M+H⁺], R_t 3.00 minutes.

Synthesis 89-B

4-Fluoro-2-(4-((3S,5R)-5-(hydroxymethyl)pyrrolidin-3-ylamino)quinazolin-2-yl)phenol (A-082)

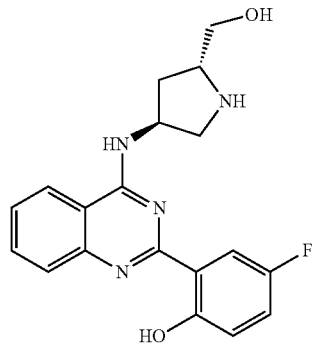

A solution of LiAlH₄ (0.132 mL of a 1M sol. in diethyl ether, 0.132 mmol) was added to a solution of (2R,4R)-1-tert-butyl 2-methyl 4-(2-(5-fluoro-2-hydroxyphenyl)quinazolin-4-ylamino)borolane-1,2-dicarboxylate (0.032 g, 0.066 mmol) in THF (1 mL) at 0° C. After 5 min, diethyl ether (5 mL) was added followed by 1M NaOH (0.050 mL) and the resulting mixture stirred for 30 min. The mixture was purified by ion exchange chromatography on SCX-2 Isolute acidic resin (2 g), eluting with methanol and then 1 M ammonia in methanol. Concentration of the basic filtrate gave the crude Boc protected amine, which was stirred with 4M HCl in dioxane (5 mL) for 1 h. The mixture was concentrated and the crude purified by ion exchange chromatography on SCX-2 (solute acidic resin (2 g), eluting with methanol and then 1 M ammonia in methanol. Further purification by silica column chromatography (3 cm plug of silica), eluting with 20% methanol in dichloromethane, gave the title compound as a solid (0.015 g, 64%).

LC-MS (LCT3B) m/z 355 [M+H⁺], R_t 2.01 minutes. ¹H NMR (MeOD) δ 8.21 (dd, J 8.0, 1.0 Hz, 1H), 8.17 (dd, J 10.0, 3.0 Hz, 1H), 7.80 (ddd, J 8.5, 7.0, 1.5 Hz, 1H), 7.74 (dd, J 8.5, 1.0 Hz, 1H), 7.52 (ddd, J 8.5, 7.0, 1.5 Hz, 1H), 7.09 (ddd, J 9.0, 8.0, 3.5 Hz, 1H), 6.90 (dd, J 9.0, 4.5 Hz, 1H), 4.97-4.91 (m, 1H), 3.69 (dd, J 11.0, 5.5 Hz, 1H), 3.65 (dd, J 11.0, 5.5 Hz, 1H), 3.61-3.54 (m, 2H), 3.06 (dd, J 11.5, 5.5 Hz, 1H), 2.17 (t, J 7.0 Hz, 2H).

Synthesis 90

2-(4-trans-4-(3-Chlorophenyl)pyrrolidin-3-ylamino)quinazolin-2-yl)-4-fluorophenol (A-083)

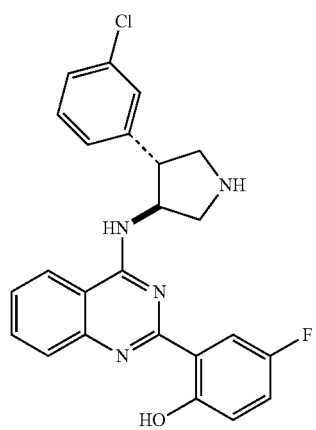

The title compound was prepared in a method analogous to that described in Synthesis 97, replacing (E)-1-methoxy-4-(2-nitrovinyl)benzene with (E)-1-chloro-3-(2-nitrovinyl)benzene in Synthesis 97-A.

LC-MS (LCT4) m/z 434 [M+H$^+$], Rt 2.08 minutes. $^1$H NMR (500 MHz, MeOD) δ 8.24-8.13 (m, 1H), 7.89-7.75 (m, 2H), 7.75-7.66 (m, 1H), 7.59-7.49 (m, 1H), 7.49-7.43 (m, 1H), 7.42-7.31 (m, 1H), 7.33-7.23 (m, 1H), 7.24-7.16 (m, 1H), 7.11-7.00 (m, 1H), 6.93-6.78 (m, 1H), 5.33-5.21 (m, 1H), 3.79-3.69 (m, 1H), 3.69-3.59 (m, 1H), 3.59-3.48 (m, 1H), 3.26-3.11 (m, 2H).

Synthesis 91

(3R,4S)-Ethyl 4-(2-(5-fluoro-2-hydroxyphenyl)quinazolin-4-ylamino)pyrrolidine-3-carboxylate (A-084)

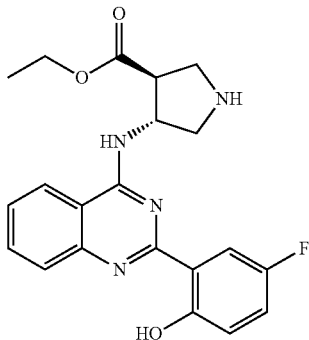

Chiral semi-prep separation of trans-ethyl 4-(2-(5-fluoro-2-hydroxyphenyl)quinazolin-4-ylamino)pyrrolidine-3-carboxylate (Synthesis 84) was performed on a Gilson GX281 with a 322 pump with a CHIRALCEL OD-H250×10 mm i.d. column at a temperature of 17° C. and a flow rate of 2.5 mL/minute using 20% IPA in hexane.

LC-MS (LCT5) m/z 397 [M+H$^+$], Rt 17.09 minutes.

Synthesis 92

(3S,4R)-Ethyl 4-(2-(5-fluoro-2-hydroxyphenyl)quinazolin-4-ylamino)pyrrolidine-3-carboxylate (A-085)

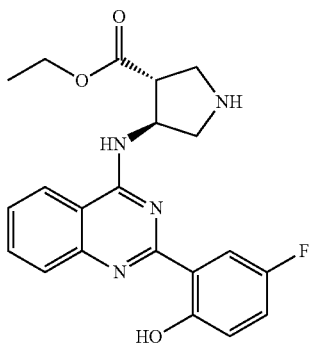

Chiral semi-prep separation of trans-ethyl 4-(2-(5-fluoro-2-hydroxyphenyl)quinazolin-4-ylamino)pyrrolidine-3-carboxylate (Synthesis 84) was performed on a Gilson GX281 with a 322 pump with a CHIRALCEL OD-H250×10 mm i.d. column at a temperature of 17° C. and a flow rate of 2.5 mL/minute using 20% IPA in hexane.

LC-MS (LCT5) m/z 397 [M+H$^+$], Rt 15.14 minutes.

Synthesis 93

4-Fluoro-2-(4-((3S,5R)-5-(2-hydroxypropan-2-yl)pyrrolidin-3-ylamino)quinazolin-2-yl)phenol (A-086)

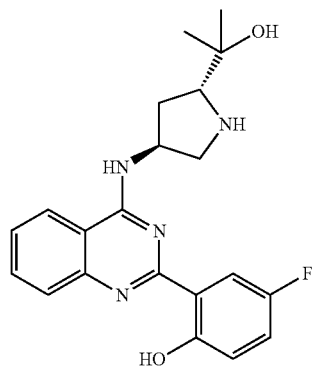

A Grignard solution of MeMgI (0.270 mL, 3M in diethyl ether, 0.810 mmol) was added to a solution of (2R,4R)-1-tert-butyl 2-methyl 4-(2-(5-fluoro-2-hydroxyphenyl)quinazolin-4-ylamino)borolane-1,2-dicarboxylate (0.039 g, 0.081 mmol, prepared as described in Synthesis 89-A) in THF (1 mL) and the solution refluxed for 10 h. Saturated aqueous ammonium chloride (20 mL) was added and the aqueous phase extracted with ethyl acetate (3×20 mL). Organic phases were combined, dried (MgSO$_4$) and concentrated. The resulting crude Boc-protected amine was stirred with 4M HCl in dioxane (6 mL) for 1 h. The mixture was concentrated and the crude purified by ion exchange chromatography on SCX-2 Isolute acidic resin (2 g), eluting with methanol and then 1 M ammonia in methanol. Further purification by silica column chromatography (3 cm plug of silica), eluting with 20% methanol in dichloromethane, gave the title compound as a solid (0.012 g, 31%).

LC-MS (LCT3B) m/z 383 [M+H$^+$], R$_t$ 2.14 minutes. $^1$H NMR (MeOD) δ 8.17 (dd, J 10.0, 3.0 Hz, 1H), 7.80-7.73 (m, 3H), 7.46 (t, J 7.5 Hz, 1H), 7.08 (dt, J 8.5, 3.0 Hz, 1H), 6.96 (dd, J 9.0, 4.5 Hz, 1H), 6.09 (d, J 5.5 Hz, 1H), 4.90-4.85 (m, 1H), 3.55 (dd, J 11.0, 5.5 Hz, 1H), 3.40-3.37 (m, 1H), 3.20 (dd, J 11.0, 3.0 Hz, 1H), 2.26 (ddd, J 13.5, 9.5, 7.0 Hz, 1H), 1.98 (ddd, J 13.5, 7.0, 3.0 Hz, 1H), 1.26 (s, 3H), 1.22 (s, 3H).

Synthesis 94

4-Fluoro-2-(4-((3S,5R)-5-(hydroxymethyl)pyrrolidin-3-ylamino)-7-methoxyquinazolin-2-yl)phenol (A-087)

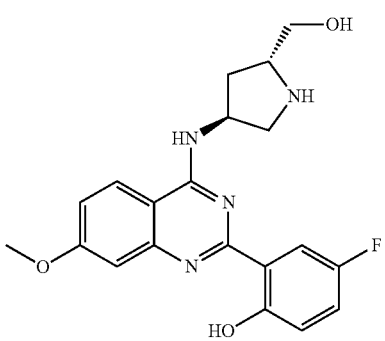

The title compound was prepared using methods analogous to those described in Synthesis 80-A, 30-A, 76-B and 89-B, replacing 2-amino-5-methoxybenzoic acid with 2-amino-4-methoxybenzoic acid in Synthesis 80-A, replacing (S)-(−)-1-boc-3-aminopyrrolidine with (2R,4S)-4-aminopyrrolidine-1,2-dicarboxylic acid 1-tert-butyl ester 2-methyl ester in Synthesis 30-A, replacing 2-hydroxyphenylboronic acid with 5-fluoro-2-hydroxyphenylboronic acid in Synthesis 76-B (using the crude Boc-protected amine in Synthesis 89-B), and replacing (2R,4S)-1-tert-butyl 2-methyl 4-(2-(5-fluoro-2-hydroxyphenyl)quinazolin-4-ylamino)pyrrolidine-1,2-dicarboxylate with (2R,4S)-1-tert-butyl 2-methyl 4-(2-(5-fluoro-2-hydroxyphenyl)-7-methoxyquinazolin-4-ylamino)pyrrolidine-1,2-dicarboxylate in Synthesis 89-B.

LC-MS (LCT3B) m/z 385 [M+H$^+$], R$_t$ 2.04 minutes. $^1$H NMR (MeOD) δ 8.11 (dd, J 10.0, 3.5 Hz, 1H), 8.04 (d, J 9.0 Hz, 1H), 7.08-7.04 (m, 3H), 6.88 (dd, J 9.0, 4.5 Hz, 1H), 4.87-4.81 (m, 1H), 3.94 (s, 3H), 3.65 (dd, J 11.0, 5.5 Hz, 1H), 3.62 (dd, J 11.0, 5.5 Hz, 1H), 3.54-3.46 (m 2H), 2.98 (dd, J 11.5, 5.5 Hz, 1H), 2.12-2.09 (m, 2H).

Synthesis 95-A tert-Butyl 3-(2-(5-fluoro-2-hydroxyphenyl)quinazolin-4-ylamino)-trans-4-(hydroxymethyl)pyrrolidine-1-carboxylate

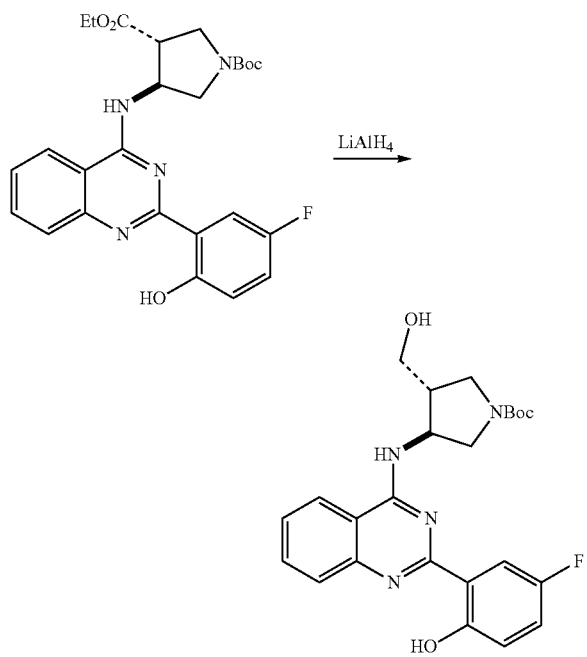

trans-1-tert-Butyl 3-ethyl 4-(2-(5-fluoro-2-hydroxyphenyl)-3,4-dihydroquinazolin-4-ylamino)pyrrolidine-1,3-dicarboxylate (0.093 g, 0.19 mmol, synthesised using methods outlined in Synthesis 84) was dissolved in THF (1.8 mL) and cooled to 0° C. A 1 M solution of LiAlH$_4$ in THF (0.375 mL, 0.38 mmol) was added dropwise and the mixture was stirred at this temperature for 15 min. The reaction was quenched with sodium potassium tartrate (2 drops) and diluted with water (10 mL). The mixture was extracted with dichloromethane (3×50 mL) and the combined organic extracts were dried (MgSO$_4$) and concentrated in vacuo. The residue was purified by silica column chromatography eluting with 25% ethyl acetate in hexane to give the title compound as a yellow solid (0.026 g, 30%).

LC-MS (LCT3B) m/z 455 [M+H$^+$], Rt 2.87 minutes.

Synthesis 95-B

4-Fluoro-2-(4-(trans-4-(hydroxymethyl)pyrrolidin-3-ylamino)quinazolin-2-yl)phenol (A-088)

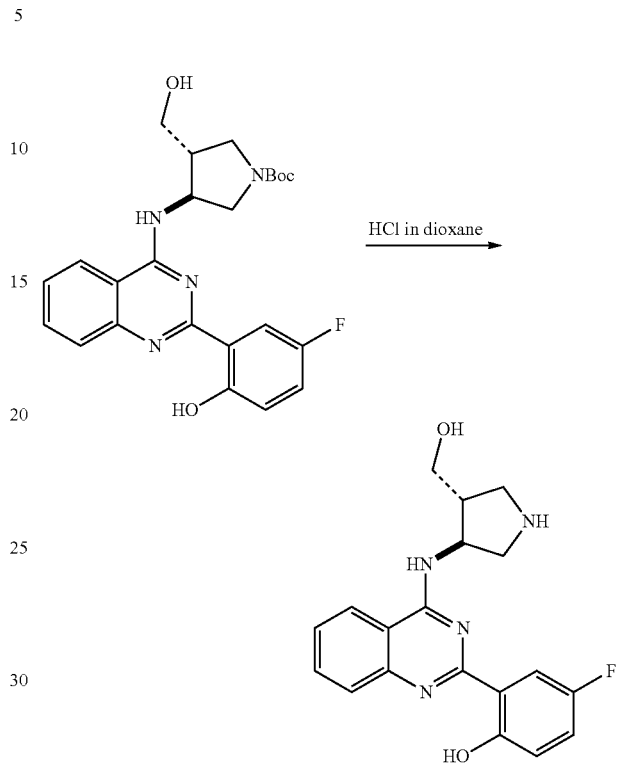

The title compound was prepared using a method analogous to that used in Synthesis 2, replacing (R)-3-[2-(2-hydroxyphenyl)-quinazolin-4-yl-amino]-piperidine-1-carboxylic acid tert-butyl ester with tert-butyl 3-(2-(trans-5-fluoro-2-hydroxyphenyl)quinazolin-4-ylamino)-4-(hydroxymethyl)pyrrolidine-1-carboxylate.

LC-MS (LCT3B) m/z 355 [M+H$^+$], Rt 1.92 minutes. $^1$H NMR (500 MHz, MeOD) δ 8.27-8.17 (m, 2H), 7.87-7.78 (m, 1H), 7.76 (d, J 8.5 Hz, 1H), 7.60-7.44 (m, 1H), 7.14-7.02 (m, 1H), 6.92 (dd, J 9.0, 4.5 Hz, 1H), 4.83-4.77 (m, 1H), 3.84 (dd, J 11.0, 5.5 Hz, 1H), 3.75 (dd, J 11.0, 7.0 Hz, 1H), 3.49 (dd, J 11.5, 7.0 Hz, 1H), 3.33-3.28 (m, 1H), 2.98 (dd, J 11.5, 5.5 Hz, 1H), 2.93 (dd, J 11.5, 6.5 Hz, 1H), 2.55-2.50 (m, 1H).

Synthesis 96 trans-4-(2-(5-Fluoro-2-hydroxyphenyl)quinazolin-4-ylamino)pyrrolidine-3-carboxylic acid (A-089)

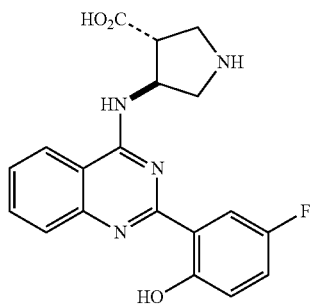

The title compound was prepared in a method analogous to that described in Synthesis 2, replacing 2-methoxybenzoyl chloride and (R)-3-amino-piperidine-1-carboxylic acid tert-butyl ester with 5-fluoro-2-methoxybenzoyl chloride and trans-4-amino-1-(tert-butoxycarbonyl)pyrrolidine-3-carboxylic acid.

LC-MS (LCT3B) m/z 369 [M+H$^+$], Rt 2.00 minutes. $^1$H NMR (500 MHz, MeOD) δ 8.19 (dd, J 10.0, 3.0 Hz, 1H), 8.01 (d, J 8.0 Hz, 1H), 7.83-7.76 (m, 1H), 7.76-7.71 (m, 1H), 7.53 (t, J 7.0 Hz, 1H), 7.13-7.05 (m, 1H), 6.91 (dd, J 9.0, 4.5 Hz, 1H), 4.91-4.83 (m, 1H), 3.50 (br. s, 1H), 3.42-3.34 (m, 2H), 3.20-3.09 (m, 2H).

Synthesis 97-A trans-1-Benzyl-3-(4-methoxyphenyl)-4-nitropyrrolidine

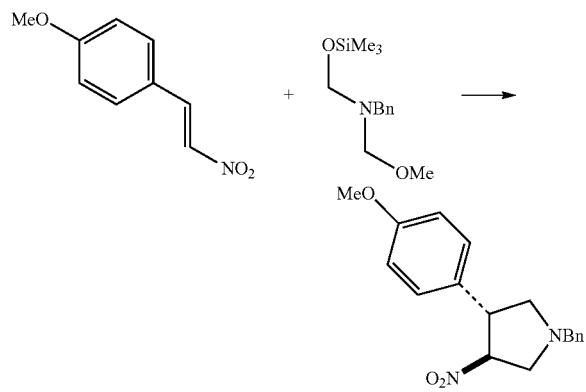

(E)-1-Methoxy-4-(2-nitrovinyl)benzene (0.390 g, 2.18 mmol) and trifluoroacetic acid (0.017 mL, 0.22 mmol) were dissolved in dichloromethane (5 mL) and cooled to 0° C. N-(Methoxymethyl)-N-trimethylsilylmethyl)benzylamine (1.04 g, 4.36 mmol) in dichloromethane (5 mL) was added drop wise over 20 mins and the solution was warmed to room temperature over 48 h. The crude reaction mixture was concentrated in vacuo. Purification of the residue by silica column chromatography eluting with 10% ethyl acetate in petroleum ether gave the title compound as a colourless oil (0.658 g, 97%).

$^1$H NMR (500 MHz, CDCl$_3$) δ 7.40-7.31 (m, 4H), 7.31-7.20 (m, 3H), 6.93-6.84 (m, 2H), 4.98-4.81 (m, 1H), 3.99 (dd, J 13.0, 7.5 Hz, 1H), 3.81 (s, 3H), 3.73 (q, J 13.0 Hz, 2H), 3.44-3.36 (m, 1H), 3.32-3.23 (m, 1H), 3.12 (dd, J 11.0, 8.0 Hz, 1H), 2.68 (dd, J 9.5, 7.5 Hz, 1H).

Synthesis 97-B trans-1-Benzyl-4-(4-methoxyphenyl)pyrrolidin-3-amine

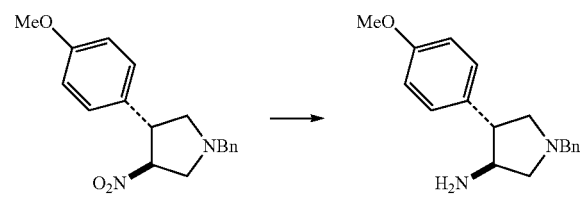

trans-1-Benzyl-3-(4-methoxyphenyl)-4-nitropyrrolidine (0.205 g, 0.66 mmol) was dissolved in methanol (10 mL) and hydrogenated under a hydrogen atmosphere at atmospheric pressure in the presence of Raney nickel (~8 mL). After stirring for 2 h the solution was concentrated in vacuo and purified by ion exchange chromatography on SCX-2 (solute acidic resin (2 g), eluting with methanol and then 1 M ammonia in methanol to give the title compound (0.116 g, 62%) as a colourless oil that was used without further purification.

$^1$H NMR (500 MHz, CDCl$_3$) δ 7.41-7.16 (m, 7H), 6.86 (d, J 8.5 Hz, 2H), 3.80 (s, 3H), 3.73 (d, J 13.0 Hz, 1H), 3.67 (d, J 13.0 Hz, 1H), 3.49-3.40 (m, 1H), 3.13 (t, J 9.0 Hz, 1H), 3.06-2.97 (m, 1H), 2.95-2.84 (m, 1H), 2.71-2.62 (m, 1H), 2.62-2.54 (m, 1H).

Synthesis 97-C 2-(4-(1-Benzyl-4-trans-(4-methoxyphenyl)pyrrolidin-3-ylamino)quinazolin-2-yl)-4-fluorophenol

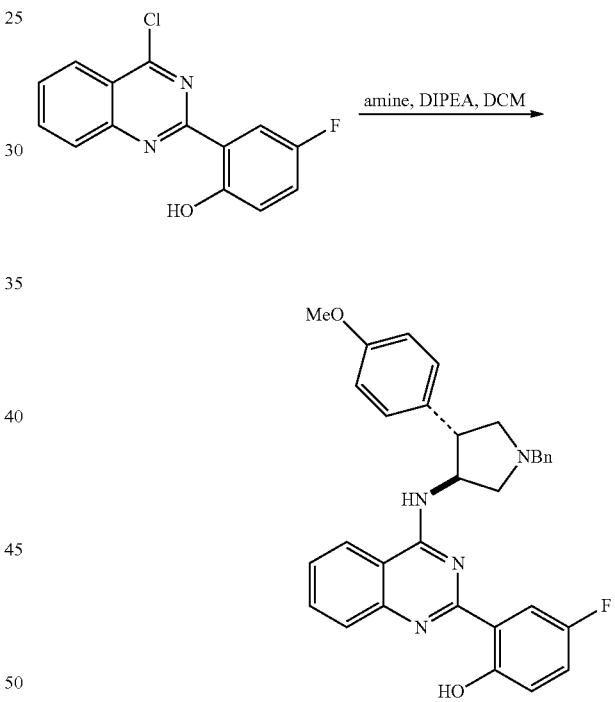

2-(4-Chloroquinazolin-2-yl)-4-fluorophenol was dissolved in DCM (5 mL) and trans-1-benzyl-4-(4-methoxyphenyl)pyrrolidin-3-amine (0.177 g, 0.63 mmol) was added followed by DIPEA (0.29 mL, 1.88 mmol) and the solution was heated at reflux for 16 h. The mixture was cooled, diluted with DCM (50 mL) and washed with saturated NH$_4$Cl (10 mL). The organic phase was dried (MgSO4) and concentrated in vacuo and the residue was purified by silica column chromatography eluting with 25% ethyl acetate in hexane to provide the title compound as a yellow solid (0.072 g, 22%).

LC-MS (LCT2B) m/z 521 [M+H$^+$], Rt 2.48 minutes.

Synthesis 97-D

4-Fluoro-2-(4-(trans-4-(4-methoxyphenyl)pyrrolidin-3-ylamino)quinazolin-2-yl)phenol (A-090)

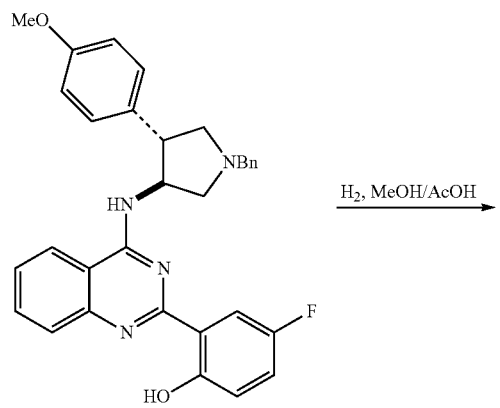

→ H₂, MeOH/AcOH

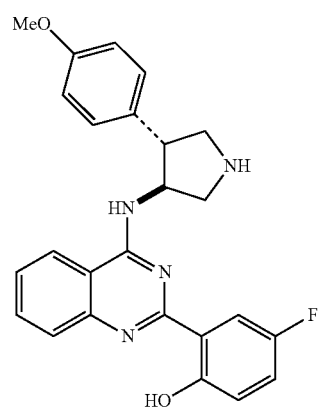

2-(4-(1-Benzyl-4-trans-(4-methoxyphenyl)pyrrolidin-3-ylamino)quinazolin-2-yl)-4-fluorophenol (0.050 g, 0.096 mmol) was dissolved in 10% acetic acid in methanol (15 mL) and hydrogenated at 40° C. using an H-Cube hydrogenator under full H₂ conditions. The solution was concentrated in vacuo and purified by silica column chromatography eluting with a gradient from 1% to 6% methanol in dichloromethane to give the title compound (0.026 g, 64%) as a yellow solid.

LC-MS (LCT3B) m/z 431 [M+H⁺], Rt 2.32 minutes. ¹H NMR (500 MHz, CDCl₃) δ 8.26 (d, J 8.2 Hz, 1H), 7.97 (dd, J 10.0, 3.0 Hz, 2H), 7.83-7.72 (m, 2H), 7.49 (t, J 7.0 Hz, 1H), 7.39 (d, J 8.5 Hz, 2H), 7.11-7.03 (m, 1H), 6.99-6.92 (m, 3H), 5.23 (s, 1H), 3.90-3.69 (m, 3H), 3.83 (s, 3H), 3.58 (d, J 11.5 Hz, 1H), 3.55-3.47 (m, 1H).

Synthesis 98

4-Fluoro-2-(4-(trans-4-(3-methoxyphenyl)pyrrolidin-3-ylamino)quinazolin-2-yl)phenol (A-091)

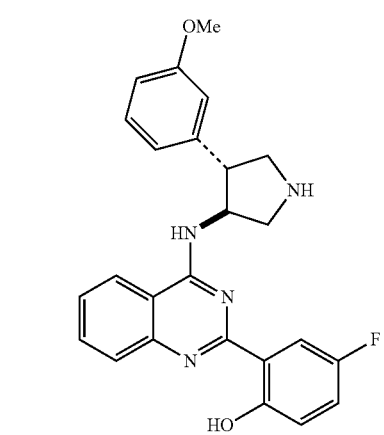

The title compound was prepared in a method analogous to that described in Synthesis 97, replacing (E)-1-methoxy-4-(2-nitrovinyl)benzene with (E)-1-methoxy-3-(2-nitrovinyl)benzene in Synthesis 97-A.

LC-MS (LCT3B) m/z 431 [M+H⁺], Rt 2.31 minutes. ¹H NMR (500 MHz, CDCl₃) δ 8.26 (d, J 8.0 Hz, 1H), 8.13 (s, 1H), 7.93 (dd, J 10.0, 3.0 Hz, 1H), 7.80-7.70 (m, 2H), 7.48 (t, J 6.5 Hz, 1H), 7.35 (t, J 8.0 Hz, 1H), 7.10-7.01 (m, 2H), 7.00-6.93 (m, 2H), 6.87 (dd, J 8.0, 2.5 Hz, 1H), 5.30 (d, J 7.0 Hz, 1H), 3.86 (dd, J 12.0, 8.0 Hz, 1H), 3.80 (s, 3H), 3.79-3.67 (m, 2H), 3.56 (d, J 12.0 Hz, 1H), 3.54-3.47 (m, 1H).

Synthesis 99

4-Fluoro-2-(4-trans(4-(2-methoxyphenyl)pyrrolidin-3-ylamino)quinazolin-2-yl)phenol (A-092)

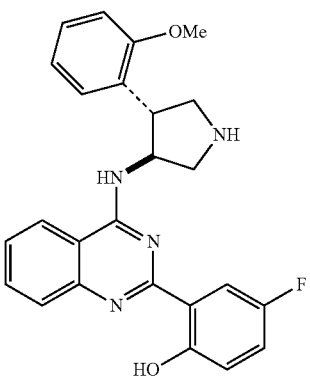

The title compound was prepared in a method analogous to that described in Synthesis 97, replacing (E)-1-methoxy-4-(2-nitrovinyl)benzene with (E)-1-methoxy-2-(2-nitrovinyl)benzene in Synthesis 97-A.

LC-MS (LCT3B) m/z 431 [M+H⁺], Rt 2.34 minutes. ¹H NMR (500 MHz, MeOD) δ 8.15 (d, J 8.0 Hz, 1H), 7.92 (dd, J 10.0, 3.5 Hz, 1H), 7.81-7.75 (m, 1H), 7.72 (d, J 8.0 Hz, 1H), 7.52 (t, J 7.5 Hz, 1H), 7.34-7.29 (m, 1H), 7.24-7.17 (m, 1H), 7.10-7.03 (m, 1H), 6.98 (d, J 7.5 Hz, 1H), 6.91-6.84 (m, 2H), 5.68 (dd, J 16.5, 8.0 Hz, 1H), 4.00-3.87 (m, 2H), 3.90 (s, 3H), 3.84-3.77 (m, 1H), 3.54-3.46 (m, 1H), 3.42-3.36 (m, 1H).

Synthesis 100

(S)-4-Fluoro-2-(7-(3-hydroxy-3-methylbut-1-ynyl)-4-(pyrrolidin-3-ylamino)quinazolin-2-yl)phenol (A-093)

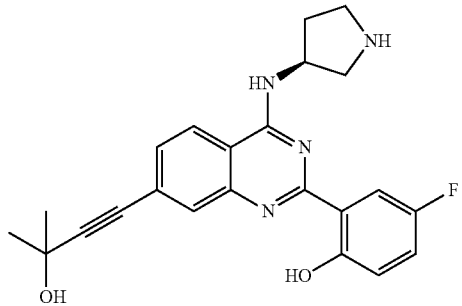

The title compound was prepared using a method analogous to that described in Synthesis 79, replacing propargyl alcohol with dimethyl propargyl alcohol. LC-MS (LCT3B) m/z 407 [M+H⁺], R_t 2.20 minutes. ¹H NMR (MeOD) δ 8.16-8.12 (m, 2H), 7.74 (d, J 1.5 Hz, 1H), 7.46 (dd, J 8.5, 1.5 Hz, 1H), 7.09 (ddd, J 9.0, 8.0, 3.0 Hz, 1H), 6.90 (dd, J 9.0, 4.5 Hz, 1H), 4.95-4.80 (m, 1H), 3.42 (dd, J 11.5, 6.5 Hz, 1H), 3.20-3.15 (m, 1H), 3.09-3.04 (m, 1H), 3.00 (dd, J 12.0, 5.0 Hz, 1H), 2.42-2.35 (m, 1H), 2.09-1.99 (m, 1H), 1.62 (s, 6H).

Synthesis 101

(S)-4-Fluoro-2-(7-(2-methoxyethoxy)-4-(pyrrolidin-3-ylamino)quinazolin-2-yl)phenol (A-094)

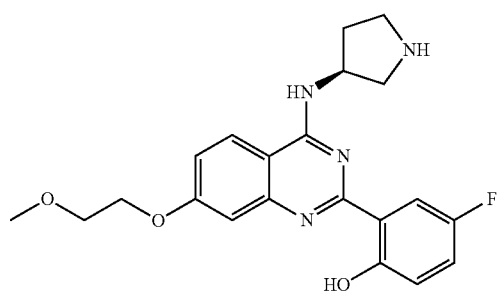

The title compound was prepared using a method analogous to that described in Synthesis 74, replacing 2-hydroxyphenylboronic acid with 5-fluoro-2-hydroxyphenylboronic acid.
LC-MS (LCT3B) m/z 399 [M+H⁺], R_t 1.98 minutes. ¹H NMR (MeOD) δ 8.13 (dd, J 10.0, 3.0 Hz, 1H), 8.06 (d, J 9.0 Hz, 1H), 7.12-7.05 (m, 3H), 6.89 (dd, J 9.0, 4.5 Hz, 1H), 4.86-4.82 (m, 1H), 4.28-4.26 (m, 2H), 3.83-3.81 (m, 2H), 3.46 (s, 3H), 3.90 (dd, J 12.0, 6.5 Hz, 1H), 3.18-3.13 (m, 1H), 3.07-3.02 (m, 1H), 2.97 (dd, J 12.0, 5.0 Hz, 1H), 2.40-2.33 (m, 1H), 2.02-1.96 (m, 1H).

Synthesis 102

(S)-4-Fluoro-2-(6-(2-methoxyethoxy)-4-(pyrrolidin-3-ylamino)quinazolin-2-yl)phenol (A-095)

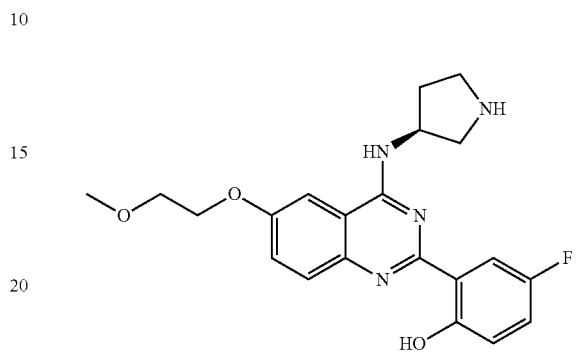

The title compound was prepared using a method analogous to that described in Synthesis 74, replacing methyl 4-fluoro-2-nitrobenzoate with methyl 5-fluoro-2-nitrobenzoate and replacing 2-hydroxyphenylboronic acid with 5-fluoro-2-hydroxyphenylboronic acid.
LC-MS (LCT3B) m/z 399 [M+H⁺], R_t 2.10 minutes. ¹H NMR (MeOD) δ 8.14 (dd, J 10.0, 3.0 Hz, 1H), 7.68 (d, J 9.0 Hz, 1H), 7.62 (d, J 2.5 Hz, 1H), 7.45 (dd, J 9.0, 2.5 Hz, 1H), 7.06 (ddd, J 9.0, 8.0, 3.0 Hz, 1H), 6.89 (dd, J 9.0, 4.5 Hz, 1H), 4.90-4.85 (m, 1H), 4.28-4.26 (m, 2H), 3.84-3.82 (m, 2H), 3.47 (s, 3H), 3.43 (dd, J 12.0, 6.5 Hz, 1H), 3.20-3.15 (m, 1H), 3.10-3.05 (m, 1H), 3.01 (dd, J 12.0, 5.0 Hz, 1H), 2.47-2.37 (m, 1H), 2.07-2.01 (m, 1H).

Synthesis 103

(S)-2-(6-(2-Methoxyethoxy)-4-(pyrrolidin-3-ylamino)quinazolin-2-yl)phenol (A-096)

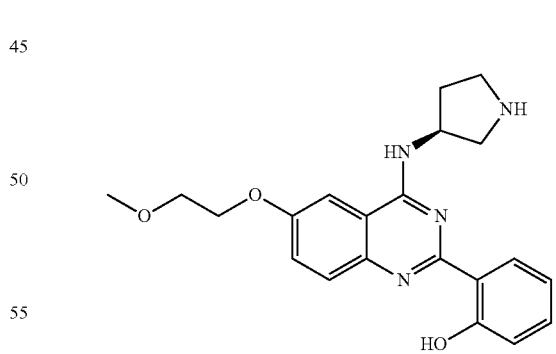

The title compound was prepared using a method analogous to that described in Synthesis 74, replacing methyl 4-fluoro-2-nitrobenzoate with methyl 5-fluoro-2-nitrobenzoate.
LC-MS (LCT3B) m/z 381 [M+H⁺], R_t 1.86 minutes. ¹H NMR (MeOD) δ 8.48 (dd, J 8.0, 1.5 Hz, 1H), 7.67 (d, J 9.0 Hz, 1H), 7.61 (d, J 2.5 Hz, 1H), 7.43 (dd, J 9.0, 2.5 Hz, 1H), 7.31 (ddd, J 8.0, 7.5, 1.5 Hz, 1H), 6.91-6.89 (m, 2H), 4.90-4.85 (m, 1H), 4.27-4.25 (m, 2H), 3.83-3.81 (m, 2H), 3.47 (s, 3H), 3.42

(dd, J 12.0, 6.5 Hz, 1H), 3.20-3.15 (m, 1H), 3.09-3.05 (m, 1H), 3.01 (dd, J 12.0, 5.0 Hz, 1H), 2.43-2.36 (m, 1H), 2.07-2.00 (m, 1H).

Synthesis 104

(S)-4-Fluoro-2-(7-(3-hydroxy-3-methylbutyl)-4-(pyrrolidin-3-ylamino)quinazolin-2-yl)phenol (A-097)

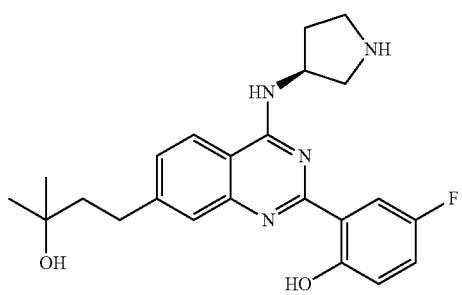

The title compound was prepared using a method analogous to that described in Synthesis 78, replacing propargyl alcohol with dimethyl propargyl alcohol.

LC-MS (LCT3B) m/z 411 [M+H$^+$], R$_t$ 2.15 minutes. $^1$H NMR (MeOD) δ 8.15 (dd, J 10.0, 3.5 Hz, 1H), 8.08 (d, J 8.5 Hz, 1H), 7.54 (s, 1H), 7.38 (dd, J 8.5, 1.5 Hz, 1H), 7.07 (ddd, J 9.0, 8.0, 3.5 Hz, 1H), 6.89 (dd, J 9.0, 4.5 Hz, 1H), 4.90-4.85 (m, 1H), 3.44-3.38 (m, 1H), 3.20-3.13 (m, 1H), 3.10-2.97 (m, 2H), 2.89-2.85 (m, 2H), 2.42-2.35 (m, 1H), 2.04-1.98 (m, 1H), 1.97-1.84 (m, 1H), 1.30 (s, 6H).

Synthesis 105

4-Fluoro-2-(4-(trans-4-(2-hydroxypropan-2-yl)pyrrolidin-3-ylamino)quinazolin-2-yl)phenol (A-098)

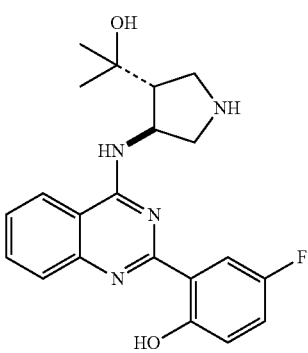

The title compound was prepared using a method analogous to that described in Synthesis 93, replacing (2R,4S)-1-tert-butyl 2-methyl 4-(2-(5-fluoro-2-hydroxyphenyl)quinazolin-4-ylamino)pyrrolidine-1,2-dicarboxylate with tert-butyl 3-(2-(trans-5-fluoro-2-hydroxyphenyl)quinazolin-4-ylamino)-4-(hydroxymethyl)pyrrolidine-1-carboxylate.

LC-MS (LCT3B) m/z 383 [M+H$^+$], Rt 2.04 minutes. $^1$H NMR (500 MHz, MeOD) δ 8.27-8.18 (m, 2H), 7.87-7.80 (m, 1H), 7.78 (d, J 7.5, 1H), 7.60-7.51 (m, 1H), 7.16-7.05 (m, 1H), 6.93 (dd, J 9.0, 4.5, 1H), 5.23 (dd, J 12.0, 6.5, 1H), 3.61 (dd, J 12.0, 7.0, 1H), 3.48 (dd, J 11.5, 8.5, 1H), 3.24 (dd, J 12.0, 8.0, 1H), 3.16 (dd, J 12.0, 5.0, 1H), 2.62 (dd, J 14.5, 8.5, 1H), 1.35 (s, 3H), 1.31 (s, 3H).

Synthesis 106

4-Fluoro-2-(4-(trans-4-methylpyrrolidin-3-ylamino)quinazolin-2-yl)phenol (A-099)

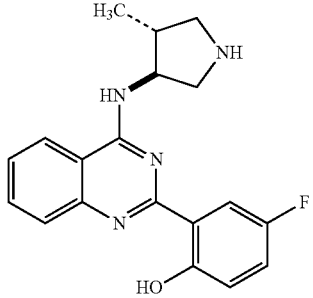

The title compound was prepared in a method analogous to that described in Synthesis 97, replacing (E)-1-methoxy-4-(2-nitrovinyl)benzene with (E)-1-nitroprop-1-ene in Synthesis 97-A.

LC-MS (LCT3B) m/z 339 [M+H$^+$], Rt 2.17 minutes. $^1$H NMR (500 MHz, MeOD) δ 8.21 (d, J 8.0 Hz, 1H), 8.08 (dd, J 10.0, 3.5 Hz, 1H), 7.83-7.73 (m, 1H), 7.70 (d, J 8.5 Hz, 1H), 7.57-7.45 (m, 1H), 7.11-6.99 (m, 1H), 6.88 (dd, J 9.0, 4.5 Hz, 1H), 4.78 (dd, J 14.5, 7.5 Hz, 1H), 3.96 (dd, J 12.0, 7.5 Hz, 1H), 3.69 (dd, J 11.5, 7.5 Hz, 1H), 3.12 (dd, J 11.5, 8.5 Hz, 1H), 2.71 (dt, J 14.5, 7.5 Hz, 1H), 1.32 (d, J 7.0 Hz, 3H).

Synthesis 107

(S)-4'-Fluoro-3-(4-(pyrrolidin-3-ylamino)quinazolin-2-yl)biphenyl-4-ol (A-100)

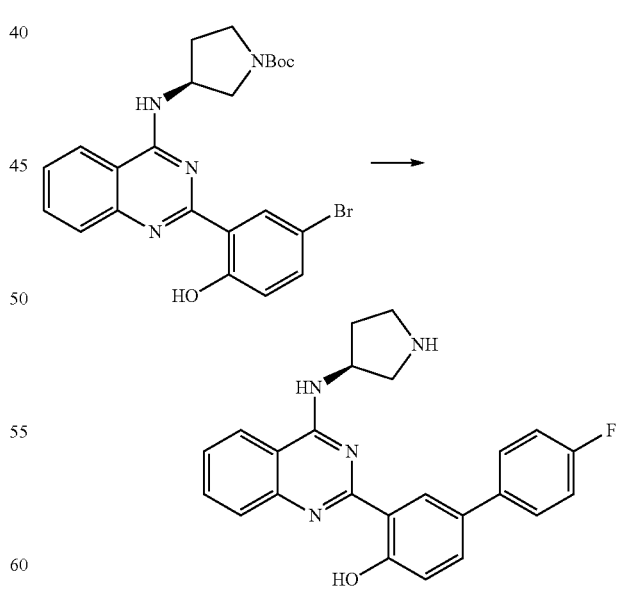

(S)-tert-Butyl 3-(2-(5-bromo-2-hydroxyphenyl)quinazolin-4-ylamino)pyrrolidine-1-carboxylate (0.051 g, 0.105 mmol, prepared in a method analogous to that described in Synthesis 2-A), 4-fluorobenzene boronic acid (0.016 g, 0.114 mmol), palladium tetrakistriphenyl phosphine (0.028 g, 0.024 mmol) and potassium phosphate (0.051 g, 0.243 mmol) were dissolved in dimethyl acetamide (0.7 mL) and water (0.3 mL) and the mixture was heated in a microwave for 10 mins at 150° C. The mixture was filtered through a short plug of silica using ethyl acetate as eluent and the filtrate concentrated in vacuo. The residue was dissolved in methanol (1.2 mL) and 4M HCl in dioxane (1.2 mL) was added and the mixture stirred for 16 h. The mixture was concentrated and purified by ion exchange chromatography on SCX-2 Isolute acidic resin (2 g), eluting with methanol and then 1 M ammonia in methanol. The basic fractions were combined and purified by silica column chromatography, eluting with dichloromethane then 10% methanol in dichloromethane, to give the title compound as a yellow solid (0.013 g, 27%).

LC-MS (LCT3B) m/z 401 [M+H$^+$], Rt 2.57 minutes. $^1$H NMR (500 MHz, MeOD) δ 8.64 (d, J 2.5 Hz, 1H), 8.21 (d, J 8.0 Hz, 1H), 7.83-7.74 (m, 1H), 7.72 (d, J 8.5 Hz, 1H), 7.61 (dd, J 5.5, 8.0 Hz, 2H), 7.56 (dd, J 2.5, 8.5 Hz, 1H), 7.50 (t, J 7.5 Hz, 1H), 7.16 (t, J 8.5 Hz, 2H), 6.99 (d, J 8.5 Hz, 1H), 5.05-4.95 (m, 1H), 3.73 (dd, J 12.5, 6.5 Hz, 1H), 3.53 (ddd, J 17.5, 12.0, 6.0 Hz, 2H), 3.47-3.39 (m, 1H), 2.53 (dq, J 15.0, 7.5 Hz, 1H), 2.36 (dt, J 13.5, 5.5 Hz, 1H).

Synthesis 108

(S)-4'-Hydroxy-3'-(4-(pyrrolidin-3-ylamino)quinazolin-2-yl)biphenyl-4-carboxamide (A-101)

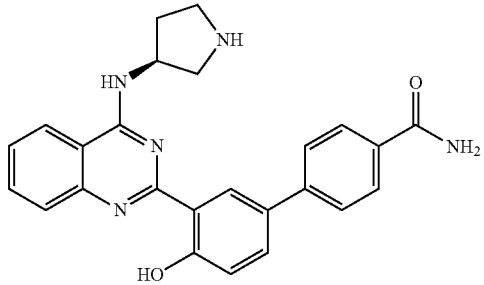

The title compound was prepared using a method analogous to that described in Synthesis 107, replacing 4-fluorobenzene boronic acid with 4-carbamoylphenylboronic acid.

LC-MS (LCT4) m/z 426 [M+H$^+$], Rt 1.82 minutes. $^1$H NMR (500 MHz, MeOD) δ 8.83 (d, J 2.5 Hz, 1H), 8.29 (d, J 8.0 Hz, 1H), 7.98 (d, J 8.0 Hz, 2H), 7.90-7.80 (m, 2H), 7.77 (d, J 8.5 Hz, 2H), 7.74-7.69 (m, 1H), 7.63-7.53 (m, 1H), 7.08 (d, J 8.5 Hz, 1H), 5.20-5.07 (m, 1H), 3.92-3.76 (m, 1H), 3.69-3.58 (m, 2H), 3.58-3.47 (m, 1H), 2.70-2.53 (m, 1H), 2.53-2.39 (m, 1H).

Synthesis 109

(S)-4-Fluoro-2-(6-(3-hydroxy-3-methylbutyl)-4-(pyrrolidin-3-ylamino)quinazolin-2-yl)phenol (A-102)

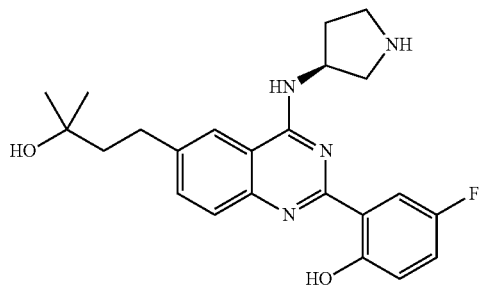

The title compound was prepared using methods analogous to those described in Synthesis 59 and 60, replacing propargyl alcohol and (S)-tert-butyl 3-(6-bromo-2-(2-hydroxyphenyl)quinazolin-4-ylamino)pyrrolidine-1-carboxylate with dimethyl propargyl alcohol and (S)-tert-butyl 3-(6-bromo-2-(5-fluoro-2-hydroxyphenyl)quinazolin-4-ylamino)pyrrolidine-1-carboxylate in Synthesis 59-A.

LC-MS (LCT3B) m/z 411 [M+H$^+$], R$_t$ 2.41 minutes. $^1$H NMR (MeOD) δ 8.08 (dd, J 10.0, 3.5 Hz, 1H), 7.96 (s, 1H), 7.61 (d, J 8.5 Hz, 1H), 7.58 (d, J 8.5 Hz, 1H), 7.04 (ddd, J 9.0, 8.0, 3.5 Hz, 1H), 6.87 (dd, J 9.0, 4.5 Hz, 1H), 4.89-4.84 (m, 1H), 3.48-3.43 (m, 1H), 3.26-3.21 (m, 1H), 3.15-3.05 (m, 1H), 2.85-2.82 (m, 2H), 2.43-2.36 (m, 1H), 2.10-2.04 (m, 1H), 1.85-1.82 (m, 2H), 1.30 (s, 6H).

Synthesis 110-A

Methyl 5-hydroxy-4-methoxy-2-nitrobenzoate

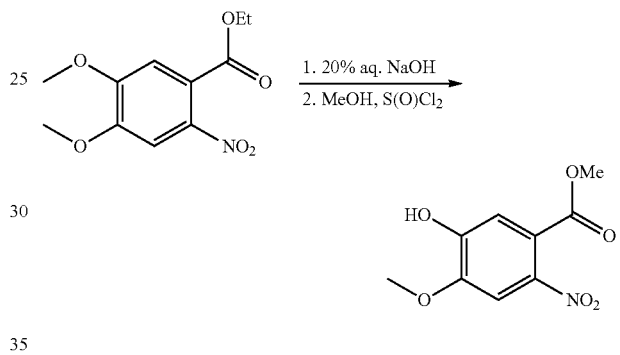

Ethyl 4,5-dimethoxy-2-nitrobenzoate (10.22 g, 40.04 mmol) was refluxed in 20% aqueous NaOH (50 mL) for 2 days. The solution was cooled, acidifed to pH 2 using concentrated HCl, and the resulting solid filtered, washed with water and dried. The solid was dissolved in methanol (90 mL) and thionyl chloride (3.1 mL, 42.75 mmol) cautiously added. After refluxing for 3 days, the solution was cooled, concentrated and diluted with dichloromethane (280 mL). The organic phase was washed with water (200 mL) and the aqueous layer further extracted with dichlormethane (100 mL). Organic layers were combined, dried (MgSO$_4$) and concentrated to give the title compound as a yellow solid (6.00 g, 66%).

LC-MS (LCT3B) m/z 250 [M+Na$^+$], R$_t$ 1.83 minutes. $^1$H NMR (DMSO) δ 10.9 (br s, 1H), 7.61 (s, 1H), 7.07 (s, 1H), 3.91 (s, 3H), 3.80 (s, 3H).

Synthesis 110-B

Methyl 4-methoxy-5-(2-methoxypthoxy)-2-nitrobenzoate

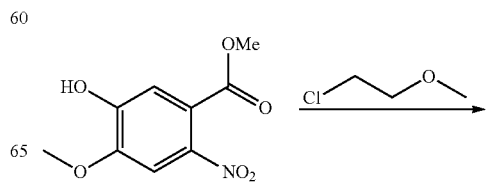

-continued

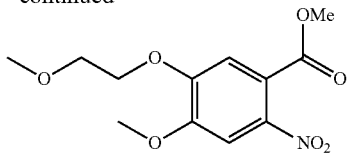

A suspension of ethyl 5-hydroxy-4-methoxy-2-nitrobenzoate (5.43 g, 23.92 mmol), $K_2CO_3$ (7.60 g, 55.01 mmol) and TBAI (0.35 g, 0.96 mmol) in acetone (35 mL) was stirred for 30 min. 1-Chloro-2-methoxyethane (17.20 g, 81.76 mmol) was added and the mixture was refluxed for 14 days. The suspension was cooled, diether ether (200 mL) added and the remaining solid filtered off, washing with a further portion of diethyl ether (200 mL). The filtrate was concentrated to give the title compound as a solid (6.50 g, 95%).

LC-MS (LCT3B) m/z 308 [M+Na$^+$], R$_t$ 2.05 minutes. $^1$H NMR (CDCl$_3$) δ 7.45 (s, 1H), 7.28 (s, 1H), 7.14 (s, 1H), 4.28-4.26 (m, 2H), 3.96 (s, 3H), 3.91 (s, 3H), 3.83-3.81 (m, 2H), 3.46 (s, 3H).

Synthesis 110-C

Methyl 2-amino-4-methoxy-5-(2-methoxyethoxy)benzoate

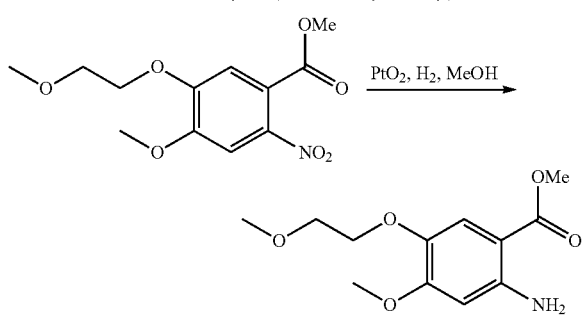

A solution of methyl 4-methoxy-5-(2-methoxyethoxy)-2-nitrobenzoate (3.39 g, 11.88 mmol) in methanol (40 mL) was hydrogenated at 50 psi hydrogen gas in the presence of PtO$_2$ (0.050 g) using a Parr hydrogenator for 24 h. The reaction mixture was filtered and concentrated to give the title compound as an oil (2.51 g, 83%).

LC-MS (LCT3B) m/z 256 [M+H$^+$], R$_t$ 1.90 minutes. $^1$H NMR (MeOD) δ 7.36 (s, 1H), 6.36 (s, 1H), 4.03-4.01 (m, 2H), 3.84 (s, 3H), 3.83 (s, 3H), 3.71-3.69 (m, 2H), 3.43 (s, 3H).

Synthesis 110-D (S)-4-Fluoro-2-(7-methoxy-6-(2-methoxyethoxy)-4-(pyrrolidin-3-ylamino)quinazolin-2-yl)phenol (A-103)

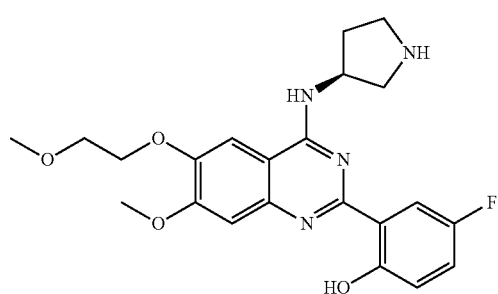

The title compound was prepared using a method analogous to that described in Synthesis 80, replacing 2-amino-5-methoxybenzoic acid with methyl 2-amino-4-methoxy-5-(2-methoxyethoxy)benzoate.

LC-MS (LCT3B) m/z 429 [M+H$^+$], R$_t$ 1.99 minutes. $^1$H NMR (CDCl$_3$) δ 8.16 (dd, J 10.0, 3.0 Hz, 1H), 7.23 (s, 1H), 7.12 (s, 1H), 7.05 (ddd, J 9.0, 8.0, 3.0 Hz, 1H), 6.95 (dd, J 9.0, 5.0 Hz, 1H), 6.38 (d, J 6.5 Hz, 1H), 5.00-4.95 (m, 1H), 4.33-4.31 (m, 1H), 4.00 (s, 3H), 3.86-3.84 (m, 2H), 3.48 (s, 3H), 3.37 (dd, J 11.0, 6.0 Hz, 1H), 3.28-3.23 (m, 1H), 3.19-3.16 (m, 1H), 3.12-3.07 (m, 1H), 2.47-2.40 (m, 1H), 2.03-1.96 (m, 1H).

Synthesis 111-A

Ethyl 3,4-bis(2-methoxyethoxy)benzoate

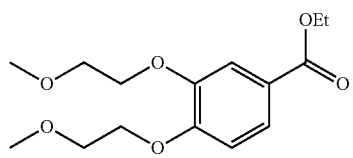

The title compound was prepared using a method analogous to that described in Synthesis 110-B, replacing ethyl 5-hydroxy-4-methoxy-2-nitrobenzoate with ethyl 3,4-dihydroxybenzoate.

LC-MS (LCT3B) m/z 321 [M+Na$^+$], R$_t$ 2.30 minutes. $^1$H NMR (DMSO) δ 7.56 (dd, J 8.5, 2.0 Hz, 1H), 7.47 (d, J 2.0 Hz, 1H), 4.27 (q, J 7.0 Hz, 1H), 4.18-4.16 (m, 2H), 4.14-4.12 (m, 2H), 3.69-3.66 (m, 4H), 3.32 (s, 3H), 3.32 (s, 3H), 1.30 (t, J 7.0 Hz, 3H).

Synthesis 111-B

Ethyl 4,5-bis(2-methoxyethoxy)-2-nitrobenzoate

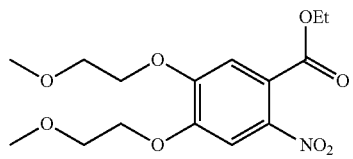

A solution of ethyl 3,4-bis(2-methoxyethoxy)benzoate (23.23 g, 77.87 mmol) in acetic acid (80 mL) was added dropwise to concentrated nitric acid (21 mL) cooled with an ice bath at such a rate as to keep the internal temperature below 5° C. After 30 min, the solution was allowed to warm to room temperature and stirred for 48 h. The solution was poured onto iced water (400 mL) and extracted with ethyl acetate (3×100 mL). The organic phases were combined and washed cautiously with saturated aqueous sodium bicarbonate (3×200 mL) and brine (2×100 mL). The organic phase was dried (Na$_2$SO$_4$) and concentrated to give the title compound as a solid (24.82 g, 93%).

Synthesis 111-C (S)-2-(6,7-bis(2-Methoxyethoxy)-4-(pyrrolidin-3-ylamino)quinazolin-2-yl)-4-fluorophenol (A-104)

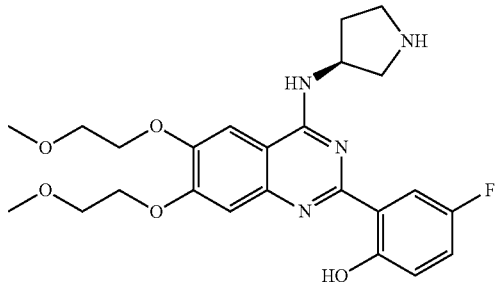

The title compound was prepared using a method analogous to that described in Synthesis 110-C and 110-D, replacing 4-methoxy-5-(2-methoxyethoxy)-2-nitrobenzoate with ethyl 4,5-bis(2-methoxyethoxy)-2-nitrobenzoate in Synthesis 110-C.

LC-MS (LCT3B) m/z 473 [M+H⁺], $R_t$ 2.01 minutes. ¹H NMR (CDCl₃) δ 8.16 (dd, J 10.0, 3.0 Hz, 1H), 7.23 (s, 1H), 7.12 (s, 1H), 7.05 (ddd, J 9.0, 8.0, 3.0 Hz, 1H), 6.95 (dd, J 9.0, 5.0 Hz, 1H), 6.33 (d, J 6.0 Hz, 1H), 4.99-4.94 (m, 1H), 4.30-4.27 (m, 4H), 3.88-3.83 (m, 4H), 3.49 (s, 3H), 3.48 (s, 3H), 3.39-3.35 (m, 1H), 3.28-3.23 (m, 1H), 3.18-3.15 (m, 1H), 3.12-3.06 (m, 1H), 2.46-2.39 (m, 1H), 2.01-1.95 (m, 1H).

Synthesis 112

(S)-4-(1H-Pyrazol-4-yl)-2-(4-(pyrrolidin-3-ylamino)quinazolin-2-yl)phenol (A-105)

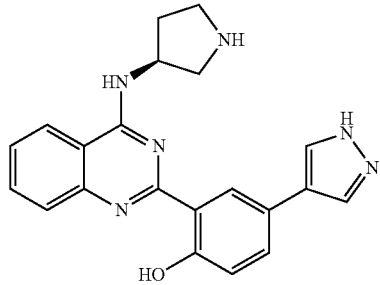

The title compound was prepared using a method analogous to that described in Synthesis 107, replacing 4-fluorobenzene boronic acid with tert-butyl 4-(4,4,5,5-tetramethyl-1,3,2-dioxaborolan-2-yl)-1H-pyrazole-1-carboxylate.

LC-MS (LCT3B) m/z 373 [M+H⁺], Rt 2.05 minutes. ¹H NMR (500 MHz, MeOD) δ 8.86 (d, J 2.0, 1H), 8.16 (d, J 8.0, 1H), 7.81-7.67 (m, 3H), 7.65 (d, J 2.0, 1H), 7.47 (ddd, J 8.0, 7.0, 1.5, 1H), 6.97 (d, J 8.5, 1H), 6.60 (d, J 2.0, 1H), 4.99-4.91 (m, 1H), 3.46 (dd, J 2.0, 6.5, 1H), 3.24-3.15 (m, 1H), 3.13-3.02 (m, 2H), 2.48-2.35 (m, 1H), 2.10-1.99 (m, 1H).

Synthesis 113

(S)-4-(1H-Pyrazol-3-yl)-2-(4-(pyrrolidin-3-ylamino)quinazolin-2-yl)phenol (A-106)

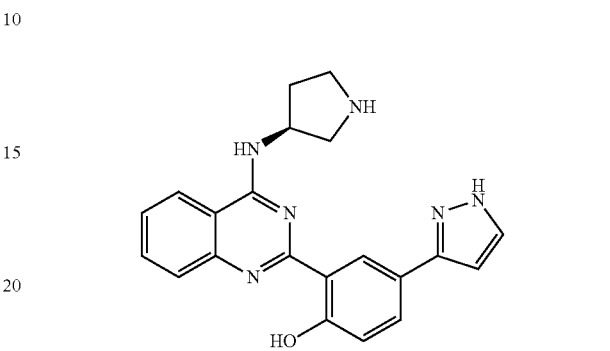

The title compound was prepared using a method analogous to that described in Synthesis 107, replacing 4-fluorobenzene boronic acid with 3-(4,4,5,5-tetramethyl-1,3,2-dioxaborolan-2-yl)-1-((2-(trimethylsilyl)ethoxy)methyl)-1H-pyrazole.

LC-MS (LCT4) m/z 373 [M+H⁺], Rt 2.09 minutes. ¹H NMR (500 MHz, MeOD) δ 8.65 (d, J 2.0 Hz, 1H), 8.17 (d, J 8.0 Hz, 1H), 7.89 (s, 2H), 7.80-7.70 (m, 2H), 7.54 (dd, J 8.5, 2.5 Hz, 1H), 7.48 (dd, J 8.0, 7.0 Hz, 1H), 6.94 (d, J 8.5 Hz, 1H), 4.90-4.83 (m, 1H), 3.43 (dd, J 12.0, 6.5 Hz, 1H), 3.23-3.12 (m, 1H), 3.06 (dt, J 11.0, 6.0 Hz, 2H), 2.41 (dt, J 15.0, 8.0 Hz, 1H), 2.05 (dt, J 13.0, 5.5 Hz, 1H).

Synthesis 114

(S)-3'-Fluoro-3-(4-(pyrrolidin-3-ylamino)quinazolin-2-yl)biphenyl-4-ol (A-107)

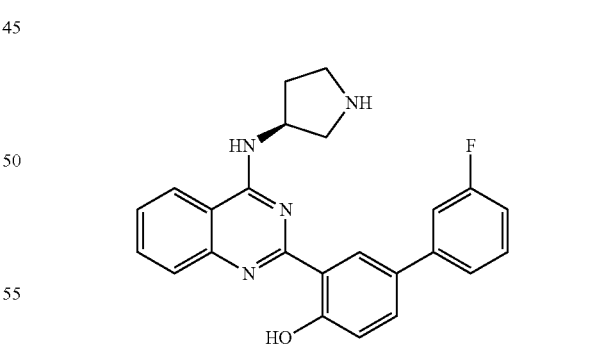

The title compound was prepared using a method analogous to that described in Synthesis 107, replacing 4-fluorobenzene boronic acid with 3-fluorophenylboronic acid.

LC-MS (LCT3B) m/z 401 [M+H⁺], Rt 2.84 minutes. ¹H NMR (500 MHz, MeOD) δ 8.65 (d, J 2.5 Hz, 1H), 8.22 (d, J 8.0 Hz, 1H), 7.80-7.74 (m, 1H), 7.71 (d, J 8.0 Hz, 1H), 7.58 (dd, J 2.5, 8.5 Hz, 1H), 7.50 (t, J 7.5 Hz, 1H), 7.45-7.39 (m, 2H), 7.31 (d, J 11.0 Hz, 1H), 7.06-7.01 (m, 1H), 7.00 (d, J 8.5

Hz, 1H), 5.07-4.96 (m, 1H), 3.74 (dd, J 6.5, 12.0 Hz, 1H), 3.63-3.49 (m, 2H), 3.49-3.39 (m, 1H), 2.65-2.45 (m, 1H), 2.44-2.31 (m, 1H).

Synthesis 115

(S)-2-(4-(Pyrrolidin-3-ylamino)quinazolin-2-yl)-4-(thiophen-3-yl)phenol (A-108)

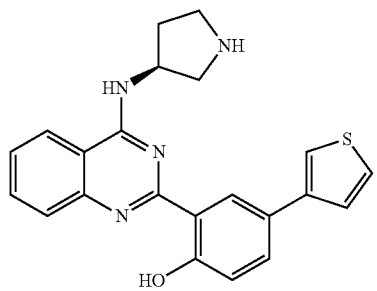

The title compound was prepared using a method analogous to that described in Synthesis 107, replacing 4-fluorobenzene boronic acid with thiophen-3-ylboronic acid.

LC-MS (LCT3B) m/z 389 [M+H$^+$], Rt 2.39 minutes $^1$H NMR (500 MHz, MeOD) δ 8.78 (d, J 2.5 Hz, 1H), 8.27 (d, J 8.5 Hz, 1H), 7.88-7.83 (m, 1H), 7.83-7.79 (m, 1H), 7.68 (dd, J 8.5, 2.5 Hz, 1H), 7.61-7.53 (m, 2H), 7.50 (dq, J 5.0, 2.0 Hz, 2H), 7.01 (d, J 8.5 Hz, 1H), 5.15-5.08 (m, 1H), 3.85 (dd, J 12.5, 6.5 Hz, 1H), 3.65-3.54 (m, 2H), 3.54-3.45 (m, 1H), 2.67-2.53 (m, 1H), 2.49-2.36 (m, 1H).

Synthesis 116

(S)-4-Fluoro-2-(6-(3-hydroxy-3-methylbut-1-ynyl)-4-(pyrrolidin-3-ylamino)quinazolin-2-yl)phenol (A-109)

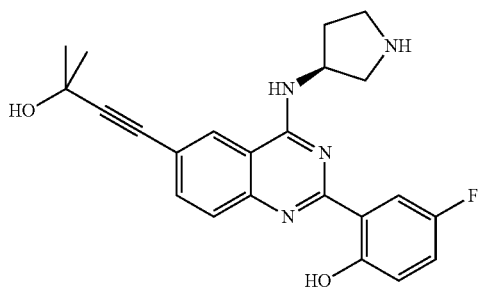

The title compound was prepared using a method analogous to that described in Synthesis 59, replacing propargyl alcohol and (S)-tert-butyl 3-(6-bromo-2-(2-hydroxyphenyl)quinazolin-4-ylamino)pyrrolidine-1-carboxylate with dimethyl propargyl alcohol and (S)-tert-butyl 3-(6-bromo-2-(5-fluoro-2-hydroxyphenyl)quinazolin-4-ylamino)pyrrolidine-1-carboxylate in Synthesis 59-A.

LC-MS (LCT3B) m/z 407 [M+H$^+$], R$_t$ 2.28 minutes. $^1$H NMR (MeOD) δ 8.14 (s, 1H), 7.97 (dd, J 10.0, 3.0 Hz, 1H), 7.61 (d, J 8.5 Hz, 1H), 7.50 (d, J 8.5 Hz, 1H), 7.05-7.00 (m, 1H), 6.82 (dd, J 9.0, 4.5 Hz, 1H), 4.75-4.71 (m, 1H), 3.38-3.34 (m, 1H), 3.18-3.13 (m, 1H), 3.07-3.01 (m, 1H), 2.99 (dd, J 12.0, 4.5 Hz, 1H), 2.39-2.29 (m, 1H), 2.03-1.96 (m, 1H), 1.62 (s, 6H).

Synthesis 117-A (S)-tert-Butyl 3-(2-(5-formyl-2-methoxyphenyl)quinazolin-4-ylamino)pyrrolidine-1-carboxylate

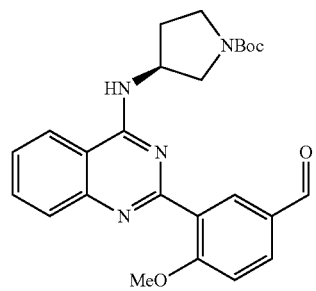

The title compound was prepared using a method analogous to that described in Synthesis 30-B replacing 5-methyl-2-methoxyphenylboronic acid with 5-formyl-2-methoxyphenylboronic acid.

LC-MS (LCT4) m/z 449 [M+H$^+$], Rt 2.08 minutes. $^1$H NMR (500 MHz, CDCl$_3$) δ 9.96 (s, 1H), 8.28 (s, 1H), 7.94 (dd, J 20.0, 8.0, 3H), 7.73 (d, J 7.0, 1H), 7.45 (d, J 12.0, 1H), 7.13 (d, J 8.0, 1H), 6.41 (br. m, 1H), 4.89 (br. s, 1H), 3.95 (s, 3H), 3.83 (s, 1H), 3.67-3.33 (m, 3H), 2.30 (s, 1H), 2.19-2.03 (m, 1H), 1.47 (s, 9H).

Synthesis 117-B (S)-4-(5-Amino-1,3,4-thiadiazol-2-yl)-2-(4-(pyrrolidin-3-ylamino)quinazolin-2-yl)phenol (A-110)

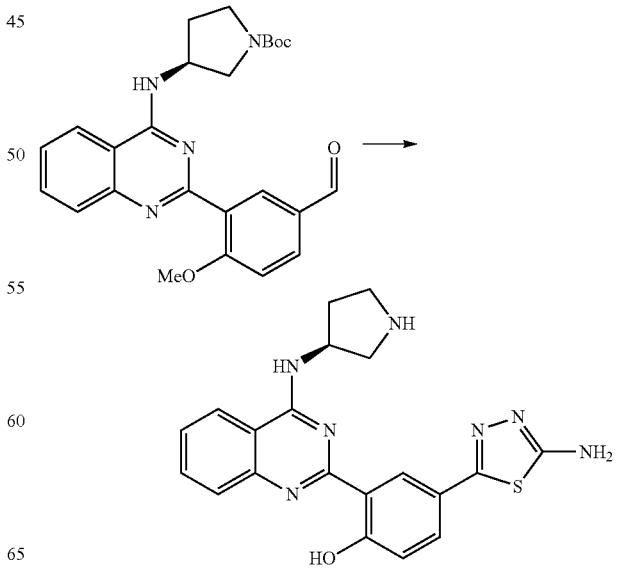

(S)-tert-Butyl 3-(2-(5-formyl-2-methoxyphenyl)quinazo-lin-4-ylamino)pyrrolidine-1-carboxylate (0.160 g, 0.357 mmol) was dissolved in ethanol (2 mL) and thiosemicarba-zide (0.033 g, 0.362 mmol) was added and the solution was stirred at room temperature for 16 h. The solid was filtered off and washed with ethanol (2×1 mL). The solid was suspended in water (16 mL) and ferric chloride (0.267 g, 1.00 mmol) was added and the solution was heated at 60° C. for 16 h. A further portion of ferric chloride (0.267 g, 1.00 mmol) was added and the solution heated at 90° C. for 2.5 h. The reaction mixture was partitioned between water (20 mL) and dichloromethane (20 mL), but the bright yellow product was visibly in the aqueous phase so the aqueous phase was concentrated in vacuo and the residue was purified by ion exchange chroma-tography on SCX-2 (solute acidic resin (2 g), eluting with methanol and then 1 M ammonia in methanol. The basic fractions were combined and purified by HPLC. Semi-prep HPLC was performed on an Agilent 1200 series with a Phe-nomex Gemini 250 mm×10 mm i.d. column at a temperature of 20 C and a flow rate of 5 mL/min using a gradient of 10%-100% acetonitrile in water over 30 mins.

LC-MS (LCT4) m/z 406 [M+H$^+$], Rt 2.07 minutes. $^1$H NMR (500 MHz, MeOD) δ 9.08 (d, J 2.5, 1H), 8.26 (d, J 8.0, 1H), 7.91-7.78 (m, 2H), 7.68-7.56 (m, 2H), 7.04 (d, J 8.5, 1H), 5.22-5.14 (m, 1H), 3.98 (dd, J 12.0, 7.0, 1H), 3.69-3.61 (m, 1H), 3.59-3.53 (m, 1H), 3.49 (dd, J 12.0, 5.5, 1H), 2.65-2.57 (m, 1H), 2.48-2.39 (m, 1H).

Synthesis 118-A (3R,4S)-1-tert-butyl 3-ethyl 4-(2-(5-bromo-2-hy-droxyphenyl)quinazolin-4-ylamino)pyrrolidine-1,3-dicarboxylate

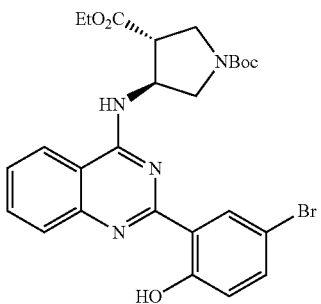

The title compound was prepared using a method analo-gous to that described in Synthesis 52, replacing 4-chloro-2-(2-methoxyphenyl)quinazoline with 4-bromo-2-(4-chloro-quinazolin-2-yl)phenol and tert-butyl-3-aminoazepane-1-carboxylate with (3R,4S)-1-tert-butyl 3-ethyl 4-aminopyrrolidine-1,3-dicarboxylate. (3R,4S)-1-tert-Butyl 3-ethyl 4-aminopyrrolidine-1,3-dicarboxylate was prepared as described in *J. Am. Chem. Soc.*, 2006, 10638.

$^1$H NMR (500 MHz, DMSO) δ 8.58 (d, J 2.5 Hz, 1H), 8.23 (d, J 8.5 Hz, 1H), 7.83 (t, J 8.0 Hz, 1H), 7.77 (d, J 8.5 Hz, 1H), 7.55 (t, J 7.5 Hz, 1H), 7.43 (dd, J 8.5, 2.5 Hz, 1H), 6.87 (d, J 8.5 Hz, 1H), 5.38-5.33 (m, 1H), 4.17-4.11 (m, 2H), 4.05-3.95 (m, 1H), 3.82-3.78 (m, 2H), 3.62-3.56 (m, 1H), 3.41-3.35 (m, 1H), 1.53 (s, 9H), 1.10 & 1.09 (2×t, J 7.0 Hz, 3H).

Synthesis 118-B 2-(4-((3S,4R)-4-(2-Hydroxypropan-2-yl)pyrrolidin-3-ylamino)quinazolin-2-yl)-4-(1H-pyrazol-4-yl)phe-nol (A-111)

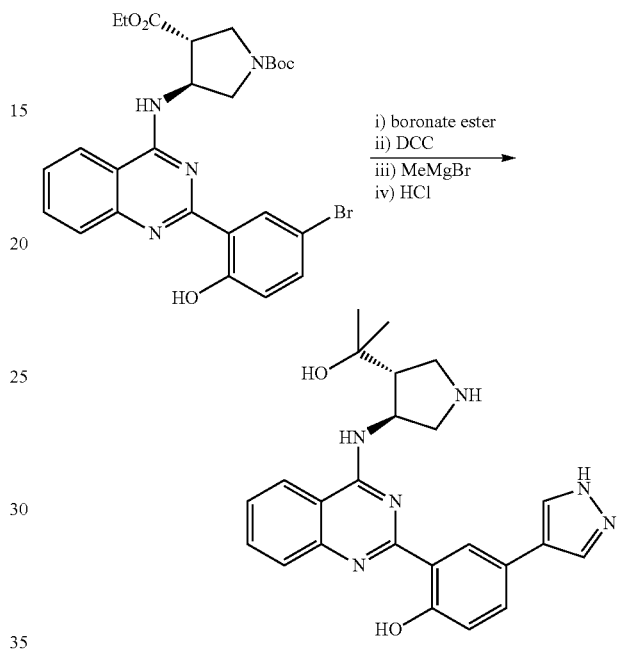

(3R,4S)-1-tert-Butyl 3-ethyl 4-(2-(5-bromo-2-hydrox-yphenyl)quinazolin-4-ylamino)pyrrolidine-1,3-dicarboxy-late (0.203 g, 0.36 mmol), tert-butyl 4-(4,4,5,5-tetramethyl-1,3,2-dioxaborolan-2-yl-1H-pyrazole-1-carboxylate (0.114 g, 0.39 mmol), palladium tetrakistriphenylphosphine (0.084 g, 0.07 mmol) and potassium phosphate (0.154 g, 0.073 mmol) was dissolved in DMA (2.1 mL) and water (0.9 mL). The mixture was heated at 150° C. for 10 mins in a micro-wave. The resulting mixture was filtered through a 3 cm plug of silica eluting with ethyl acetate and the concentrated filtrate was submitted to silica column chromatography eluting on a gradient from DCM to 5% MeOH in DCM. The resulting (3R,4S)-1-(tert-butoxycarbonyl)-4-(2-(2-hydroxy-5-(1H-pyrazol-4-yl)phenyl)quinazolin-4-ylamino)pyrrolidine-3-carboxylic acid (20 mg, 0.036 mmol) was dissolved in DCM (1.0 mL) and MeOH (0.3 mL) was added followed by DMAP (14 mg, 0.01 mmol) and DCC (16 mg, 0.072 mmol) and the solution was stirred at room temperature for 18 h. The mixture was concentrated in vacuo and purified by silica column chromatography eluting with a gradient from DCM to 5% MeOH in DCM to give (3R,4S)-1-tert-butyl-3-(methylcar-boxylate)-4-(2-(2-hydroxy-5-(1H-pyrazol-4-yl)phenyl) quinazolin-4-ylamino)pyrrolidine-1-carboxylate (11 mg, 56%). (3R,4S)-1-tert-butyl-3-(methylcarboxylate)-4-(2-(2-hydroxy-5-(1H-pyrazol-4-yl)phenyl)quinazolin-4-ylamino) pyrrolidine-1-carboxylate was dissolved in THF (0.57 mL) and MeMgBr (20 eq.) was added drop wise. The solution was heated at reflux overnight. The mixture was cooled and water (0.5 mL) was cautiously added followed by saturated NH$_4$Cl (1 mL) the mixture was concentrated in vacuo and water was added (20 mL) and the aqueous phase was extracted with DCM (3×50 mL). The combined organic extracts were dried (MgSO₄) and concentrated in vacuo and purified by silica column chromatography eluting with a gradient of 1% MeOH in DCM to 5% DCM in MeOH to afford the title compound.

LC-MS (LCT3) m/z 431 [M+H⁺], R$_t$ 2.03 minutes.

Synthesis 119

2-(4-((3S,4R)-4-(2-Hydroxypropan-2-yl)pyrrolidin-3-ylamino)quinazolin-2-yl)-4-(1H-pyrazol-3-yl)phenol (A-112)

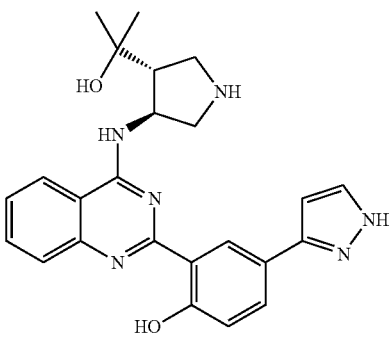

The title compound was prepared in a method analogous to that described in Synthesis 118, replacing tert-butyl 4-(4,4,5,5-tetramethyl-1,3,2-dioxaborolan-2-yl)-1H-pyrazole-1-carboxylate with 3-(4,4,5,5-tetramethyl-1,3,2-dioxaborolan-2-yl)-1-((2-(trimethylsilyl)ethoxy)methyl)-1H-pyrazole.

LC-MS (LCT3B) m/z 431 [M+H⁺], R$_t$ 2.08 minutes.

Synthesis 120

2-(4-((3S,4R)-4-(2-Hydroxypropan-2-yl)pyrrolidin-3-ylamino)quinazolin-2-yl)-4-(1-methyl-1H-pyrazol-4-yl)phenol (A-113)

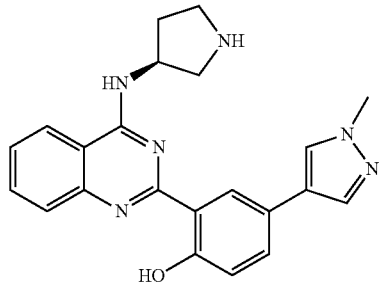

The title compound was prepared in a method analogous to that described in synthesis 107, replacing 4-fluorobenzene boronic acid with 1-methyl-4-(4,4,5,5-tetramethyl-1,3,2-dioxaborolan-2-yl)-1H-pyrazole.

LC-MS (LCT3B) m/z 387 [M+H⁺], R$_t$ 1.96 minutes. ¹H NMR (500 MHz, DMSO) δ 9.12 (br. s, 1H), 8.71 (d, J 5.5 Hz, 1H), 8.57 (d, J 2.5 Hz, 1H), 8.48 (d, J 8.0 Hz, 1H), 8.12 (s, 1H), 7.92-7.76 (m, 3H), 7.65-7.49 (m, 2H), 6.95 (d, J 8.5, 1H), 5.04 (s, 1H), 3.89 (s, 3H), 3.73 (dd, J 12.0, 6.5 Hz, 1H), 3.50-3.37 (m, 3H), 2.43 (dd, J 13.5, 7.5 Hz, 1H), 2.33-2.27 (m, 1H).

Synthesis 121

(S)-4-Fluoro-2-(7-fluoro-4-(pyrrolidin-3-ylamino)quinazolin-2-yl)phenol (A-114)

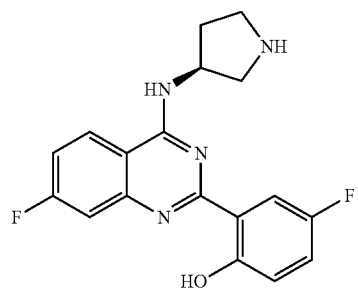

The title compound was prepared using a method analogous to that described in Synthesis 80, replacing 2-amino-5-methoxybenzoic acid with 2-amino-4-fluorobenzoic acid in Synthesis 80-A.

LC-MS (LCT3B) m/z 343 [M+H⁺], R$_t$ 2.17 minutes. ¹H NMR (DMSO) δ 8.16 (dd, J 9.0, 5.5 Hz, 1H), 8.02 (dd, J 10.0, 3.5 Hz, 1H), 7.28 (dd, J 10.0, 2.5 Hz, 1H), 7.21 (dd, J 8.5, 2.5 Hz, 1H), 7.05 (ddd, J 9.0, 8.0, 3.5 Hz, 1H), 6.84 (dd, J 9.0, 4.5 Hz, 1H), 4.81-4.76 (m, 1H), 3.41 (dd, J 12.0, 6.5 Hz, 1H), 3.21-3.15 (m, 1H), 3.10-3.05 (m, 1H), 3.00 (dd, J 12.0, 5.0 Hz, 1H), 2.40-2.32 (m, 1H), 2.05-1.98 (m, 1H).

Synthesis 122

4-Fluoro-2-(4-((3S,4R)-4-(2-hydroxypropan-2-yl)pyrrolidin-3-ylamino)quinazolin-2-yl)phenol (A-115)

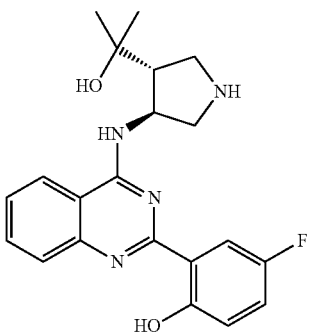

The title compound was prepared using methods analogous to those described in Synthesis 84 and 93, replacing trans-1-tert-butyl 3-ethyl 4-(2-(5-fluoro-2-hydroxyphenyl)-3,4-dihydroquinazolin-4-ylamino)pyrrolidine-1,3-dicarboxylate with (3R,4S)-1-tert-butyl 3-ethyl 4-aminopyrrolidine-1,3-dicarboxylate in Synthesis 84. (3R,4S)-1-tert-Butyl 3-ethyl 4-aminopyrrolidine-1,3-dicarboxylate was prepared as described in J. Am. Chem. Soc., 2006, 10638.

LC-MS (LCT3B) m/z 383 [M+H⁺], Rt 2.04 minutes. ¹H NMR (500 MHz, MeOD) δ 8.27-8.18 (m, 2H), 7.87-7.80 (m, 1H), 7.78 (d, J 7.5, 1H), 7.60-7.51 (m, 1H), 7.16-7.05 (m, 1H), 6.93 (dd, J 9.0, 4.5, 1H), 5.23 (dd, J 12.0, 6.5, 1H), 3.61 (dd, J 12.0, 7.0, 1H), 3.48 (dd, J 11.5, 8.5, 1H), 3.24 (dd, J 12.0, 8.0, 1H), 3.16 (dd, J 12.0, 5.0, 1H), 2.62 (dd, J 14.5, 8.5, 1H), 1.35 (s, 3H), 1.31 (s, 3H).

Synthesis 123

4-Fluoro-2-(4-((3S,4R)-4-(hydroxymethyl)pyrrolidin-3-ylamino)quinazolin-2-yl)phenol (A-116)

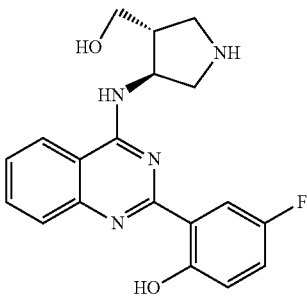

The title compound was prepared using methods analogous to those described in Synthesis 84 and 95, replacing trans-1-tert-butyl 3-ethyl 4-(2-(5-fluoro-2-hydroxyphenyl)-3,4-dihydroquinazolin-4-ylamino)pyrrolidine-1,3-dicarboxylate with (3R,4S)-1-tert-butyl 3-ethyl 4-aminopyrrolidine-1,3-dicarboxylate in Synthesis 84. (3R,4S)-1-tert-Butyl 3-ethyl 4-aminopyrrolidine-1,3-dicarboxylate was prepared as described in *J. Am. Chem. Soc.*, 2006, 10638.

LC-MS (LCT3B) m/z 355 [M+H$^+$], Rt 1.92 minutes. $^1$H NMR (500 MHz, MeOD) δ 8.27-8.17 (m, 2H), 7.87-7.78 (m, 1H), 7.76 (d, J 8.5 Hz, 1H), 7.60-7.44 (m, 1H), 7.14-7.02 (m, 1H), 6.92 (dd, J 9.0, 4.5 Hz, 1H), 4.83-4.77 (m, 1H), 3.84 (dd, J 11.0, 5.5 Hz, 1H), 3.75 (dd, J 11.0, 7.0 Hz, 1H), 3.49 (dd, J 11.5, 7.0 Hz, 1H), 3.33-3.28 (m, 1H), 2.98 (dd, J 11.5, 5.5 Hz, 1H), 2.93 (dd, J 11.5, 6.5 Hz, 1H), 2.55-2.50 (m, 1H).

Synthesis 124

4-Fluoro-2-(4-((3S,4R)-4-(2-hydroxypropan-2-yl)pyrrolidin-3-ylamino)-6,7-dimethoxyquinazolin-2-yl)phenolphenol (A-117)

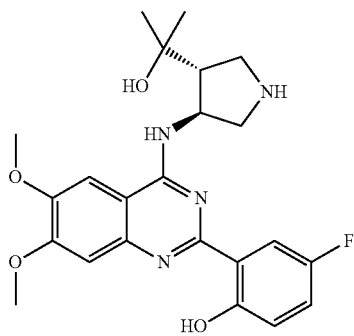

The title compound was prepared using methods analogous to those described in Synthesise 77 and 95, replacing (S)-(−)-1-boc-3-aminopyrrolidine with (3R,4S)-1-tert-butyl 3-ethyl 4-aminopyrrolidine-1,3-dicarboxylate. (3R,4S)-1-tert-Butyl 3-ethyl 4-aminopyrrolidine-1,3-dicarboxylate was prepared as described in *J. Am. Chem. Soc.*, 2006, 10638.

LC-MS (LCT3B) m/z 355 [M+H$^+$], Rt 1.92 minutes. $^1$H NMR (500 MHz, MeOD) δ 8.13 (dd, J 10.0, 3.0 Hz, 1H), 7.51 (s, 1H), 7.09 (s, 1H), 7.03 (ddd, J 9.0, 8.0, 3.0 Hz, 1H), 6.86 (dd, J 9.0, 4.5 Hz, 1H), 5.06-5.02 (m, 1H), 3.98 (s, 3H), 3.97 (s, 3H), 3.40-3.25 (m, 2H), 3.05-2.94 (m, 2H), 2.46 (dd, J 14.0, 8.0 Hz, 1H), 1.32 (s, 3H), 1.30 (s, 3H).

Synthesis 125

4-Fluoro-2-(4-((3S,4R)-4-(2-hydroxypropan-2-yl)pyrrolidin-3-ylamino)-6-methoxy-7-(2-methoxyethoxy)quinazolin-2-yl)phenol (A-118)

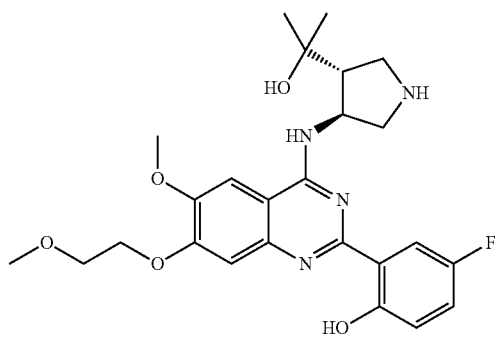

The title compound was prepared using methods analogous to those described in Synthesise 88 and 95, replacing (S)-(−)-1-boc-3-aminopyrrolidine with (3R,4S)-1-tert-butyl 3-ethyl 4-aminopyrrolidine-1,3-dicarboxylate. (3R,4S)-1-tert-Butyl 3-ethyl 4-aminopyrrolidine-1,3-dicarboxylate was prepared as described in *J. Am. Chem. Soc.*, 2006, 10638.

LC-MS (LCT3B) m/z 487 [M+H$^+$], Rt 2.02 minutes. $^1$H NMR (500 MHz, MeOD) δ 8.15 (dd, J 10.0, 3.0 Hz, 1H), 7.55 (s, 1H), 7.14 (s, 1H), 7.05 (dt, J 8.5, 3.0 Hz, 1H), 6.88 (dd, J 9.0, 4.5 Hz, 1H), 5.08-5.05 (m, 1H), 4.29-4.27 (m, 2H), 3.99 (s, 3H), 3.85-3.84 (m, 2H), 3.47 (s, 3H), 3.45-3.38 (m, 1H), 3.34-3.28 (m, 1H), 3.09-2.96 (m, 2H), 2.50-2.46 (m, 1H), 1.33 (s, 3H), 1.30 (s, 3H).

Biological Methods

CHK2 Kinase Activity Assay

Measurement of inhibition of CHK2 kinase activity in vitro. CHK2 kinase activity was measured in a DELFIA® assay that monitors phosphorylation of a CDC25C peptide using a specific phospho antibody. The enzyme reaction was carried out in 96-well polypropylene plates (Greiner). The reaction mix (total volume 25 μL) contained enzyme and peptide mix (15 μL) (containing CHK2, prepared in-house, 1 nM; Biotin-KKKVSRSGLYRSPSMPENLNRPR, 1 μM), ATP (30 μM, 5 μL) and either DMSO (2.5%) or test compound (5 μL) diluted to a give a range of concentrations (0-100 μM in 2.5% DMSO, final concentrations) in assay buffer (40 mM HEPES (pH7.4), 40 mM KCl, 2 mM MgCl$_2$, 10 mM DTT and 0.02% Tween 20). The reaction mixture was incubated for 30 minutes at room temperature and stopped by the addition of buffer (125 μL) containing 40 mM EDTA, 0.05% Tween 20, 0.1% BSA in TBS (10× concentrate, Sigma). An aliquot (100 μL) of the reaction mix was transferred to a black neutravidin-coated 96-well plate (Perbio) and incubated for 1 hour on a shaker (Titertek, Flow Laboratories) at room temperature. The plates were washed four times with wash buffer (25 mM Tris (pH 8), 150 mM NaCl and 0.1% Tween 20) (WellWash4, Thermo Life Sciences) and incubated for 1 hour as before with antibody mix (100 µL) consisting of anti-phospho CDC25C (diluted 1/4000 equivalent to 0.35 nM-1.25 nM, #9528, Cell Signalling Technology) and europium-labelled anti-rabbit IgG, (0.3 µg/mL, AD0105, PerkinElmer Life Sciences) diluted in DELFIA assay buffer (PerkinElmer Life Sciences). The plates were washed a further four times with wash buffer before the addition of enhancement solution (100 µL/well, PerkinElmer Life Sciences). The plate was read on a Victor$^2$ 1420 multilabel counter (PerkinElmer Life Sciences) using a time-resolved measurement mode reading fluorescence at 615 nM. The concentration of test compound required to inhibit enzyme activity by 50% was calculated ($IC_{50}$).

CHK2 Band Shift Assay

Measurement of CHK2 inhibition in cells. U2OS cells were plated at $2\times10^5$ cells per well in 6-well plates and left for 48 hours before treatment. Cells were then pre-treated with test compound at the indicated concentrations for 1 hour before the addition of DMSO control or 50 µM etoposide for 6 hours. Cells are then washed with ice-cold phosphate buffered saline (PBS), harvested, lysates prepared and protein estimations performed. Samples of 30 µg total protein in sample buffer were separated by SDS-PAGE on 7% NuPAGE gels and transferred to 0.45 µm Immobilon-P transfer membrane (Millipore). The membranes were blocked for 1 hour in blocking solution comprising 5% non-fat dried milk in TNT buffer (50 mM Tris pH 8.0, 150 mM NaCl, 0.1% Tween-20) before incubating at 4° C. and shaking overnight with the CHK2 antibody sc-8813 (Santa Cruz Biotechnology) diluted to 1:2000 in the blocking solution. The membranes were then washed in TNT buffer before incubating in bovine anti-goat HRP-conjugated secondary antibody (Santa Cruz Biotechnology) in blocking solution at 1:10,000 for 1 hour at room temperature. Bands were visualised with ECL Western Blotting Detection Reagents (Pierce) and developed using Hyperfilm (Amersham Biosciences). The test compounds were assessed for their ability to prevent the band shift on the gel seen in control samples where cells were incubated with etoposide in the absence of test compound.

Biological Data

The ability of several compounds to inhibit CHK2 kinase activity was determined using the method described above under the heading "Measurement of inhibition of CHK2 kinase activity in vitro".

The following compounds were tested: A-001, A-002, A-003, A-004, A-005, A-006, A-007, A-008, A-009, A-010, A-011, A-012, A-013, A-014, A-015, A-016, A-017, A-018, A-019, A-020, A-021, A-022, A-023, A-024, A-025, A-026, A-027, A-028, A-029, A-030, A-031, A-032, A-033, A-034, A-035, A-036, A-037, A-038, A-039, A-040, A-041, A-042, A-043, A-044, A-045, A-046, A-047, A-048, A-049, A-050, A-051, A-052, A-053, A-054, A-055, B-001, B-002, B-003, B-004, C-001, D-001, D-002.

All of those compounds have an IC50 of less than 100 µM.

The following compounds have an IC50 of less than 3 µM: A-001, A-002, A-003, A-004, A-006, A-008, A-009, A-010, A-013, A-014, A-015, A-016, A-018, A-019, A-020, A-023, A-024, A-026, A-027, A-028, A-029, A-030, A-031, A-032, A-033, A-034, A-035, A-036, A-037, A-038, A-039, A-040, A-041, A-042, A-043, A-044, A-045, A-046, A-047, A-048, A-049, A-050, A-051, A-052, A-053, A-054, A-055, B-003, B-004.

The following compounds have an IC50 of 3 µM or more, and less than 30 µM: A-005, A-007, A-011, A-012, A-017, A-021, A-022, A-025, B-001, B-002, C-001, D-002.

Following further studies, the following compounds were tested: A-001 through AA-110, AA-114 through AA-118, B-001, B-002, B-003, B-004, C-001, D-001, D-002.

All of those compounds have an IC50 of less than 100 µM.

The following compounds have an IC50 of less than or equal to 0.3 µM: A-002, A-004, A-013, A-014, A-015, A-019, A-023, A-026, A-027, A-030, A-033, A-034, A-037, A-038, A-040, A-041, A-043, A-044, A-045, A-046, A-048, A-050, A-052, A-053, A-054, A-055, A-057, A-058, A-059, A-060, A-061, A-062, A-065, A-066, A-067, A-068, A-069, A-070, A-071, A-072, A-073, A-074, A-075, A-076, A-077, A-078, A-079, A-080, A-081, A-082, A-085, A-087, A-088, A-090, A-091, A-093, A-094, A-095, A-096, A-097, A-098, A-099, A-102, A-103, A-104, A-105, A-106, A-110, A-114, A-115, A-116, A-117, A-118.

The following compounds have an IC50 of more than 0.3 µM and less than or equal to 3 µM: A-001, A-003, A-006, A-008, A-009, A-010, A-016, A-018, A-020, A-024, A-028, A-029, A-031, A-032, A-035, A-036, A-039, A-042, A-047, A-049, A-051, A-056, A-063, A-083, A-084, A-086, A-089, A-092, A-107, A-108, A-109, B-003, B-004.

The following compounds have an IC50 of more than 3 µM and less than or equal to 30 µM: A-005, A-007, A-011, A-012, A-017, A-021, A-022, A-025, A-064, A-100, A-101, B-001, B-002, C-001, D-002.

One compound, compound A-001, has an IC50 value of 1.6 µM.

One compound, compound B-002, has an IC50 value of 3.8 µM.

One compound, compound C-001, has an IC50 value of 4.4 µM.

One compound, compound D-002, has an IC50 value of 8.2 µM.

The ability of compounds to inhibit CHK2 kinase activity in cells was examined using the CHK2 band shift assay as described above. See, for example, FIG. 1, which shows a photograph of a gel with bands for Chk2 and GAPDH, with lanes for a DMSO control (without and with etoposide) and for 25 µM compound A-004 (denoted "Ex 4") (again, without and with etoposide). Compound A-004 prevented the etoposide-induced CHK2 band shift on the gel when the cells were exposed to a concentration of 25 µM of the compound.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Arienti, K. L., et al., 2005, "Checkpoint kinase inhibitors: SAR and radioprotective properties of a series of 2-arylbenzimidazoles", *J. Med. Chem., Vol.* 48, pp. 1873-1855.
Bartkova, J., et al., 2005, "DNA damage response as a candidate anti-cancer barrier in early human tumorigenesis", *Nature*, Vol. 434, pp. 864-870.
Chehab, N. H., et al., 2000, "CHK2/hCds1 functions as a DNA damage checkpoint in G(1) by stabilizing p53", *Genes Dev.*, Vol. 14, No. 3, pp. 278-288.
Gibson, S. L., et al., 2005, "Hypoxia-induced phosphorylation of Chk2 in an ataxia telangiectasia mutated-dependent manner", *Cancer Res.*, Vol. 65, No. 23, pp. 10734-10741.
Gorgoulis, V. G., et al., 2005, "Activation of the DNA damage checkpoint and genomic instability in human precancerous lesions", *Nature*, Vol. 434, pp. 907-913.
Hirao, A., et al., 2000, "DNA damage-induced activation of p53 by the checkpoint kinase CHK2," *Science*, Vol. 287, pp. 1824-1827.
Komarov, P. G., et al., 1999, "A chemical inhibitor of p53 that protects mice from the side effects of cancer therapy", *Science*, Vol. 285, p. 1733.
Matsuoka, S., et al., 1998, "Linkage of ATM to cell cycle regulation by the CHK2 protein kinase", *Science*, Vol. 282, pp. 1893-1897.
Melchionna, R., et al., 2000, "Threonine 68 is required for radiation-induced phosphorylation and activation of Cds1," *Nat. Cell Biol.*, Vol. 2. pp. 762-765.
Murakami, H., et al., 1995, "A kinase from fission yeast responsible for blocking mitosis in S phase," *Nature*, Vol. 374, pp. 817-819.
Oliver, A. W., et al., 2006, "Trans-activation of the DNA-damage signalling protein kinase CHK2 by T-loop exchange," *EMBO J.*, Vol. 25, pp. 3179-3190.
Pommier, Y., et al., 2005, "Targeting CHK2 kinase: molecular interaction maps and therapeutic rationale," *Curr. Pharm. Des.*, Vol. 11, No. 22, pp. 2855-2872.
Simpson, G. L., et al., 2006, "Glycosylated Foldamers To Probe the Carbohydrate-Carbohydrate Interaction" *J. Am. Chem. Soc.*, Vol. 128, pp. 10638-10639.
Takai, H., et al., 2002, "Chk2-deficient mice exhibit radioresistance and defective p53-mediated transcription. *EMBO J.*, Vol. 21, pp. 5195-5205.

The invention claimed is:

1. A compound selected from compounds of the following formula, and pharmaceutically acceptable salts thereof:

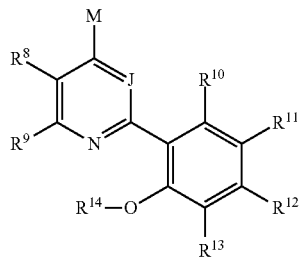

wherein
=J- is independently =N— or =CH—;
—$R^{10}$ is independently —H or -$G^1$;
—$R^{11}$ is independently —H or -$G^1$;
—$R^{12}$ is independently —H or -$G^1$;
—$R^{13}$ is independently —H or -$G^1$; and
—$R^{14}$ is independently —H or -$G^2$;
and wherein
either (i):
—$R^8$ is independently —$R^{19}$; and
—$R^9$ is independently —$R^{20}$;
wherein
—$R^{19}$ is independently —H or -$G^3$; and
—$R^{20}$ is independently —H or -$G^4$;
or (ii):
the group:

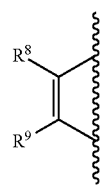

is independently a group:
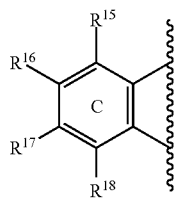
wherein
— $R^{15}$ is independently —H or -$G^5$;
— $R^{16}$ is independently —H or -$G^5$;
— $R^{17}$ is independently —H or -$G^5$; and
— $R^{18}$ is independently —H or -$G^5$;
and wherein
-M is independently selected from:
(MX-4)
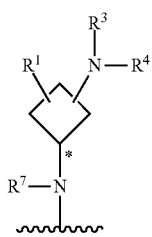
(MX-5)
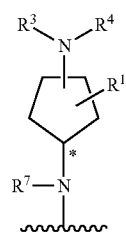
(MX-6)
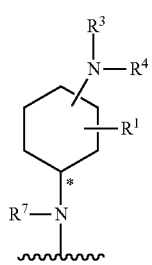
(MX-7)
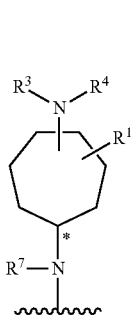
(MN-4)
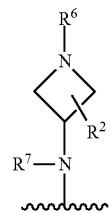
(MN-5)
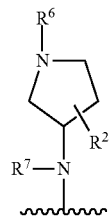
(MN-6-m)
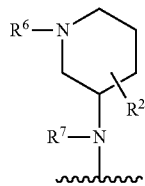
(MN-6-p)
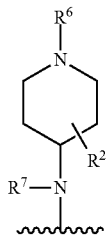
(MN-7-m)
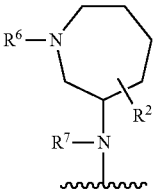
(MN-7-p)
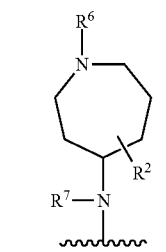
(MNN-7)

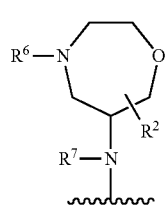

(MNO-7)

wherein
—$R^1$ is independently —H or a group -$D^1$;
—$R^2$ is independently —H or a group -$D^1$;
the group —$NR^3R^4$ is attached to a ring carbon atom other than the ring carbon atom to which is attached the group —$NR^7$—;
if —$R^3$ and —$R^4$ are present, then:
either: each of —$R^3$ and —$R^4$ is independently —H or -$D^2$;
or: —$R^3$ and —$R^4$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
—$R^5$ is independently —H or -$D^2$;
—$R^6$ is independently —H or -$D^2$; and
—$R^7$ is independently —H or -$D^2$;
and wherein
each -$D^1$ is independently
—$R^{5A1}$,
—OH, -$L^{5A}$-OH,
—$OR^{5A1}$, -$L^{5A}OR^{5A1}$,
—$NH_2$, —$NHR^{5A1}$, —$NR^{5A1}{}_2$, —$NR^{5A2}R^{5A3}$,
-$L^{5A}$-$NH_2$, -$L^{5A}$-$NHR^{5A1}$, -$L^{5A}$-$NR^{5A1}{}_2$, -$L^{5A}$-$NR^{5A2}R^{5A3}$,
—C(=O)OH, —C(=O)$OR^{5A1}$,
—C(=O)$NH_2$, —C(=O)$NHR^{5A1}$, —C(=O)$NR^{5A1}{}_2$, —C(=O)$NR^{5A2}R^{5A3}$, or
—C(=O)$R^{5A1}$;
with the limitation that if a -$D^1$ is —OH, —$OR^{5A1}$, —$NH_2$, —$NHR^{5A1}$, —$NR^{5A1}{}_2$, or —$NR^{5A2}$, $R^{5A3}$, then that -$D^1$ is not attached to a carbon atom that is attached to a nitrogen atom;
wherein
each -$L^{5A}$- is independently saturated aliphatic $C_{1-5}$alkylene;
in each group —$NR^{5A2}R^{5A3}$, —$R^{5A2}$ and —$R^{5A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{5A1}$ is independently
—$R^{5B1}$, —$R^{5B2}$, —$R^{5B3}$, —$R^{5B4}$, —$R^{5B5}$, —$R^{5B6}$, —$R^{5B7}$, —$R^{5B8}$,
-$L^{5B}$-$R^{5B4}$, -$L^{5B}$-$R^{5B5}$, -$L^{5B}$-$R^{5B6}$, -$L^{5B}$-$R^{5B7}$, or -$L^{5B8}$;
wherein
each —$R^{5B1}$ is independently saturated aliphatic $C_{1-6}$alkyl;
each —$R^{5B2}$ is independently aliphatic $C_{2-6}$alkenyl;
each —$R^{5B3}$ is independently aliphatic $C_{2-6}$alkynyl;
each —$R^{5B4}$ is independently saturated $C_{3-6}$cycloalkyl;
each —$R^{5B5}$ is independently $C_{3-6}$cycloalkenyl;
each —$R^{5B6}$ is independently non-aromatic $C_{3-7}$heterocyclyl;
each —$R^{5B7}$ is independently $C_{6-10}$-carboaryl;
each —$R^{5B8}$ is independently $C_{5-10}$heteroaryl;
each -$L^{5B}$- is independently saturated aliphatic $C_{1-3}$alkylene;
and wherein
each —$R^{5B4}$, —$R^{5B5}$, —$R^{5B6}$, —$R^{5B7}$, and —$R^{5B8}$ is optionally substituted with one or more substituents —$R^{5C1}$ and/or one or more substituents —$R^{1C2}$, and
each —$R^{5B1}$, —$R^{5B2}$, —$R^{5B3}$, and -$L^{5B}$- is optionally substituted with one or more substituents —$R^{5C2}$,
wherein
each —$R^{5C1}$ is independently saturated aliphatic $C_{1-4}$alkyl, phenyl, or benzyl;
each —$R^{5C2}$ is independently
—F, —Cl, —Br, —I,
—$CF_3$, —$OCF_3$,
—OH, -$L^{5D}$—OH, —O-$L^{5D}$-OH,
—$OR^{5D1}$, -$L^{5D}$-$OR^{5D1}$, —O-$L^{5D}$-$OR^{5D1}$,
—SH, —$SR^{5D1}$,
—CN,
—$NO_2$,
—$NH_2$, —$NHR^{5D1}$, —$NR^{5D1}{}_2$, —$NR^{5D2}R^{5D3}$,
-$L^{5D}$-$NH_2$, -$L^{5D}$-$NHR^{5D1}$, -$L^{5D}$-$NR^{5D1}{}_2$, -$L^{5D}$-$NR^{5D2}R^{5D3}$,
—O-$L^{5D}$-$NH_2$, —O-$L^{5D}$-$NHR^{5D1}$, —O-$L^{5D}$-$NR^{5D1}{}_2$, —O-$L^{5D}$-$NR^{5D2}R^{5D3}$,
—C(=O)OH, —C(=O)$OR^{5D1}$,
—C(=O)$NH_2$, —C(=O)$NHR^{5D1}$, —C(=O)$NR^{5D1}{}_2$, or —C(=O)$NR^{5D2}R^{5D3}$;
wherein
each —$R^{5D1}$ is independently saturated aliphatic $C_{1-4}$alkyl, phenyl, or benzyl;
each -$L^{5D}$- is independently saturated aliphatic $C_{1-5}$alkylene; and
in each group —$NR^{5D2}R^{5D3}$, —$R^{5D2}$ and —$R^{5D3}$ together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
and wherein
each -$D^2$ is independently saturated aliphatic $C_{1-4}$alkyl,
and wherein
each -$G^1$ is independently
—F, —Cl, —Br, —I,
$R^{1A1}$,
—$CF_3$, —$OCF_3$,
—OH, -$L^{1A}$-OH, —O-$L^{1A}$-OH,
—$OR^{1A1}$, -$L^{1A}$-$OR^{1A1}$, —O-$L^{1A}OR^{1A1}$,
—SH, —$SR^{1A1}$,
—CN,
—$NO_2$,
—$NH_2$, —$NHR^{1A1}$, —$NR^{1A1}{}_2$, —$NR^{1A2}R^{1A3}$,
-$L^{1A}$-$NH_2$, -$L^{1A}$-$NHR^{1A1}$, -$L^{1A}$-$NR^{1A1}{}_2$, -$L^{1A}$-$NR^{1A2}R^{1A3}$,
—O-$L^{1A}$-$NH_2$, —O-$L^{1A}$-$NHR^{1A1}$, —O-$L^{1A}$-$NR^{1A1}{}_2$, —O-$L^{1A}$-$NR^{1A2}R^{1A3}$,
—C(=O)OH, —C(=O)$OR^{1A1}$,
—C(=O)$NH_2$, —C(=O)$NHR^{1A1}$, —C(=O)$NR^{1A1}{}_2$, —C(=O)$NR^{1A2}R^{1A3}$,
—C(=O)$NHOR^{1A1}$, —C(=O)$NR^{1A1}OR^{1A1}$,
—NHC(=O)$R^{1A1}$, —$NR^{1A1}$C(=O)$R^{1A1}$,
—NHC(=O)$OR^{1A1}$, —$NR^{1A1}$C(=O)$OR^{1A1}$, —OC(=O)NH$_2$, —OC(=O)NHR$^{1A1}$, —OC(=O)NR$^{1A1}$$_2$, —OC(=O)NR$^{1A2}$R$^{1A3}$,
—C(=O)R$^{1A1}$,
—NHC(=O)NH$_2$, —NHC(=O)NHR$^{1A1}$,
—NHC(=O)NR$^{1A1}$$_2$, —NHC(=O)NR$^{1A2}$R$^{1A3}$,
—NR$^{1A1}$C(=O)NH$_2$, —NR$^{1A1}$C(=O)NHR$^{1A1}$,
—NR$^{1A1}$C(=O)NR$^{1A1}$$_2$, —NR$^{1A1}$C(=O)NR$^{1A2}$R$^{1A3}$,
—NHS(=O)$_2$R$^{1A1}$, —NR$^{1A1}$S(=O)$_2$R$^{1A1}$,
—S(=O)$_2$NH$_2$, —S(=O)$_2$NHR$^{1A1}$, —S(=O)$_2$NR$^{1A1}$$_2$, —S(=O)$_2$NR$^{1A2}$R$^{1A3}$,
—S(=O)R$^{1A1}$, —S(=O)$_2$R$^{1A1}$, —OS(=O)$_2$R$^{1A1}$, or —S(=O)$_2$OR$^{1A1}$;

wherein
each -L$^{1A}$- is independently saturated aliphatic C$_{1-5}$alkylene;
in each group —NR$^{1A1}$R$^{1A3}$, —R$^{1A2}$ and —R$^{1A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —R$^{1A1}$ is independently
—R$^{1B1}$, —R$^{1B2}$, —R$^{1B3}$, —R$^{1B4}$, —R$^{1B5}$, —R$^{1B6}$, —R$^{1B7}$, —R$^{1B8}$,
-L$^{1B}$-R$^{1B4}$, -L$^{1B}$-R$^{1B5}$, -L$^{1B}$-R$^{1B6}$, -L$^{1B}$-R$^{1B7}$, or -L$^{1B}$-R$^{1B8}$;
wherein
each —R$^{1B1}$ is independently saturated aliphatic C$_{1-6}$alkyl;
each —R$^{1B2}$ is independently aliphatic C$_{2-6}$alkenyl;
each —R$^{1B3}$ is independently aliphatic C$_{2-6}$alkynyl;
each —R$^{1B4}$ is independently saturated C$_{3-6}$cycloalkyl;
each —R$^{1B5}$ is independently C$_{3-6}$cycloalkenyl;
each —R$^{1B6}$ is independently non-aromatic C$_{3-7}$heterocyclyl;
each —R$^{1B7}$ is independently C$_{6-10}$carboaryl;
each —R$^{1B8}$ is independently C$_{5-10}$heteroaryl;
each -L$^{1B}$- is independently saturated aliphatic C$_{1-3}$alkylene;
and wherein
each —R$^{1B4}$, —R$^{1B5}$, —R$^{1B6}$, —R$^{1B7}$, and —R$^{1B8}$ is optionally substituted with one or more substituents —R$^{1C1}$ and/or one or more substituents —R$^{1C2}$, and
each —R$^{1B1}$, —R$^{1B2}$, —R$^{1B3}$, and -L$^{1B}$- is optionally substituted with one or more substituents —R$^{1C2}$,
wherein
each —R$^{1C1}$ is independently saturated aliphatic C$_{1-4}$alkyl, phenyl, or benzyl;
each —R$^{1C2}$ is independently
—F, —Cl, —Br, —I,
—CF$_3$, —OCF$_3$,
—OH, -L$^{1D}$-OH, —O-L$^{1D}$-OH,
—OR$^{1D1}$, -L$^{1D}$-OR$^{1D1}$, —O-L$^{1D}$-OR$^{1D1}$,
—SH, —SR$^{1D1}$,
—CN,
—NO$_2$,
—NH$_2$, —NHR$^{1D1}$, —NR$^{1D1}$$_2$, —NR$^{1D2}$R$^{1D3}$,
-L$^{1D}$-NH$_2$, -L$^{1D}$-NHR$^{1D1}$, -L$^{1D}$-NR$^{1D1}$$_2$, or -L$^{1D}$-NR$^{1D2}$R$^{1D3}$,
—O-L$^{1D}$-NH$_2$, —O-L$^{1D}$-NHR$^{1D1}$, —O-L$^{1D}$-NR$^{1D1}$$_2$, —O-L$^{1D}$-NR$^{1D2}$R$^{1D3}$,
—C(=O)OH, —C(=O)OR$^{1D1}$,
—C(=O)NH$_2$, —C(=O)NHR$^{1D1}$, —C(=O)NR$^{1D1}$$_2$, —C(=O)NR$^{1D2}$R$^{1D3}$, —S(=O)$_2$NH$_2$, —S(=O)$_2$NHR$^{1A1}$, —S(=O)$_2$NR$^{1A1}$$_2$, —S(=O)$_2$NR$^{1A1}$R$^{1A3}$, or
—S(=O)$_2$R$^{1A1}$;
wherein
each —R$^{1D1}$ is independently saturated aliphatic C$_{1-4}$alkyl, phenyl, or benzyl;
each -L$^{1D}$- is independently saturated aliphatic C$_{1-5}$alkylene; and
in each group —NR$^{1D2}$R$^{1D3}$, —R$^{1D2}$ and —R$^{1D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
and wherein
-G$^2$ is independently saturated aliphatic C$_{1-4}$alkyl;
and wherein
-G$^3$ is independently -G$^{3A}$, -G$^{3B}$, or -G$^{3C}$, wherein
-G$^{3A}$ is independently -G$^A$;
-G$^{3B}$ is independently -G$^B$; and
-G$^{3C}$ is independently -G$^C$;
and wherein
-G$^4$ is independently -G$^{4A}$, -G$^{4B}$, or -G$^{4C}$, wherein
-G$^{4A}$ is independently -G$^A$;
-G$^{4B}$ is independently -G$^B$; and
-G$^{4C}$ is independently -G$^C$;
and wherein
each -G$^A$ is independently
—F, —Cl, —Br, —I,
R$^{2A1}$,
—CF$_3$, —OCF$_3$,
—OH, -L$^{2A}$-OH, —O-L$^{2A}$-OH,
—OR$^{2A1}$, -L$^{2A}$-OR$^{2A1}$, —O-L$^{2A}$-OR$^{2A1}$,
—SH, —SR$^{2A1}$,
—CN,
—NO$_2$,
—NH$_2$, —NHR$^{2A1}$, —NR$^{2A1}$$_2$, —NR$^{2A2}$R$^{2A3}$,
-L$^{2A}$-NH$_2$, -L$^{2A}$-NHR$^{2A1}$, -L$^{2A}$-NR$^{2A1}$$_2$, -L$^{2A}$-NR$^{2A2}$R$^{2A3}$,
—O-L$^{2A}$-NH$_2$, —O-L$^{2A}$-NHR$^{2A1}$, —O-L$^{2A}$-NR$^{2A1}$$_2$, —O-L$^{2A}$-NR$^{2A2}$R$^{2A3}$,
—C(=O)OH, —C(=O)OR$^{2A1}$,
—C(=O)NH$_2$, —C(=O)NHR$^{2A1}$, —C(=O)NR$^{2A1}$$_2$, —C(=O)NR$^{2A2}$R$^{2A3}$,
—NHC(=O)R$^{2A1}$, —NR$^{2A1}$C(=O)R$^{2A1}$,
—NHC(=O)OR$^{2A1}$, —NR$^{2A1}$C(=O)OR$^{2A1}$,
—OC(=O)NH$_2$, —OC(=O)NHR$^{2A1}$, —OC(=O)NR$^{2A1}$$_2$, —OC(=O)NR$^{2A2}$R$^{2A3}$,
—C(=O)R$^{2A1}$,
—NHC(=O)NH$_2$, —NHC(=O)NHR$^{2A1}$,
—NHC(=O)NR$^{2A1}$$_2$, —NHC(=O)NR$^{2A2}$R$^{2A3}$,
—NR$^{2A1}$C(=O)NH$_2$, —NR$^{2A1}$C(=O)NHR$^{2A1}$,
—NR$^{2A1}$C(=O)NR$^{2A1}$$_2$, —NR$^{2A1}$C(=O)NR$^{2A2}$R$^{2A3}$,
—NHS(=O)$_2$R$^{2A1}$, —NR$^{2A1}$S(=O)$_2$R$^{2A1}$,
—S(=O)$_2$NH$_2$, —S(=O)$_2$NHR$^{2A1}$, —S(=O)$_2$NR$^{2A1}$$_2$, —S(=O)$_2$NR$^{2A2}$R$^{2A3}$,
—S(=O)R$^{2A1}$, —S(=O)$_2$R$^{2A1}$, —OS(=O)$_2$R$^{2A1}$, or —S(=O)$_2$OR$^{2A1}$;
wherein
each -L$^{2A}$- is independently saturated aliphatic C$_{1-5}$alkylene;
in each group —NR$^{2A2}$R$^{2A3}$, —R$^{2A2}$ and —R$^{2A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —$R^{2A1}$ is independently
—$R^{2B1}$, —$R^{2B2}$, —$R^{2B3}$, —$R^{2B4}$, —$R^{2B5}$, —$R^{2A6}$, —$R^{2B7}$, —$R^{2B8}$,
-$L^{2B}$-$R^{2B4}$, -$L^{2B}$-$R^{2B5}$, -$L^{2B}$-$R^{2B6}$, -$L^{2B}$-$R^{2B7}$, or -$L^{2B}$-$R^{2B8}$;

wherein
each —$R^{2B1}$ is independently saturated aliphatic $C_{1-6}$alkyl;
each —$R^{2B2}$ is independently aliphatic $C_{2-6}$alkenyl;
each —$R^{2B3}$ is independently aliphatic $C_{2-6}$alkynyl;
each —$R^{2B4}$ is independently saturated $C_{3-6}$cycloalkyl;
each —$R^{2B5}$ is independently $C_{3-6}$cycloalkenyl;
each —$R^{2B6}$ is independently non-aromatic $C_{3-7}$heterocyclyl;
each —$R^{2B7}$ is independently $C_{6-10}$carboaryl;
each —$R^{2B8}$ is independently $C_{5-10}$heteroaryl;
each -$L^{2B}$- is independently saturated aliphatic $C_{1-3}$alkylene;

and wherein
each —$R^{2B4}$, —$R^{2B5}$, —$R^{2B6}$, —$R^{2B7}$, and —$R^{2B8}$ is optionally substituted with one or more substituents —$R^{2C1}$ and/or one or more substituents —$R^{2C2}$, and
each —$R^{2B1}$, —$R^{2B2}$, —$R^{2B3}$, and -$L^{2B}$- is optionally substituted with one or more substituents —$R^{2C2}$, wherein
each —$R^{2C1}$ is independently saturated aliphatic $C_{1-4}$alkyl, phenyl, or benzyl;
each —$R^{2C2}$ is independently
—F, —Cl, —Br, —I,
—$CF_3$, —$OCF_3$,
—OH, -$L^{2D}$-OH,
—$OR^{2D1}$, -$L^{2D}$-$OR^{2D1}$,
—SH, —$SR^{2D1}$,
—CN,
—$NO_2$,
—$NH_2$, —$NHR^{2D1}$, —$NR^{2D1}{}_2$, —$NR^{2D2}R^{2D3}$,
-$L^{2D}$-$NH_2$, -$L^{2D}$-$NHR^{2D1}$, -$L^{2D}$-$NR^{2D1}{}_2$, -$L^{2D}$-$NR^{2D2}R^{2D3}$,
—C(=O)OH, —C(=O)$OR^{2D1}$,
—C(=O)$NH_2$, —C(=O)$NHR^{2D1}$, —C(=O)$NR^{2D1}{}_2$, or —C(=O)$NR^{2D2}R^{2D3}$;

wherein
each —$R^{2D1}$ is independently saturated aliphatic $C_{1-4}$alkyl, phenyl, or benzyl;
each -$L^{2D}$- is independently saturated aliphatic $C_{1-5}$alkylene; and
in each group —$NR^{2D2}R^{2D3}$, —$R^{2D2}$ and —$R^{2D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

and wherein
each -$G^B$ is independently phenyl, and is optionally substituted with one or more substituents, -$Q^1$;

and wherein
each -$G^C$ is independently $C_{5-6}$heteroaryl, and is optionally substituted with one or more substituents, -$Q^1$;

and wherein
each -$Q^1$ is independently
—F, —Cl, —Br, —I,
—$R^{3A1}$,
—$CF_3$, —$OCF_3$,
—OH, -$L^{3A}$-OH, —O-$L^{3A}$-OH,
—$OR^{3A1}$, -$L^{3A}$-$OR^{3A1}$, —O-$L^{3A}$-$OR^{3A1}$,
—SH, —$SR^{3A1}$,
—CN,
—$NO_2$,
—$NH_2$, —$NHR^{3A1}$, —$NR^{3A1}{}_2$, —$NR^{3A2}R^{3A3}$,
-$L^{3A}$-$NH_2$, -$L^{3A}$-$NHR^{3A1}$, -$L^{3A}$-$NR^{3A1}{}_2$, -$L^{3A}$-$NR^{3A2}R^{3A3}$,
—O-$L^{3A}$-$NH_2$, —O-$L^{3A}$-$NHR^{3A1}$, —O-$L^{3A}$-$NR^{3A1}{}_2$, —O-$L^{3A}$-$NR^{3A2}R^{3A3}$,
—C(=O)OH, —C(=O)$OR^{3A1}$,
—C(=O)$NH_2$, —C(=O)$NHR^{3A1}$, —C(=O)$NR^{3A1}{}_2$, —C(=O)$NR^{3A2}R^{3A3}$,
—C(=O)$NHOR^{3A1}$, —C(=O)$NR^{3A1}OR^{3A1}$,
—NHC(=O)$R^{3A1}$, —$NR^{3A1}$C(=O)$R^{3A1}$,
—NHC(=O)$OR^{3A1}$, —$NR^{3A1}$C(=O)$OR^{3A1}$,
—OC(=O)$NH_2$, —OC(=O)$NHR^{3A1}$, —OC(=O)$NR^{3A1}{}_2$, —OC(=O)$NR^{3A2}R^{3A3}$,
—C(=O)$R^{3A1}$,
—NHC(=O)$NH_2$, —NHC(=O)$NHR^{3A1}$,
—NHC(=O)$NR^{3A1}{}_2$, —NHC(=O)$NR^{3A2}R^{3A3}$,
—$NR^{3A1}$C(=O)$NH_2$, —$NR^{3A1}$C(=O)$NHR^{3A1}$,
—$NR^{3A1}$C(=O)$NR^{3A1}{}_2$, —$NR^{3A1}$C(=O)$NR^{3A2}R^{3A3}$,
—NHS(=O)$_2R^{3A1}$, —$NR^{3A1}$S(=O)$_2NR^{3A1}$,
—S(=O)$_2NH_2$, —S(=O)$_2NHR^{3A1}$, —S(=O)$_2NR^{3A1}{}_2$, —S(=O)$_2NR^{3A2}R^{3A3}$,
—S(=O)$R^{3A1}$, —S(=O)$_2R^{3A1}$, —OS(=O)$_2R^{3A1}$, or —S(=O)$_2OR^{3A1}$;

wherein
each -$L^{3A}$- is independently saturated aliphatic $C_{1-5}$alkylene;
in each group —$NR^{3A2}R^{3A3}$, —$R^{3A2}$ and —$R^{3A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —$R^{3A1}$ is independently
—$R^{3B1}$, —$R^{3B2}$, —$R^{3B3}$, —$R^{3B4}$, —$R^{3B5}$, —$R^{3B6}$, —$R^{3B7}$, —$R^{3B8}$,
-$L^{3B}$-$R^{3B4}$, -$L^{3B}$-$R^{3B5}$, -$L^{3B}$-$R^{3B6}$, -$L^{3B}$-$R^{3B7}$, or -$L^{3B}$$R^{3B8}$;

wherein
each —$R^{3B1}$ is independently saturated aliphatic $C_{1-6}$alkyl;
each —$R^{3B2}$ is independently aliphatic $C_{2-6}$alkenyl;
each —$R^{3B3}$ is independently aliphatic $C_{2-6}$alkynyl;
each —$R^{3B4}$ is independently saturated $C_{3-6}$cycloalkyl;
each —$R^{3B5}$ is independently $C_{3-6}$cycloalkenyl;
each —$R^{3B6}$ is independently non-aromatic $C_{3-7}$heterocyclyl;
each —$R^{3B7}$ is independently $C_{6-10}$carboaryl;
each —$R^{3B8}$ is independently $C_{5-10}$heteroaryl;
each -$L^{3B}$- is independently saturated aliphatic $C_{1-3}$alkylene;

and wherein
each —$R^{3B4}$, —$R^{3B5}$, —$R^{3B6}$, —$R^{3B7}$, and —$R^{3B8}$ is optionally substituted with one or more substituents —$R^{3C1}$ and/or one or more substituents —$R^{1C2}$, and
each —$R^{3B1}$, —$R^{3B2}$, —$R^{3B3}$, and -$L^{3B}$- is optionally substituted with one or more substituents —$R^{3C2}$, wherein
each —$R^{3C1}$ is independently saturated aliphatic $C_{1-4}$alkyl, phenyl, or benzyl;

each —$R^{3C2}$ is independently
- —F, —Cl, —Br, —I,
- —$CF_3$, —$OCF_3$,
- —OH, -$L^{3D}$-OH, —O-$L^{3D}$-OH,
- —$OR^{3D1}$, -$L^{3D}$-$OR^{3D1}$, —O-$L^{3D}$-$OR^{3D1}$,
- —SH, —$SR^{3D1}$,
- —CN,
- —$NO_2$,
- —$NH_2$, —$NHR^{3D1}$, —$NR^{3D1}{}_2$, —$NR^{3D2}R^{3D3}$,
- -$L^{3D}$-$NH_2$, -$L^{3D}$-$NHR^{3D1}$, -$L^{3D}$-$NR^{3D1}{}_2$, or -$L^{3D}$-$NR^{3D2}R^{3D3}$,
- —O-$L^{3D}$-$NH_2$, —O-$L^{3D}$-$NHR^{3D1}$, —O-$L^{3D}$-$NR^{3D1}{}_2$, —O-$L^{3D}$-$NR^{3D2}R^{3D3}$,
- —C(=O)OH, —C(=O)$OR^{3D1}$,
- —C(=O)$NH_2$, —C(=O)$NHR^{3D1}$, —C(=O)$NR^{3D1}{}_2$, —C(=O)$NR^{3D2}R^{3D3}$,
- —S(=O)$_2$$NH_2$, —S(=O)$_2$$NHR^{3A1}$, —S(=O)$_2$$NR^{3A1}{}_2$, —S(=O)$_2$$NR^{3A2}R^{3A3}$, or S(=O)$_2$$R^{3A1}$;

wherein
each —$R^{3D1}$ is independently saturated aliphatic $C_{1-4}$alkyl, phenyl, or benzyl;
each -$L^{3D}$- is independently saturated aliphatic $C_{1-5}$alkylene; and
in each group —$NR^{3D2}R^{3D3}$, —$R^{3D2}$ and —$R^{3D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

and wherein
each -$G^5$ is independently
- —F, —Cl, —Br, —I,
- —$R^{4A1}$,
- —$CF_3$, —$OCF_3$,
- —OH, -$L^{4A}$-OH, —O-$L^{4A}$-OH,
- —$OR^{4A1}$, -$L^{4A}$-$OR^{4A1}$, —O-$L^{4A}$-$OR^{4A1}$,
- —SH, —$SR^{4A1}$,
- —CN,
- —$NO_2$,
- —$NH_2$, —$NHR^{4A1}$, —$NR^{4A1}{}_2$, —$NR^{4A2}R^{4A3}$,
- -$L^{4A}$-$NH_2$, -$L^{4A}$-$NHR^{4A1}$, -$L^{4A}$-$NR^{4A1}{}_2$, -$L^{4A}$-$NR^{4A2}R^{4A3}$,
- —O-$L^{4A}$-$NH_2$, —O-$L^{4A}$-$NHR^{4A1}$, —O-$L^{4A}$-$NR^{4A1}{}_2$, —O-$L^{4A}$-$NR^{4A2}R^{4A3}$,
- —C(=O)OH, —C(=O)$OR^{4A1}$,
- —C(=O)$NH_2$, —C(=O)$NHR^{4A1}$, —C(=O)$NR^{4A1}{}_2$, —C(=O)$NR^{4A2}R^{4A3}$,
- —NHC(=O)$R^{4A1}$, —$NR^{4A1}$C(=O)$R^{4A1}$,
- —NHC(=O)$OR^{4A1}$, —$NR^{4A1}$C(=O)$OR^{4A1}$,
- —OC(=O)$NH_2$, —OC(=O)$NHR^{4A1}$, —OC(=O)$NR^{4A1}{}_2$, —OC(=O)$NR^{4A2}R^{4A3}$,
- —C(=O)$R^{4A1}$,
- —NHC(=O)$NH_2$, —NHC(=O)$NHR^{4A1}$,
- —NHC(=O)$NR^{4A1}{}_2$, —NHC(=O)$NR^{4A2}R^{4A3}$,
- —$NR^{4A1}$C(=O)$NH_2$, —$NR^{4A1}$C(=O)$NHR^{4A1}$,
- —$NR^{4A1}$C(=O)$NR^{4A1}{}_2$, —$NR^{4A1}$C(=O)$NR^{4A2}R^{4A3}$,
- —NHS(=O)$_2$$R^{4A1}$, —$NR^{4A1}$S(=O)$_2$$R^{4A1}$,
- —S(=O)$_2$$NH_2$, —S(=O)$_2$$NHR^{4A1}$, —S(=O)$_2$$NR^{4A1}{}_2$, —S(=O)$_2$$NR^{4A2}R^{4A3}$,
- —S(=O)$R^{4A1}$, —S(=O)$_2$$R^{4A1}$, —OS(=O)$_2$$R^{4A1}$, or —S(=O)$_2$$OR^{4A1}$;

wherein
each -$L^{4A}$- is independently saturated aliphatic $C_{1-5}$alkylene;
in each group —$NR^{4A2}R^{4A3}$, —$R^{4A2}$ and —$R^{4A3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{4A1}$ is independently
- —$R^{4B1}$, —$R^{4B2}$, —$R^{4B3}$, —$R^{4B4}$, —$R^{4B5}$, —$R^{4B6}$, —$R^{4B7}$, —$R^{4B8}$,
- -$L^{4B}$-$R^{4B4}$, -$L^{4B}$-$R^{4B5}$, -$L^{4B}$-$R^{4B6}$, -$L^{4B}$-$R^{4B7}$, or -$L^{4B}$-$R^{4B8}$;

wherein
each —$R^{4B1}$ is independently saturated aliphatic $C_{1-6}$alkyl;
each —$R^{4B2}$ is independently aliphatic $C_{2-6}$alkenyl;
each —$R^{4B3}$ is independently aliphatic $C_{2-6}$alkynyl;
each —$R^{4B4}$ is independently saturated $C_{3-6}$cycloalkyl;
each —$R^{4B5}$ is independently $C_{3-6}$cycloalkenyl;
each —$R^{4B6}$ is independently non-aromatic $C_{3-7}$heterocyclyl;
each —$R^{4B7}$ is independently $C_{6-10}$ carboaryl;
each —$R^{4B8}$ is independently $C_{5-10}$heteroaryl;
each -$L^{4B}$- is independently saturated aliphatic $C_{1-3}$alkylene;

and wherein
each —$R^{4B4}$, —$R^{4B5}$, —$R^{4B6}$, —$R^{4B7}$, and —$R^{4B8}$ is optionally substituted with one or more substituents —$R^{4C1}$ and/or one or more substituents —$R^{4C2}$, and
each —$R^{4B1}$, —$R^{4B2}$, —$R^{4B3}$, and -$L^{4B}$- is optionally substituted with one or more substituents —$R^{4C2}$, wherein
each —$R^{4C1}$ is independently saturated aliphatic $C_{1-4}$alkyl, phenyl, or benzyl;
each —$R^{4C2}$ is independently
- —F, —Cl, —Br, —I,
- —$CF_3$, —$OCF_3$,
- —OH, -$L^{4D}$-OH,
- —$OR^{4D1}$, -$L^{4D}$-$OR^{4D1}$,
- —SH, —$SR^{4D1}$,
- —CN,
- —$NO_2$,
- —$NH_2$, —$NHR^{4D1}$, —$NR^{4D1}{}_2$, —$NR^{4D2}R^{4D3}$,
- -$L^{4D}$-$NH_2$, -$L^{4D}$-$NHR^{4D1}$, -$L^{4D}$-$NR^{4D1}{}_2$, -$L^{4D}$-$NR^{4D2}R^{4D3}$,
- —C(=O)OH, —C(=O)$OR^{4D1}$,
- —C(=O)$NH_2$, —C(=O)$NHR^{4D1}$, —C(=O)$NR^{4D1}{}_2$, or —C(=O)$NR^{4D2}R^{4D3}$;

wherein
each —$R^{4D1}$ is independently saturated aliphatic $C_{1-4}$alkyl, phenyl, or benzyl;
each -$L^{4D}$- is independently saturated aliphatic $C_{1-5}$alkylene; and
in each group —$NR^{4D2}R^{4D3}$, —$R^{4D2}$ and —$R^{4D3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

with the proviso that the compound is not a compound selected from the following compounds:

(PR-E) 2-{7-Chloro-4-[methyl-(1-methyl-pyrrolidin-3-yl)-amino]-quinazolin-2-yl}-phenol;
(PR-F) 2-{7-Methyl-4-[methyl-(1-methyl-pyrrolidin-3-yl)-amino]-quinazolin-2-yl}-phenol;
(PR-G) 2-{6-Fluoro-4-[methyl-(1-methyl-pyrrolidin-3-yl)-amino]-quinazolin-2-yl}-phenol;
(PR-H) 2-{7-Chloro-4-[methyl-(1-methyl-piperidin-4-yl)-amino]-quinazolin-2-yl}-phenol;
(PR-I) 2-{7-Methyl-4-[methyl-(1-methyl-piperidin-4-yl)-amino]-quinazolin-2-yl}-phenol;
(PR-J) 2-{6-Fluoro-4-[methyl-(1-methyl-piperidin-4-yl)-amino]-quinazolin-2-yl}-phenol;
(PR-K) 2-Amino-6-(2-hydroxy-phenyl)-4-(piperidin-3-ylamino)-nicotinonitrile; and
(PR-L) 2-Amino-6-(2-hydroxy-phenyl)-4-(piperidin-4-ylamino)-nicotinonitrile.

2. A compound according to claim 1, wherein the compounds are selected from compounds of Formula (I), and pharmaceutically acceptable salts thereof:

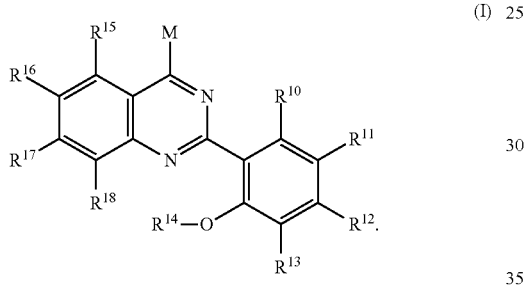

(I)

3. A compound according to claim 2, wherein -M is independently selected from:
groups of Formula (MN-5),
groups of Formula (MN-6-m), and
groups of Formula (MN-6-p).

4. A compound according to claim 2, wherein -M is independently selected from groups of Formula (MN-5).

5. A compound according to claim 4, wherein —$R^2$ is independently —H or a group -$D^1$; wherein -$D^1$ is independently
—$R^{5A1}$,
—$OR^{5A1}$, -$L^{5A}$-$OR^{5A1}$,
-$L^{5A}$-$NH_2$, -$L^{5A}$-$NHR^{5A1}$, -$L^{5A}$-$NR^{5A1}{}_2$, -$L^{5A}$-$NR^{5A2}R^{5A3}$,
—C(=O)OH, —C(=O)$OR^{5A1}$,
—C(=O)$NH_2$, —C(=O)$NHR^{5A1}$, —C(=O)$NR^{5A1}{}_2$, or —C(=O)$NR^{5A2}R^{5A3}$.

6. A compound according to claim 4, wherein —$R^2$ is independently —H or a group -$D^1$; wherein -$D^1$ is independently
—$R^{5A1}$,
—$OR^{5A1}$, or -$L^{5A}$-$OR^{5A1}$.

7. A compound according to claim 4, wherein —$R^2$ is independently —H or a group -$D^1$; wherein -$D^1$ is independently —$R^{5A1}$; wherein —$R^{5A1}$ is independently —$R^{5B1}$; and wherein —$R^{5C2}$ is independently —OH.

8. A compound according to claim 7, wherein
—$R^{10}$ is independently —H;
—$R^{11}$ is independently -$G^1$;
—$R^{12}$ is independently —H;
—$R^{13}$ is independently —H;
—$R^{14}$ is independently —H; and
-G' is independently
—F, —Cl, —Br, —I,
—$R^{1A1}$,
—$CF_3$, —$OCF_3$,
—$OR^{1A1}$, -$L^{1A}$-$OR^{1A1}$,
—CN,
—$NH_2$, —$NHR^{1A1}$, —$NR^{1A1}{}_2$, —$NR^{1A2}R^{1A3}$,
-$L^{1A}$-$NH_2$, -$L^{1A}$-$NHR^{1A1}$, -$L^{1A}$-$NR^{1A1}{}_2$, -$L^{1A}$-$NR^{1A2}R^{1A3}$,
—C(=O)$OR^{1A1}$,
—C(=O)$NH_2$, —C(=O)$NHR^{1A1}$, —C(=O)$NR^{1A1}{}_2$, —C(=O)$NR^{1A2}R^{1A3}$, or —C(=O)$NHOR^{1A1}$.

9. A compound according to claim 7, wherein
—$R^{10}$ is independently —H;
—$R^{11}$ is independently -$G^1$;
—$R^{12}$ is independently —H;
—$R^{13}$ is independently —H;
—$R^{14}$ is independently —H; and
-G' is independently —F, —Cl, —Br, —I, —$R^{1A1}$, or —C(=O)$OR^{1A1}$.

10. A compound according to claim 7, wherein
—$R^{10}$ is independently —H;
—$R^{11}$ is independently -$G^1$;
—$R^{12}$ is independently —H;
—$R^{13}$ is independently —H;
—$R^{14}$ is independently —H; and
-G' is independently —$R^{1A1}$.

11. A compound according to claim 10, wherein —$R^{1A1}$ is independently —$R^{1B8}$.

12. A compound according to claim 11, wherein —$R^{1B8}$ is independently $C_{5-6}$heteroaryl, and is optionally substituted.

13. A compound according to claim 11, wherein —$R^{1B8}$ is independently furanyl, thienyl, pyrrolyl, imidazolyl, pyrazolyl, triazolyl, oxazolyl, isoxazolyl, thiazolyl, isothiazolyl, pyridyl, pyrimidinyl, pyrazinyl, or pyridazinyl, and is optionally substituted.

14. A compound according to claim 13, wherein
—$R^{15}$ is independently —H;
—$R^{15}$ is independently —H or -$G^5$;
—$R^{16}$ is independently —H or -$G^5$;
—$R^{18}$ is independently —H; and
each -$G^5$ is independently
—F, —Cl, —Br, —I,
—$R^{4A1}$,
—$CF_3$,
-$L^{4A}$-OH, —O-$L^{4A}$-OH,
—$OR^{4A1}$, -$L^{4A}$-$OR^{4A1}$, —O-$L^{4A}$-$OR^{4A1}$,
—CN,
—$NH_2$, —$NHR^{4A1}$, —$NR^{4A1}{}_2$, —$NR^{4A2}R^{4A3}$,
-$L^{4A}$-$NH_2$, -$L^{4A}$-$NHR^{4A1}$, -$L^{4A}$-$NR^{4A1}{}_2$, —O-$L^{4A}$-$NR^{4A2}R^{4A3}$,
—O-$L^{4A}$-$NH_2$, —O-$L^{4A}$-$NHR^{4A1}$, —O-$L^{4A}$-$NR^{4A1}{}_2$, or —O-$L^{4A}$-$NR^{4A2}R^{4A3}$.

15. A compound according to claim 13, wherein
—$R^{15}$ is independently —H;
—$R^{16}$ is independently —H;
—$R^{17}$ is independently —H; and
—$R^{18}$ is independently —H.

16. A compound according to claim 1, selected from the following compounds, and pharmaceutically acceptable salts thereof:

(A-001)
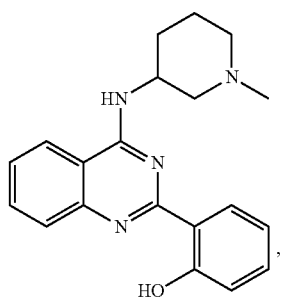
(A-002)
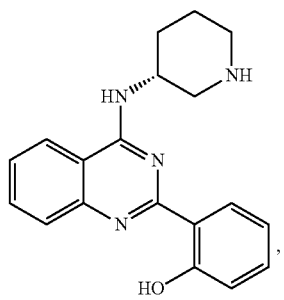
(A-003)
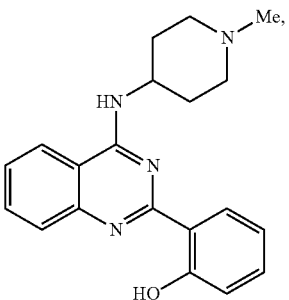
(A-004)
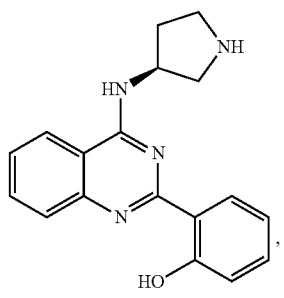
(A-005)
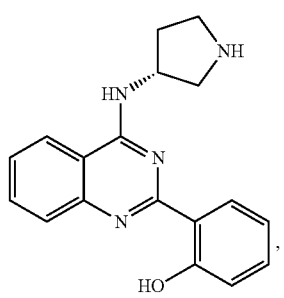
(A-006)
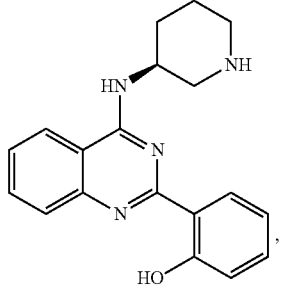
(A-007)
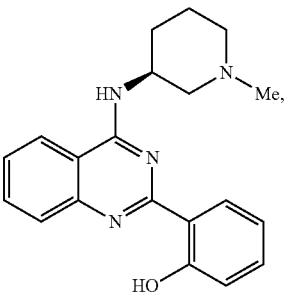
(A-008)
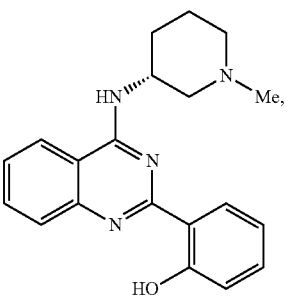
(A-009)
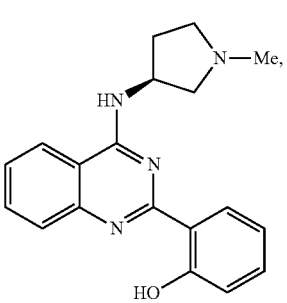
(A-010)
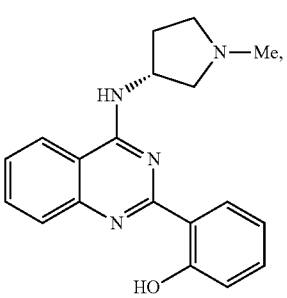

(A-011) 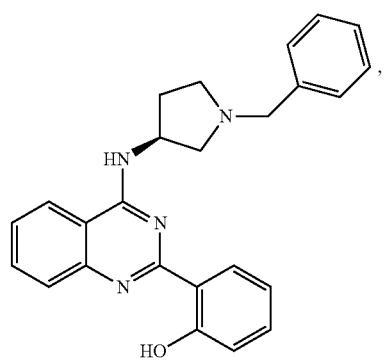
(A-012) 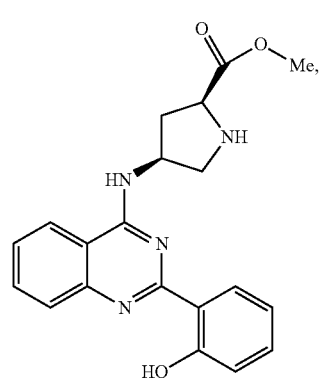
(A-013) 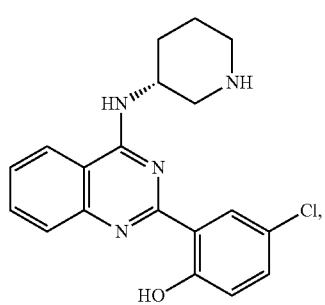
(A-014) 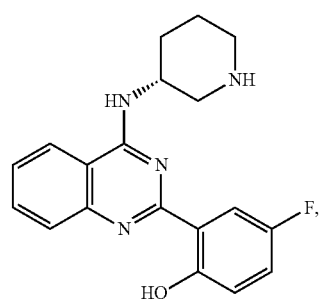
(A-015) 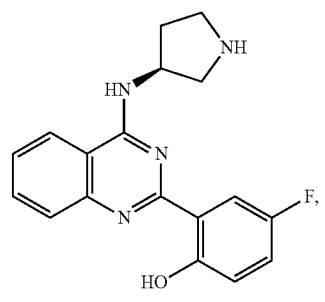
(A-016) 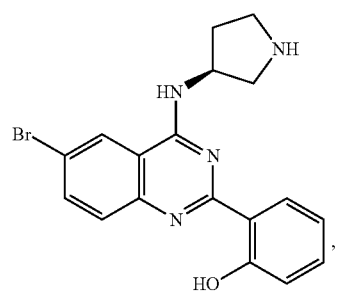
(A-017) 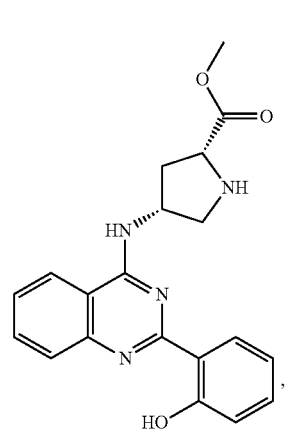
(A-018) 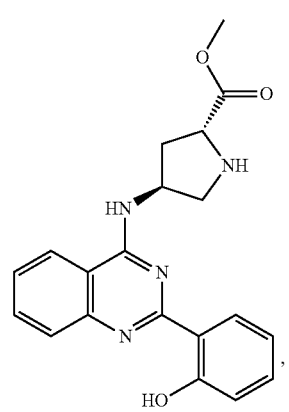
(A-019) 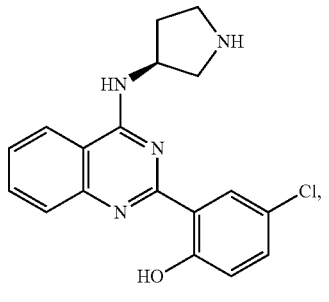

-continued
(A-020)
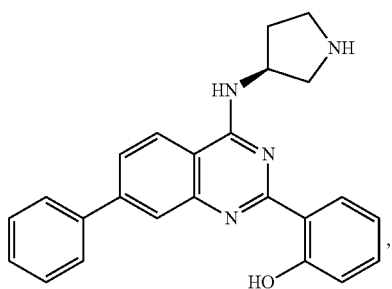
(A-021)
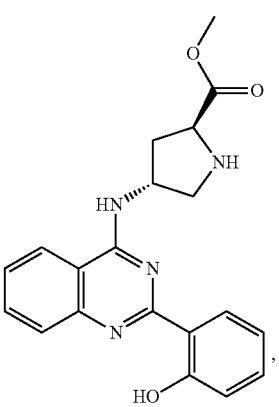
(A-022)
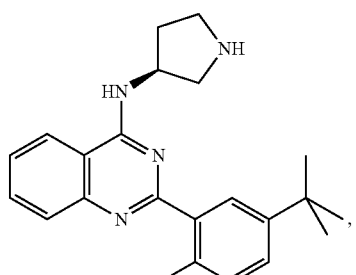
(A-023)
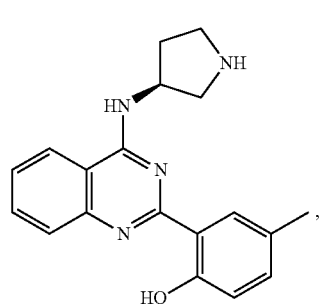
(A-024)
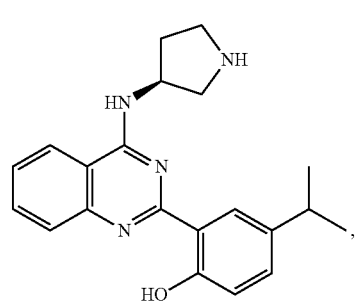
-continued
(A-025)
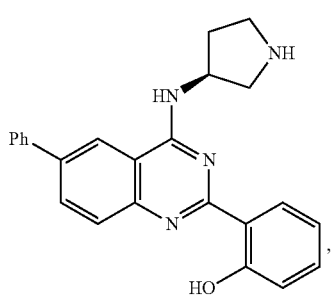
(A-026)
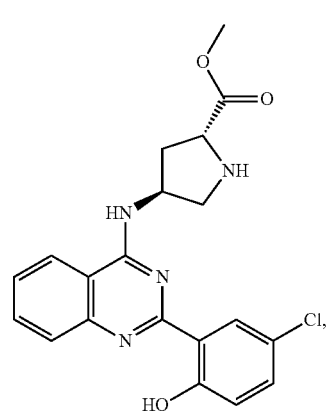
(A-027)
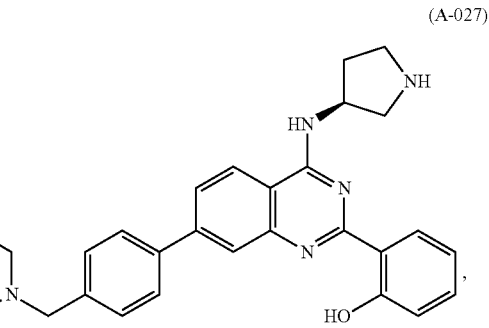
(A-028)
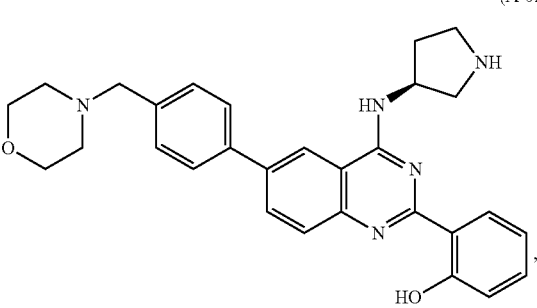
(A-029)
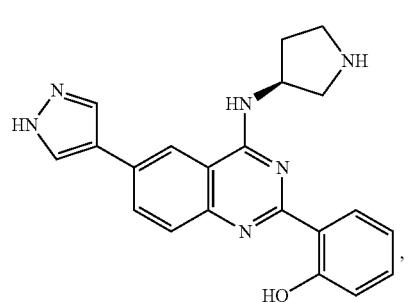

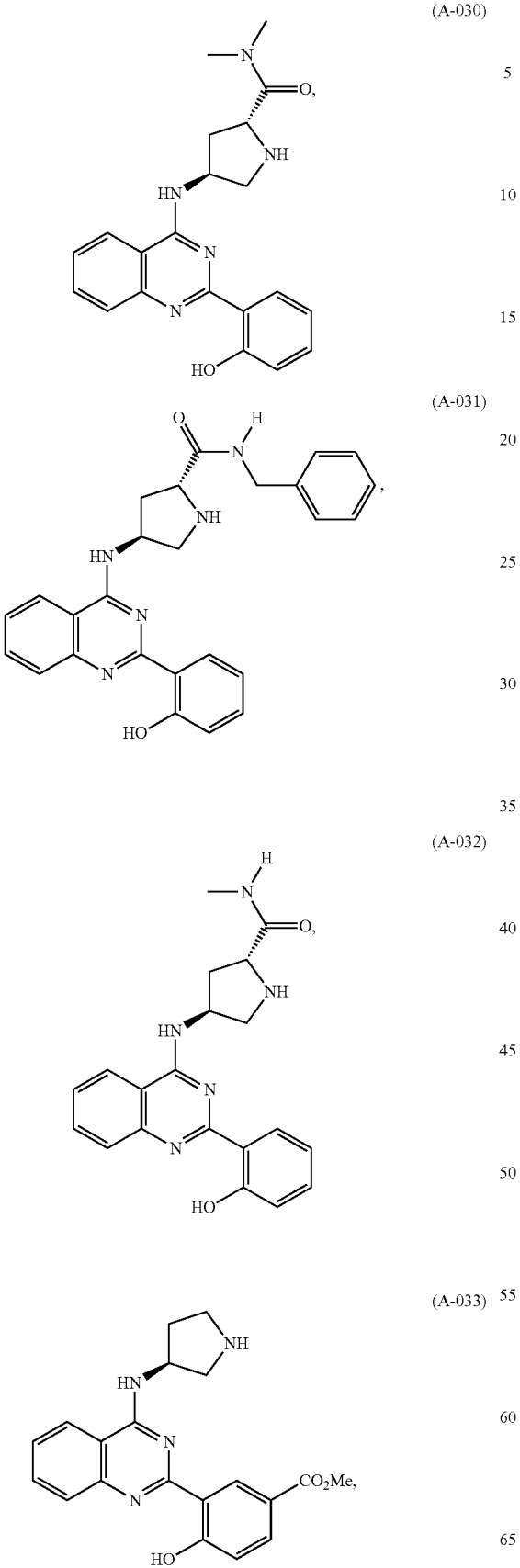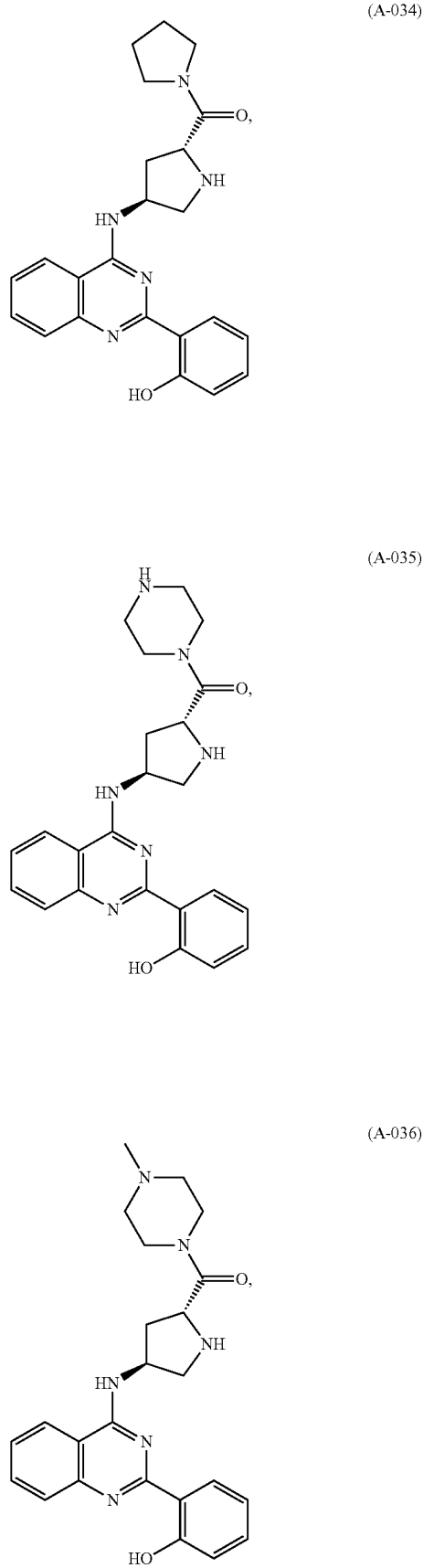

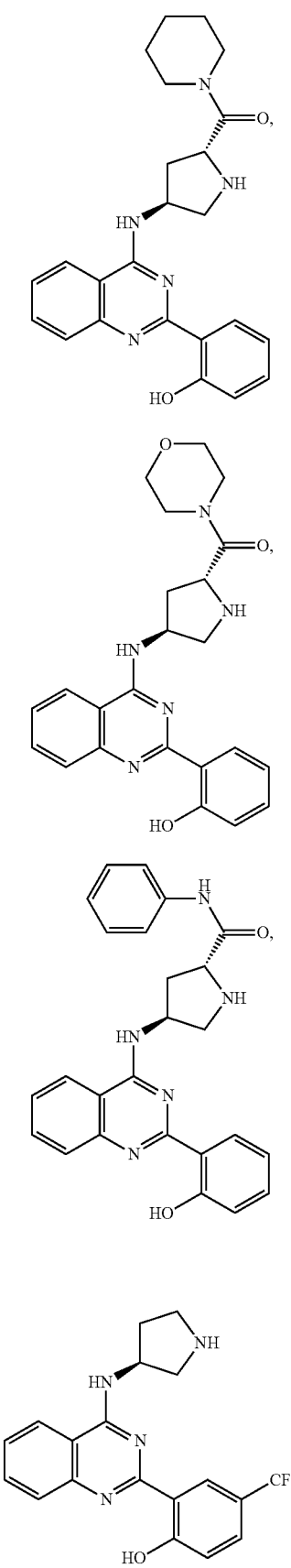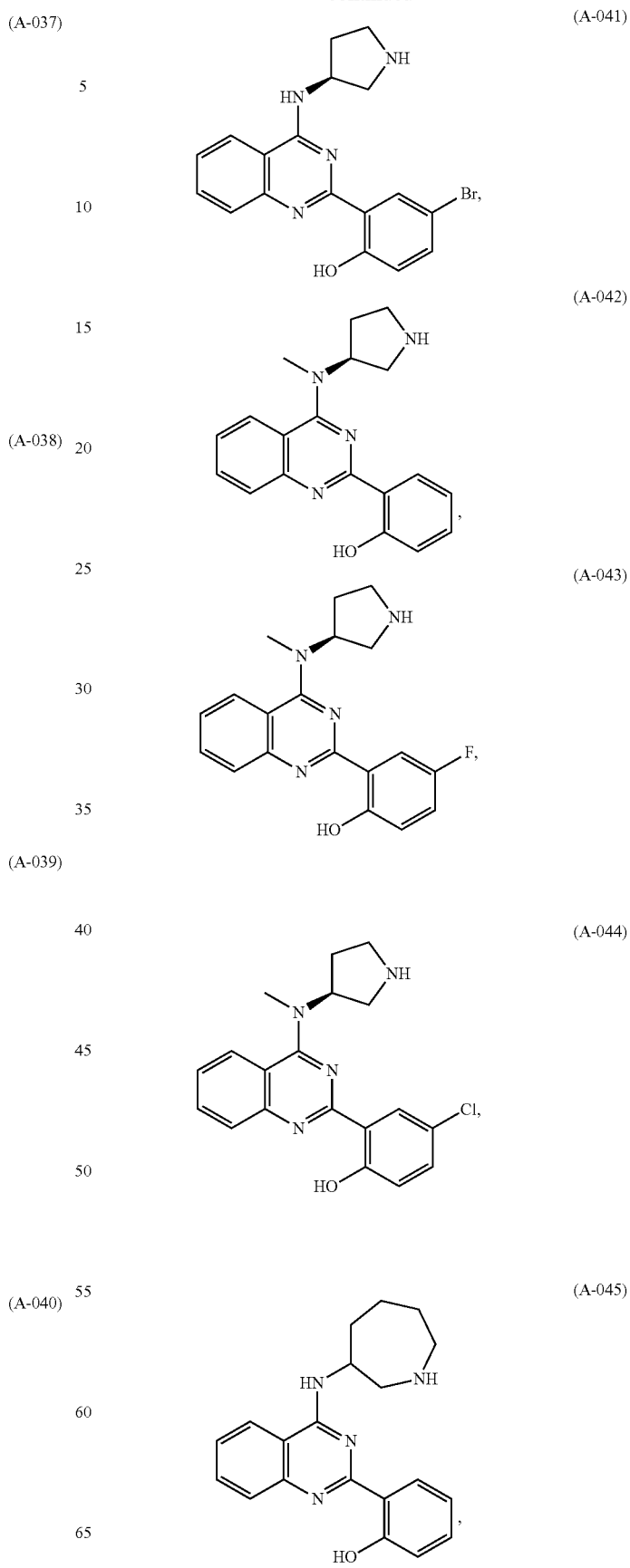

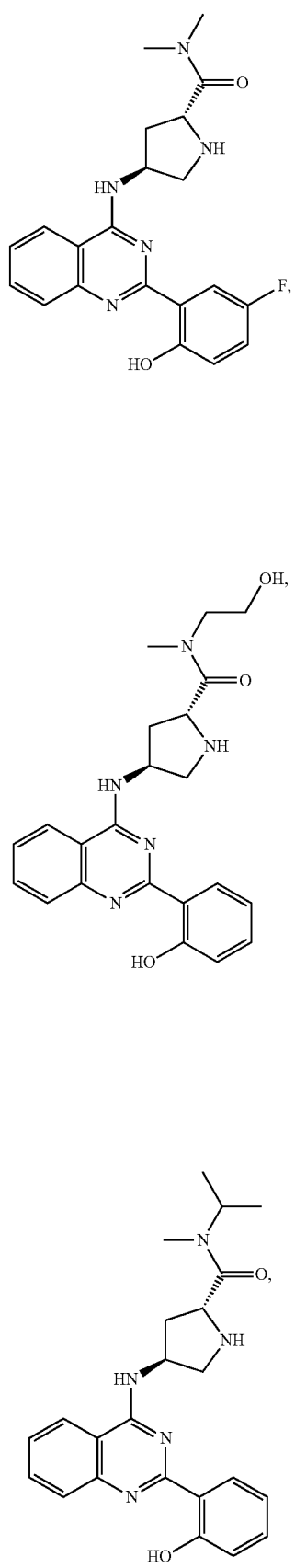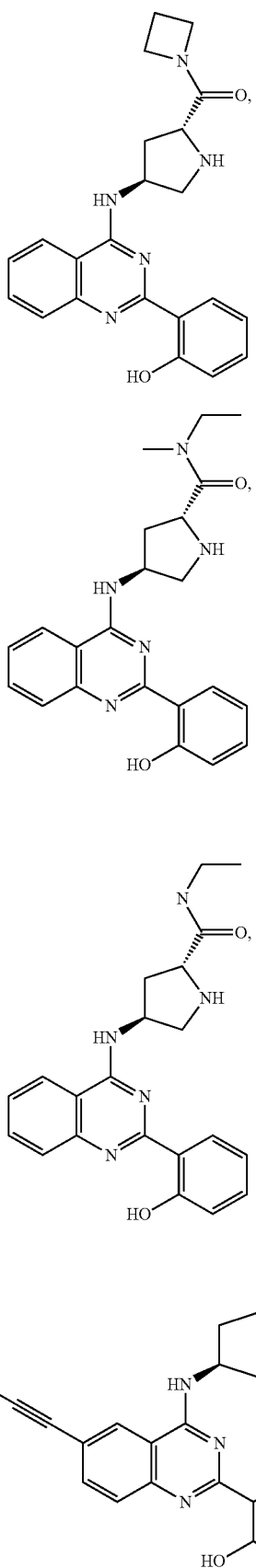

(A-053)
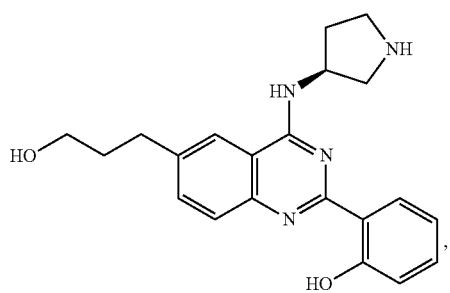
(A-054)
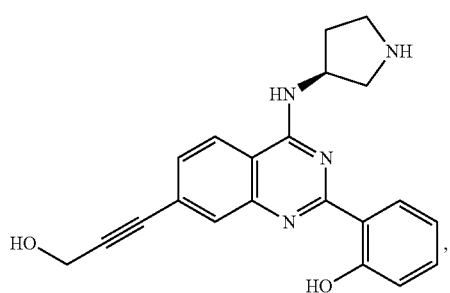
(A-055)
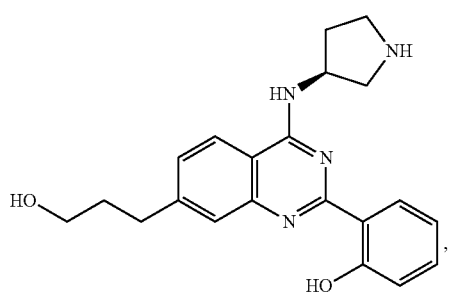
(A-056)
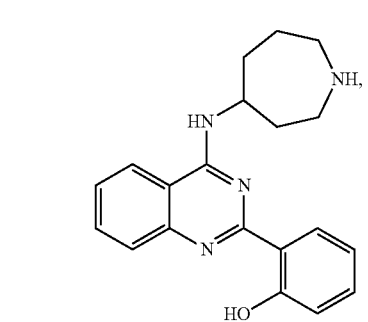
(A-057)
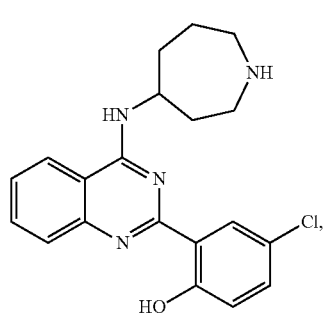
(A-058)
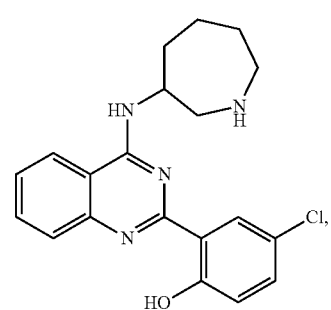
(A-059)
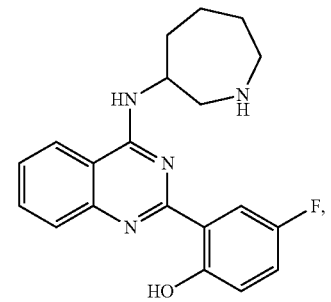
(A-060)
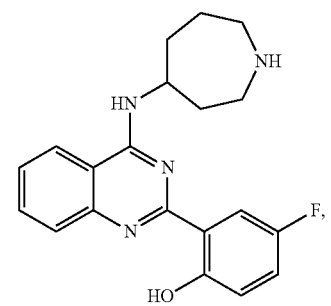
(A-061)
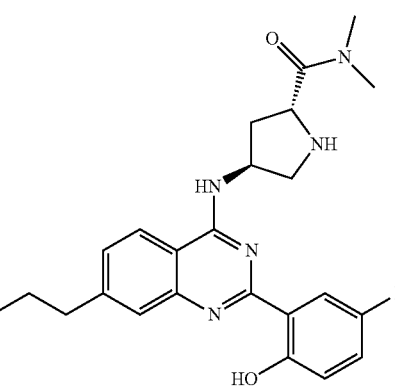
(A-062)
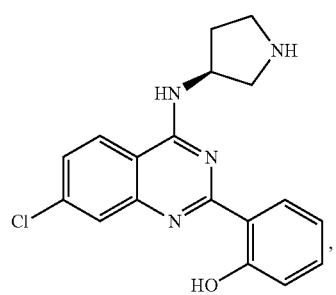

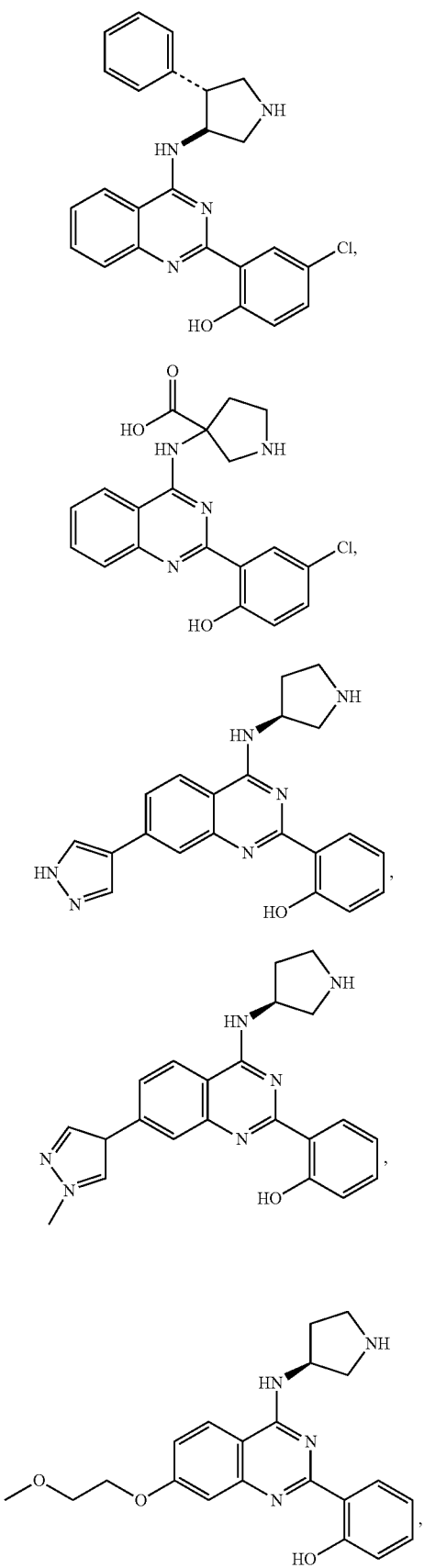
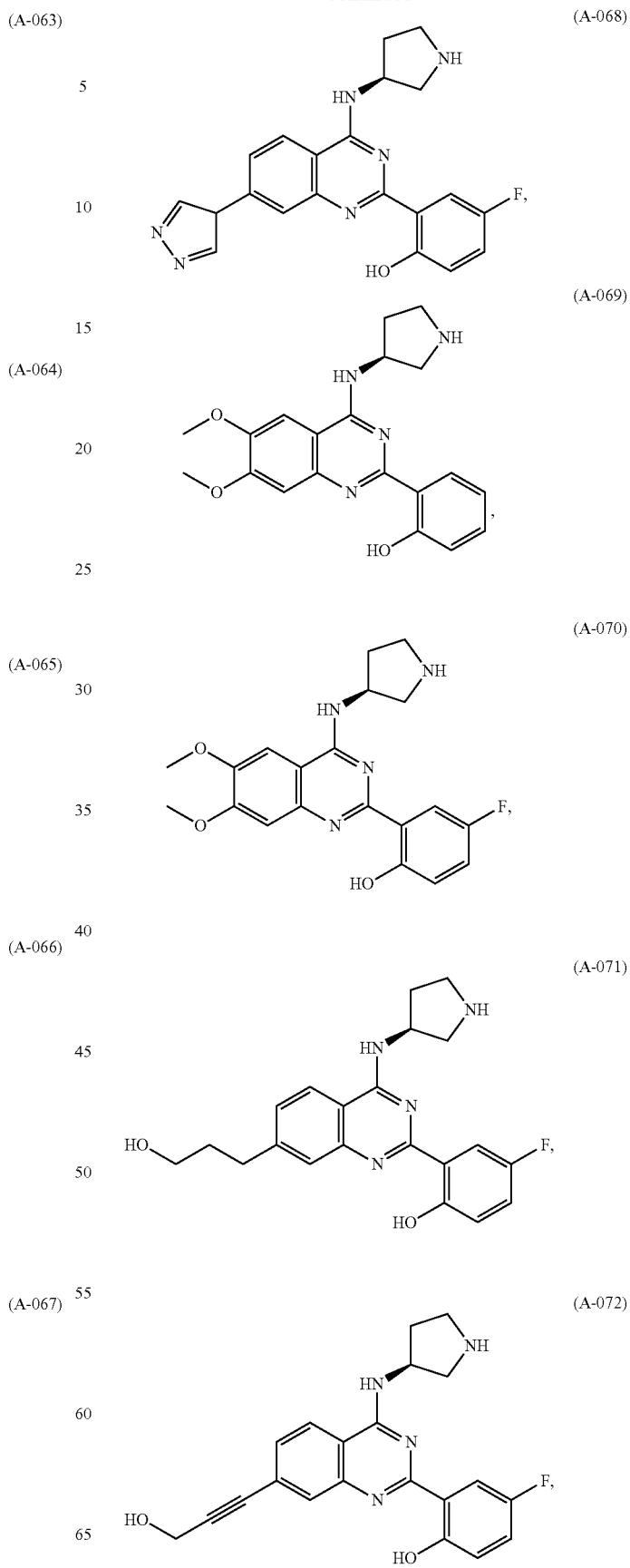

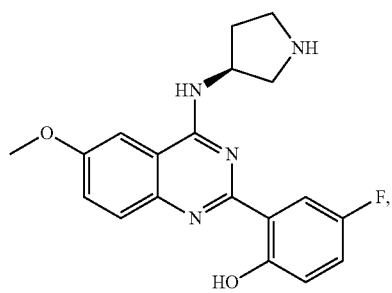 (A-073)
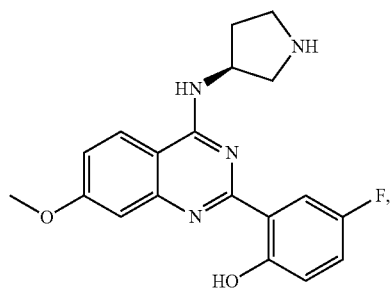 (A-074)
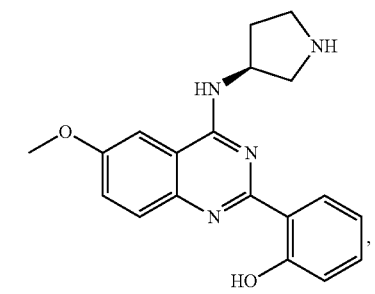 (A-075)
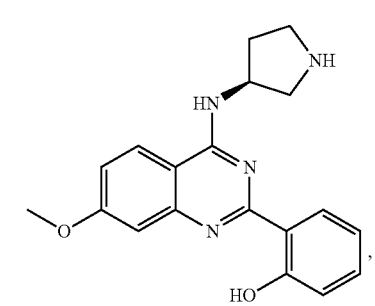 (A-076)
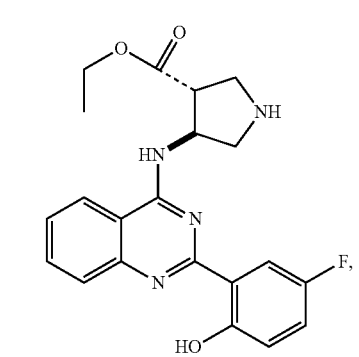 (A-077)
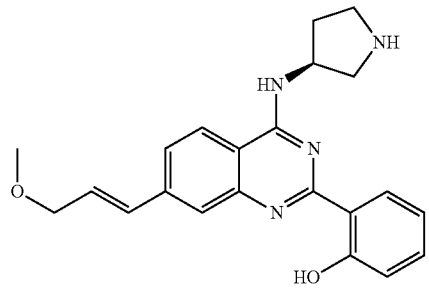 (A-078)
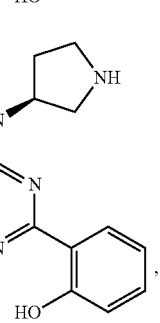 (A-079)
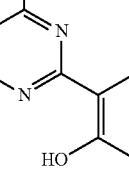 (A-080)
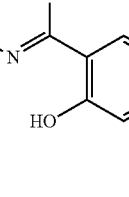 (A-081)
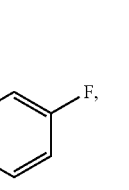 (A-082)

227
-continued
(A-083)
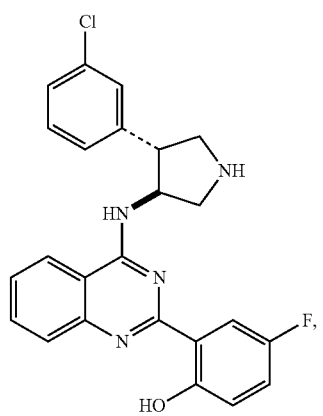
(A-084)
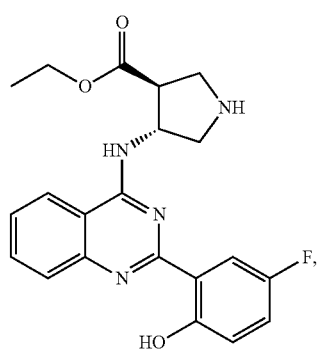
(A-085)
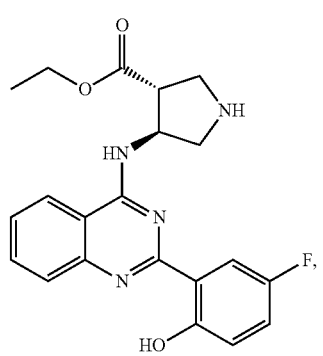
(A-086)
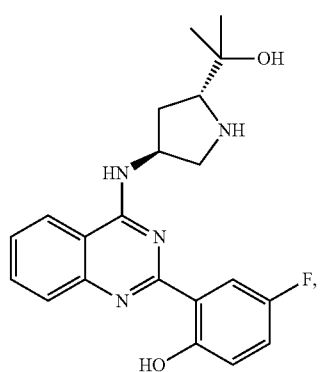
228
-continued
(A-087)
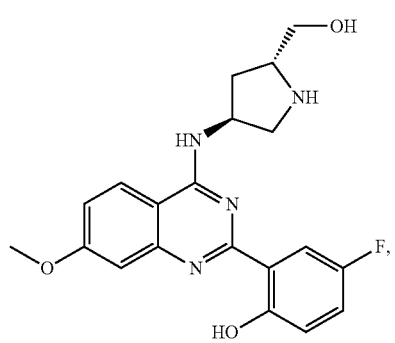
(A-088)
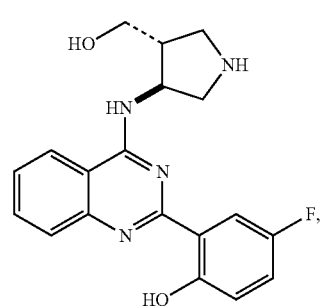
(A-089)
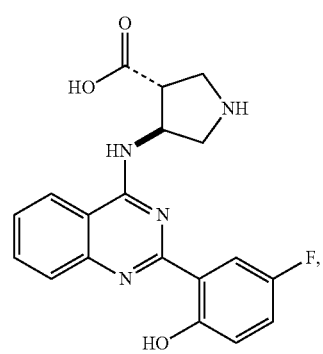
(A-090)
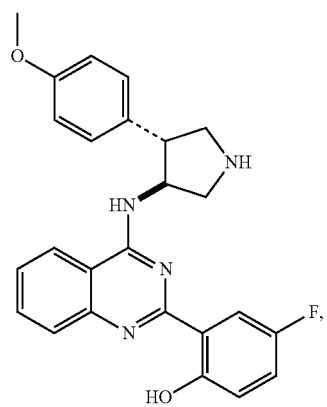

(A-091)
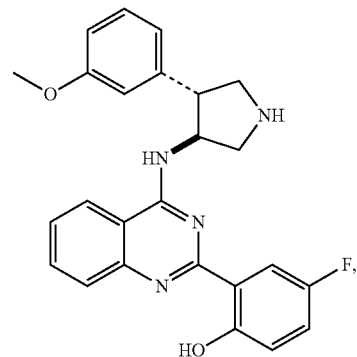
(A-092)
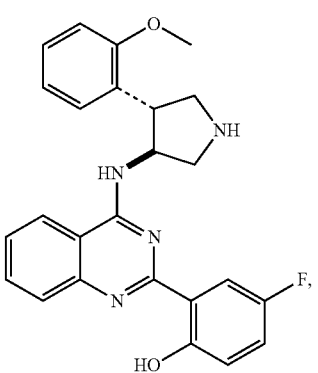
(A-093)
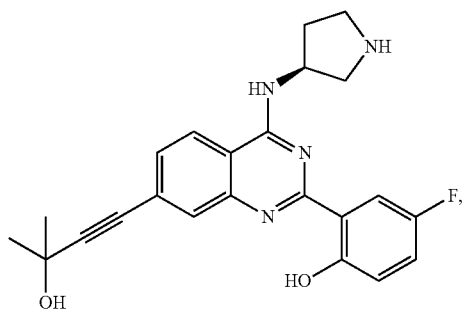
(A-094)
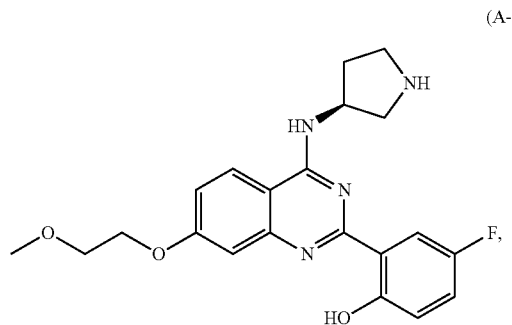
(A-095)
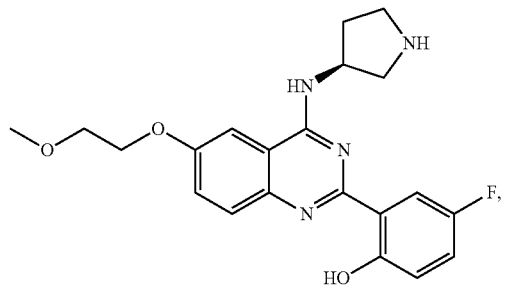
(A-096)
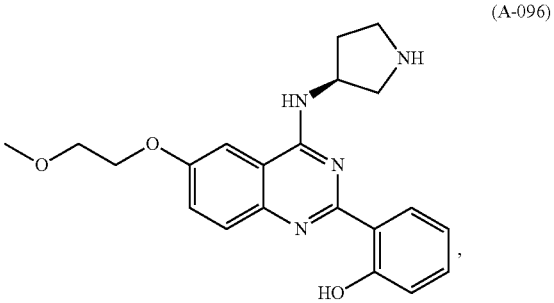
(A-097)
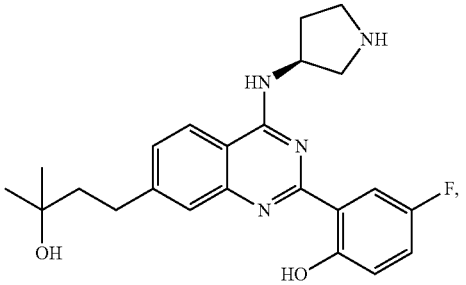
(A-098)
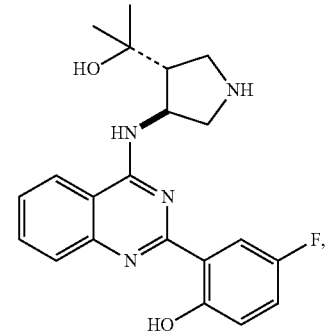
(A-099)
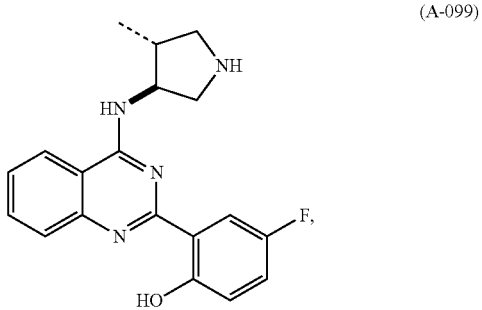

(A-100)
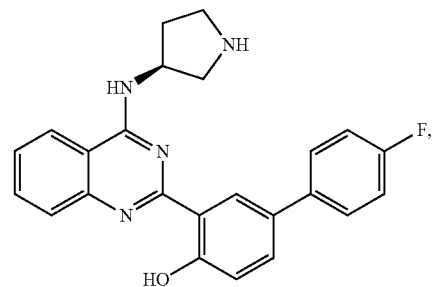
(A-101)
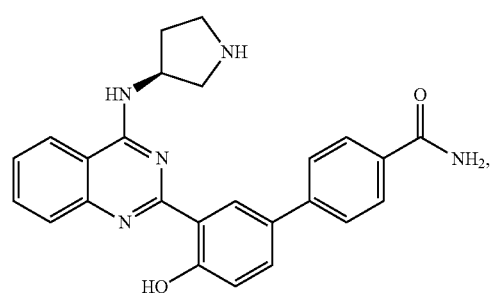
(A-102)
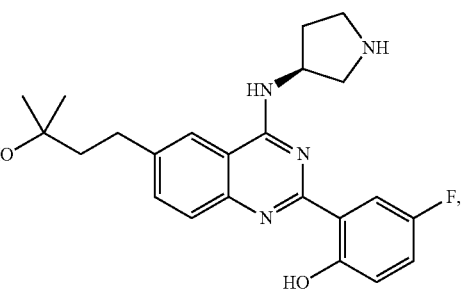
(A-103)
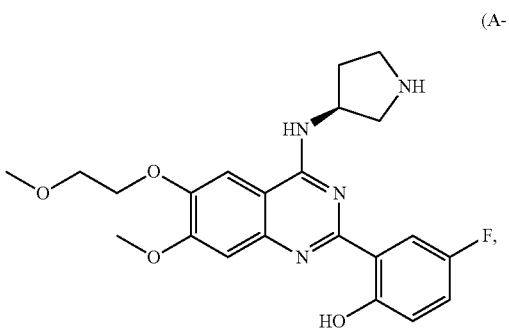
(A-104)
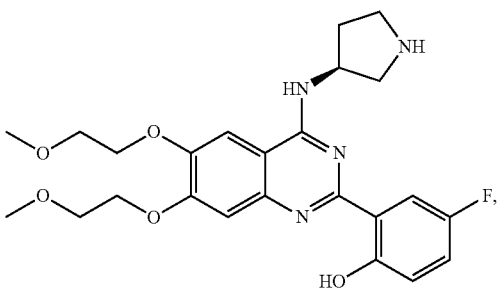
(A-105)
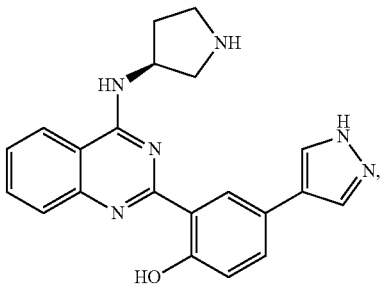
(A-106)
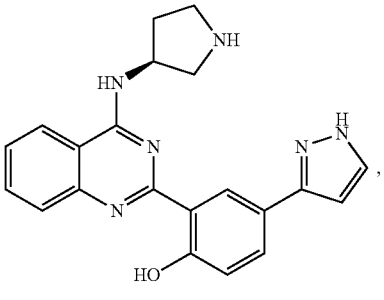
(A-107)
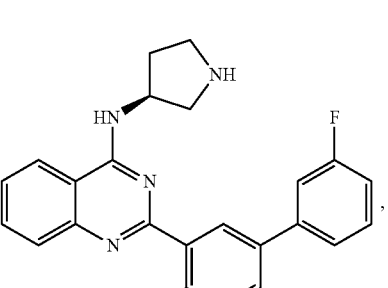
(A-108)
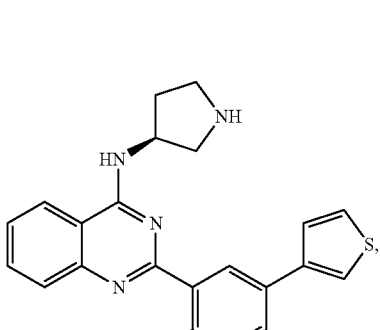
(A-109)
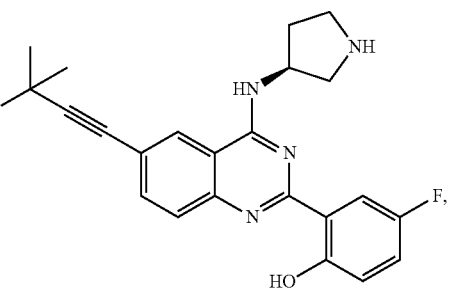

-continued
(A-110)
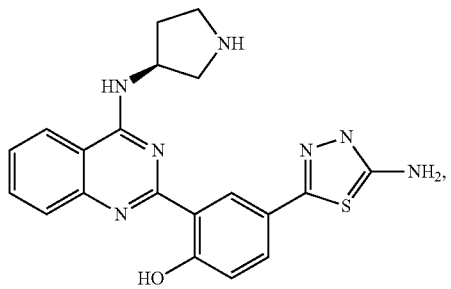
(A-111)
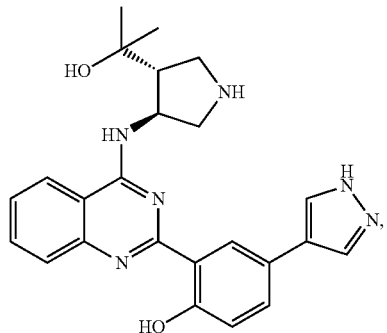
(A-112)
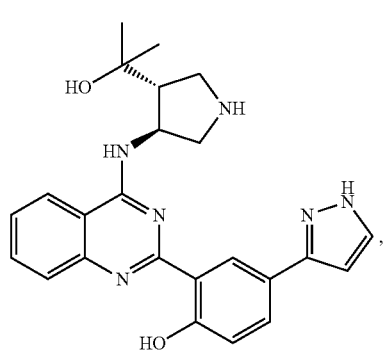
(A-113)
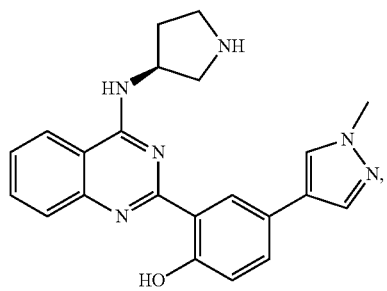
(A-114)
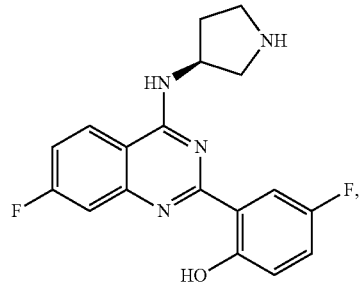
-continued
(A-115)
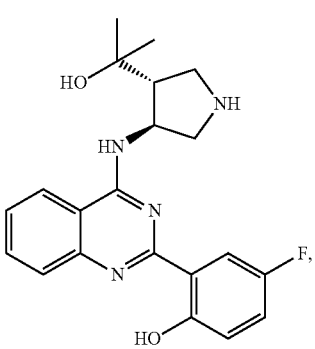
(A-116)
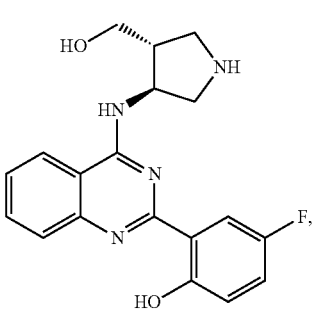
(A-117)
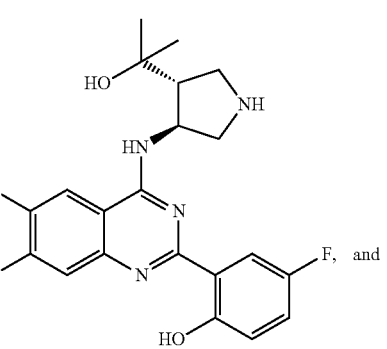
and
(A-118)
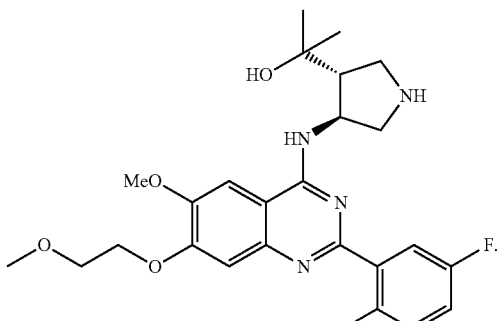
17. A pharmaceutical composition comprising a compound according to claim 1 and a pharmaceutically acceptable carrier or diluent.
* * * * *

```
                        SEQUENCE LISTING

<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide

<400> SEQUENCE: 1

Lys Lys Lys Val Ser Arg Ser Gly Leu Tyr Arg Ser Pro Ser Met Pro
1               5                   10                  15

Glu Asn Leu Asn Arg Pro Arg
            20
```